United States Patent
Davidsohn et al.

(10) Patent No.: US 12,281,154 B2
(45) Date of Patent: Apr. 22, 2025

(54) GENE THERAPY METHODS FOR AGE-RELATED DISEASES AND CONDITIONS

(71) Applicant: President and Fellows of Harvard College, Cambridge, MA (US)

(72) Inventors: Noah Davidsohn, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/302,865

(22) PCT Filed: May 22, 2017

(86) PCT No.: PCT/US2017/033815
§ 371 (c)(1),
(2) Date: Nov. 19, 2018

(87) PCT Pub. No.: WO2017/201527
PCT Pub. Date: Nov. 23, 2017

(65) Prior Publication Data
US 2019/0345224 A1 Nov. 14, 2019

Related U.S. Application Data

(60) Provisional application No. 62/421,665, filed on Nov. 14, 2016, provisional application No. 62/339,182, filed on May 20, 2016.

(51) Int. Cl.
*C07K 14/71* (2006.01)
*A61K 48/00* (2006.01)
(Continued)

(52) U.S. Cl.
CPC ............... *C07K 14/71* (2013.01); *A61P 3/04* (2018.01); *A61P 9/04* (2018.01); *C07K 14/50* (2013.01);
(Continued)

(58) Field of Classification Search
CPC .... C07K 14/71; C07K 14/50; C07K 2319/30; C07K 2319/31; A61P 3/04; A61P 9/04;
(Continued)

(56) References Cited

U.S. PATENT DOCUMENTS

| 5,824,655 A * | 10/1998 | Border ..................... A61P 1/16 514/44 R |
| 9,006,400 B2 * | 4/2015 | Boettcher ................. A61P 1/00 530/399 |
| 10,882,894 B2 * | 1/2021 | Philip ....................... A61P 1/16 |
| 2003/0072938 A1 * | 4/2003 | Kappes .................. C12N 15/86 428/341 |

(Continued)

FOREIGN PATENT DOCUMENTS

| CA | 2813163 A1 * | 4/2012 | ........... A61K 31/713 |
| CN | 103203027 A | 7/2013 | |

(Continued)

OTHER PUBLICATIONS

Lin HY, Moustakas A, Knaus P, et al. The soluble exoplasmic domain of the type II transforming growth factor (TGF)-β receptor: a heterogeneously glycosylated protein with high affinity and selectivity for TGF-β ligands. Journal of Biological Chemistry. Feb. 10, 1995;270(6):2747-54. (Year: 1995).*

(Continued)

*Primary Examiner* — Jeremy C Flinders
*Assistant Examiner* — Thomas R. Amick
(74) *Attorney, Agent, or Firm* — Banner & Witcoff, Ltd.

(57) ABSTRACT

Methods of gene therapy are provided for treating or preventing age-related diseases or conditions by regulating one (Continued)

or more functional proteins associated with age-related diseases or conditions.

22 Claims, 26 Drawing Sheets

Specification includes a Sequence Listing.

(51) Int. Cl.
    *A61P 3/04* (2006.01)
    *A61P 9/04* (2006.01)
    *C07K 14/50* (2006.01)
    *C12N 15/86* (2006.01)

(52) U.S. Cl.
    CPC .............. *C12N 15/86* (2013.01); *A61K 48/00* (2013.01); *C07K 2319/30* (2013.01); *C12N 2750/14132* (2013.01); *C12N 2750/14143* (2013.01); *C12N 2830/48* (2013.01)

(58) Field of Classification Search
    CPC . A61P 3/10; A61P 43/00; C12N 15/86; C12N 2750/14132; C12N 2750/14143; C12N 2830/48; A61K 48/00; A61K 48/005
    See application file for complete search history.

(56) References Cited

U.S. PATENT DOCUMENTS

| | | | |
|---|---|---|---|
| 2005/0002907 A1* | 1/2005 | Mitrophanous | C12N 9/0071 424/93.2 |
| 2006/0239972 A1 | 10/2006 | Zolotukhin et al. | |
| 2008/0262004 A1* | 10/2008 | Diefenbacher | C07D 519/00 514/265.1 |
| 2009/0053233 A1* | 2/2009 | De Romeuf | C07K 16/2887 424/141.1 |
| 2010/0003218 A1 | 1/2010 | Duan et al. | |
| 2010/0119516 A1* | 5/2010 | Wu | A61P 35/00 424/139.1 |
| 2010/0222280 A1* | 9/2010 | Herrerías | A61K 38/1841 514/21.2 |
| 2013/0039911 A1* | 2/2013 | Bedi | A61P 35/00 424/134.1 |
| 2013/0315996 A1* | 11/2013 | Steinberg | A61P 43/00 536/23.1 |
| 2014/0213512 A1* | 7/2014 | Ellison | A61P 3/08 514/4.8 |
| 2015/0018405 A1 | 1/2015 | Cohen et al. | |
| 2016/0120959 A1 | 5/2016 | Sun | |
| 2017/0189476 A1* | 7/2017 | Sung | A61P 1/04 |

FOREIGN PATENT DOCUMENTS

| | | | |
|---|---|---|---|
| CN | 103665166 A * | 3/2014 | ............. A61K 38/21 |
| EP | 2548570 A1 * | 1/2013 | ......... A61K 38/1825 |
| JP | 2001-515360 A | 9/2001 | |
| JP | 2009-532025 A | 9/2009 | |
| JP | 2014-526441 A | 10/2014 | |
| JP | 2014-534172 A | 12/2014 | |
| WO | WO-2006116002 A2 * | 11/2006 | ................. A61P 9/10 |
| WO | WO-2007079820 A1 * | 7/2007 | ............... A61P 25/28 |
| WO | 2008/033518 A2 | 3/2008 | |
| WO | WO-2008157367 A1 * | 12/2008 | ............. C07K 14/71 |
| WO | WO-2016065326 A2 * | 4/2016 | ............. A61K 38/00 |
| WO | WO-2016114633 A1 * | 7/2016 | ......... A61K 38/1825 |
| WO | WO-2015157469 A9 * | 10/2016 | ........... A61K 9/0014 |

OTHER PUBLICATIONS

Lijnen PJ, Petrov VV, Fagard RH. Induction of cardiac fibrosis by transforming growth factor-β1. Molecular genetics and metabolism . Sep. 1, 2000;71(1-2):418-35. (Year: 2000).*

Hills CE, Squires PE. TGF-β1-induced epithelial-to-mesenchymal transition and therapeutic intervention in diabetic nephropathy. American journal of nephrology. 2010;31(1):68-74. (Year: 2010).*

Dobaczewski M, Chen W, Frangogiannis NG. Transforming growth factor (TGF)-β signaling in cardiac remodeling. Journal of molecular and cellular cardiology. Oct. 1, 2011;51(4):600-6 (Year: 2011).*

Nishioka A, Ogawa Y, Mima T, et al. Histopathologic amelioration of fibroproliferative change in rat irradiated lung using soluble transforming growth factor-beta (TGF-β) receptor mediated by adenoviral vector. International Journal of Radiation Oncology* Biology* Physics. Mar. 15, 2004;58(4):1235-41. (Year: 2004).*

Liu SQ, Ma XL, Qin G, Liu Q, Li YC, Wu YH. Trans-system mechanisms against ischemic myocardial injury. Compr Physiol. Jan. 2015;5(1):167-92. doi: 10.1002/cphy.c140026. PMID: 25589268. (Year: 2015).*

Gimeno RE, Moller DE. FGF21-based pharmacotherapy-potential utility for metabolic disorders. Trends in Endocrinology & Metabolism. Jun. 1, 2014;25(6):303-11. (Year: 2014).*

Itoh N, Ohta H. Pathophysiological roles of FGF signaling in the heart. Frontiers in Physiology. Sep. 6, 2013;4:247. (Year: 2013).*

Kharitonenkov A, Adams AC. Inventing new medicines: the FGF21 story. Molecular metabolism. Jun. 1, 2014;3(3):221-9. Excellent review FGF21. (Year: 2014).*

Gray SJ, Foti SB, Schwartz JW, et al. Optimizing promoters for recombinant adeno-associated virus-mediated gene expression in the peripheral and central nervous system using self-complementary vectors. Human gene therapy. Sep. 1, 2011;22(9):1143-53. (Year: 2011).*

Wu Z, Sun J, Zhang T, Yin C, Yin F, Van Dyke T, Samulski RJ, Monahan PE. Optimization of self-complementary AAV vectors for liver-directed expression results in sustained correction of hemophilia B at low vector dose. Molecular Therapy. Feb. 1, 2008;16(2):280-9. (Year: 2008).*

Furler S, Paterna JC, Weibel M, Bueler H. Recombinant AAV vectors containing the foot and mouth disease virus 2A sequence confer efficient bicistronic gene expression in cultured cells and rat substantia nigra neurons. Gene therapy. Jun. 2001;8(11):864-73. (Year: 2001).*

Piek A, De Boer RA, Sillje HH. The fibrosis-cell death axis in heart failure. Heart failure reviews. Mar. 1, 2016;21(2):199-211. (Year: 2016).*

Kim JH, Lee SR, Li LH, Park HJ, Park JH, Lee KY, Kim MK, Shin BA, Choi SY. High cleavage efficiency of a 2A peptide derived from porcine teschovirus-1 in human cell lines, zebrafish and mice. PloS one. Apr. 29, 2011;6(4):e18556. (Year: 2011).*

Tang L, Sampson C, Dreitz MJ, McCall C. Cloning and characterization of cDNAs encoding four different canine immunoglobulin γ chains. Veterinary immunology and immunopathology. Aug. 10, 2001;80(3-4):259-70. (Year: 2001).*

Dai, J., & Rabie, A. (2007). Recombinant adeno-associated virus vector hybrids efficiently target different skeletal cells. Frontiers in bioscience : a journal and virtual library, 12, 4280-7 . (Year: 2007).*

Sequence alignment from IFW search results SEQ ID No. 20 Results 10 and 12 from file 20210513_133710_us-16-302-865-20. rge; May 14, 2021 (Year: 2021).*

Rabbani ZN, Anscher MS, Zhang X, Chen L, Samulski TV, Li CY, Vujaskovic Z. Soluble TGFβ type II receptor gene therapy ameliorates acute radiation-induced pulmonary injury in rats. International Journal of Radiation Oncology* Biology* Physics. Oct. 1, 2003;57(2):563-72. (Year: 2003) .*

Machine translation (WIPO) of GUO-CN 103665166A_MT (English) (Year: 2014).*

Mehal WZ, Schuppan D. Antifibrotic therapies in the liver. InSeminars in liver disease May 2015 (vol. 35, No. 2, p. 184). NIH Public Access. (Year: 2015).*

Yata Y, Gotwals P, Koteliansky V, Rockey DC. Dose-dependent inhibition of hepatic fibrosis in mice by a TGF-β soluble receptor: implications for antifibrotic therapy. Hepatology. May 1, 2002;35(5):1022-30 (Year: 2002).*

Xu P, Zhang Y, Liu Y, Yuan Q, Song L, Liu M, Liu Z, Yang Y, Li J, Li D, Ren G. Fibroblast growth factor 21 attenuates hepatic

(56) References Cited

OTHER PUBLICATIONS fibrogenesis through TGF-β/smad2/3 and NF-κB signaling pathways. Toxicology and applied pharmacology. Jan. 1, 2016;290:43-53. (Year: 2016).*
Kumar R, Sreenivasa BP, Tamilselvan RP. Construction and characterization of recombinant human adenovirus type 5 expressing foot-and-mouth disease virus capsid proteins of Indian vaccine strain, O/IND/R2/75. Vet World. Feb. 2015;8(2):147-55. doi: 10.14202/vetworld.2015.147-155. Epub Feb. 10, 2015. (Year: 2015).*
Chira S, Jackson CS, Oprea I, Ozturk F, Pepper MS, Diaconu I, Braicu C, Raduly LZ, Calin GA, Berindan-Neagoe I. Progresses towards safe and efficient gene therapy vectors. Oncotarget. Oct. 13, 2015;6(31):30675-703. doi: 10.18632/oncotarget.5169. PMID: 26362400; PMCID: PMC4741561 (Year: 2015).*
Rayssac A, Neveu C, Pucelle M, Van den Berghe L, Prado-Lourenco L, Arnal JF, Chaufour X, Prats AC. IRES-based vector coexpressing FGF2 and Cyr61 provides synergistic and safe therapeutics of lower limb ischemia. Molecular Therapy. Dec. 1, 2009; 17(12):2010-9 (Year: 2009).*
Pohlers D, Brenmoehl J, Loffler I, Muller CK, et al. TGF-β and fibrosis in different organs-molecular pathway imprints. Biochimica et Biophysica Acta (BBA)—Molecular Basis of Disease. Aug. 1, 2009;1792(8):746-56 (Year: 2009).*
Russo LM, del Re E, Brown D, Lin HY. Evidence for a role of transforming growth factor (TGF)-β1 in the induction of postglomerular albuminuria in diabetic nephropathy: amelioration by soluble TGF-β type II receptor. Diabetes. Feb. 1, 2007;56(2):380-8 (Year: 2007).*
Rabbani ZN, Anscher MS, Zhang X, Chen L, Samulski TV, Li CY, Vujaskovic Z. Soluble TGFβ type II receptor gene therapy ameliorates acute radiation-induced pulmonary injury in rats. International Journal of Radiation Oncology* Biology* Physics. Oct. 1, 2003;57(2):563-72; cited in prior action. (Year: 2003).*
Rayssac A, Neveu C, Pucelle M, Van den Berghe L, Prado-Lourenco L, Arnal JF, Chaufour X, Prats AC. IRES-based vector coexpressing FGF2 and Cyr61 provides synergistic and safe therapeutics of lower limb ischemia. Molecular Therapy. Dec. 1, 2009; 17(12):2010-9; cited in prior action. (Year: 2009).*
Zhang C, Wang KZ, Qiang H, Tang YL, Li Q, Li M, Dang XQ. Angiopoiesis and bone regeneration via co-expression of the hVEGF and hBMP genes from an adeno-associated viral vector in vitro and in vivo. Acta Pharmacologica Sinica. Jul. 2010;31(7):821-30 (Year: 2010).*
Bosch MK, Nerbonne JM, Ornitz DM. Dual transgene expression in murine cerebellar Purkinje neurons by viral transduction in vivo. PLoS One. Aug. 5, 2014;9(8):e104062 (Year: 2014).*
Jazwa A, Tomczyk M, Taha HM, Hytonen E, Stoszko M, Zentilin L, Giacca M, Yla-Herttuala S, Emanueli C, Jozkowicz A, Dulak J. Arteriogenic therapy based on simultaneous delivery of VEGF-A and FGF4 genes improves the recovery from acute limb ischemia. Vascular cell. Dec. 2013;5(1):1-1 (Year: 2013).*
Choi JH, Yu NK, Baek GC, Bakes J, Seo D, Nam HJ, Baek SH, Lim CS, Lee YS, Kaang BK. Optimization of AAV expression cassettes to improve packaging capacity and transgene expression in neurons. Molecular brain. Dec. 2014;7(1):1-0; cited in instant specification p. 32 final paragraph. (Year: 2014).*
Yero CD, Pajón FR, Caballero ME, Cobas AK,, et al. Immunization of mice with Neisseria meningitidis serogroup B genomic expression libraries elicits functional antibodies and reduces the level of bacteremia in an infant rat infection model. Vaccine. Jan. 4, 2005;23(7):932-9. (Year: 2005).*
Alignments of SV40 late poly A sequences; alignments performed on Nov. 18, 2021. (Year: 2021).*
Carswell S, Alwine JC. Efficiency of utilization of the simian virus 40 late polyadenylation site: effects of upstream sequences. Molecular and Cellular Biology. Oct. 1989;9(10):4248-58. (Year: 1989).*
Renaud-Gabardos E, Hantelys F, Morfoisse F, Chaufour X, Garmy-Susini B, Prats AC. Internal ribosome entry site-based vectors for combined gene therapy. World journal of experimental medicine. Feb. 20, 2015;5(1):11. (Year: 2015).*
Borkham-Kamphorst E, Herrmann J, Stoll D, Treptau J, Gressner AM, Weiskirchen R. Dominant-negative soluble PDGF-β receptor inhibits hepatic stellate cell activation and attenuates liver fibrosis. Laboratory investigation. Jun. 2004;84(6):766-77 (Year: 2004).*
Prud'homme GJ, Glinka Y, Khan AS, Draghia-Akli R. Electroporation-enhanced nonviral gene transfer for the prevention or treatment of immunological, endocrine and neoplastic diseases. Current Gene Therapy. Apr. 1, 2006;6(2):243-73 (Year: 2006).*
Tsang ML, Zhou L, Zheng BL, Wenker J, Fransen G, Humphrey J, Smith JM, O'Connor-McCourt M, Lucas R, Weatherbee JA. Characterization of recombinant soluble human transforming growth factor-β receptor type II (rhTGF-βsRII). Cytokine. Jul. 1, 1995;7(5):389-97 (Year: 1995).*
Wang ZG, Zhao W, Ramachandra M, Seth P. An oncolytic adenovirus expressing soluble transforming growth factor-β type II receptor for targeting breast cancer: in vitro evaluation. Molecular cancer therapeutics. Feb. 1, 2006;5(2):367-73 (Year: 2006).*
Komesli S, Vivien D, Dutartre P. Chimeric extracellular domain of type II transforming growth factor (TGF)-β receptor fused to the Fc region of human immunoglobulin as a TGF-β antagonist. European Journal of Biochemistry. Jun. 15, 1998;254(3):505-13 (Year: 1998).*
Ueno H, Sakamoto T, Nakamura T, Qi Z, Astuchi N, Takeshita A, Shimizu K, Ohashi H. A soluble transforming growth factor beta receptor expressed in muscle prevents liver fibrogenesis and dysfunction in rats. Human gene therapy. Jan. 1, 2000;11(1):33-42 ( Year: 2000).*
Zhu HJ, Sizeland AM. Extracellular domain of the transforming growth factor-β receptor negatively regulates ligand-independent receptor activation. Journal of Biological Chemistry. Oct. 8, 1999;274(41):29220-7 (Year: 1999).*
Alignment of Kyostio-Moore SEQ ID No. 4 and SEQ ID No. 8 (Year: 2022).*
Alignment of GeneBank LC600803.1 and SEQ ID No. 5 (Year: 2022).*
Choi JH, Yu NK, Baek GC, Bakes J, Seo D, Nam HJ, Baek SH, et al. Optimization of AAV expression cassettes to improve packaging capacity and transgene expression in neurons. Molecular brain. Dec. 2014;7(1):1-0; cited in instant specification p. 32 final paragraph; cited in prior action. (Year: 2014).*
Yero CD, Pajón FR, Caballero ME, Cobas AK,, et al. Immunization of mice with Neisseria meningitidis serogroup B genomic expression libraries elicits functional antibodies and reduces the level of bacteremia in an infant rat infection model. Vaccine. Jan. 4, 2005;23(7):932-9; cited in prior action. (Year: 2005).*
Chira S, Jackson CS, Oprea I, Ozturk F, Pepper MS, Diaconu I, Braicu C, Raduly LZ, Calin GA, Berindan-Neagoe I. Progresses towards safe and efficient gene therapy vectors. Oncotarget. Oct. 13, 2015;6(31):30675-703. doi: 10.18632/oncotarget.5169. PMID: 26362400; PMCID: PMC4741561; cited in prior action. (Year: 2015).*
Borkham-Kamphorst E, Herrmann J, Stoll D, Treptau J, Gressner AM, Weiskirchen R. Dominant-negative soluble PDGF-B receptor inhibits hepatic stellate cell activation and attenuates liver fibrosis. Laboratory investigation. Jun. 2004;84(6):766-77; cited in prior action. (Year: 2004).*
Prud'homme GJ, Glinka Y, Khan AS, Draghia-Akli R. Electroporation-enhanced nonviral gene transfer for the prevention or treatment of immunological, endocrine and neoplastic diseases. Current Gene Therapy. Apr. 1, 2006;6(2):243-73; cited in prior action. (Year: 2006).*
Lenski M, Kazakov A, Marx N, Bohm M, Laufs U. Effects of DPP-4 inhibition on cardiac metabolism and function in mice. Journal of molecular and cellular cardiology. Dec. 1, 2011;51(6):906-18. (Year: 2011).*
Carswell S, Alwine JC. Efficiency of utilization of the simian virus 40 late polyadenylation site: effects of upstream sequences. Molecular and Cellular Biology. Oct. 1989;9(10):4248-58; cited in prior action. (Year: 1989).*
Kumar R, Sreenivasa BP, et al. Construction and characterization of recombinant human adenovirus type 5 expressing foot-and-mouth disease virus capsid proteins of Indian vaccine strain, O/IND/R2/75. Vet World. Feb. 2015;8(2):147-55. Epub Feb. 10, 2015; cited in prior action. (Year: 2015).*

(56) References Cited

OTHER PUBLICATIONS

Gimeno RE, Moller DE. FGF21-based pharmacotherapy-potential utility for metabolic disorders. Trends in Endocrinology & Metabolism. Jun. 1, 2014;25(6):303-11; cited in prior action May 2021 (Year: 2014).*

Alignments of SV40 late poly A sequences; alignments performed on Nov. 18, 2021; cited in prior action. (Year: 2021).*

Machine translation (WIPO) of GUO-CN103665166A_MT (English); cited in prior action. (Year: 2014).*

Alignment of Kyostio-Moore SEQ ID No. 4 and SEQ ID No. 8; cited in prior action. (Year: 2022).*

Yang (Yang et al, Recombinant AAV-DJ Vector-Mediated FGF-21/FGF-21-GLP-1 Long-Term Expression in db/db Mice With Type 2 Diabetes Mellitus, Diabetes, Metabolic and Genetic Diseases, vol. 22, Supplement 1, S1329-S140, May 2014.) (Year: 2014).*

Yuan et al., A Versatile Adena-Associated Virus Vector Producer Cell Line Method for Scalable Vector Production of Different Serotypes. Human Gene Therapy, May 2011, vol. 22, pp. 613?624. Abstract; p. 614, col. 2, para 2; p. 615, col. 1, last para-col. 2, first para; p. 615, col. 2, last para-p. 616, col. 1, first para.

Cui, Xuezhi et al., "Inhibitory effect of a soluble transforming growth factor (beta) type II receptor on the activation of at hepatic stellate cells in primary culture", Journal of Hepatology, vol. 39, No. 5, Nov. 1, 2003 (Nov. 1, 2003), pp. 731-737, XP55623163, Amsterdam, NL.

European Search Report issued on Sep. 30, 2019 for EP Application No. 17800329.9.

Gao, Mingming et al., "Hydrodynamic delivery of FGF21 gene alleviates obesity and fatty liver in mice fed a high-fat diet", Journal of controlled release, Elsevier, Amsterdam, NL, vol. 185, Apr. 18, 2014 (Apr. 18, 2014), pp. 1-11, XP028854107.

Martin Fisher, Ffolliott et al., "Understanding the Physiology of FGF21", Annual Review of Physiology., vol. 78, No. 1, Feb. 10, 2016 (Feb. 10, 2016) pp. 223-241, XP55623554.

Zhang et al., "Effect of recombinant adenovirus pAd-sTGF-ß R? on ventricular remodeling after myocardial infarction in rats," Chin. J. Biologicals, vol. 47, No. 6, pp. 643-648 (2011).

Urabe et al., "Adeno-associated virus vectors and gene therapy," Virus, vol. 47, No. 2, pp. 221-230 (1997).

Suzuki et al., "Soluble Type II Transforming Growth Factor-ß Receptor Inhibits Established Murine Malignant Mesothelioma Tumor Growth by Augmenting Host Antitumor Immunity," Clin Cancer Res., vol. 10, No. 17, pp. 5907-5918 (Sep. 1, 2004).

Fisher, Ffolliott et al., "Understanding the Physiology of FGF21", Annual Review of Physiology, 2016, vol. 78, pp. 223-241.

Koichi Miyake et al., "Gene Delivery and Expression Series Viral Vector Mediated Gene Delivery and Expression (4),", Journal of Nippon Medical School, vol. 8, No. 2, Aug. 2012, pp. 150-156.

Tamio Iwamoto et al., "Motor Dysfunction in Type 5 Adenylyl Cyclase-null Mice*," Journal of Biological Chemistry, vol. 278, No. 19, May 2003, pp. 16936-16940.

Raphael Carapito et al., "A De Novo ADCY5 Mutation Causes Early-Onset Autosomal Dominant Chorea and Dystonia," Movement Disorders, vol. 30, No. 3, Mar. 2015, pp. 423-427.

* cited by examiner

Control 2 right            2000 Right

GENE THERAPY METHODS FOR AGE-RELATED DISEASES AND CONDITIONS

RELATED APPLICATIONS

This application is a National Stage Application under 35 U.S.C. 371 of PCT application PCT/US17/33815 designating the United States and filed May 22, 2017; which claims the benefit of U.S. Provisional Application No. 62/421,665 filed on Nov. 14, 2016 and to U.S. Provisional Application No. 62/339,182 filed on May 20, 2016 each of which are hereby incorporated by reference in their entireties.

STATEMENT OF GOVERNMENT INTERESTS

This invention was made with Government Support under HG005550 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Jun. 21, 2017, is named 010498_00961-WO_SL.txt and is 221,563 bytes in size.

BACKGROUND

Aging is the gradual loss of function and deterioration at the cellular, tissue, and organ level, leading to increased susceptibility to disease and external stressors, and eventually death. All organisms age, but the effects of aging can be slowed or minimized or manipulated. Numerous experiments have shown the ability to increase maximal lifespan as well as healthspan with decreased susceptibility to other age related pathologies. Aging interventions tested to date have included environmental manipulation such as calorie restriction (CR), small molecule drugs such as rapamycin, and genetic manipulations accomplished through the creation of transgenic animals such as the Ames and Snell dwarf mice. While these experiments have led to a greater understanding of the mechanisms involved in aging, they are not amenable to translation to aging human and pet populations. Calorie restriction requires strict adherence to dietary constraints and evidence to date suggests this is not a likely avenue for treatment. Rapamycin has immune modulation effects that can increase vulnerability to certain pathogens. And creating transgenic animals does not apply to all the existing living organisms. AAV delivery of hTERT into a cancer resistant genetic background mouse is described in Bernardes de Jesus B. et al., (2012) *EMBO Mol Med.* 4 (8): 691-704.

Gene therapy methods are known. For example GLY-BERA is a human gene therapy from uniQure that treats lipoprotein lipase deficiency (LPLD) by adding a working copy of the involved gene through intramuscular injections of AAV (adeno-associated virus). SPK-RPE65 is from Spark Therapeutics and is a human gene therapy that treats a rare blinding condition from a non-functioning RPE65 gene.

SUMMARY

The present disclosure provides gene therapy methods, such as combinational gene therapy methods to provide or regulate one or more endogenous proteins. The disclosure provides a method of treating or preventing age-related diseases and conditions or the aging phenotype using gene therapy. The disclosure provides the identification of genes related to certain diseases and conditions that may be associated with aging. The disclosure provides for the regulation of such genes either by increasing a protein related to a gene or decreasing a protein related to a gene. The disclosure provides for increasing a functional protein related to a gene by introducing a nucleic acid encoding the functional protein which is expressed within a cell. The expression results in the increased amount of the functional protein that can either be intracellular or be secreted providing a therapeutic effect or prophylactic effect. The disclosure provides for the inhibition of a gene thereby decreasing the functional protein associated with the gene by introducing a nucleic acid encoding an inhibitory RNA which when expressed binds to the gene or the messenger RNA to inhibit expression of the functional protein. The disclosure provides for the inhibition of a functional protein thereby decreasing the activity of the functional protein by introducing a nucleic acid encoding a protein inhibitor, such as a soluble receptor protein, which when expressed, binds to the functional protein. The disclosure provides for gene therapy methods using genetic constructs targeting cells in an animal and the delivery of such genetic constructs using vectors, such as viral vectors. The disclosure provides for gene therapy methods using genetic constructs targeting cells in an animal and the delivery of such genetic constructs using methods such as liposomes, synthetic or naturally occurring polymers, electroporation, coated or non-coated nano-particle delivery, bolistic particle delivery, laser mediate transfection (optoporation or phototransfection). See, e.g., Kim, T. K. et al., (2010) *Analytical and Bioanalytical Chemistry.* 397 (8): 3173-3178. The disclosure provides for gene therapy methods using genetic constructs targeting cells in an animal and the delivery of such genetic constructs wherein the genetic construct has been processed from the original DNA into miRNA, shRNA, RNAi, or mRNA (where the mRNA consists of a 5' Cap and a 3' poly A or equivalent). According to additional aspects, the RNA is targeted to the ribosome for translation using a 5' Cap analogue known to those of skill in the art or 3' poly A analogue known to those of skill in the art. For the gene therapy methods described herein, the disclosure provides for the use of a gene or gene product or DNA encoding the gene or mRNA corresponding to the gene or processed pri-mRNA or miRNA corresponding to the gene in the methods of gene therapy described herein insofar as the gene or gene product or DNA encoding the gene or mRNA corresponding to the gene or processed pri-mRNA or miRNA corresponding to the gene are altered or regulated to provide a cellular effect in the therapeutic or prophylactic methods described herein.

The regulation or providing of certain proteins associated with age-related diseases and conditions provide prophylactic methods or therapeutic methods to address age-related diseases and conditions. The regulation or providing of certain proteins or genes or gene products or DNA encoding the gene or mRNA corresponding to the gene or processed pri-mRNA or miRNA corresponding to the gene associated with age-related diseases and conditions provide methods of rejuvenating organisms including humans and other mammals. The disclosure provides gene therapy methods where one or more or a plurality of nucleic acids, such as genes, are delivered to one or more target cells in an animal. The disclosure provides the delivery to a cell of a plurality of nucleic acids including a single promoter driving their expression using a single vector. The one or more or plurality of nucleic acids are expressed to produce one or more corresponding proteins and the one or more proteins alter a condition of the organism. The disclosure provides for combination therapy where different cell types are targeted by the one or more or plurality of nucleic acids in the animal.

The disclosure provides for combination therapy where one or more cellular processes within a cell are targeted by the one or more or plurality of nucleic acids. The disclosure provides for gene therapy using a viral vector such as a parvoviral virion. The disclosure provides for gene therapy using a viral vector such as an adeno-associated virus ("AAV"). The adeno-associated virus will insert an exogenous gene into a cell and the protein encoded by the exogenous gene will be expressed. In this manner, the protein, whether a functional protein, an inhibitory RNA or an inhibitory protein, will alter the cell and/or the organism harboring the cell.

The disclosure provides for the slowing, inhibiting, forestalling or reversing of age-related diseases or conditions. Exemplary age-related or other diseases or conditions include one or more of cardiovascular diseases, diabetes, atherosclerosis, obesity, cancer, infection, and neurological disorders. The disclosure provides long-term gene therapy treatments to treat and/or prevent age-related or other diseases or conditions. The methods include reversing age-related diseases and conditions and correcting these pathological states resulting in an increased healthspan (years of good quality of life) and lifespan.

The disclosure provides a method for identifying a gene or set of genes to be regulated which prevent or treat one or more diseases or conditions, such as diseases or conditions associated with aging. The gene or set of genes are identified as being related to age-related diseases or conditions. The genes are determined to be associated or non-associated with a particular tissue type so that appropriate regulation of the gene using desired methods can be determined. In addition, genes associated with a particular tissue type may benefit from regulation using particular vectors that deliver to a particular tissue type cell a nucleic acid, inhibitory RNA or inhibitory protein to regulate the amount or activity of the protein within the particular tissue type cell. Tissue specific promoters may be used to express the nucleic acid.

Exemplary nucleic acids encoding particular functional proteins, inhibitory RNA or inhibitory proteins are provided at Appendix A, the sequences of which are provided in Appendix A or are readily known or available in the literature. Likewise, sequences for the functional proteins, inhibitory RNA or inhibitory proteins are known to those of skill in the art or can be derived from the nucleic acid sequences. Appendix B includes the DNA and amino acid sequences for the mouse versions of genes as well as the pri-miRNA DNA constructs that target multiple RNA species.

Functional proteins as described herein can be the full length proteins or proteins which vary from the full length proteins but retain the activity in whole or in part of the full length protein.

Further features and advantages of certain embodiments of the present invention will become more fully apparent in the following description of embodiments and drawings thereof, and from the claims.

DETAILED DESCRIPTION

Figure 1:
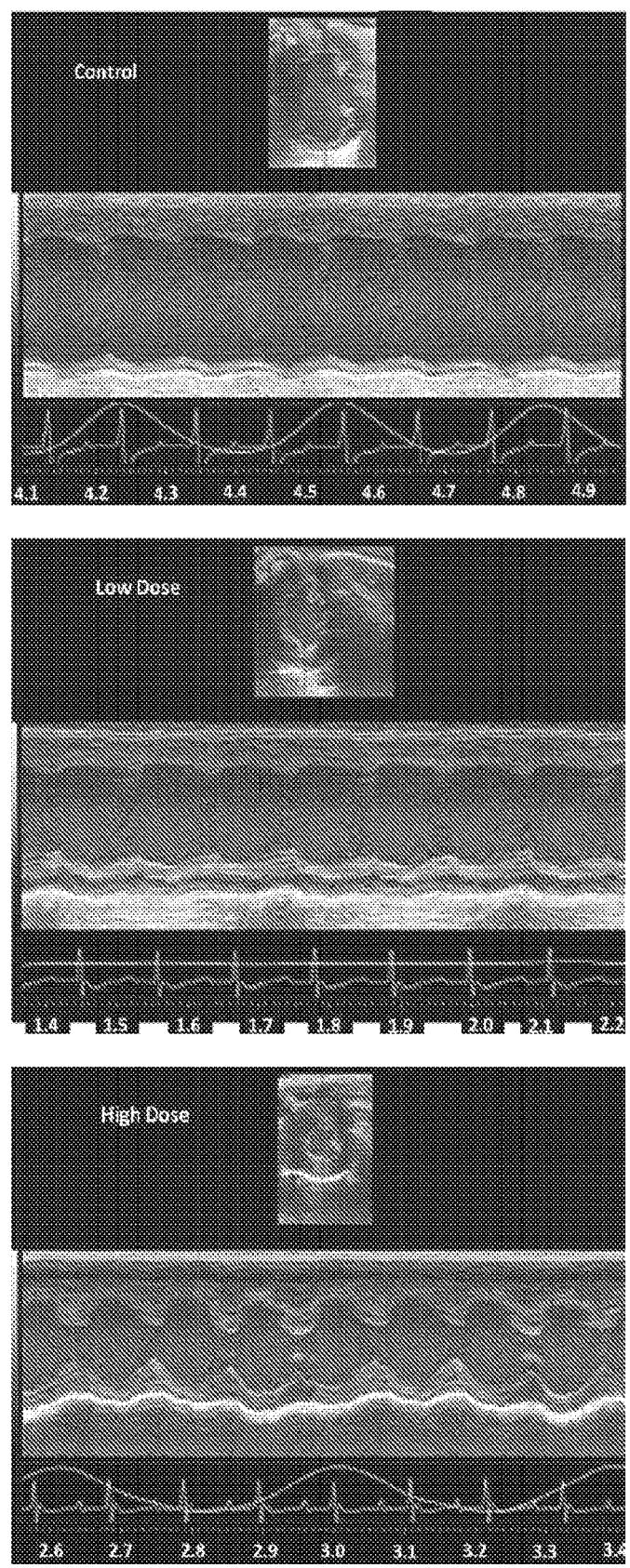
FIG. 1 are representative echocardiograms after 7 weeks post AAC surgery.

The present disclosure provides gene therapy methods where one or more or a plurality of nucleic acids encoding a functional protein, an inhibitory RNA or an inhibitory protein are provided to cells within a subject. The one or more nucleic acids are administered by one or more vectors or combined into a single viral vector, such as an AAV, to treat or prevent diseases or conditions associated with aging and age-related physiological decline.

As used in this specification and the appended claims, the singular forms "a", "an" and "the" include plural referents unless the context clearly indicates otherwise. Thus, for example, reference to "a protein" includes more than one protein, and reference to "an excipient" includes more than one excipient.

It is further to be understood that use of "or" means "and/or" unless stated otherwise. Similarly, "comprise," "comprises," "comprising" "include," "includes," and "including" are interchangeable and not intended to be limiting. Also, where descriptions of various embodiments use the term "comprising," those skilled in the art would understand that in some specific instances, an embodiment can be alternatively described using language "consisting essentially of" or "consisting of."

The foregoing general description, including the drawings, and the following detailed description are exemplary and explanatory only and are not restrictive of this disclosure.

The section headings used herein are for organizational purposes only and not to be construed as limiting the subject matter described.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Gene" as used herein refers to a nucleic acid region, also referred to as a transcribed region, which expresses a polynucleotide, such as an RNA. The transcribed polynucleotide can have a sequence encoding a polypeptide, such as a functional protein, which can be translated into the encoded polypeptide when placed under the control of an appropriate regulatory region. A gene may comprise several operably linked fragments, such as a promoter, a 5' leader sequence, a coding sequence and a 3' nontranslated sequence, such as a polyadenylation site. A chimeric or recombinant gene is a gene not normally found in nature, such as a gene in which, for example, the promoter is not associated in nature with part or all of the transcribed DNA region. "Expression of a gene" refers to the process wherein a gene is transcribed into an RNA and/or translated into a functional protein.

"Gene delivery" or "gene transfer" refers to methods for introduction of recombinant or foreign DNA into host cells. The transferred DNA can remain non-integrated or preferably integrates into the genome of the host cell. Gene delivery can take place for example by transduction, using viral vectors, or by transformation of cells, using known methods, such as electroporation, cell bombardment.

"Transgene" refers to a gene that has been introduced into a host cell. The transgene may comprise sequences that are native to the cell, sequences that do not occur naturally in the cell, or combinations thereof. A transgene may contain sequences coding for one or more proteins that may be operably linked to appropriate regulatory sequences for expression of the coding sequences in the cell.

"Transduction" refers to the delivery of a nucleic acid molecule into a recipient host cell, such as by a gene delivery vector, such as rAAV. For example, transduction of a target cell by a rAAV virion leads to transfer of the rAAV vector contained in that virion into the transduced cell. "Host cell" or "target cell" refers to the cell into which the nucleic acid delivery takes place.

"Functional protein" includes variants, mutations, homologues, and functional fragments of the full length proteins. One of skill will readily be able to construct proteins homologous to the full length proteins which retain the activity, in whole or in part, of the full length protein.

"Vector" refers generally to nucleic acid constructs suitable for cloning and expression of nucleotide sequences. One example of a vector is a viral vector. The term vector may also sometimes refer to transport vehicles comprising the vector, such as viruses or virions, which are able to transfer the vector into and between host cells.

"AAV vector" or "rAAV vector" refers to a recombinant vector derived from an adeno-associated virus serotype, such as AAV1, AAV2, AAV3, AAV4, AAV5, AAV6, AAV7, AAV8, AAV9, AAV10, AAV11, AAV12, AAV2.5, AAvDJ, AAVrh10.XX and others. rAAV vectors can have one or preferably all wild type AAV genes deleted, but still comprise functional ITR nucleic acid sequences. Functional ITR sequences are necessary for the replication, rescue and packaging of AAV virions. The ITR sequences may be wild type sequences or substantially identical sequences (as defined below) or may be altered by for example in insertion, mutation, deletion or substitution of nucleotides, as long as they remain functional.

"Therapeutically effective amount" refers to an amount effective, at dosages and for periods of time necessary, to achieve the desired therapeutic result, such as results directed at age-related diseases or conditions. A therapeutically effective amount of a parvoviral virion or pharmaceutical composition may vary according to factors such as the disease state, age, sex, and weight of the individual, and the ability of the parvoviral virion or pharmaceutical composition to elicit a desired response in the individual. Dosage regimens may be adjusted to provide the optimum therapeutic response. A therapeutically effective amount is also typically one in which any toxic or detrimental effects of the parvoviral virion or pharmaceutical composition are outweighed by the therapeutically beneficial effects.

"Prophylactically effective amount" refers to an amount effective, at dosages and for periods of time necessary, to achieve the desired prophylactic result, such as preventing or inhibiting various age-related diseases or conditions, A prophylactic dose may be used in subjects prior to or at an earlier stage of disease, and a prophylactically effective amount may be more or less than a therapeutically effective amount in some cases.

"Nucleic acid" includes any molecule composed of or comprising monomeric nucleotides. The term "nucleotide sequence" may be used interchangeably with "nucleic acid" herein. A nucleic acid may be an oligonucleotide or a polynucleotide. A nucleic acid may be a DNA or an RNA. A nucleic acid may be a gene. A nucleic acid may be chemically modified or artificial. Artificial nucleic acids include peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule. Also, phosphorothioate nucleotides may be used.

"Nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell. One type of nucleic acid construct is an "expression cassette" or "expression vector". These terms refers to nucleotide sequences that are capable of effecting expression of a gene in host cells or host organisms compatible with such sequences. Expression cassettes or expression vectors typically include at least suitable transcription regulatory sequences and optionally, 3' transcription termination signals. Additional factors necessary or helpful in effecting expression may also be present, such as expression enhancer elements. A nucleic acid construct can also be a vector in which it directs expression or repression of a protein by operating as RNA instead of DNA. In the case of increasing expression of a target protein this nucleic acid construct can be mRNA or similar in which the cell or more specifically the ribosome would recognize and create many copies of the protein. In the case of repressing expression of a target sequence the RNA can be in the form that acts through preventing the ribosome from creating protein, this can be done through mechanisms of RNAi or shRNA or miRNA or Pri-miRNA. One could also imagine through Boolean logic that if one represses a known repressor of a target sequence one would in turn actually get an increase in the target sequence through repression and one skilled in the art can abstract away from the target protein such that any combination of "inversions" or "imply's" through the delivery of either mRNA (or similar) or shRNA (or similar) can produce the regulation of the target sequence. This can also be done through the vector that provides DNA that must be expressed as in the AAV.

"Operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signals for introns, 2A peptide sequences (that allow multicistronic expression) and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a poly A tail, i.e., a string of adenine residues at the 3'-end of a mRNA, which may be referred to as poly A sequences. It also can be designed to enhance mRNA stability. Expression control sequences which affect the transcription and translation stability, e.g., promoters, as well as sequences which effect the translation, e.g., Kozak sequences, suitable for use in insect cells are well known to those skilled in the art. Expression control sequences can be of such nature as to modulate the nucleotide sequence to which it is operably linked such that lower expression levels or higher expression levels are achieved.

One can also fuse functional domains to already known proteins. Such is the case where a mitochondrial signal is fused to CAT (catalase) such that the catalase is targeted to be shuttled to the mitochondria and perform its function inside or near the mitochondria instead of its natural location. One can also add targeting signals to other proteins to have them targeted to other parts of the cell or even secreted from the cell. In the case of some proteins a better known version can replace the natural sequence for enhanced effect, such as taking the human or mouse secretion signal for TGFbR2 and fusing it to the dog version of the protein.

"Promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter, including e.g. attenuators or enhancers, but also silencers. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells. The disclosure provides for the operable linking of nucleic acid constructs to a mammalian cell-compatible expression control sequence, e.g., a promoter. Many such promoters are known in the art (see Sambrook and Russell, 2001, supra). Constitutive promoters that are broadly expressed in many cell types, such as the CMV and hEf1α promoter are disclosed. Variations of the full-length hEf1α are also disclosed which are shorter but still provide effective constitutive expression. Disclosed are promoters that are inducible, tissue-specific, cell-type-specific, or cell cycle-specific. In a disclosed embodiment, the nucleotide sequence encoding the porphobilinogen deaminase is operably linked to a liver-specific promoter. Liver-specific promoters are particularly preferred for use in conjunction the non-erythroid deaminase. Preferably, in a construct of the disclosure an expression control sequence for liver-specific expression are e.g. selected from the group consisting of an a1-anti-trypsin (AAT) promoter, a thyroid hormone-binding globulin promoter, an albumin promoter, a thyroxin-binding globulin (TBG) promoter, an Hepatic Control Region (HCR)-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumour-selective, and, in particular, neurological cell tumour-selective expression (Parr et al., (1997) *Nat. Med.* 3:1145-9) or the IL-2 promoter for use in mononuclear blood cells (Hagenbaugh et al., (1997) *J Exp Med;* 185:2101-10).

"3' UTR" or "3' non-translated sequence" (also often referred to as 3' untranslated region, or 3'end) refers to the nucleic acid sequence found downstream of the coding sequence of a gene, which comprises, for example, a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Naturally occurring sequence" or "native sequence" as used herein refers to a polynucleotide or amino acid isolated from a naturally occurring source. Included within "native sequence" are recombinant forms of a native polypeptide or polynucleotide which have a sequence identical to the native form.

"Mutant" or "variant" as used herein refers to an amino acid or polynucleotide sequence which has been altered by substitution, insertion, and/or deletion. In some embodiments, a mutant or variant sequence can have increased, decreased, or substantially similar activities or properties in comparison to the parental sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, (1981) Adv. Appl. Math. 2:482, by the homology alignment algorithm of Needleman and Wunsch, (1970) J. Mol. Biol. 48:443, by the search for similarity method of Pearson and Lipman, (1988) Proc. Natl. Acad. Sci. USA 85:2444, by computerized implementations of these algorithms (GAP, BESTFIT, FASTA, and TFASTA), or by visual inspection (see generally, Current Protocols in Molecular Biology, F. M. Ausubel et al., eds., Current Protocols, Greene Publishing Associates, Inc. and John Wiley & Sons, Inc., (1995 Supplement)).

Examples of algorithms that are suitable for determining percent sequence identity and sequence similarity are the BLAST and BLAST 2.0 algorithms, which are described in Altschul et al., (1990), J. Mol. Biol. 215:403-410 and Altschul et al., (1977) Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value: the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, (1989) Proc. Natl. Acad. Sci. USA 89:10915).

The degree of percent amino acid sequence identity can also be obtained by ClustalW analysis (version W 1.8) by counting the number of identical matches in the alignment and dividing such number of identical matches by the length of the reference sequence, and using the following default ClustalW parameters to achieve slow/accurate pairwise optimal alignments-Gap Open Penalty: 10: Gap Extension Penalty: 0.10; Protein weight matrix: Gonnet series: DNA weight matrix: IUB: Toggle Slow/Fast pairwise alignments=SLOW or FULL Alignment.

"Subject" or "patient" refers to a mammal, such as a non-primate (e.g., cow, pig, horse, cat, dog, rat, etc.) or a primate (e.g., monkey or human). Preferably, the mammal is a domesticated animal, such as a dog, a cat, a mouse, a cow, a sheep, a goat, a horse, a pig, or a human subject. In some embodiments, the human is an adult patient. In some embodiments, the human is a pediatric patient.

Gene Therapy by Expressing Functional Proteins and Regulating Functional Protein Expression As summarized above, the present disclosure provides for the regulation of one or more or a plurality of genes or their associated functional proteins in a method of treating or preventing diseases or conditions associated with the targeted genes. In particular the individual targeted gene or one or more of a combination of the targeted genes is associated with age-related diseases or conditions and/or affecting biological lifespan. The genes or gene products targeted by the described gene therapy are involved in diverse cellular roles, such as metabolic activity, insulin-like growth factor activity pathway (i.e., IGF1/GH/mTOR axis), mitochondrial function, inflammatory/fibrosis, autophagy, neural function, genome stability, etc. The gene therapy can be based on, by way of example and not limitation, one or more of a nucleic acid or gene which overexpress a functional protein or a mutant form thereof; expression of a functional protein which regulates another target gene/protein: expression of polynucleotides, such as inhibitory RNA, to regulate expression of a target gene; and expression of gene editing systems that modify in situ the target gene. Such nucleic acids can be a "synthetic nucleotide sequence" which is herein understood to mean that the nucleotide sequence does not occur as such in nature, but rather was designed, engineered and/or constructed by human intervention. The term "synthetic" thus does not necessarily imply that the sequence is exclusively and/or entirely obtained through chemical synthesis.

Rather, although parts of the synthetic sequence may at one stage have been obtained through chemical synthesis, molecules comprising a synthetic sequence of the invention will usually be obtained from biological sources such as (cultured, for example recombinant) cells.

In some embodiments, the gene for therapeutic applications and the corresponding expressed gene product are provided in Table 1 which may be administered, for example, by a viral vector system or a Cas9 guide RNA system.

TABLE 1

| No. | Gene | Expressed product of the Gene | Description of biological effect of Gene expression |
|---|---|---|---|
| 1 | ADcy5 | Inhibitory pri-miRNA/shRNA | Decrease ADcy5 in order to decrease cAMP/PKA and increase RAF/MEK/ERK to increase anti-apoptotic effect and cell survival and oxidative resistance. |
| 2 | Adiponectin | over express protein | Agonist of pParg and AMPK |
| 3 | Adra1a (mut) | over express protein | Constitutively active receptor leads to neurogenesis and plasticity and enhanced learning |
| 4 | Agtr1a | Inhibitory pri-miRNA/shRNA | Increases mitochondrial biogenesis and NAMPT and Sirt3 and decreases oxidative damage, especially in kidney and heart |
| 5 | Akt1 | Inhbitory Pri-miRNA/shRNA | Akt1+/− mice showed a decrease of TOR signaling, but phosphorylation of the forkhead transcription factors (FOXO) was not down-regulated, Decreasing Akt1 decreases ribsomal gene expression and lower mitochondrial biomass only need 50% reduction for effect |
| 6 | AMPK | over express protein | Metabolic involvement and energy expenditure |
| 7 | Atg5 | over express protein | Increases autophagy and increased levels of glutathione |
| 8 | BubR1 | over express protein | BubR1 overabundance exerts a protective effect by correcting mitotic checkpoint impairment and microtubule-kinetochore attachment defects. Furthermore, sustained high-level expression of BubR1 extends lifespan and delays age-related deterioration and aneuploidy in several tissues. |
| 9 | MCAT | over express protein | mitochondrial targeting signal attached to a catalase that enables the catalase to act in/near the mitochondria to decrease oxidative damage |
| 10 | Cebpalpha | Inhbitory pri-miRNA/shRNA | Decrease cebpa and increase cebpb |
| 11 | Cebpbeta | over express protein | acts by turning WAT to BAT by increasing mitochondria biogenesis and UCP1 |
| 12 | Cisd2d | over express protein | Mitochondrial membrane protein, Cisd2 may function as an autophagy regulator and may be involved in the Bcl-2-mediated regulation of autophagy and calcium homeostasis |
| 13 | Coq7 | Inhibitory pri-miRNA/shRNA | Loss of Coq7 (or mClk-1) results in decreased ROS and oxidative DNA damage the effect seems to come from the liver. |
| 14 | Ctf1 | Inhibitory pri-miRNA/shRNA | CT-1-null mice shows decreased levels of inflammatory, apoptotic, and senescence pathways, whereas telomere-linked proteins, DNA repair proteins, and antioxidant enzyme activities were increased. |
| 15 | Dgat1 | Inhibitory pri-miRNA/shRNA | Involved in fat synthesis fat such that knocking down expressom can result in less fat and thus less igf1 and increased lifespan |
| 16 | FGF21 | over express protein | Decreases IGF1 signaling, modulates metabolism, changes differentiation of osteoblast and osteoclasts, curbs appetite |
| 17 | GDF15 (hNAG) | over express protein | Acts through decreasing IGF1/mTOR/insulin signaling . . . Reduces weight in mice to prevent them from getting age associated obesity |
| 18 | HAS2 naked mole rat (nmr) | over express protein | Anti-Cancer, Believed to create contact inhibition signals through the body by making the environment more viscous |
| 19 | humanizeFoxP2 | over express protein | Learning and striatal neuroplasticity. Foxp2(hum/hum) mice learn stimulus-response associations faster than their WT littermates |
| 20 | Ikbkb | Inhibitory pri-miRNA/shRNA | Acts through NFKB and GnRH development via immune-neuroendocrine integration, and immune inhibition or GnRH restoration in the hypothalamus/brain |
| 21 | Insr | Inhibitory pri-miRNA/shRNA | Fat Specific Knockout. Makes fat smaller and acts on metabolism and insulin resistance |
| 22 | Klotho | over express protein | Klotho protein functions as a circulating hormone that binds to a cell-surface receptor and represses intracellular signals of insulin and insulin-like growth factor 1 (IGF1) as well as other effects |
| 23 | Mt1 | over express protein | Decreases anti-oxidants and increases resistance to stress in cardiac function. Delays onset of age associated phenotypes. |
| 24 | mTOR | Inhibitory pri-miRNA/shRNA | Acts through NFkb. Active mTORC1 enhances processes including glycolysis, protein, lipid and nucleotide biosynthesis, and it inhibits autophagy. By blocking mTOR you get health and lifespan inprovements in mice. |

TABLE 1-continued

| No. | Gene | Expressed product of the Gene | Description of biological effect of Gene expression |
|---|---|---|---|
| 25 | NEU1 | over express protein | Reduces B amyloid plaques and decreases AD development |
| 26 | nf-kb | Inhibitory pri-miRNA/shRNA | Acts through inflammatory responses and immune modulation |
| 27 | NGF | over express protein | Makes mice smarter; is a neuropeptide primarily involved in the regulation of growth, maintenance, proliferation, and survival of certain target neurons. Can increase pain in different areas and is a target for knockdown in neuropathy. |
| 28 | Nrf2 | over express protein | Expression of antioxidant and other protective proteins that protect against oxidative damage triggered by injury and inflammation. |
| 29 | NUDT1 | over express protein | Overexpression prevents the age-dependent accumulation of DNA 8-oxoguanine that occurs in wild-type mice. These lower levels of oxidized guanines are associated with increased longevity and hMTH1-Tg animals live significantly longer than their wild-type littermates |
| 30 | Pappa | Inhibiory pri-miRNA/shRNA | Activates IGF1 so a knockout decreases expression of IGF1 |
| 31 | Par4 SAC domain | over express protein | Anti-cancer, pro-apoptotic to cancer cells only, works through decreasing NFKb, activated by PKA in tumor cells |
| 32 | Pck1 | over express protein | Basically extra GTP, Activates mitochondrial biogenesis and energy production. Creates extra fat in in muscles to account for the high amount of energy needed. Is involved in the citric acid cycle flux |
| 33 | PCSK9 | Inhibitory pri-miRNA/shRNA | Decreases bad cholesterol |
| 34 | PDE4b | Inhibitory pri-miRNA/shRNA | Disruption of PDE4b increases cAMP levels in the brain makes mice smarter and less anxious |
| 35 | Prkar2b | Inhibitory pri-miRNA/shRNA | Turns on UCP1 and is mediated by increasing intracellular cAMP levels through the modulation of adenylyl cyclase (AC) activity |
| 36 | Rps6kb1 (S6K1) | Inhibitory pri-miRNA/shRNA | part of the mTOR complex, Increases AMPK activation when S6k1 is deleted |
| 37 | sIFG1r-fc | over express soluble receptor protein | Decreases IGF1 signaling |
| 38 | Sirt1 | over express protein | Sirt1 as a negative regulator of nuclear factor-κB (NF-κB)15, 17 and as a positive effector of PGC1α and FoxO through increased orexin type 2 receptor (Ox2r) expression. |
| 39 | Sirt6 | over express protein | Decreases IGF1 signaling and increases mito |
| 40 | Slc13a1 | Inhibitory pri-miRNA/shRNA | Increases Sirt1 (by ≈60%), Cat (by ≈48%), Hdac3 (by ≈22%), Trp53 and Cd55 |
| 41 | Slc13a5 (INDY) | Inhibitory pri-miRNA/shRNA | By decreasing INDY you can activate hepatic AMPK, induces PGC-1α, inhibits ACC-2, and reduces SREBP-1c levels. This signaling network promotes hepatic mitochondrial biogenesis, lipid oxidation, and energy expenditure and attenuates hepatic de novo lipogenesis |
| 42 | TERT | over express protein | Telomerase extends DNA ends and also promotes other anti aging effects and possible cell immortalization |
| 43 | TFAM | over express protein | Mitochondrial biogenesis and decreased ROS |
| 44 | TFEB | over express protein | Increases lysosomal biogenesis It encodes a transcription factor that coordinates expression of lysosomal hydrolases, membrane proteins and genes involved in autophagy. |
| 45 | sTGFbR2 (e.g., sTGFbR2-Fc) | over express soluble receptor protein | Decreases fibrosis and inflammatory signaling by blocking the effects of TGFB1 and has immune modulating effects and can rejuvenate aged neurons and skeletal muscle |
| 46 | Txn1 | over express protein | Acts through AP1 and NFkb by decreasing some parts of NFkb signaling and protecting from oxidative DNA damage and other protein redox states |
| 47 | Ubd | Inhibitory pri-miRNA/shRNA | AMPK and UCP1, FAT10/Ubd regulates lifespan through pleiotropic actions on metabolism and inflammation. |
| 48 | UCP1 | over express protein | Fat only. Increases thermogenesis and energy expenditure |
| 49 | BMP2 | over express protein | Increases Bone mass by increasing Osteoblasts |
| 50 | BMP4 | over express protein | Increases Bone mass by increasing Osteoblasts |
| 51 | Sema3a | over express protein | Increases Bone mass by decreasing osteoclasts and increasing osteoblasts |
| 52 | GDF8 | Inhibitory pri-miRNA/shRNA | Increases Muscle mass |
| 53 | Follistatin | over express protein | Increases Muscle mass |

The description in Table 1 identifies exemplary genes and whether the gene is over expressed in the method ("over expressed") or inhibited ("pri-miRNA/shRNA"). As such, where the description makes reference to "overexpressed" gene, the gene therapy refers to use of a nucleic acid encoding the indicated protein product and where the protein product is overexpressed. Thus, in such descriptions, a reference to an identified gene also refers to the protein encoded by the gene. For example, "klotho" may refer to both the gene and the protein encoded by the gene. In some embodiments, the nucleic acid can encode a protein product, which is a mutated form of the naturally occurring expressed protein. By way of example and not limitation, Adra1a (mut) refers to a nucleic acid sequence encoding a mutated form of the naturally occurring Adra1a protein product, where the expressed mutated form of the receptor protein is constitutively active. Where the description in Table 1 makes reference to "pri-miRNA/shRNA," the gene therapy refers to use of a nucleic acid which has a sequence for an expressed pri-miRINA/shRNA where the expressed pri-miRINA/shRNA inhibits or ultimately attenuates expression of the gene product of the target gene.

In some embodiments, a nucleic acid for gene therapy can use sequences which are homologous to the gene sequences provided herein or known in the art and are functional as the reference protein, inhibitory RNA or inhibitory protein. Accordingly, the present disclosure contemplates the nucleic acid sequences described herein and those that are at least 80%, at least 85%, at least 90%, at least 95%, at least 96%, at least 97%, at least 98% or at least 99% homologous thereto. Likewise, the present disclosure contemplates the amino acid sequences described herein and those that are at least 80%, at least 85%, at least 90%, at least 95%, at least 96%, at least 97%, at least 98% or at least 99% homologous thereto, such that the protein retains function or activity, at least in whole or in part. It is to be understood that one of skill can readily design different nucleic acid sequences than those identified herein or known in the art to encode a known protein based on the degeneracy of the genetic code. Accordingly, it is to be understood that identification of specific nucleic acid sequences herein is not intended to be limiting.

It is to be understood that each gene and thus the corresponding nucleic acid in Table 1 can be separately used in the gene therapy method to produce the desired physiological (e.g., therapeutic) effect. In some embodiments, a combination of the nucleic acids in Table 1 can be used in the gene therapy method to produce the desired therapeutic effect. As such, the present disclosure encompasses each and every possible combination of the gene and corresponding nucleic acid in Table 1 for use in gene therapy, as described herein. In some embodiments, the gene therapy includes combinations of any 2, 3, 4, 5, 6, 7, 8, 9, 10, 11, 12, 13, 14, 15 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or all of the nucleic acids in Table 1, where the combination has the intended therapeutic effect, particularly with regards to treating or preventing an age-related disease or condition. It is to be understood that one of skill in the art can readily envision combinations and subcombinations of the nucleic acids for use in a therapeutic method.

According to one aspect, one or more of the genes in Table 1, such as FGF21 or Klotho, can be operably linked to a stabilizing peptide, such as is exemplified by sTGFbR2-FC, so as to increase its half life. One of skill can readily identify suitable fusion peptides, an example of which is FC. Also, the present disclosure contemplates the modification of one or more of the genes listed in Table 1, such as FGF21 and Klotho, so as to increase stability or half life of the protein encoded by the gene.

According to one aspect, one or more of the genes in Table 1, such as FGF21 or Klotho, can be operably linked to a secretion signal, such that the secretion signal is attached to the secreted protein in a manner to enhance expression. One of skill can readily identify suitable secretion signals and methods of adding a secretion signal to a secreted protein for enhanced expression.

In some embodiments identified in Table 2, a method of gene therapy for treating or preventing age related diseases or conditions comprises administering to a subject in need thereof an effective amount of a vector or plurality of vectors expressing the following genes, which express the gene product(s) as described in Table 1 above.

TABLE 2

| Therapy group | The unique combination of genes used for a particular therapy and administered by viral vector or a Cas9 guide RNA system |
|---|---|
| 1 | GDF15; |
| 2 | TERT and BubR1; |
| 3 | GDF15, TERT and BubR1; |
| 4 | GDF15, TERT, BubR1, Agtra1a, Adcy5, and Coq7; |
| 5 | GDF15, TERT, BubR1, Agtra1a, Adcy5, Coq7, Slc13a1, and Ikbkb; |
| 6 | BubR1, Cis2d, Txn1, FGF21, BubR1, Agtr1a, ikbkb, mTOR, Nudt1, Slc13a5, pappa, Coq7, Sdcy5, Agtr1a and Ctf1/akt1; |
| 7 | FGF21, Nrf2, sTGFbR2-Fc, HAS2, Nudt1, TERT, BubR1, Par4, Ubd, Dgat1, Ctf1, Coq7 Adcy5, Agtr1a, and mTOR; |
| 9 | Atg5, Nudt1, Adra1a (mut), NGF, NEU1, humanized foxP2, TFEB, PDE4b, mTOR, Slc13a5, Slc13a5, Coq7, Akt1, ikbkb and Slc13a1; |
| 10 | klotho, GDF15 (hNAG), sIGF1r-Fc, Mt1, Adra1a(mut), Nrf2, Rps6kb1, PCsk9, Prkar2b, Dgat, Ctf1, Coq7, papa, and ikbkb. |
| 11 | Atg5, Cebpa, pb, Ctf1, akt1, Pck1, adiponectin, PcsK9, Nrf2, Cisd2, papa, Dgat, Ctf1, Coq7, and mTOR. |
| 12 | FGF21, GDF15, klotho, Adra1a (mut), Sirt6, Bubr1, Par4, Coq7, Adcy5, Agtr1a, Agtr1a, ikbkb, mTOR, Slc13a1, papa, Ctf1, Ctf1, and Slc13a5 |
| 13 | FGF21, GDF15, klotho, TERT, sIGF1r-Fc, Bubr1, Par4, Rps6kb1, PCSk9, Adcy5, Coq7, Agtr1a, ikbkb, mTOR, and Slc13a1. |
| 14 | klotho, Txn1, Nrf2, TFEB, sTGFbr2-Fc, Nudt1, mt1, Atg5, Bubr1, Par4, Ctf1, Coq7 and ikbkb. |
| 15 | FGF21, sIGF1r-Fc, klotho, sTGFbr2-Fc, GDF15, HAS2, Mt1, Txn1, Nrf2, mCAT, Adra1a (mut), TFEB, Bubr1, Par4, Atg5, Cisd2, Nudt1, Sirt1, Sirt6, mTOR, slc13a5, pappa, ikbkb, adcy5, agtr1a and akt1. |

TABLE 2-continued

Therapy: The unique combination of genes used for a particular therapy and administered by
group viral vector or a Cas9 guide RNA system

| | |
|---|---|
| 16 | TFEB, Atg5, klotho, UCP1, Cebpbeta, miCebpa, adiponectin, Mt1, Txn1, Nrf2, mCAT, TERT, Bubr1, Par4, TFAM, Cisd2, Nudt1, Neu1, NGF, Sirt6, Dgat, prkar2b, insr, ubd, Coq7, Ctf1, mTOR, and Slc13a5 |
| 17 | sTGFbR2-FC and Nrf2 |
| 18 | FGF21, TERT, BubR1, Agtra1a, Adcy5, Coq7, Slc13a1, Ikbkb, Klotho, GDF15, CTF1, mTOR, Slc13a5, Pappa, Pcsk9, and Rps6kb1 |
| 19 | FGF21, GDF15, Klotho, Adra1a (mut), Sirt6, BubR1, Agtra1a, Adcy5, Akt1, MCAT, Slc13a1, Ikbkb, Ctf1, mTOR, Coq7, and Slc13a5 |
| 20 | Txn1, Sirt6, Mt1, TFEB, Pck1, Adiponectin, Cisd2, Nudt1, Atg5, Ctf1, Ikbkb, and Coq7 |
| 21 | Fgf21, Nrf2, sTGFbR2-FC, Has2, NudT1, TERT, BubR1, Dgat1, Pappa, Ctf1, mTOR, Coq7, Slc13a5, Agtra1a, Adcy5, and Akt1 |
| 22 | Ctf1, Coq7, Agtra1a, Adcy5, mTOR, Cisd2, MCAT, FGF21, GDF15, Klotho, Slc13a1, Ikbkb, Txn1, and Sirt6 |
| 23 | Klotho, GDF15, Neu1, Mt1, Adra1a, hFoxP2, PCSK9, Rps6kb1, Ctf1, Ikbkb, Coq7, Slc13a1, mTOR, and NudT1 |
| 24 | Atg5, Ctf1, Akt1, BubR1, Pck1, Adiponectin, TERT, Nrf2, Cisd2, Dgat1, Pappa, Ctf1, mTOR, Coq7, and Slc13a5 |
| 25 | FGF21 and BMP2 |
| 26 | FGF21 and BMP4 |
| 27 | FGF21 and Sema3a |
| 28 | FGF21, BMP2, and BMP4 |
| 29 | FGF21, BMP2, and Sema3a |
| 30 | FGF21, BMP4, and Sema3a |
| 31 | FGF21, BMP2, BMP4, and Sema3a |
| 32 | FGF21 and Klotho |
| 33 | FGF21 and sTGFbR2-FC |
| 34 | Klotho and sTGFbR2-FC |
| 35 | FGF21, Klotho, and sTGFbR2-FC |

In the foregoing exemplary embodiments, where there are two or more genes used for the gene therapy, the genes can be contained in separate gene delivery vectors, either individually or where permissible (e.g., based on the capacity of the viral gene therapy vector) in certain combinations, such as based on the intended target tissue, as further described below.

As further described in detail herein, the nucleic acids in Table 1 and corresponding nucleic acid constructs, expression cassettes, expression vectors, expression control sequences, promoters and other elements related to the delivery of the nucleic acid sequence can be constructed as a gene delivery vector, such as a viral vector. The vector is administered to a mammal under conditions that result in expression of the nucleic acid which alters the levels of a functional protein in a manner to provide a preventative or therapeutic effect. Accordingly, the present disclosure also contemplates a vector, particularly a viral vector, more particularly an AAV vector for each and every one of the genes and corresponding nucleic acids listed in Table 1. Details of such viral vectors are described below.

In some embodiments, the nucleic acids of Table 1 can be collectively regulated to produce the desired therapeutic effect. The gene therapy and the corresponding nucleic acid used can be grouped based on the desired effect, including, among others, effects on metabolism, IGF1 or GH signaling, protein synthesis or autophagy, inflammation, fibrosis or immune response, genome stability, cancer, mitochondrial fitness number or function, oxidation or neuronal function.

Table 3 identifies exemplary genes and their grouping based on the effects on the indicated biological function which can be collectively regulated to achieve a desired effect.

TABLE 3

| Category | Gene | Reported literature effect on median lifespan or expected |
|---|---|---|
| | Metabolism | |
| | FGF21 | 36 |
| | GDF15 (hNAG) | 35 |
| | Slc13a1 | 25 |
| | mTOR | 20 |
| | Cebpa/Cebpb | 20 |
| | Dgat1 | 20 |
| | Insr | 18 |
| | Ubd | 15 |
| | Prkar2b | 14 |
| | UCP1 | 10* |
| | Pck1 | 10* |
| | Sirt1 | 10* |
| | Adiponectin | 0* |
| | AMPK | 0* |
| | PCSK9 | 0* |
| | Slc13a5 (INDY) | 0* |
| | IGF1/GH | |
| | FGF21 | 36 |
| | GDF15 (hNAG) | 35 |
| | Pappa | 30 |
| | Klotho | 21 |
| | mTOR | 20 |
| | Sirt6 | 12 |
| | sIFG1r-Fc | 8 |
| | Akt1 | 8 |
| | Rps6kb1 (S6K1) | 0* |
| | Protein Synthesis/Autophagy | |
| 20 | mTOR | 20 |
| 20 | Cisd2 | 20 |
| 17 | Atg5 | 17 |
| 8 | Akt1 | 8 |
| 0* | TFEB | 0* |
| | Inflammatory/fibrosis/immune | |
| | Klotho | 21 |
| | Ctf1 | 18 |

TABLE 3-continued

| Category | Gene | Reported literature effect on median lifespan or expected |
|---|---|---|
| | Txn1 | 15 |
| | Nrf2 | 10* |
| | Sirt1 | 10* |
| | sTGFbR2-FC | 0* |
| Genome Stability/Cancer | | |
| | Coq7 | 23 |
| | Ctf1 | 18 |
| | NUDT1 | 16 |
| | BubR1 | 15 |
| | TERT | 15 |
| | Par4 SAC domain | 10 |
| | HAS2 | 0* |
| Mitochondrial/Oxidative | | |
| | Adcy5 | 30 |
| | Agtr1a | 26 |
| | Slc13a1 | 25 |
| | Coq7 | 23 |
| | Cisd2 | 20 |
| | MCAT | 20 |
| | Mt1 | 14 |
| | Sirt6 | 12 |
| | Pck1 | 10* |
| | Nrf2 | 10* |
| | TFAM | 0* |
| Neurological | | |
| | Ikbkb | 23 |
| | NUDT1 | 16 |
| | Adra1a (mut) | 10* |
| | NGF | 0* |
| | NEU1 | 0* |
| | humanizeFoxP2 | 0* |
| | PDE4b | 0* |
| Bone and Muscle | | |
| | BMP2 | 0* |
| | BMP4 | 0* |
| | Sema3a | 0* |
| | Follistatin | 0* |
| | GDF8 | 0* |

10* indicates an hypothesized effect.
0* indicates a positive effect on lifespan.

In some embodiments, the gene therapy method is directed to the exemplary combinations of the nucleic acids (i.e. the genes) provided in each of the groups in Tables 2 or 3. In some embodiments, the gene therapy includes use of the combination or subcombination of nucleic acids for FGF21, GDF15 (hNAG), Slc13a1, mTOR, Cebpa/Cebpb, Dgat1, Insr, Ubd, Prkar2b, UCP1, Pck1, Sirt1, Adiponectin, AMPK, PCSK9 and Slc13a5 (INDY), as provided in Table 1, such as for treating or preventing metabolic conditions or diseases associated with aging.

In some embodiments, the gene therapy includes use of the combination or subcombination of nucleic acids for FGF21, GDF15 (hNAG), Pappa, Klotho, mTOR, Sirt6, sIFG1r-Fc, Akt1, and Rps6 kb1 (S6K1), as provided in Table 1, such as for treating or preventing conditions or diseases associated with IGF1/GH activity, particularly with regards to such activity involved in an age related disease or condition.

In some embodiments, the gene therapy includes use of the combination or subcombination of nucleic acids for mTOR, Cisd2, Atg5, Akt1, TFEB, as provided in Table 1, such as for treating or preventing conditions or diseases associated with protein synthesis and autophagy, particularly with regards to such activity involved in an age related disease or condition.

In some embodiments, the gene therapy includes use of the combination or subcombination of nucleic acids for Klotho, FGF21, Ctf1, Txn1, Nrf2, Sirt1 and sTGFbR2-FC, as provided in Table 1, such as for treating or preventing inflammation, fibrosis, immune conditions or diseases particularly with regards to such activity involved in an age related disease or condition. Exemplary gene combinations include FGF21 and Klotho: FGF21 and sTGFbR2-FC: Klotho and sTGFbR2-FC or FGF21, Klotho, and sTGFbR2-FC.

In some embodiments, the gene therapy includes use of the combination or subcombination of nucleic acids for Coq7, Ctf1, NUDT1, BubR1, TERT, Par4 SAC domain, and HAS2, as provided in Table 1, such as for treating or preventing DNA damage, genome instability or cancer, particularly with regards to such activity, e.g., DNA damage or genome instability, involved in an age related disease or condition.

In some embodiments, the gene therapy includes use of the combination or subcombination of nucleic acids for Adcy5, Agtr1a, Cisd2, Coq7, mCAT, Mt1, Pck1, Sirt6, Slc13a1, Nrf2, and TFAM, as provided in Table 1, such as for treating or preventing conditions or diseases associated with mitochondrial function or oxidative damage, particularly with regards to such activity involved in an age related disease or condition.

In some embodiments, the gene therapy includes use of the combination or subcombination of nucleic acids for Ikbkb, NUDT1, Adra1a (mut), NGF, NEU1, humanize-FoxP2 and PDE4b, as provided in Table 1, such as for treating or preventing neurological conditions or diseases, such as cognitive impairment or cognitive decline, particularly with regards neurological conditions or diseases associated with aging.

It is also to be understood that the groups of the genes and corresponding nucleic acids used for treating or preventing conditions or diseases in the corresponding class of biological processes can be used in combination with one or more of the other groups of the genes and corresponding nucleic acids to treat more than one class of biological processes, particularly as those biological processes are associated with aging. Accordingly, encompassed within the present disclosure are gene therapy methods using every possible combination of the genes and corresponding nucleic acids listed in Table 1 or identified in the different groups in Table 2 or Table 3 above. Groups of the genes and corresponding nucleic acids used in gene therapy for (i) treating or preventing metabolic conditions or diseases, (ii) IGF1/GH activity associated conditions or diseases, (iii) conditions or diseases associated with protein synthesis and autophagy, (iv) inflammation, fibrosis, immune conditions or diseases, (v) DNA damage, genome instability or cancer, (vi) conditions or diseases associated with mitochondrial function or oxidative damage; and (vii) neurological conditions or diseases, can be used in combination or subcombination to treat multiple classes of diseases or conditions, particularly those multiple diseases or conditions relate to aging. By way of example, the combination or subcombination of the group of genes and corresponding nucleic acids for treating or preventing neurological diseases or conditions (vii) can be used together with the combination or subcombination of the group of genes and corresponding nucleic acids for treating or preventing diseases or conditions associated with mitochondrial function, i.e., group and oxidative damage, i.e., group (iv). Other such exemplary combinations include, by way of example and not limitation, combinations of 2, 3, 4, 5, 6 or all 7 of the foregoing groups (i) to (vii).

In some embodiments, the set of genes and corresponding nucleic acids for gene therapy methods herein can also be selected based on the tissue type targeted for gene therapy. Appropriate gene delivery constructs for expression in a specified tissue can incorporate the relevant nucleic acids for gene therapy. In some embodiments, the tissue specific delivery is based on choice of the appropriate viral vectors and viral packaging systems. The viral vectors can incorporate suitable promoters and other transcription regulators that allow expression of the gene product in the targeted tissue. The viral packaging systems can use the host cell range specificity of the viral components used to package the viral vectors so that the gene therapy vector is delivered to the targeted tissue. In the context of AAV vectors and capsid design, AAV serotypes, either naturally occurring or synthetic derivatives, can be used to manipulate the tropism range for gene therapy applications, as further described in detail below. For example, neuronal targeted genes may use a viral capsid designed to cross the blood-brain barrier, such as AAV9, and a liver targeted genes may use AAV8 which does not cross the blood-brain barrier to the same extent but does accumulate in the liver and muscle.

Other tissue specific methods can be used to limit expression in the tissue of interest, including, among others, use of tissue specific promoters and miRNA binding sites targeting those sequences expressed in the target tissue(s). Table 4 provides exemplary gene therapy nucleic acid as defined herein, the targeted cell or tissue, the AAV serotype or combination of serotypes having the appropriate tropism for the target tissue, exemplary promoters which function in the specific cell or target tissue to regulate expression, the administration route, and the size of the gene: A=adipose tissue, M=muscle tissue, B=brain tissue, L=liver tissue, E=systemic delivery throughout the organism, N=Not brain tissue, and H=cardiac tissue. Table 4 also indicates whether the gene product is an expressed protein or an inhibitor RNA. In some embodiments, the nucleic acid for gene therapy includes an expression inhibitor element which when expressed inhibits or attenuates expression of the gene product in one or more non-target tissue, also referred to as detargeting (see, e.g., Broderick et a., (2011) Gene Ther. 18 (2): 1104-1110, incorporated herein by reference). In Table 4, an exemplary inhibitor element is a sequence for a miRNA at the 3' UTR of the expressed mRNA such that the mRNA (or other transcribed RNA such as pri-miRNA/shRNA) is silenced in the specified non-target tissue, such as the liver. Various miRNAs for use in detargeting expression in non-target tissues include, among others, miRNA-122 for silencing expression in hepatocytes, miRNA-124 for silencing expression in neuronal cells, and miRNA-142 for silencing expression in hematopoietic cells. Other miRNAs known in the art for inhibiting expression in particular cells and tissues can be used in the present gene therapy applications by the person of skill in the art. One or a combination of such silencing miRNA targeting sequences can be used to inhibit or attenuate undesirable expression of the gene therapy construction in one or more non-target cells and tissues, where the non-target tissues can be different from each other.

TABLE 4

| | Gene | Target Tissue | AAV type | Promoter | 3' miRNA silencer | Expressed Gene product | Size |
|---|---|---|---|---|---|---|---|
| 1 | UCP1 | A | AAV:2/8 | adipose | prevent liver expression | over express protein | 924 |
| 2 | Cebpbeta | A | AAV:2/8 | adipose | prevent liver expression | over express protein | 891 |
| 3 | Adiponectin | S, A | AAV:2/8 | adipose | prevent liver expression | over express protein | 800 |
| 4 | sIFG1r-fc | S, L | AAV:2/8 | hEf1a | None | over express soluble receptor protein | 3507 |
| 5 | sTGFbr2-Fc | S, L | AAV:2/8 | hEf1a | None | over express soluble Rec | 1251 |
| 6 | FGF21 | S, L | AAV:2/8 | hEf1a | None | over express protein | 633 |
| 7 | GDF15 (hNAG) | S, L | AAV:2/8 | hEf1a | None | over express protein | 912 |
| 8 | Klotho | S, L | AAV:2/8 | hEf1a | None | over express protein | 3045 |
| 9 | HAS2 | S, N | AAV:2/8 | hEf1a | None | over express protein | 1659 |
| 10 | Mt1 | H | AAV:2/9 | hEf1a | None | over express protein | 399 |
| 11 | Nrf2 | E | AAV:2/9 | hEf1a | None | over express protein | 1794 |
| 12 | Par4 SAC domain 137-195 | E, B | AAV:2/9 | hEf1a | None | over express protein | 180 |
| 13 | Txn1 | E | AAV:2/9 | hEf1a | None | over express protein | 318 |
| 14 | mCat | M, H | AAV9 | hEf1a | None | over express protein | 1671 |
| 15 | Pck1 | M | AAV:2/9 | muscle specific | prevent liver expression | over express protein | 1869 |

TABLE 4-continued

| | Gene | Target Tissue | AAV type | Promoter | 3' miRNA silencer | Expressed Gene product | Size |
|---|---|---|---|---|---|---|---|
| 16 | Adra1a (mut) | B, H | AAV:2/PHP B | hEf1a | None | over express protein | 1401 |
| 17 | BubR1 | E | AAV:2/PHP B | hEf1a | None | over express protein | 3159 |
| 18 | TERT | E | AAV:2/PHP B | hEf1a | None | over express protein | 3424 |
| 19 | TFAM | E | AAV:2/PHP B | hEf1a | None | over express protein | 732 |
| 20 | TFEB | E | AAV:2/PHP B | hEf1a | None | over express protein | 1605 |
| 21 | Humanized FoxP2 | B | AAV:2/PHP B | Brain | prevent liver expression | over express protein | 2145 |
| 22 | NEU1 | B | AAV:2/PHP B | Brain | prevent liver expression | over express protein | 1230 |
| 23 | NGF | B | AAV:2/PHP B | Brain | prevent liver expression | over express protein | 1124 |
| 24 | Atg5 | E | AAV:2/PHP B or AAV:2/9 | hEf1a | None | over express protein | 828 |
| 25 | Cisd2 | E, M, B | AAV:2/PHP B or AAV:2/9 | hef1a | None | over express protein | 408 |
| 26 | NUDT1 | E, B | AAV:2/PHP B or AAV:2/9 | hEf1a | None | over express protein | 471 |
| 27 | Sirt1 | E, B | AAV:2/PHP B or AAV:2/9 | hEf1a | None | over express protein | 2214 |
| 28 | Sirt6 | E | AAV:2/PHP B or AAV:2/9 | hEf1a | None | over express protein | 993 |
| 29 | Dgat1 | A | AAV:2/8 | adipose | prevent liver expression | Inhibitory pri-miRNA/shRNA | 363 |
| 30 | Prkar2b | A | AAV:2/8 | adipose | prevent liver expression | Inhibitory pri-miRNA/shRNA | 363 |
| 31 | Insr | A | AAV:2/8 | adipose | prevent liver expression | Inhibitory pri-miRNA/shRNA | 363 |
| 32 | Ubd | A | AAV:2/8 | adipose | prevent liver expression | Inhibitory pri-miRNA/shRNA | 363 |
| 33 | Cebpalpha | A | AAV:2/8 | adipose | prevent liver expression | Inhibitory pri-miRNA/shRNA | 363 |
| 34 | PCSK9 | L | AAV:2/8 | hEf1a | None | Inhibitory pri-miRNA/shRNA | 363 |
| 35 | Rps6kb1 (S6K1) | L | AAV:2/8 | hEf1a | None | Inhibitory pri-miRNA/shRNA | 363 |
| 36 | Slc13a5 (INDY) | L | AAV:2/8 | hEf1a | None | Inhibitory pri-miRNA/shRNA | 363 |
| 37 | Pappa | E, M | AAV:2/9 | hEf1a | None | Inhibitory pri-miRNA/shRNA | 363 |
| 38 | Ikbkb | B | AAV:2/PHP B | hEf1a | none | Inhibitory pri-miRNA/shRNA | 363 |
| 39 | ADcy5 | E | AAV:2/PHP B | hEf1a | None | Inhibitory pri-miRNA/shRNA | 363 |
| 40 | Agtr1a | E | AAV:2/PHP B | hEf1a | None | Inhibitory pri-miRNA/shRNA | 363 |
| 41 | Akt1 | E | AAV:2/PHP B | hEf1a | None | Inhibitory pri-miRNA/shRNA | 363 |
| 42 | Coq7 | E | AAV:2/PHP B | hef1a | None | Inhibitory pri-miRNA/shRNA | 363 |
| 43 | Ctf1 | E | AAV:2/PHP B | hef1a | None | Inhibitory pri-miRNA/shRNA | 363 |
| 44 | PDE4b | B | AAV:2/PHP B | hEf1a | none | Inhibitory pri-miRNA/shRNA | 363 |
| 45 | mTOR | E | AAV:2/PHP B or AAV:2/9 | hEf1a | None | Inhibitory pri-miRNA/shRNA | 363 |
| 46 | Slc13a1 | E | AAV:2/PHP B or AAV:2/9 | hEf1a | None | Inhibitory pri-miRNA/shRNA | 363 |

TABLE 4-continued

| Gene | Target Tissue | AAV type | Promoter | 3' miRNA silencer | Expressed Gene product | Size |
|---|---|---|---|---|---|---|
| 47 AMPK | M | AAV:2/PHP B or AAV:2/9 | Muscle and adipose | Prevent Liver | Over express Protein | 1680 |
| 48 Nf-Kb | E | AAV:2/PHP B or AAV:2/9 | hEf1a | None | Inhibitory pri-miRNA/shRNA | 363 |
| 49 BMP2 | L | AAV:2/8 | hEf1a | None | Over express Protein | |
| 50 BMP4 | L | AAV:2/8 | hEf1a | None | Over express Protein | |
| 51 Sema3a | Bone | AAV:2/8 | hEf1a | None | Over express Protein | |
| 52 GDF8 | L | AAV:2/8 | hEf1a | None | Over express Protein | |
| 53 Follistatin | L | AAV:2/8 | hEf1a | None | Over express Protein | |

In view of the description in Table 4, the present disclosure is directed to an exemplary gene therapy vector containing the elements (i.e., gene, promoter, miRNA silencer) specified for each of embodiments 1-53 in Table 4. In some embodiments, the gene therapy vector can be based on vector construct hEf1a-WPRE3-SV40, where Hef1a refers to human elongation factor 1a promoter; WPRE3 is a truncated version of the woodchuck hepatitis posttranscriptional regulatory element; and SV40 is a truncated version of the SV40 polyadenylation site (PMCID: PMC3975461). The present disclosure is directed to recombinant AAV viral particles having the specific AAV serotype and specified vector elements for each of embodiments 1-53 in Table 4. The AAV capsid protein specifying the serotype of the recombinant viral particle can be provided using the appropriate AAV helper viruses. See, e.g., Yuan et al., 2011, *Hum Gene Ther.* 22 (5): 613-24, incorporated herein by reference). The hEf1α can also refer to a truncated version of the hEf1α promoter that is 231 bp long and referenced as SEQ ID NO:18.

In view of the capacity of gene therapy vectors for delivering nucleic acids into target cells, in some embodiments, the viral vector can have two or more nucleic acids for expression of two or more corresponding functional proteins, inhibitory RNA, or inhibitory proteins. Each of the nucleic acids for expressing the different gene expression products can have its own transcription regulatory elements, and if expressing a protein, separate translational regulatory elements, such that separate RNAs are expressed. In some embodiments, a single RNA can be expressed in a cistronic form, where the gene products are expressed from the single RNA. Thus in some embodiments, the gene therapy vector can have polycistronic elements, such as internal ribosome entry sites (IRES) or 2A sequences (PMCID: PMC3084703) for inducing ribosome skipping as they may be required to express the different gene therapy products from the single RNA.

In some embodiments, in gene therapy with a plurality of nucleic acids expressing a plurality of different gene products, two or more gene delivery vectors, particularly viral vectors, are administered to a mammal. Accordingly, in some embodiments, the present disclosure provides for the concurrent or separate administration of 2, 3, 4, 5, 6, 7, 8, 9, 10, 11, 12, 13, 14, 15, 16, 17, 18, 19, 20 or more separate vectors for delivering the relevant genes in methods of gene therapy. Amounts of each separate vector to be administered alone or as a combination of vectors can be determined based upon, among others, the vector design, the nucleic acid sequences to be delivered, efficiency of delivery to target tissue, mode of administration, and the intended therapeutic effect. In various embodiments, the optimal ratio of each viral vector to be administered concurrently can be assessed from the maximum viral dose for each subject and by the effectiveness of each individual vector. A person of skill can determine the proper ratios and doses based on the present disclosure.

An exemplary set of viral vectors with one or more genes for gene therapy are given in Table 2. For gene therapy with a combination of genes expressing the referenced protein and/or inhibitory RNA, a plurality of viruses as described are administered to a mammal in a method of gene therapy. Accordingly, the disclosure provides methods of administering multiple viruses including one or more or multiple genes, inhibitory RNAs or inhibitory proteins, examples and combinations of which are provided below, particularly for treating or preventing diseases or conditions associated with aging.

In Group 1, virus 1 includes AAV8-GFP as a control and virus 2 includes AAV9: GFP as a control.

In Group 2, a single virus including a single gene, GDF15, is administered to a mammal in a method of gene therapy.

In Group 3, virus 1 includes TERT and virus 2 includes BubR1.

In Group 4, virus 1 includes GDF15, virus 2 includes TERT and virus 3 includes BubR1.

In Group 5, virus 1 includes GDF15, virus 2 includes TERT, virus 3 includes FGF21 and virus 4 includes BubR1.

In Group 6, virus 1 includes GDF15, virus 2 includes TERT, virus 3 includes FGF21, virus 4 includes Klotho and virus 5 includes BubR1.

In Group 7, virus 1 includes BubR1, p2A and Par4, virus 2 includes Cis2d, virus 3 includes Txn1, virus 4 includes FGF21, virus 5 includes BubR1, virus 6 includes Agtr1a, ikbkb and mTOR, virus 7 includes Nudt1, virus 8 includes Slc 13a5 and pappa, virus 9 includes Coq7, ASdcy5 and Agtr1a and virus 10 includes Ctf1/akt1.

In Group 8, virus 1 includes FGF21, virus 2 includes Nrf2, virus 3 includes sTGFbR2-Fc, virus 4 includes HAS2, virus 5 includes Nudt1, virus 6 includes TERT, virus 7 includes BubR1, p2A and Par4, virus 8 includes Ubd and Dgat1, virus 9 includes Ctf1 and Coq7 and virus 10 includes Adcy5, Agtr 1a and mTOR.

In Group 9, virus 1 includes Atg5, virus 2 includes Nudt1, virus 3 includes Adra1a (mut), virus 4 includes NGF, virus 5 includes NEU1, virus 6 includes humanized foxP2, virus 7 includes TFEB, virus 8 includes PDE4b, mTOR, and Slc13a5, virus 9 includes Slc13a5, Coq7 and Akt and virus 10 includes ikbkb and Slc13a1.

In Group 10, virus 1 includes klotho, virus 2 includes GDF15 (hNAG), virus 3 includes sIGF1r-Fc, virus 4 includes Mt1, virus 5 includes Adra1a (mut), virus 6 includes Nrf2, virus 7 includes Rps6 kb1 and PCsk9, virus 8 includes Prkar2b and Dgat, virus 9 includes Ctf1 and Coq7 and virus 10 includes pappa and ikbkb.

In Group 11, virus 1 includes Atg5, virus 2 includes Cebpa and Cebpb, virus 3 includes Ctf1 and akt1, virus 4 includes Pck1, virus 5 includes adiponectin, virus 6 includes PcsK9, virus 7 includes Nrf2, virus 8 includes Cisd2, virus 9 includes pappa and Dgat and virus 10 includes Ctf1, Coq7 and mTOR.

In Group 12, virus 1 includes FGF21, virus 2 includes GDF15, virus 3 includes klotho, virus 4 includes Adra1a (mut), virus 5 includes Sirt6, virus 6 includes Bubr1, p2A and Par4, virus 7 includes Coq7, Adcy5 and Agtr1a, virus 8 includes Agtr1a, ikbkb and mTOR, virus 9 includes Slc13a1, pappa and Ctf1 and virus 10 includes Ctf1, Slc13a5 (AAV9).

In Group 13, virus 1 includes FGF21, virus 2 includes GDF15, virus 3 includes klotho, virus 4 includes TERT, virus 5 includes sIGF1r-Fc, virus 6 includes Bubr1, p2A and Par4, virus 7 includes Rps6 kb1 and PCSK9, virus 8 includes Adcy5 and Coq7, virus 9 includes Agtr1a and ikbkb and virus 10 includes mTOR and Slc13a1.

In Group 14, virus 1 includes klotho, virus 2 includes Txn1, virus 3 includes Nrf2, virus 4 includes TFEB, virus 5 includes sTGFbr2-Fc, virus 6 includes Nudt1, virus 7 includes mt1, virus 8 includes Atg5, virus 9 includes Bubr1, p2A and Par4 and virus 10 includes Ctf1, Coq7 and ikbkb.

In Group 15, virus 1 includes FGF21, IRES, and sIGF1r-Fc, virus 2 includes klotho, virus 3 includes sTGFbr2-Fc, IRES and GDF15, virus 4 includes HAS2, p2A, Mt1, and Txn1, virus 5 includes Nrf2, p2A and mCAT, virus 6 includes Adra1a (mut), p2A and TFEB, virus 7 includes Bubr1, p2A and Par4, virus 8 includes Atg5, p2A, Cisd2 and Nudt1, virus 9 includes Sirt1, p2A and Sirt6 and virus 10 includes mTOR, slc13a5, pappa, ikbkb, adcy5, agtr1a and akt1.

In Group 16, virus 1 includes TFEB, p2A and Atg5, virus 2 includes klotho, virus 3 includes UCP1, p2A, Cebpbeta and miCebpa, virus 4 includes adiponectin, IRES, Mt1, p2A and Txn1, virus 5 includes Nrf2, p2A and mCAT, virus 6 includes TERT, virus 7 includes Bubr1, p2A and Par4, virus 8 includes TFAM, p2A, Cisd2 and Nudt1, virus 9 includes Neu1, p2A, NGF and Sirt6 and virus 10 includes Dgat, prkar2b, insr, ubd, Coq7, Ctf1, mTOR and Slc13a5.

In Group 17, the viruses include sTGFbR2-FC and/or Nrf2.

In Group 18, the viruses include FGF21, TERT, BubR1, Agtra1a, Adcy5, Coq7, Slc13a1, Ikbkb, Klotho, GDF15, CTF1, mTOR, Slc13a5, Pappa, Pcsk9, and/or Rps6 kb1.

In Group 19, the viruses include FGF21, GDF15, Klotho, Adra1a (mut), Sirt6, BubR1, Agtra1a, Adcy5, Akt1, MCAT, Slc13a1, Ikbkb, Ctf1, mTOR, Coq7, and/or Slc13a5.

In Group 20, the viruses include Txn1, Sirt6, Mt1, TFEB, Pck1, Adiponectin, Cisd2, Nudt1, Atg5, Ctf1, Ikbkb, and/or Coq7.

In Group 21, the viruses include Fgf21, Nrf2, sTGFbR2-FC, Has2, NudT1, TERT, BubR1, Dgat1, Pappa, Ctf1, mTOR, Coq7, Slc13a5, Agtra1a, Adcy5, and/or Akt1.

In Group 22, the viruses include Ctf1, Coq7, Agtra1a, Adcy5, mTOR, Cisd2, MCAT, FGF21, GDF15, Klotho, Slc13a1, Ikbkb, Txn1, and/or Sirt6.

In Group 23, the viruses include Klotho, GDF15, Neu1, Mt1, Adra1a, hFoxP2, PCSK9, Rps6 kb1, Ctf1, Ikbkb, Coq7, Slc 13a1, mTOR, and/or NudT1.

In Group 24, the viruses include Atg5, Ctf1, Akt1, BubR1, Pck1, Adiponectin, TERT, Nrf2, Cisd2, Dgat1, Pappa, Ctf1, mTOR, Coq7, and/or Slc13a5.

In Group 25, the viruses include FGF21 and/or BMP2.

In Group 26, the viruses include FGF21 and/or BMP4.

In Group 27, the viruses include FGF21 and/or Sema3a.

In Group 28, the viruses include FGF21, BMP2, and/or BMP4.

In Group 29, the viruses include FGF21, BMP2, and/or Sema3a.

In Group 30, the viruses include FGF21, BMP4, and/or Sema3a.

In Group 31, the viruses include FGF21, BMP2, BMP4, and/or Sema3a.

In Group 32, the viruses include FGF21 and Klotho.

In Group 33, the viruses include FGF21, sTGFbR2-FC.

In Group 34, the viruses include Klotho and sTGFbR2-FC.

In Group 35, the viruses include FGF21, Klotho and sTGFbR2-Fc.

Gene Therapy with Pri-miRNA/shRNA Against a Target Gene

In the present disclosure, a gene construct expressing a primary miRNA molecule (pri-miRNA) and/or short hairpin (shRNA) are used to inhibit or attenuate expression of a target gene. A single pri-miRNA may contain from one to six miRNA precursors, and is processed to produce miRNA, which is exported from the nucleus to the cytoplasm, where it silences expression of target RNAs. Exemplary hairpin loop structures are composed of about 70 nucleotides each. Each hairpin is flanked by sequences necessary for efficient processing.

The double-stranded RNA (dsRNA) structure of the hairpins in a pri-miRNA is recognized by a nuclear protein known as DiGeorge Syndrome Critical Region 8 (DGCR8 or "Pasha" in invertebrates), named for its association with DiGeorge Syndrome. DGCR8 associates with the enzyme Drosha, a protein that cuts RNA, to form the Microprocessor complex. See Lee, Y. et al., *Nature* 425 (6956): 415-9 (2003): Gregory RI. et al . . . (2006) *Methods Mol. Biol.* 342:33-47. In this complex, DGCR8 orients the catalytic RNase III domain of Drosha to liberate hairpins from pri-miRNAs by cleaving RNA about eleven nucleotides from the hairpin base (one helical dsRNA turn into the stem). See Han. J et al . . . (2004) *Genes & Development* 18 (24): 3016-27; Han, J. et al. (2006) *Cell* 125 (5): 887-901. The product resulting has a two-nucleotide overhang at its 3' end; it has 3' hydroxyl and 5' phosphate groups. It is often termed as a pre-miRNA (precursor-miRNA). Sequence motifs downstream of the pre-miRNA that are important for efficient processing have been identified. Conrad. T. et al., *Cell Reports* 9 (2): 542-554; Auyeung. V. et al., (2013) *Cell* 152 (4): 844-858; Ali, P. S. et al., (2012) *FEBS Letters* 586 (22): 3986-90.

Pre-miRNAs that are spliced directly out of introns, bypassing the Microprocessor complex, are known as "Mirtrons." Originally thought to exist only in *Drosophila* and *C. elegans*, mirtrons have now been found in mammals. See Berezikov E. et al. (2007) "Mammalian mirtron genes" *Mol. Cell* 28 (2): 328-36.

As many as 16% of pre-miRNAs may be altered through nuclear RNA editing. See Kawahara Y. et al., (2008) Nucleic Acids Res. 36 (16): 5270-80; Winter J. et al., (2009) *Nat. Cell Biol.* 11 (3): 228-34; Ohman M. (2007) Biochimie 89 (10): 1171-6. Most commonly, enzymes known as adenosine deaminases acting on RNA (ADARs) catalyze adenosineto inosine (A to I) transitions. RNA editing can halt nuclear processing (for example, of pri-miR-142, leading to degradation by the ribonuclease Tudor-SN) and alter downstream processes including cytoplasmic miRNA processing and target specificity (e.g., by changing the seed region of miR-376 in the central nervous system). See Kawahara Y, et al., (2008) Nucleic Acids Res. 36 (16): 5270-80.

Pre-miRNA hairpins are exported from the nucleus in a process involving the nucleocytoplasmic shuttler Exportin-5. This protein, a member of the karyopherin family, recognizes a two-nucleotide overhang left by the RNase III enzyme Drosha at the 3' end of the pre-miRNA hairpin. Exportin-5-mediated transport to the cytoplasm is energy-dependent, using GTP bound to the Ran protein. See Murchison E. P. et al., (2004) *Curr. Opin. Cell Biol.* 16 (3): 223-9.

In the cytoplasm, the pre-miRNA hairpin is cleaved by the RNase III enzyme Dicer. See Lund E. et al., (2006) *Cold Spring Harb. Symp. Quant. Biol.* 71:59-66. This endoribonuclease interacts with 5' and 3' ends of the hairpin. See Park, J. E. et al., (2011) *Nature* 475 (7355): 201-5, and cuts away the loop joining the 3' and 5' arms, yielding an imperfect miRNA: miRNA* duplex about 22 nucleotides in length. See Lund E. et al., (2006) *Cold Spring Harb. Symp. Quant. Biol.* 71:59-66. Overall hairpin length and loop size influence the efficiency of Dicer processing. The imperfect nature of the miRNA: miRNA* pairing also affects cleavage. See Lund E. et al. (2006) *Cold Spring Harb. Symp. Quant. Biol.* 71:59-66: Ji X (2008) *Current Topics in Microbiology and Immunology* 320:99-116. Some of the G-rich pre-miRNAs can potentially adopt the G-quadruplex structure as an alternative to the canonical stem-loop structure. For example, human pre-miRNA 92b adopts a G-quadruplex structure which is resistant to the Dicer mediated cleavage in the cytoplasm. See Mirihana A. et al., (2015) *Chem. Biol.* 22:262-272. Although either strand of the duplex may potentially act as a functional miRNA, only one strand is usually incorporated into the RNA-induced silencing complex (RISC) where the miRNA and its mRNA target interact.

Gene Therapy with Cas9 Mediated Regulation of Functional Proteins

The present disclosure also provides method of regulating the target genes and their corresponding functional proteins described herein using a Cas9/guide RNA system with a transcriptional regulator. It is to be understood that one of skill will be able to design suitable guide RNA for forming a co-localization complex with a target nucleic acid including a target gene as described herein.

Cas9 DNA Binding Proteins

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety. Such RNA guided DNA binding proteins may include one or m ore nuclear localization signals attached thereto for facilitating transfer of the RNA guided DNA binding protein into the nuclease.

In general, bacterial and archaeal CRISPR-Cas systems rely on short guide RNAs in complex with Cas proteins to direct degradation of complementary sequences present within invading foreign nucleic acid. See Deltcheva, E. et al., (2011) *Nature* 471, 602-607; Gasiunas, G. et al., (2012) *Proc Natl Acad Sci USA* 109, E2579-2586; Jinek, M. et al. (2012) *Science* 337, 816-821; Sapranauskas, R. et al., (2011) Nucleic Acids Res 39:9275-9282; and Bhaya, D. et al., (2011) *Ann Rev Gen* 45:273-297. A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., (2008) *J Bact* 190, 1390. Additional useful Cas proteins are from *S. thermophilis* or *S. aureus*.

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., (2011) *Nature Rev Microbiol.* 9:467; all publications incorporated herein by reference in its entirety.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., (2012) *Science* 337, 816-821, hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae: Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RSI; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua;Lactobacillus casei; Lactobacillus rhamnosus* GG; *Lactobacillus salivarius* UCC118;*Streptococcus agalactiae* A909;*Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CHI; *Streptococcus mutans* NN2025 uid46353; *Streptococcus mutans; Streptococcus pyogenes* MI GAS; *Streptococcus pyogenes* MGAS5005; *Streptococ-* cus pyogenes MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus* thermophiles CNRZ1066; *Streptococcus* thermophiles LMD-9; *Streptococcus* thermophiles LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma* mobile 163K; *Mycoplasma penetrans; Mycoplasma synoviae* 53; *Streptobacillus moniliformis* DSM 12112; *Bradyrhizobium* BTAil; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis* novicida U112; *Francisella tularensis* holarctica; *Francisella tularensis* FSC 198; *Francisella tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., (2011) *Nature* 471, 602-607, hereby incorporated by reference in its entirety.

Modification to the Cas9 protein is a representative embodiment of the present disclosure. CRISPR systems useful in the present disclosure are described in Barrangou, R. et al., (2012) *Ann Rev Food Sci Technol.* 3:143 and Wiedenheft, B. et al., (2012) *Nature* 482, 331, each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e., the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated. See Jinek et al., (2012) *Science* 337, 816-821. A Cas9 protein lacking nuclease activity is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein includes the sequence as set forth for naturally occurring Cas9 from *S. thermophiles* or *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

An exemplary CRISPR system includes the *S. thermophiles* Cas9 nuclease (ST1 Cas9) (see Esvelt, K. M. et al., (2013) *Nature Methods.* 10 (11): 1116-21, hereby incorporated by reference in its entirety). An exemplary CRISPR system includes the *S. pyogenes* Cas9 nuclease (Sp. Cas9), an extremely high-affinity (see Sternberg, S. H., et al., (2014) *Nature* 507, 62-67, hereby incorporated by reference in its entirety), programmable DNA-binding protein isolated from a type II CRISPR-associated system (see Garneau, J. E. et al., (2010) *Nature* 468, 67-71 and Jinek, M. et al., (2012) *Science* 337, 816-821, each of which are hereby incorporated by reference in its entirety). Various Cas proteins are known to those of skill in the art and include CasI (Cas3), Cas IA (Cas8a), CasIB (Cas8b), CasIC (Cas8c), CasID (Cas10d), CasIE (Csel), CasIF (Csy 1), CasIU, CasII (Cas9), CasIIA (Csn2), CasIIB (Cas4), CasIIC, CasIII (Cas10), CasIIIA (Csm2), CasIIIB (Cmr5), CasIIIC, CasIIID, CasIV (Csf1), CasIVA, CasIVB, CasV (Cpf1), C2c2, and C2cl and the like.

In a multitude of CRISPR-based biotechnology applications (see Mali, P. et al., (2013) *Nature Methods* 10:957-963: Hsu, P. D. et al., (2014) *Cell* 157, 1262-1278: Chen, B. et al., (2013) *Cell* 155:1479-1491: Shalem, O. et al., (2014) *Science* 343, 84-87; Wang, T. et al., (2014) *Science* 343:80-84; Nissim, L. et al., (2014) *Molecular Cell* 54:698-710; Ryan, O. W. et al., (2014) *eLife* 3: Gilbert, L. A. et al., (2014) *Cell* 159 (3): 647-61; and Citorik, R. J. et al., (2014) *Nature Biotechnol.* 32:1141-1145, each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

According to one aspect, the Cas9 protein is an enzymatically active Cas9 protein, a Cas9 protein wild-type protein, a Cas9 protein nickase or a nuclease null or nuclease deficient Cas9 protein. Additional exemplary Cas9 proteins include Cas9 proteins attached to, bound to or fused with functional proteins such as transcriptional regulators, such as transcriptional activators or repressors.

According to certain aspects, the Cas9 protein may be delivered directly to a cell by methods known to those of skill in the art, including injection or lipofection, or as translated from its cognate mRNA, or transcribed from its cognate DNA into mRNA (and thereafter translated into protein). Cas9 DNA and mRNA may be themselves introduced into cells through electroporation, transient and stable transfection (including lipofection) and viral transduction or other methods known to those of skill in the art.

Guide RNA

The present disclosure provides for the use of guide RNA to target a Cas protein to a target gene as described herein. Such guide RNA can be readily designed by those of skill in the art when knowing the particular target nucleic acid. A guide RNA may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed a sgRNA).

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length. According to certain aspects, the tracr mate sequence is between about 10 and about 500 nucleotides in length. In some embodiments, the tracr sequence is between about 10 and about 100 nucleotides in length. In some embodiments, the linker nucleic acid sequence is between about 10 and about 100 nucleotides in length.

In some embodiments, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

Modifying Transcription of Target Genes Using Cas9

According to one aspect, an engineered Cas9-gRNA system is provided which enables RNA-guided DNA regulation in cells such as human cells by tethering or connecting transcriptional regulation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

According to one aspect, a mutant Cas9N-fusion protein capable of transcriptional activation is provided. According to one aspect, a VP64 activation domain (see Zhang et al., Nature Biotechnology 29, 149-153 (2011) hereby incorporated by reference in its entirety) is joined, fused, connected or otherwise tethered to the C terminus of mutant Cas9N. According to one method, the transcriptional regulatory domain is provided to the site of target mitochondrial DNA by the mutant Cas9N protein. According to one method, a mutant Cas9N fused to a transcriptional regulatory domain is provided within a cell along with one or more guide RNAs. The mutant Cas9N with the transcriptional regulatory domain fused thereto bind at or near target mitochondrial DNA. The one or more guide RNAs bind at or near target mitochondrial DNA. The transcriptional regulatory domain regulates expression of the target mitochondrial nucleic acid sequence. According to a specific aspect, a mutant Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target mitochondrial DNA by the gRNA. According to one method, a gRNA fused to a transcriptional regulatory domain is provided within a cell along with a mutant Cas9N protein. The mutant Cas9N binds at or near target DNA. The one or more guide RNAs with the transcriptional regulatory protein or domain fused thereto bind at or near target DNA. The transcriptional regulatory domain regulates expression of the target gene. According to a specific aspect, a mutant Cas9N protein and a gRNA fused with a transcriptional regulatory domain activated transcription of reporter constructs, thereby displaying RNA-guided transcriptional activation.

Transcriptional regulator proteins or domains which are transcriptional activators include VP16 and VP64 and others readily identifiable by those skilled in the art based on the present disclosure. For example, one skilled in the art would be able to use Cas9-gRNA system (either with intact cutting or dCas9 with or without being fused to VP16, KRAB, HDAC, methyltransferases etc., or being able to recruit similar activators or repressors with a "spy catcher" or MS2 recruitment domain or similar) can be used to increase or decrease expression of the target genes presented herein to be used in combination for therapeutic or prophylactic effect.

Target Nucleic Acids

Target nucleic acids include any nucleic acid sequence to which a co-localization complex as described herein can be useful to regulate, such as the genes identified herein. Target nucleic acids include nucleic acid sequences capable of being expressed into proteins. For purposes of the present disclosure, a co-localization complex can bind to or otherwise co-localize with the target nucleic acid at or adjacent or near the target nucleic acid and in a manner in which the co-localization complex may have a desired effect on the target nucleic acid. One of skill based on the present disclosure will readily be able to identify or design guide RNAs and Cas9 proteins which co-localize to a target nucleic acid. One of skill will further be able to identify transcriptional regulator proteins or domains which likewise co-localize to a target nucleic acid.

Cells

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, mammalian cells, animal cells, human cells and the like. Further, cells include any in which it would be beneficial or desirable to regulate production of a functional protein. Such cells may include those which are deficient in expression of a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment. Such cells may include those which overexpress a particular protein or where production of a particular protein is desired to be reduced leading to a disease or detrimental condition. Such diseases or detrimental conditions are readily known to those of skill in the art. According to the present disclosure, the nucleic acid responsible for expressing the particular protein may be targeted by the methods described herein and a transcriptional depressor or repressor resulting in downregulation of the target nucleic acid and corresponding expression of the particular protein. In this manner, the methods described herein provide therapeutic treatment.

Delivery of Nucleic Acids Regulating Functional Proteins

Foreign nucleic acids, alternatively referred to as heterologous nucleic acids (i.e., those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. Foreign nucleic acids may be delivered to a subject by administering to the subject, such as systemically administering to the subject, such as by intravenous administration or injection, intraperitoneal administration or injection, intramuscular administration or injection, intracranial administration or injection, intraocular administration or injection, subcutaneous administration or injection, a nucleic acid or vector including a nucleic acid as described herein.

Gene therapy methods and methods of delivering genes to subjects, for example using adeno-associated viruses, are described in U.S. Pat. No. 6,967,018, WO2014/093622, US2008/0175845, US 2014/0100265, EP2432490, EP2352823, EP2384200, WO2014/127198, WO2005/122723, WO2008/137490, WO2013/142114, WO2006/128190, WO2009/134681, EP2341068, WO2008/027084, WO2009/054994, WO2014059031, U.S. Pat. No. 7,977,049 and WO 2014/059029, each of which are incorporated herein by reference in its entirety.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors include, among others, plasmids, lentiviruses, and adeno-associated viruses as is known to those of skill in the art. Vectors include, but are not limited to, nucleic acid molecules that are single-stranded, double stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus, e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in, e.g., U.S. Pat. Nos. 5,049,386, 4,946,787; and 4,897,355, incorporated herein by reference. Lipofection reagents are aso available from commercial sources (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g., in vitro or ex vivo administration) or target tissues (e.g. in vivo administration). The term native includes the protein, enzyme or guide RNA species itself and not the nucleic acid encoding the species.

In some embodiments, the gene therapy vectors for use in the methods herein are parvoviral vectors., such as animal parvoviruses, in particular dependoviruses such as infectious human or simian adeno-associated virus (AAV), and the components thereof (e.g., an animal parvovirus genome) for use as vectors for introduction and/or expression of the nucleotide sequences encoding a porphobilinogen deaminase in mammalian cells. Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth 1. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, −2 and −3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild-type (wt) AAV infection in mammalian cells the Rep genes (i.e., Rep78 and Rep52) are expressed from the P5 promoter and the P19 promoter, respectively and both Rep proteins have a function in the replication of the viral genome. A splicing event in the Rep ORF results in the expression of actually four Rep proteins (i.e., Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral" or "AAV vector" or "rAAV vector" herein refers to a vector comprising one or more polynucleotide sequences of interest, genes of interest or "transgenes" that are flanked by at least one parvoviral or AAV inverted terminal repeat sequences (ITRs). Such rAAV vectors can be replicated and packaged into infectious viral particles when present in an insect host cell that is expressing AAV rep and cap gene products (i.e., AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions. Thus, in a further aspect the invention relates to a nucleic acid construct comprising a nucleotide sequence encoding a porphobilinogen deaminase as herein defined above, wherein the nucleic acid construct is a recombinant parvoviral or AAV vector and thus comprises at least one parvoviral or AAV ITR. Preferably, in the nucleic acid construct the nucleotide sequence encoding the porphobilinogen deaminase is flanked by parvoviral or AAV ITRs on either side.

AAV is able to infect a number of mammalian cells. See, e.g., Tratschin et al., (1985) *Mol. Cell Biol.* 5:3251-3260) and Grimm et al., (1999) *Hum. Gene Ther.* 10:2445-2450). However, AAV transduction of human synovial fibroblasts is significantly more efficient than in similar murine cells, (Jennings et al., (2001) Arthritis Res, 3:1), and the cellular tropicity of AAV differs among serotypes. See, e.g., Davidson et al. (2000) *Proc. Natl. Acad. Sci. USA,* 97:3428-3432), which discuss differences among AAV2, AAV4, and AAV5 with respect to mammalian CNS cell tropism and transduction efficiency; Goncalves, (2005) *Virol J.* 2 (1): 43, which discusses approaches to modification of AAV tropism. In some embodiments, for transduction of liver cells rAAV virions with AAV1, AAV8 and AAV5 capsid proteins are preferred (Nathwani et al., (2007) *Blood* 109 (4): 1414-1421; Kitajima et al., (2006) *Atherosclerosis* 186 (1): 65-73), of which is rAAV virions with AAV5 capsid proteins may be most preferred.

AAVs are highly prevalent within the human population. See Gao, G., et al., (2004) *J Virol.* 78 (12): 6381-8; and Boutin, S., et al., (2010) *Hum Gene Ther.* 21 (6): 704-12) and are useful as viral vectors. Many serotypes exist, each with different tropism for tissue types, See Zincarelli, C., et al., (2008) *Mol Ther.* 16 (6): 1073-80), which allows specific tissues to be preferentially targeted with appropriate pseudotyping. Some serotypes, such as serotypes 8, 9, and rh10, transduce the mammalian body. See Zincarelli, C., et al., (2008) *Mol Ther.* 16 (6): 1073-80, Inagaki, K., et al., (2006) *Mol Ther.* 14 (1): 45-53; Keeler, A. M., et al., (2012) Mol Ther. 20 (6): 1131-8; Gray, S. J. et al., (2011) Mol Ther. 19 (6): 1058-69; Okada, H., et al., (2013) *Mol Ther Nucleic Acids.* 2: e95; and Foust, K. D., et al., (2009) *Nat Biotechnol.* 27 (1): 59-65. AAV9 has been demonstrated to cross the blood-brain barrier. See Foust, K. D., et al., (2009) *Nat Biotechnol.* 27 (1): 59-65; and Rahim, A. A. et al., (2011) *FASEB J.* 25 (10): 3505-18) that is inaccessible to many viral vectors and biologics. Certain AAVs have a pay load of 4.7-5.0 kb, including viral inverted terminal repeats (ITRs), which are required in cis for viral packaging). See Wu, Z. et al., (2010) Mol Ther. 18 (1): 80-6; and Dong, J. Y. et al., (1996) *Hum Gene Ther.* 7 (17): 2101-12; all publications incorporated herein by reference.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of one serotype (e.g., AAV5) and the Rep and/or ITR sequences of another AAV serotype (e.g., AAV2). Such pseudotyped rAAV particles are a part of the present invention. Herein, a pseudotyped rAAV particle may be referred to as being of the type "x/y", where "x" indicates the source of ITRs and "y" indicates the serotype of capsid, for example a ⅖ rAAV particle has ITRs from AAV2 and a capsid from AAV5. Modified "AAV" sequences also can be used in the context of the present disclosure, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having from about 75% to about 99% nucleotide sequence identity) to an AAV1, AAV2, AAV3, AAV4, AAV5, AAV6, AAV7, AAV8, AAV9, AAV 10, AAV11, AAV12, AAV2.5, AAvDJ, AAVrh10.XX ITR, Rep, or VP can be used in place of wild-type AAV ITR, Rep, or VP sequences. Preferred adenoviral vectors are modified to reduce the host response. See, e.g., Russell (2000) *J. Gen. Virol.* 81:2573-2604; US patent publication no. 20080008690; and Zaldumbide et al. (2008) *Gene Therapy* 15 (4): 239-46; all publications incorporated herein by reference.

Regulatory Elements and Terminators

Regulatory elements are contemplated for use with the gene therapy vector constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart et al, (1985) *Cell* 41:521-530) the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Takebe, Y. (1988) *Mol. Cell. Biol.* 8 (1): 466-472): SV40 enhancer; and the intron sequence between exons 2 and 3 of rabbit β-globin (O'Hare K. et al., (1981) *Proc. Natl. Acad. Sci. USA*. 78 (3): 1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Administration, Dosage and Treatment

In various embodiments, the one or more gene delivery vectors, including viral vectors, and packaged viral particles containing the viral vectors, can be in the form of a medicament or a pharmaceutical composition and may be used in the manufacture of a medicament or a pharmaceutical composition. The pharmaceutical composition may include a pharmaceutically acceptable carrier. Preferably, the carrier is suitable for parenteral administration. In particular embodiments, the carrier is suitable for intravenous, intraperitoneal or intramuscular administration. Pharmaceutically acceptable carrier or excipients are described in, for example, *Remington: The Science and Practice of Pharmacy,* Alfonso R. Gennaro (Editor) Publishing Company (1997). Exemplary pharmaceutical forms can be in combination with sterile saline, dextrose solution, or buffered solution, or other pharmaceutically acceptable sterile fluids. Alternatively, a solid carrier, may be used such as, for example, microcarrier beads.

Pharmaceutical compositions are typically sterile and stable under the conditions of manufacture and storage. Pharmaceutical compositions may be formulated as a solution, microemulsion, liposome, or other ordered structure suitable to delivery of the gene therapy vectors. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The vectors of the present disclosure may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG).

In some embodiments, the gene therapy vectors, formulated with any acceptable carriers, can be administered parenterally, such as by intravenous, intraperitoneal, subcutaneous, intramuscular administration, limb perfusion or combinations thereof. The administration can be systemic, such that the gene delivery vectors are delivered through the body of the subject. In some embodiments, the gene delivery vectors can be administered directly into the targeted tissue, such as to the heart, liver, synovium, or intrathecally for neural tissues. In some embodiments, the gene delivery vectors can be administered locally, such as by a catheter. The route of administration can be determined by the person of skill in the art, taking into consideration, for example, the nature of target tissue, gene delivery vectors, intended therapeutic effect, and maximum load that can be administered and absorbed by the targeted tissue(s).

Generally, an effective amount, particularly a therapeutically effective amount, of the gene delivery vectors are administered to a subject in need thereof. A "therapeutically effective amount" refers to an amount effective, at dosages and for periods of time necessary, to achieve the desired therapeutic result, such as treatment or amelioration of an age-related condition. An effective or therapeutically effective amount of vector may vary according to factors such as the disease state, age, sex, and weight of the individual, and the ability of the viral vector to elicit a desired response in the individual. Dosage regimens may be adjusted to provide the optimum therapeutic response.

In particular embodiments, a range for therapeutically or prophylactically effective amounts of a nucleic acid, nucleic acid construct, parvoviral virion or pharmaceutical composition may be from $1\times10^{11}$ and $1\times10^{14}$ genome copy (gc)/kg or $1\times10^{12}$ and $1\times10^{13}$ genome copy (gc)/kg. It is to be noted that dosage values may vary with the severity of the condition to be alleviated. The dosage may also vary based on the efficacy of the virion employed. For example AAV8 is better at infecting liver as compared to AAV2 and AAV9 is better at infecting brain than AAV8, in these two cases one would need less AAV8 or AAV9 for the case of liver or brain respectively. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

The tissue target may be specific, for example the liver tissue, or it may be a combination of several tissues, for example the muscle and liver tissues. Exemplary tissue targets may include liver, skeletal muscle, heart muscle, adipose deposits, kidney, lung, vascular endothelium, epithelial and/or hematopoietic cells. In some embodiments, the effective dose range for small animals (mice), following intramuscular injection, may be between $1\times10^{12}$ and $1\times10^{13}$ genome copy (gc)/kg, and for larger animals (cats or dogs) and for human subjects, between $1\times10^{11}$ and $1\times10^{12}$ gc/kg, or between $1\times10^{11}$ and $1\times10^{14}$ genome copy (gc)/kg.

In various embodiments, the gene delivery vectors can be administered as a bolus or by continuous infusion over time. In some embodiments, several divided doses can be administered over time or the dose may be proportionally reduced or increased as indicated by the exigencies of the therapeutic situation. In some embodiments, the gene delivery vectors can be administered daily, weekly, biweekly or monthly. The duration of treatment can be for at least one week, one month, 2 months, 3 months, 6 months, or 8 month or more. In some embodiments, the duration of treatment can be for up to 1 year or more, 2 years or more, 3 years or more or indefinitely.

In some embodiments, a therapeutically effective amount is administered to the subject to treat a condition or disease associated with aging, e.g., an age related disease or disorder. The application of the invention extends the period of time for which an individual is generally healthy and free of chronic illness and/or the invention ameliorates disorders that appear often in aged and ageing adult population, including one or more of cardiovascular diseases, diabetes, atherosclerosis, obesity, cancer, infection, and neurological disorders. Any well established indicators of ageing progression can be used.

In some embodiments, the gene therapy described herein is used to least one of the following indicators of aging: reducing the incidence of cancer, delaying or ameliorating cardiovascular disease, such as atherosclerosis; delaying and/or ameliorating osteoporosis: improving glucose tolerance or reducing incidence of related diseases, such as diabetes and obesity: improving or reducing the decline in memory function and other cognitive functions; improving or reducing the decline neuromuscular coordination; and improving or reducing the decline in immune function. The amelioration of age-related disorders provided by the gene therapy methods herein can be as a result of reduction of symptoms in an affected subject or a reduction of incidence of the disease or disorder in a population as compared to an untreated population. The gene therapy has the effect of treating and/or preventing various age-related conditions and diseases, as assessed by particular markers and disorders of ageing. In a further aspect, therefore, the invention refers to a gene therapy method or the use of a nucleic acid vector as described above, for use in the treatment or prevention in a subject of at least a disorder or marker of ageing that is selected from the group of reduced cardiovascular function, osteoporosis, arthrosis, glucose intolerance, insulin resistance, loss of memory, loss of neuromuscular coordination, increase in cardiovascular disease, decrease in heart, circulatory or lung function and decrease in longevity, or combinations thereof.

In some embodiments, the gene therapy described herein is used to extend the lifespan for any particular species of subject. Extended lifespan can be an increase in the average lifespan of an individual of that species who reaches adulthood and/or an extension of the maximum lifespan of that species. In some embodiments, extended lifespan can be a 5%, 10%, 15%, 20% or more increase in maximum lifespan and/or a 5%, 10%, 15%, 20% or more increase in average lifespan.

EXAMPLES

Example 1: Methods for Regulating TGFβ1

The present disclosure provides a gene therapy method for the long term regulation of TGFβ1 in an animal such as a human or other mammal such as a domesticated animal such as a dog or cat. The disclosure provides a gene therapy method for the long term regulation of TGFβ1 in an animal such as a human or other mammal such as a domesticated animal such as a dog or cat as a method of treating or preventing inflammation, remodeling, or fibrosis. The disclosure provides a gene therapy method for regulating TGFβ1 in an animal such as a human or other mammal such as a domesticated animal such as a dog or cat for treating a heart pathology, such as increased fibrosis. The disclosure provides for the regulation of TGFβ1 by a gene therapy method including the delivery of a nucleic acid to a cell, for example, by using an adeno-associated vector. The disclosure provides for the regulation of TGFβ1 by the delivery of a nucleic acid that produces a soluble circulating protein that binds TGFβ1 thereby inhibiting its ability to activate its endogenous pathway. The soluble circulating protein can be the extracellular domain of TGFβ receptor 2. One skilled in the art can also create a version from the TGFβ receptor 1 or 3 as well. The soluble TGFβ receptor 2 protein has been truncated at the transmembrane domain of the protein as predicted by annotation software and by hydrophobicity of the amino acids.

Plasmids

The vector AAV vector was created by amplifying the extracellular domain using Forward primer 5'-GCCAC-CATGGGTCGGGGGCTGC (SEQ ID NO: 118) and reverse primer 5'-GGACAGGGCTTGAT-TGTGGGCCCTCTGGGGTCGGGACTGCTGGTGGTGT-ATTCTTCCG (SEQ ID NO: 119). The bold and italicized part of the forward primer is the Kozak sequence. The bold and italicized part of the reverse primer matches the mouse igg domain that was fused C terminally by overlapping PCR.

Forward primer 5'-CGGAAGAATACAC-CACCAGCAGTCCCGACCCCAGAGGGCCCACAAT-CAAGCCCTGTCC (SEQ ID NO:1) and reverse primer 5'-TCATTTACCCGGAGTCCGGGAGAAGCTC (SEQ ID NO:2) were used to amplify the igg domain. The bold and italicized part matches the extracellular domain of TGFbR2 for overlapping PCR. The two parts were combined by using equal molar ratios of the amplified sections in a second round of PCR using the forward primer from TGFbR2 amplification and the reverse primer from igg amplification. This created the fusion protein sTGFbR2-Fc (igg2Ae) for a total length of 1251 base pairs. This was ligated into an AAV backbone using unique restriction enzyme site overhangs NotI and NheI.

AAV Production

The method of AAV production and titer quantification was carried out according to Lock, M. 2010 Human gene therapy: Kwon, O. et al., (2010) *J Histochem Cytochem.* 58 (8): 687-694. Briefly, Hek 293 cells were triple co-transfected at 75% confluency in one 10 layer Nunc™ Cell Factory™ System from Thermo Scientific (Rockford, IL) using PEI transfection reagent following manufacturer's instructions. Cells and supernatant were harvested separately after 72 hours post transfection. The cells were spun down and lysed with 3 freeze-thaw cycles and incubated with Benzonase (E1015-25KU, Sigma). They were then clarified by spinning at 10,500×G for 20 min and the supernatant was added to the rest of the media supernatant. Everything was filtered through a 0.2 uM filter and was then concentrated using lab scale TFF system (EMD Chemicals, Gibbstown, NJ) down to 15 ml. We used a Pellicon XL 100 kDa filter and followed manufactures instructions (EMD Chemicals, Gibbstown, NJ). The concentrated prep was re-clarified by centrifugation at 10,500×g and 15° C. for 20 min and the supernatant was carefully removed to a new tube. Six iodixanol step gradients were formed according to the method of Zolotukhin and colleagues. See Zolotukhin S., (1999) *Gene Ther.* 6:973-85, with some modifications as follows: Increasingly dense iodixanol (OptiPrep; Sigma-Aldrich, St Louis, MO) solutions in phosphate-buffered saline (PBS) containing 10 mM magnesium chloride and 25 mM potassium were successively underlaid in 39 ml of Quick-Seal centrifuge tubes (Beckman Instruments, Palo Alto, CA). The steps of the gradient were 4 ml of 15%, 9 ml of 25%, 9 ml of 40%, and 5 ml of 54% iodixanol. Fourteen milliliters of the clarified feedstock was then overlaid onto the gradient and the tube was sealed. The tubes were centrifuged for 70 min at 242,000×g in a VTi 50 rotor (Beckman Instruments) at 18° C. and the 40% gradient was collected through an 18-gauge needle inserted horizontally at the 54%/40% interface. The virus containing iodixanol was diafiltered using Amicon 15-Ultra and washed 5 times with final formulation buffer (PBS-35 mM NaCl), and concentrated to ~1 ml.

Vector Characterization

DNase I-resistant vector genomes were titered by TaqMan PCR amplification (Applied Biosystems, Foster City, CA), using primers and probes directed against the WPRE3 poly Adenylation signal encoded in the transgene cassette. The purity of gradient fractions and final vector lots were evaluated by sodium dodecyl sulfate-polyacrylamide gel electrophoresis (SDS-PAGE) and the proteins were visualized by SYPRO ruby staining (Invitrogen) and UV excitation.

Infection

The mice were infected through intra-peritoneal (IP), tail vein (IV) or retro orbital (RO) injection. Briefly, the IP injection location is located by drawing an imaginary line across the abdomen just above the knees. The needle is inserted along this line on the animal's right side and close to the midline. To perform an IP injection, the mouse must be well restrained so that it cannot move during the procedure. Tilt the entire mouse so that the top of the head is facing toward the ground and its hind legs are higher up and so that it's abdomen is facing you. Insert the needle into the abdomen at about a 30-degree angle, the shaft of the needle should enter to a depth of about half a centimeter. Aspirate to be sure that the needle has not penetrated a blood vessel, the intestines, or the urinary bladder. Inject the contents of the syringe and withdraw the needle and return the mouse to its cage. The recommended needle size for IP injections in the mouse is 25-27 gauge. For IV injection into the tail vein, the mouse is restrained and the tail vein is found by holding the tail over a bright light. The vein is made larger by briefly putting the mice under a heat lamp to dilate the blood vessels. Then using a 25 gauge needle the mouse is injected with up to 200ul. The RO injections are done under anesthesia. The mouse, while under, is prepared by putting slight pressure to bulge the eye and slide the needle behind the eye with only up to 150ul for an adult mouse.

Surgery

Aortic constriction (ACC) is induced in adult animal through constriction of ascending aorta. An incision will be made in the chest wall approximately at the third intercostals space. A rodent rib spreader is inserted and the ribs gently spread to allow access to the thoracic cavity. The ascending aorta is then isolated from the pulmonary artery and a sterile 8.0 prolene ligature is passed around it approximately 3 mm from the base of the heart. A blunted 27 gauge needle is placed on top of the aorta and ligation is tied around the needle. The needle is then carefully removed from under the tie. The rib spreader is closed and the lung re-inflated. The ribs, chest musculature, and skin are closed using sterile sutures (5-0) Dexons and 6-0 Prolene sutures for closing muscle and subcutaneous layers and skin, respectively). The surgeon will minimize pneumothorax by expanding the lungs in concert with the placement of the last suture closing the thoracotomy. Sham operated animals undergo similar procedure without constriction of the aorta. The animal will be closely monitored until full recovery from anesthesia. Once the animal has regained consciousness (and is able to protect its airway), the animal will be extubated. Animals will continually be closely monitored until full neurological consciousness is achieved. Suture will be removed by 10-14 days post-surgery. The date, time, and type of the surgical procedure will be noted on a clinical post-operative record, as required. ACC surgical mortality may be 30%.

Non-Invasive Echocardiography

To serially non-invasively assess cardiac structure and function, animals at designated time points (not to exceed once per week) undergo non-invasive transthoracic echocardiography. For this, animals are brought to a designated procedure room. The animal is lightly anesthetized with 1.5-5% (mice and rat) isoflurane. Sedation will be confirmed by the lack of response to gentle skin pinch. Eye ointment is applied to the anesthetized animals to prevent the eye from drying and causing irritation or ulceration. Hair will be removed from the animal's chest using #40 blade and medical grade depilatory cream for obtaining clear echo images. The animal is gently placed on a platform, and the echocardiogram probe placed on the left chest wall. The heart rate and respiratory rate of the animal is monitored with the physiologic monitor that is connected to the echo machine and the platform on which the animal is placed while the ultrasound imaging is going on. Ultrasound images are generally obtained within 15 minutes and result in no pain to the animal. During the procedure, animals are closely monitored for any signs of distress, and if any are present, the procedure is immediately terminated and the animal returned to its cage.

Euthanasia

Animals are euthanized by the slow fill method of CO2 administration according to the equipment available in the facility. Typically, animals are euthanized in the home cage out of view from other animals. A regulator is used to ensure the proper flow rate. Animals should lose consciousness rapidly ~30 sec. At the cessation of breathing (several minutes) animals will undergo a secondary physical method of euthanasia.

Tissue Harvest

Tissues are immediately harvested after euthanasia. Part of each organ was snap frozen in dry ice for qPCR analysis and sequencing and the other part of each organ was then formalin fixed overnight 24-48 hours depending on size and frozen in OCT buffer for sectioning and analysis.

Blood Collection

The mice are held by their scruff and a needle is used to puncture the mandibular vein/artery and blood is collected in heparin coated tubes.

Staining and Sectioning

The mice are sectioned using a microtome and then paraffin embedded. Deparafinization and rehydration takes place by heating the slides to 50° C. and then successive baths of xylene and ethanol and finally DI H2O. The slides are then incubated in boiling citrate buffer for 10 minutes and are cooled on the bench at room temperature. They are then washed in PBS 5× for 2 min each. The slides are blocked in 3% BSA in PBS at room temperature for 1 hour. Primary antibody was applied in 3% BSA/PBS at a 1:300 dilution overnight at 4° C. The slides are then washed in PBS 5× for 2 min each. The secondary antibody in 3% BSA/PBS is applied for 1 hr at 37° C., dilution ¹/₁₀₀. The slides are then washed in PBS 5× for 2 min each. 50 μl per slide DAPI (or Hoechst final 5 μg/ml) in PBS is applied for 30 minutes in room temperature (in humid chamber). The slides are then washed in PBS 5× for 2 min each. Mount with mounting medium without DAPI and cover.

Inhibition of Transforming Growth Factor β1 (TGFβ1)

Figure 2:
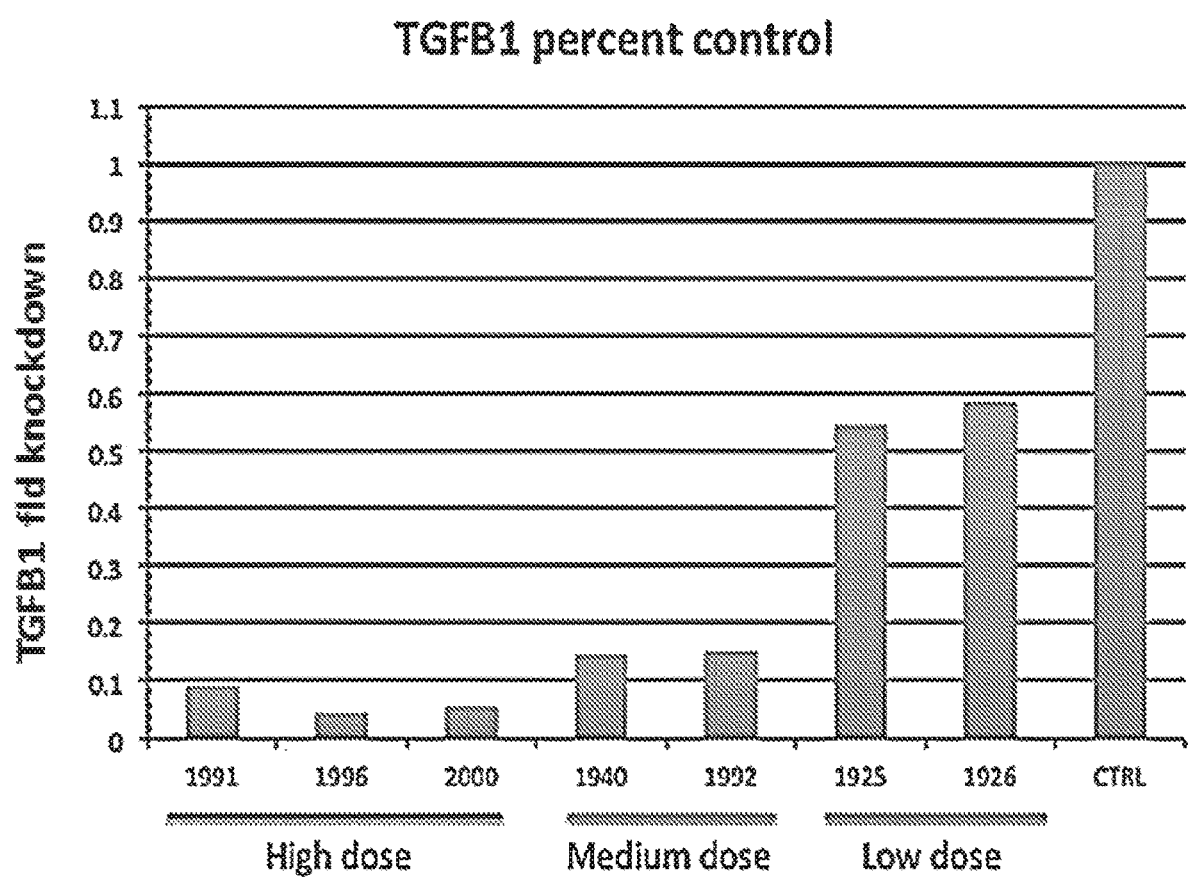
FIG. 2 is a graph of data demonstrating TGFb1 knockdown versus dosage.
Figure 7:
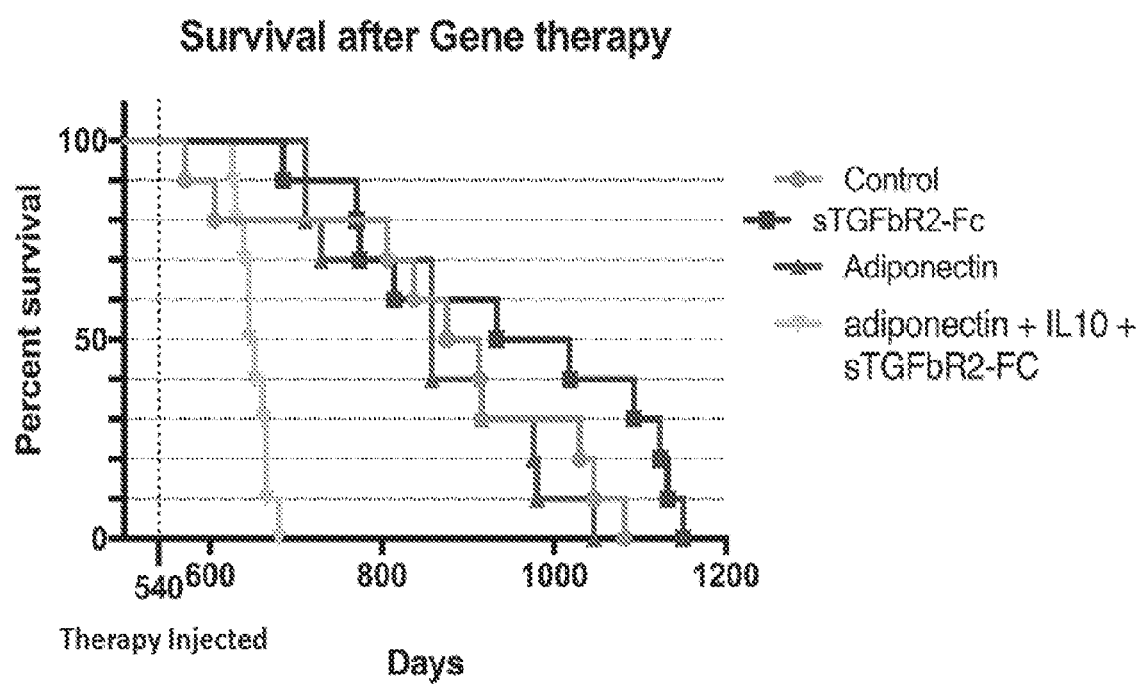
FIG. 7 is a graph of percent survival versus time in days.

A nucleic acid encoding a soluble receptor protein for Transforming Growth Factor Receptor II (TGFbRII) was delivered using an AAV to cells in a mouse model of HCM/DCM that uses aortic banding to achieve a pressure overload that eventually causes the desired phenotype. The AAV was used for the long-term permanent decrease of TGFβ1, which is beneficial for reducing heart failure and promoting longevity as indicated in the survival curve shown in FIG. 7. The soluble receptor protein binds TGFβ1 in order to reduce signaling of this pathway and alleviate fibrotic tissue induction and inflammatory responses. As indicated in FIG. 2, administration of the AAV with the nucleic acid encoding the soluble receptor protein for Transforming Growth Factor Receptor II (TGFbRII) decreased serum TGFβ1 by up to 95% leading to a reduction in TGFβ1 signaling.

Figure 3:
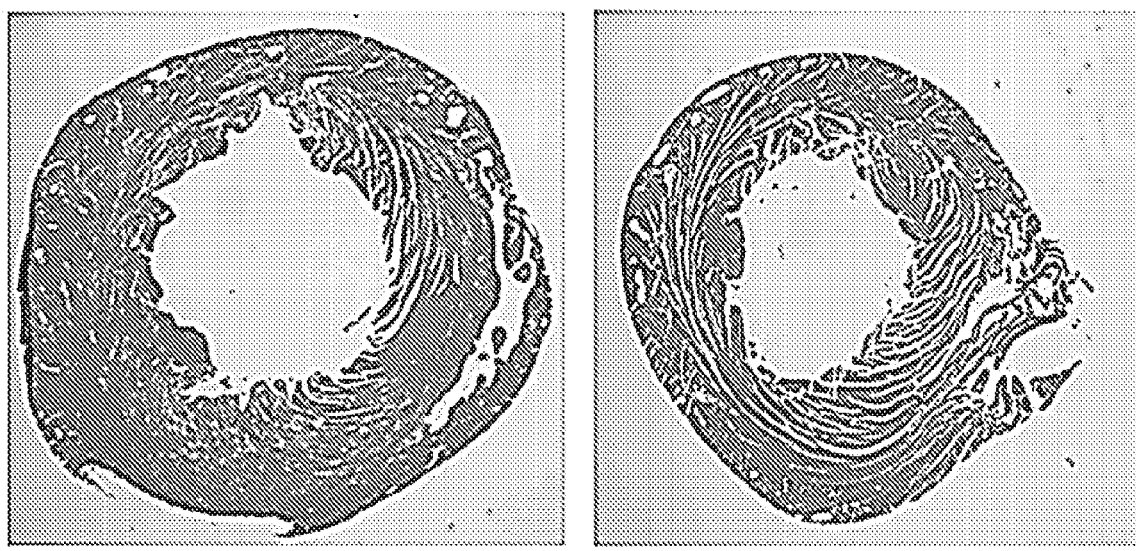
FIG. 3 is a graph of data showing percent fibrosis and related images.
Figure 3:
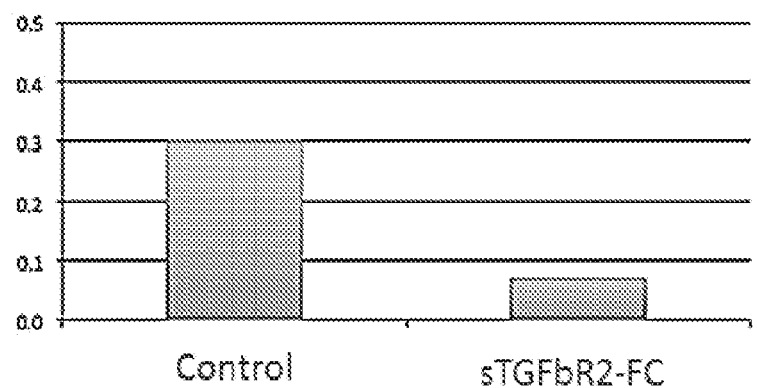
Figure 5:
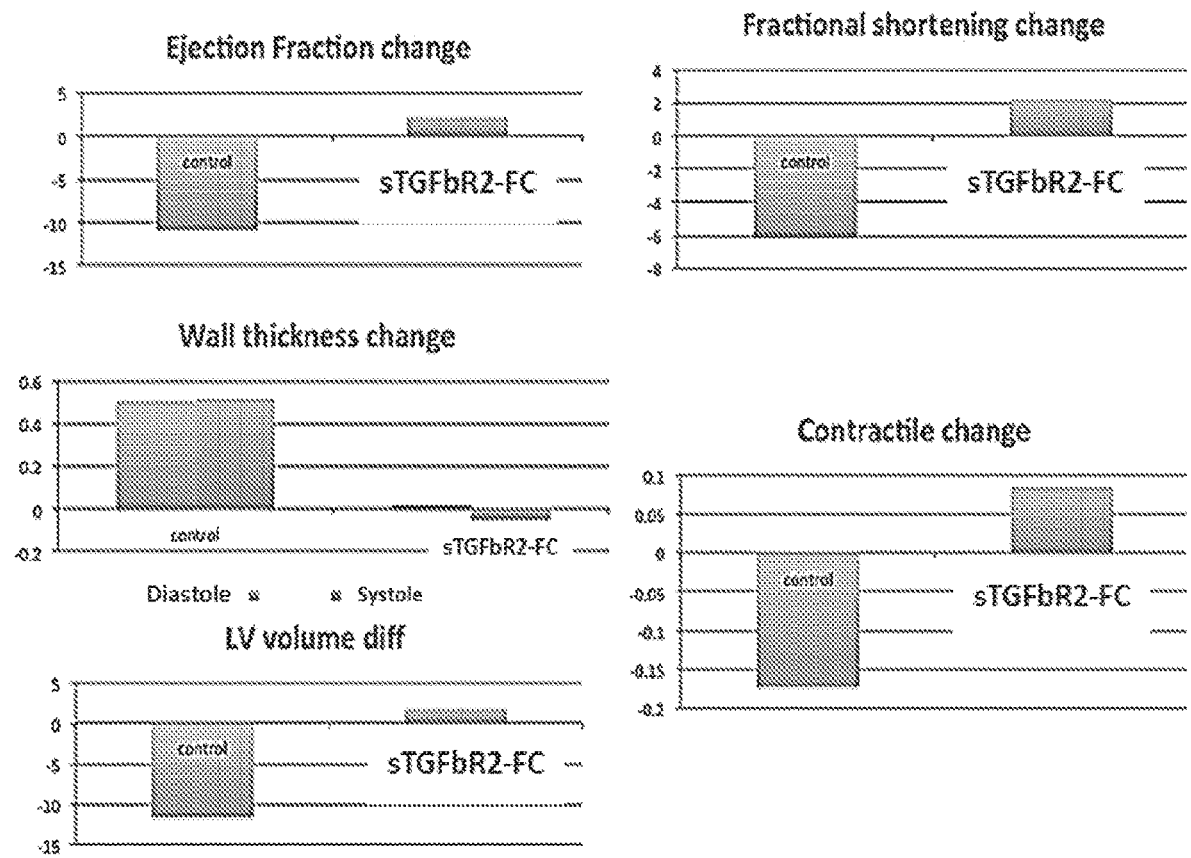
FIG. 5 is a graph of data demonstrating change in heart parameters in a control versus sTGFbR2-FC administration.

The gene therapy affected fibrotic lesion development. As indicated in FIG. 3, the control samples have approximately 30% fibrosis on the total area of sectioned heart as compared to the AAV treated mouse heart that has approximately 8%. The gene therapy also impacted the functioning of the heart 7 weeks post AAC surgery. As shown in FIG. 1, there is a large difference in the strength of heart contractility and left ventricle volume as seen in the echocardiograms. FIG. 5 demonstrates that control animals have a negative change in several parameters such as heart wall thickness, ejection fraction, fractional shortening, and left ventricle volume. The gene therapy animals have either no or a positive change in these parameters.

Figure 4:
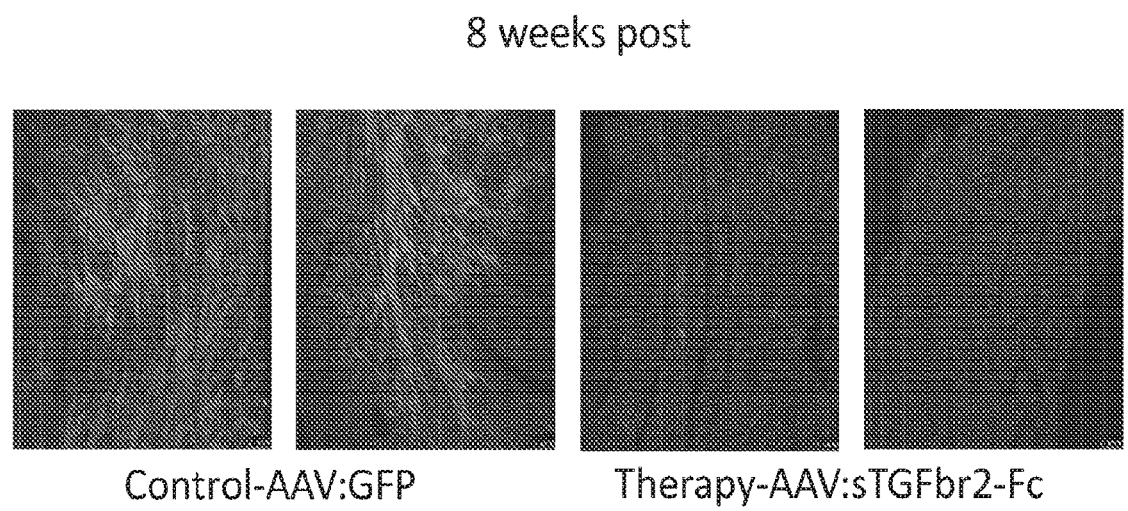
FIG. 4 are images showing WGA staining for control heart and treated heart sections.
Figure 6:
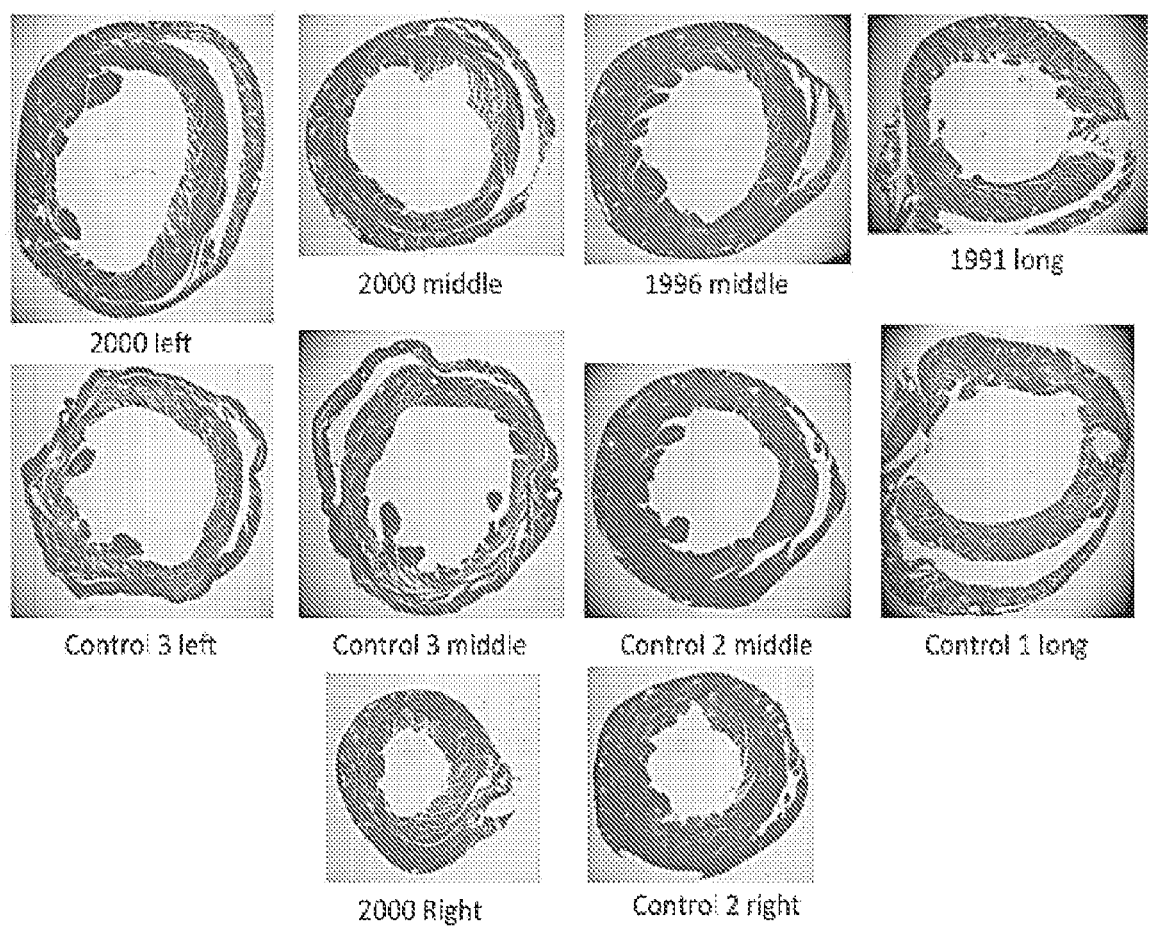
FIG. 6 are representative trichrome staining images.

FIG. 4 depicts WGA and DAPI staining for control heart.
FIG. 6 depicts representative trichrome staining images.

Example 2: Combination Gene Therapy

The disclosure provides a gene therapy method for the delivery of a nucleic acid encoding a soluble receptor protein for Transforming Growth Factor Receptor II (TGFbRII) and a nucleic acid encoding for Nrf2 (or nuclear factor (erythroid-derived 2)-like 2 Nfe2l2). Nrf2 is an antioxidant protein that protects against oxidative damage triggered by injury and inflammation. The disclosure provides a method of using each in combination by directly injecting two viruses each containing one transgene cassette. (i.e. ITR-hEf1α-sTGFbR2-Fc-WPRE3-SV40 pA-ITR AND ITR-hEf1α-Nrf2-WPRE3-SV40 pA-ITR). The disclosure provides combining both transgenes into one vector by use of the viral 2A sequences or IRES whereby two genes are expressed from one promoter. (i.e. ITR-hEf1α-sTGFbR2-Fc-P2A-Nrf2-WPRE3-SV40 pA-ITR or ITR-hEf1α-sTGFbR2-Fc-IRES-Nrf2-WPRE3-SV40 pA-ITR).

Example 3: Methods for Regulating Adiponectin

The disclosure provides a gene therapy method for regulating Adiponectin in an animal such as a human or other mammal such as a domesticated animal such as a dog or cat. An adeno-associated virus is provided including a constitutive promoter driving the expression of a nucleic acid encoding adiponectin and DsbA-L (GSTK1). The nucleic acid construct may include a 3'UTR including WPRE3 and late SV40 pA. A nucleic acid encoding adiponectin is provided in a first vector and a nucleic acid encoding DsbA-L is provided in a second vector. The first vector and the second vector are self-complimentary AAV vectors. A self-complementary adeno-associated virus (scAAV) is a viral vector engineered from the naturally occurring adeno-associated virus (AAV). The rAAV is termed "self-complementary" because the coding region has been designed to form an intra-molecular double-stranded DNA template. A rate-limiting step for the standard AAV genome involves the second-strand synthesis since the typical AAV genome is a single-stranded DNA template. However, this is not the case for scAAV genomes. Upon infection, rather than waiting for cell mediated synthesis of the second strand, the two complementary halves of scAAV will associate to form one double stranded DNA (dsDNA) unit that is ready for immediate replication and transcription. In gene therapy application utilizing rAAV, the virus transduces the cell with a single stranded DNA (ssDNA) flanked by two Inverted Terminal Repeats (ITRs). These ITRs form hairpins at the end of the sequence to serve as primers to initiate synthesis of the second strand before subsequent steps of infection can begin. The second strand synthesis is considered to be one of several blocks to efficient infection. Additional advantages of scAAV include increased and prolonged transgene expression in vitro and in vivo, as well as higher in vivo DNA stability and more effective circularization.

Example 4: Method for Treating Obesity

Figure 8A:
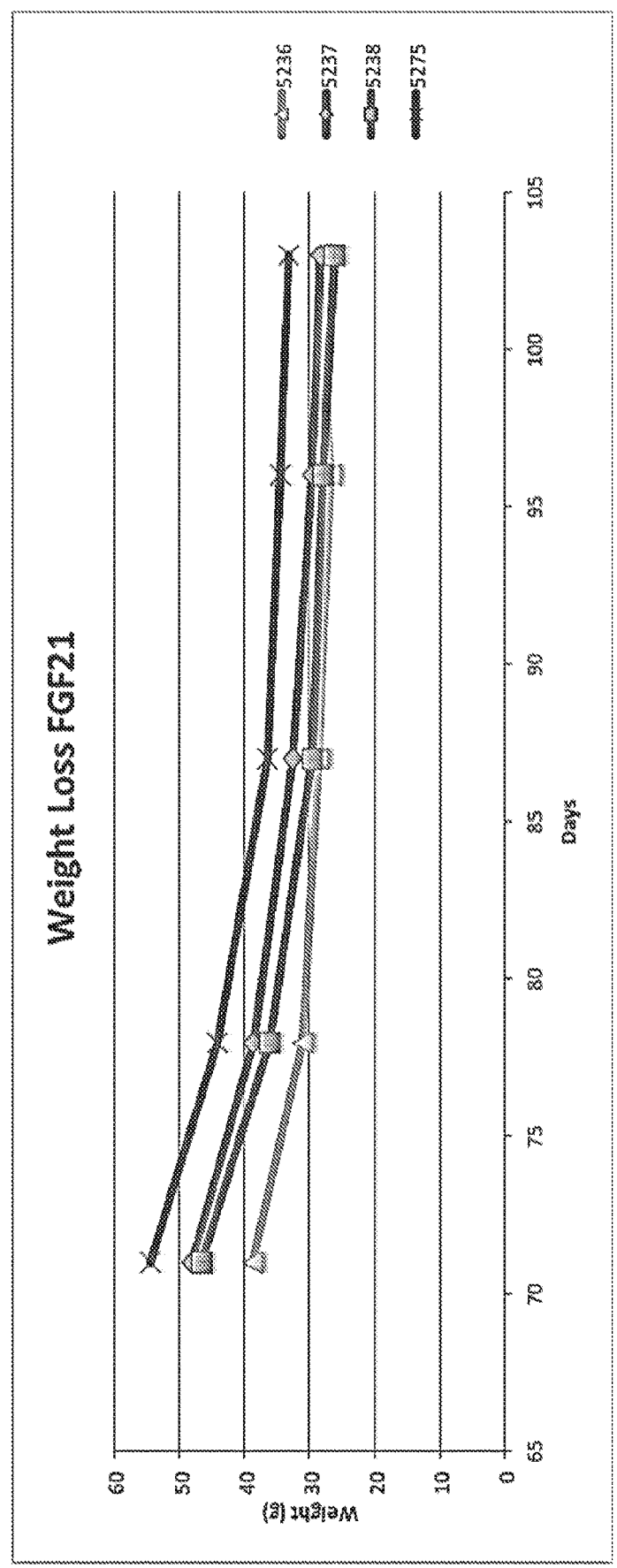
FIG. 8A is a graph of weight loss versus time in days for FGF21.
Figure 8B:
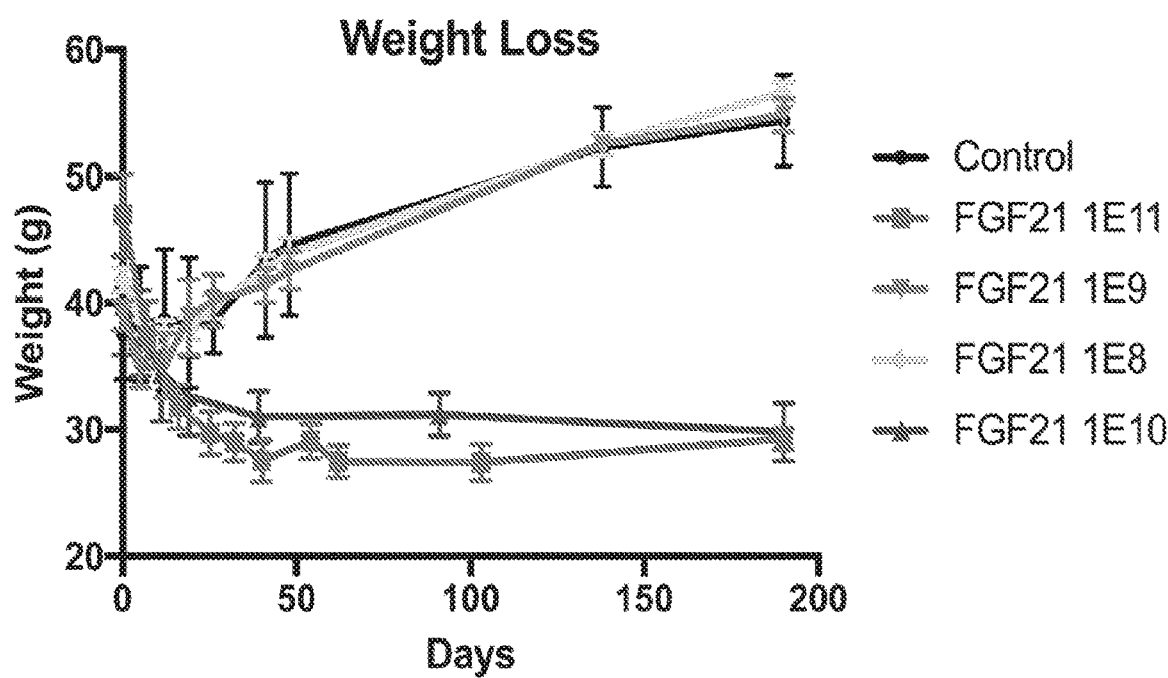
FIG. 8B is a graph of weight loss versus time in days for various FGF21 gene therapies.

The disclosure provides for a gene therapy method for the delivery of a nucleic acid encoding fibroblast growth factor 21 (FGF21) and a nucleic acid encoding either BMP2, BMP4 or Sema3a or all of them together. FGF21 is known to shift the balance of osteoblasts and osteoclasts toward osteoclastic formation through the inhibition of differentiation of cells into osteoblasts and the promotion of differentiation of cells into osteoclasts. To balance the negative side effect of bone loss from increased FGF21 expression, multiple genes are delivered. FGF21 will cause weight loss as seen in FIGS. 8A and 8B without any apparent toxicity (seen by body condition score and activity monitoring). The mice while maintained on a high fat diet were able to lose up to 40% of their body weight (back to the normal weight for a mouse their age) and seem to have plateaued into the normal range. To combat the bone loss, one or two or all of BMP2, BMP4 or Sema3a are delivered with FGF21 simultaneously or in series as part of a combination therapy to shift the balance back to homeostasis for osteoblasts and osteoclasts.

According to certain aspects, methods are provided for losing weight in an individual or increasing metabolic rate of an individual comprising delivery of a nucleic acid encoding fibroblast growth factor 21 (FGF21) to the individual in a gene therapy method, such as using an AAV or otherwise regulating, (upregulating or downregulating) FGF21.

Figure 16:
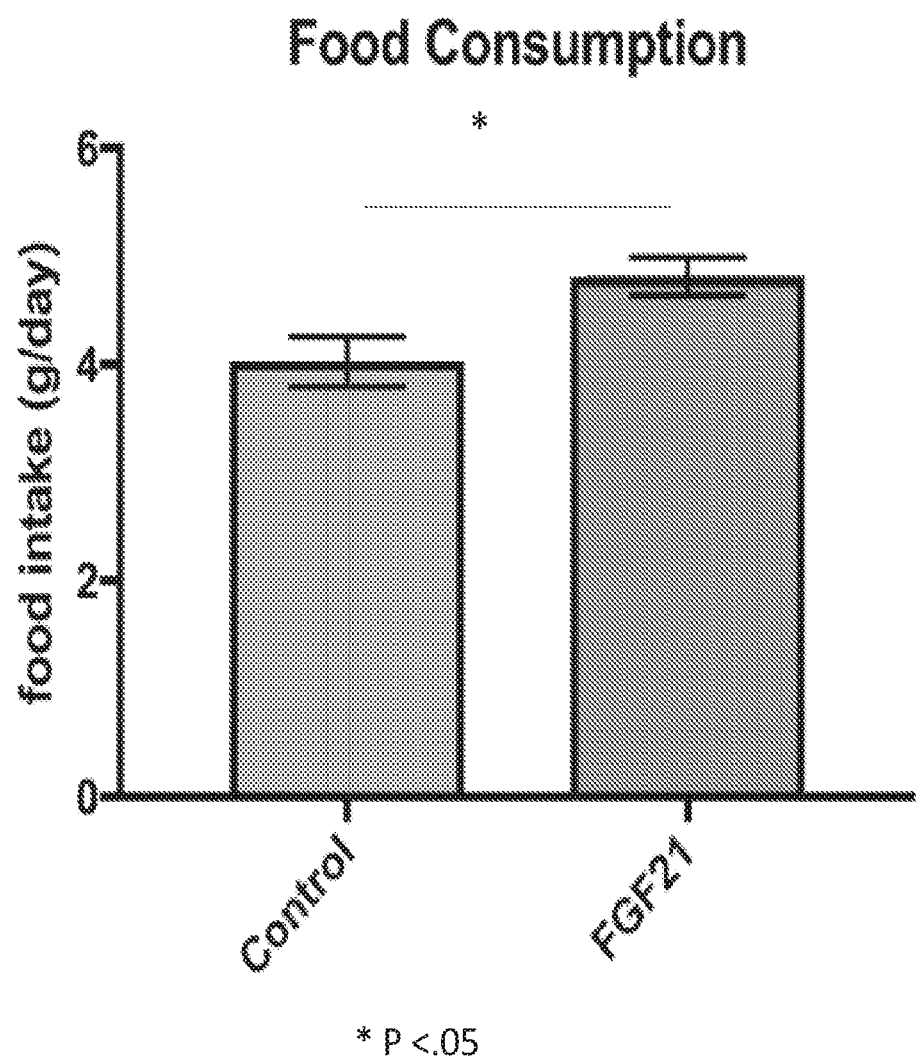
FIG. 16 is a graph of food intake of a control mice versus mice treated with FGF21.
Figure 17:
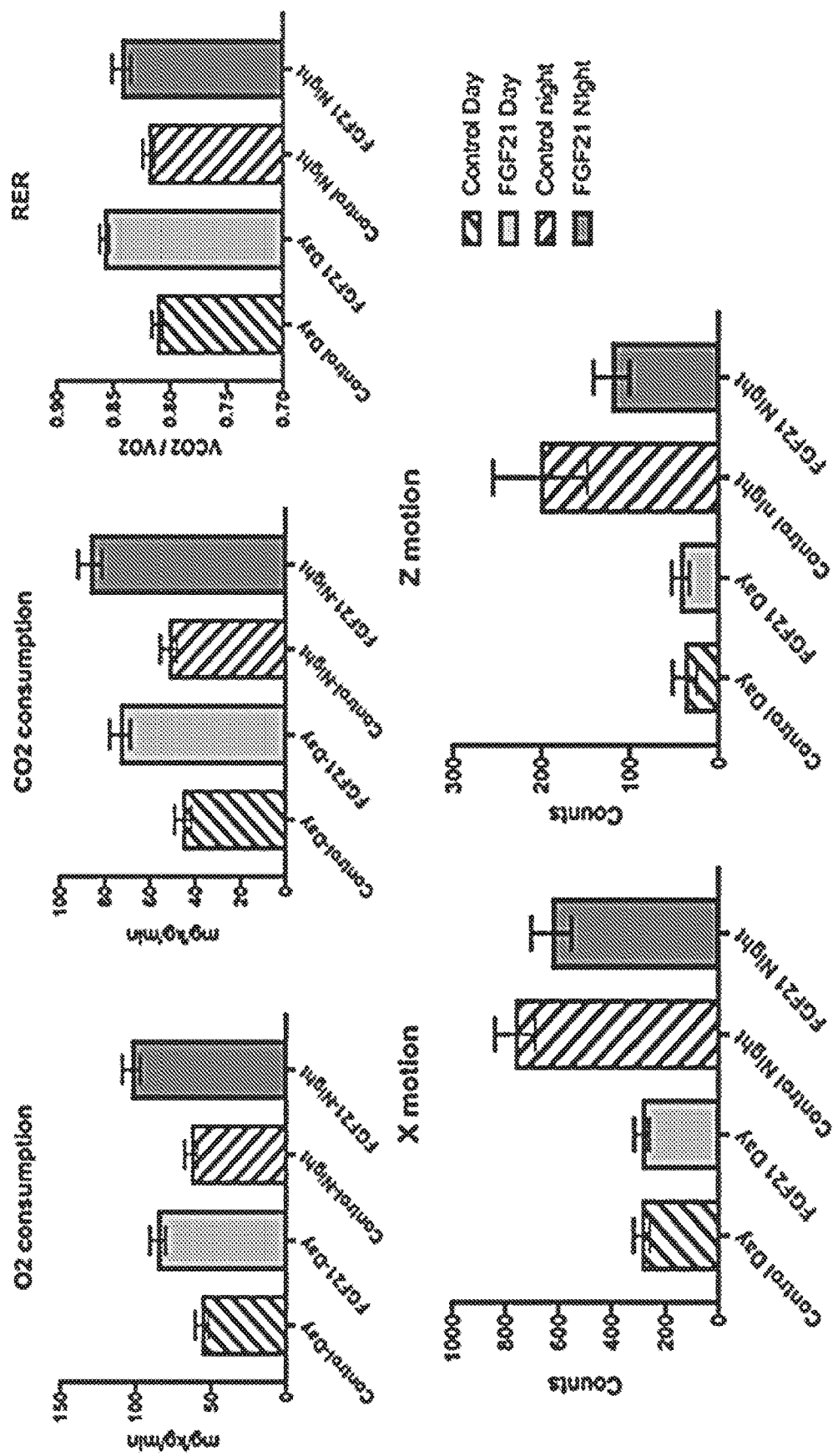
FIG. 17 depicts data of control mice versus mice treated with FGF21.

In an experiment conducted, food intake of mice was measured where the mice were provided with FGF21 as a gene therapy and mice that received the therapy consume more high fat food but are still able to maintain a normal lean mouse weight, indicating an altered metabolic state. See FIG. 16. The effect of the gene therapy on respiration rate and activity was determined. Mice treated with FGF21 were placed into the Columbus Instruments CLAMS system to measure their $O_2$ consumption, $CO_2$ production and their movement in X, Y, Z plane and the results are shown in FIG. 17. Once the mice were in the system the data was generated automatically. The FGF21 mice that maintain a lean body weight while consuming more food have higher metabolic activities as indicated by the increased $O_2$ consumptions and $CO_2$ production as compared to controls. However, as noted by motion sensors, the FGF21 mice show less movement providing another indication that their altered mitochondrial activity and metabolic state and not their behavior is responsible for their ability to maintain a lean body mass while on a high fat diet.

Figure 18:
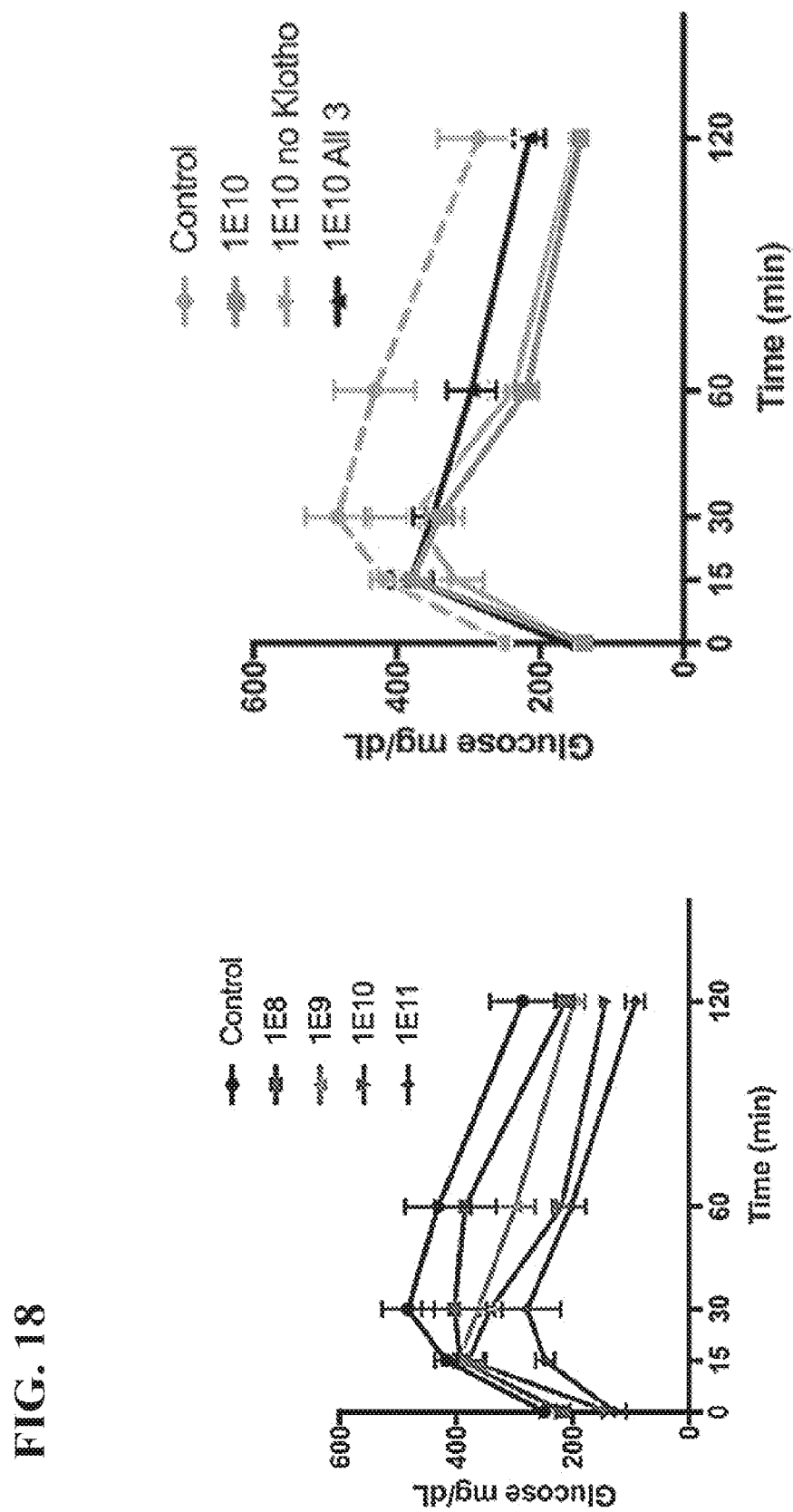
FIG. 18 depicts glucose level data.

The effect of FGF21 on glucose and insulin sensitivity was tested through the Glucose tolerance test and determined to have a large effect as indicated in FIG. 18. Briefly, mice were fasted overnight anywhere from 6-10 hours. Blood was collected to analyze baseline blood glucose levels. The mice were then given a dose of glucose solution through oral gavage with up to 500 µl of 250 mg/ml glucose in dd$H_2$O. Then blood was taken and blood glucose was measured in the following increments: 15 min, 30 min, 60 min, and 120 min. The data is shown in FIG. 18 for several different doses of FGF21 in the left hand graph and then for different combinations of other proteins with a constant 1E10 dose for FGF21. FGF21+sTGFbR2-FC, and FGF21+sTGFbR2-FC+Klotho were tested and the results presented in the right hand graph with the differences in glucose indicated.

Figure 9:
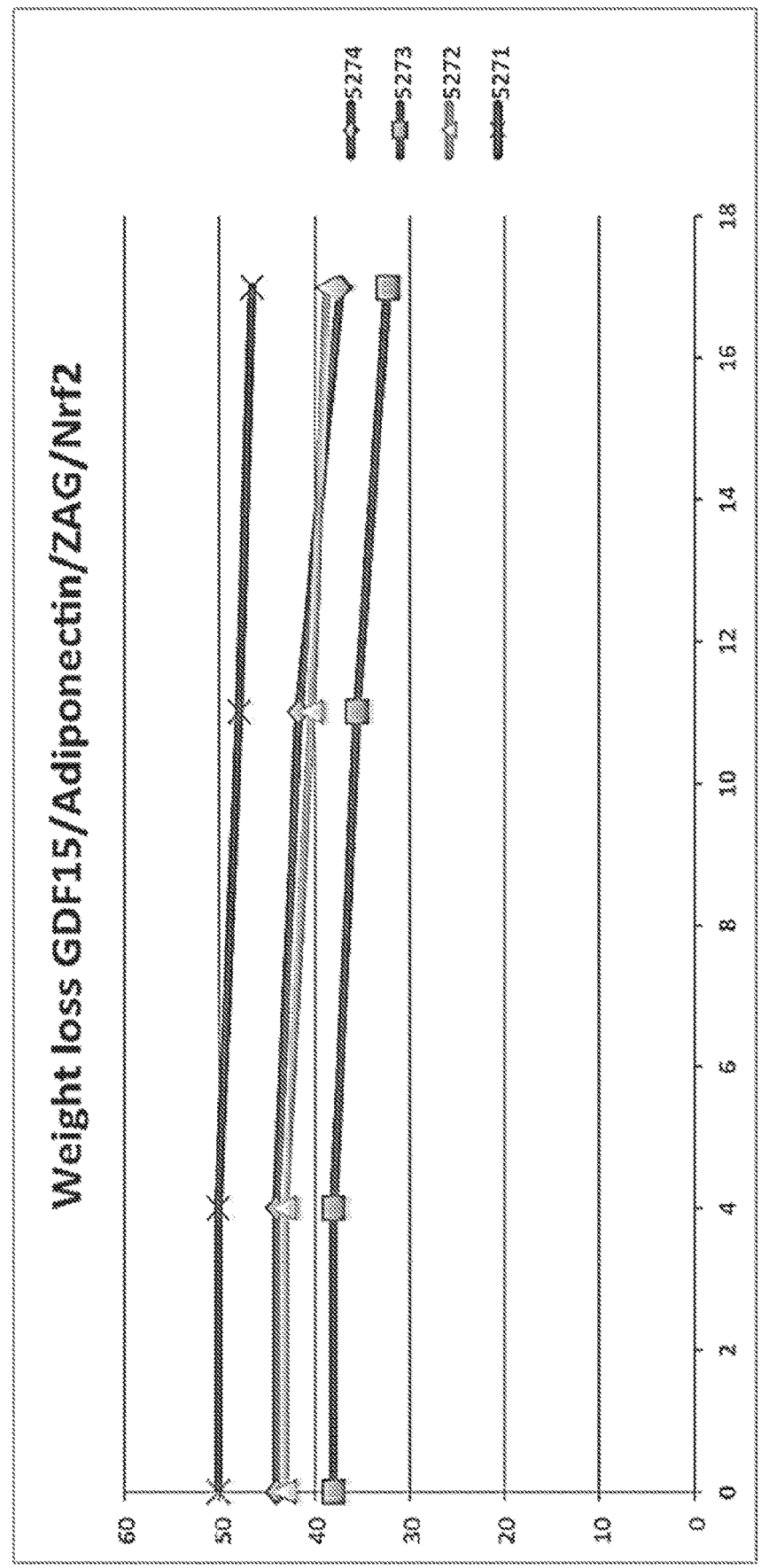
FIG. 9 is a graph of weight loss versus time in days for GDF15, adiponectin, ZAG, and Nrf2.
Figure 10:
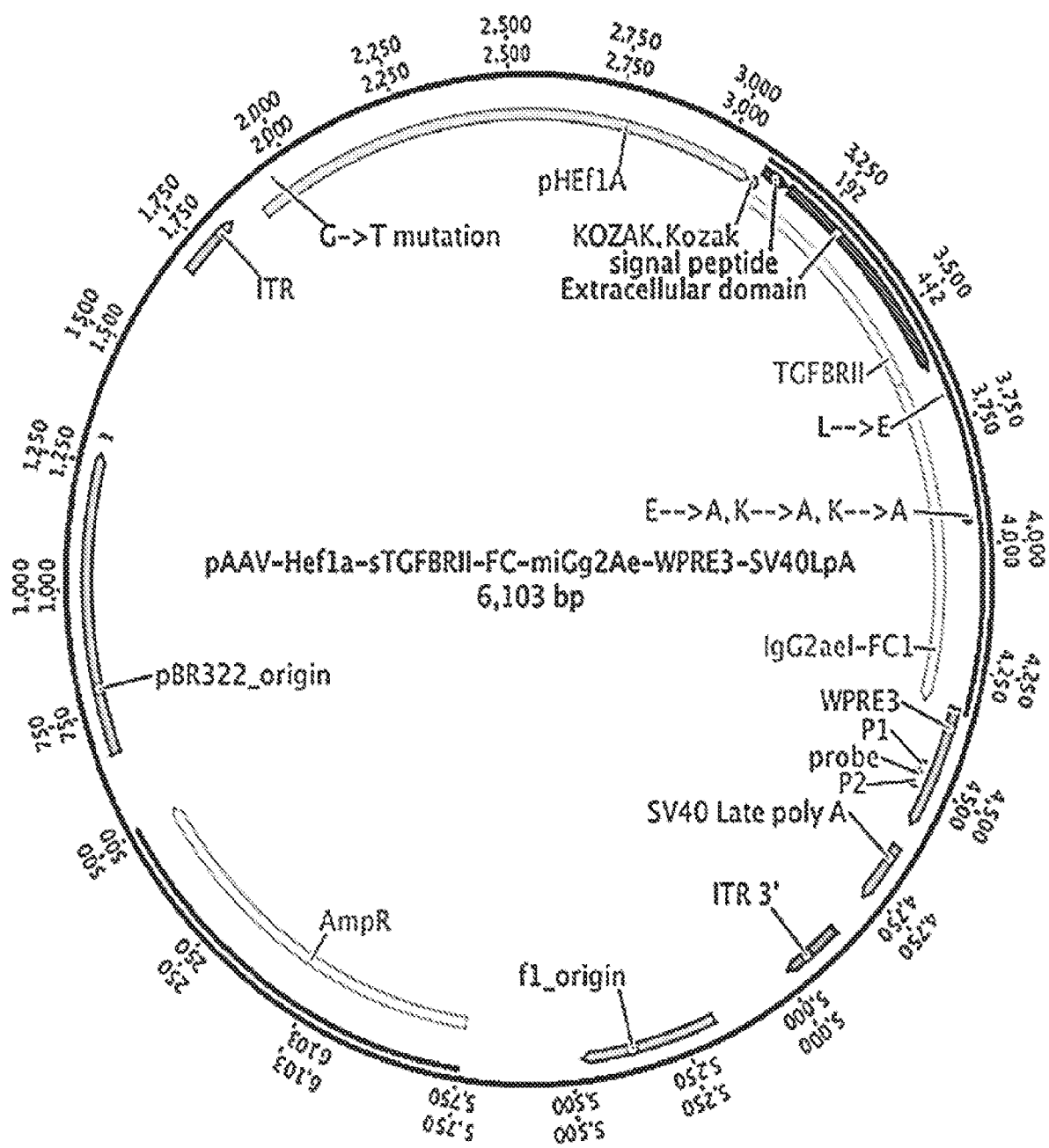
FIG. 10 is a vector map of viral construct including ITRs promoter sTGFbR2-Fc and 3'UTR.
Figure 11:
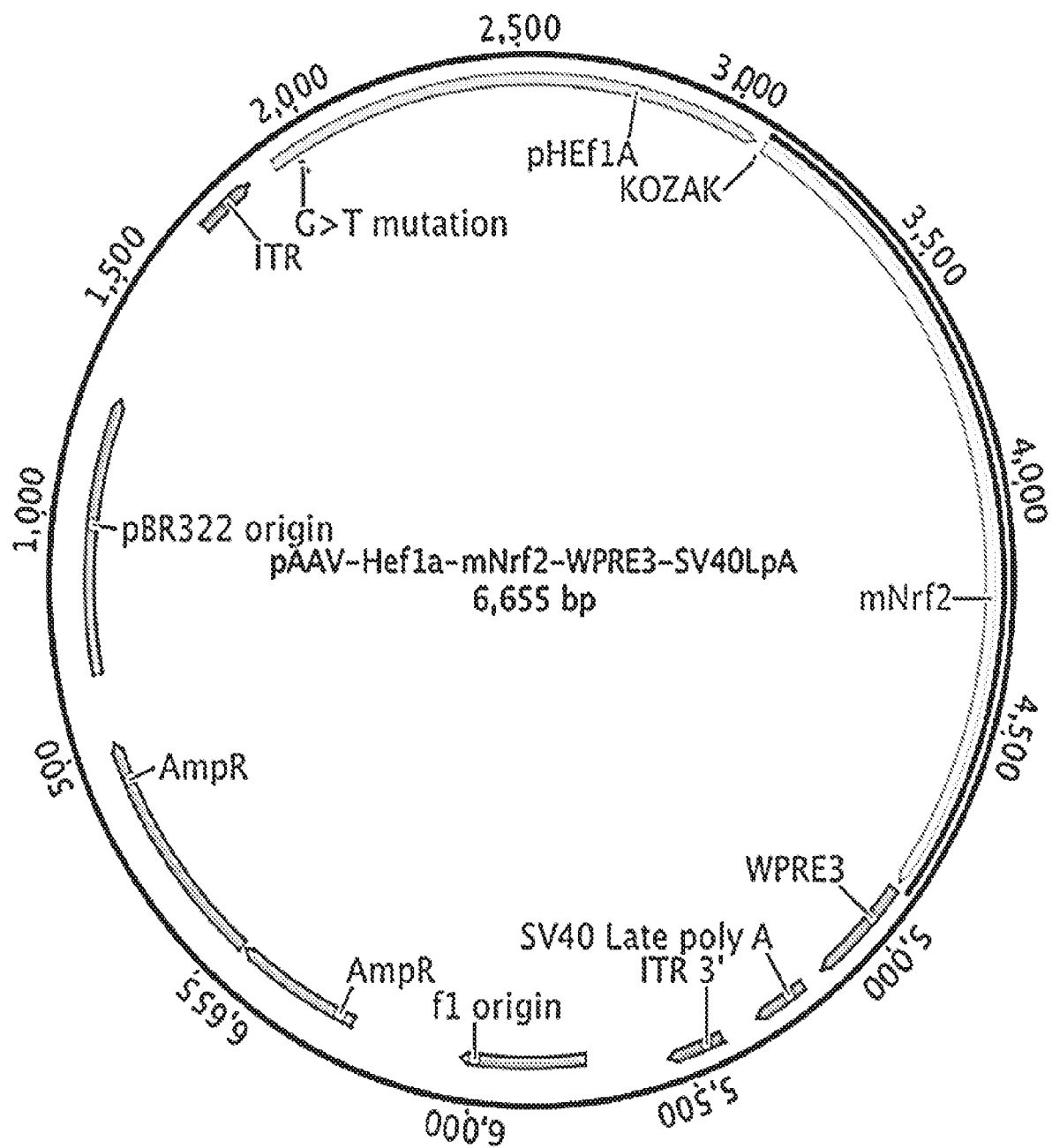
FIG. 11 is a vector map of viral construct including ITRs promoter Nrf2 and 3'UTR.
Figure 12:
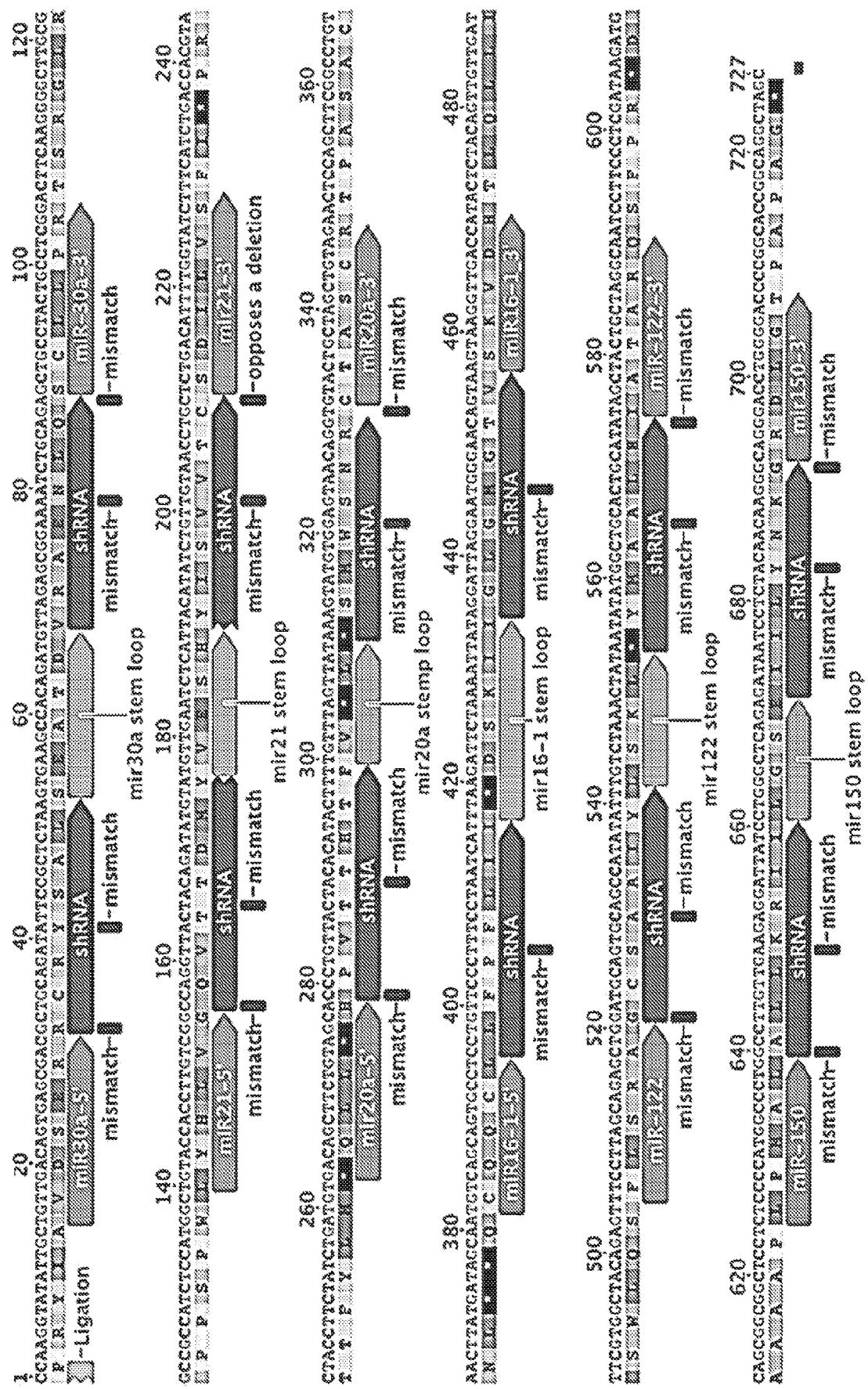
FIG. 12 is a vector map of a possible construction of 7 Pri-miRNAs and the order they are concatenated. There is also a red mark for where the mismatches are planned in the "shRNA" part for proper processing of the miRNA. Figure discloses the nucleotide sequence as SEQ ID NO: 137 and the amino acid sequences as SEQ ID NOS 138-145, respectively, in order of appearance.
Figure 13:
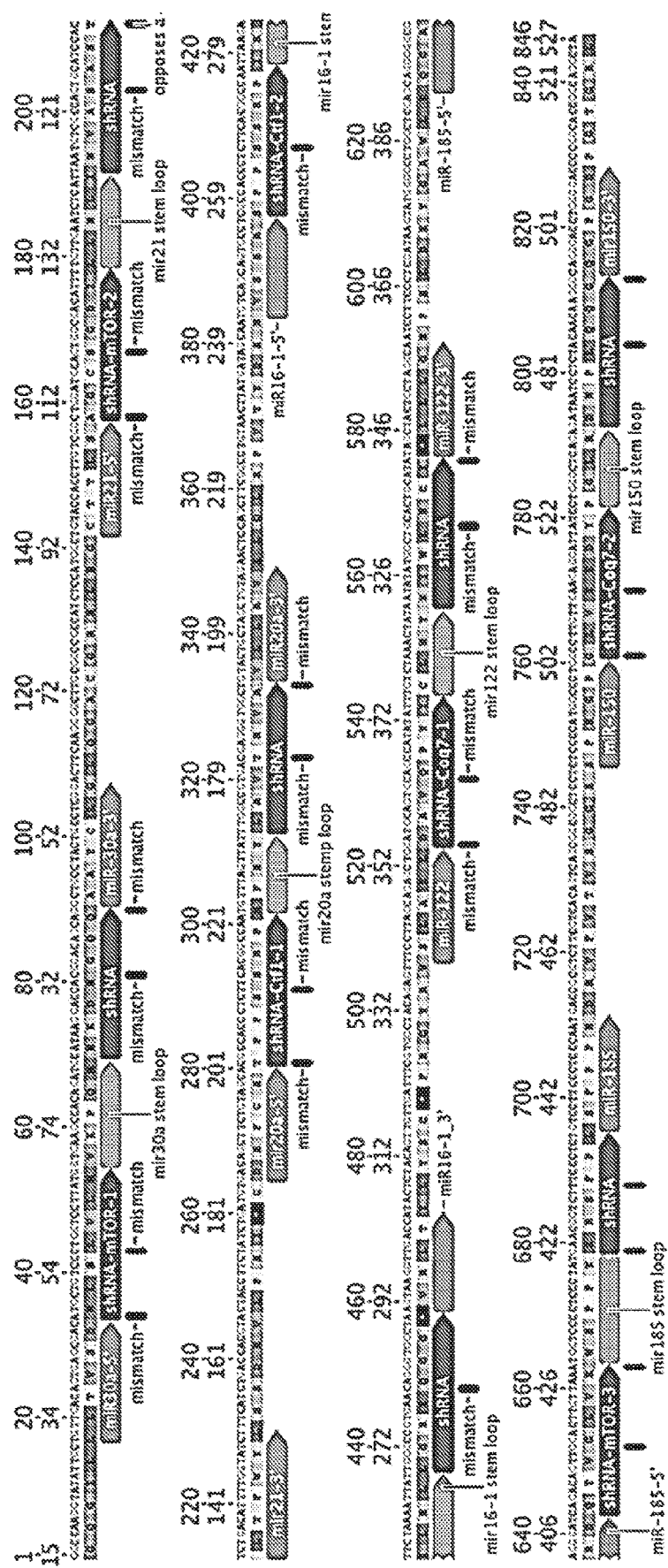
FIG. 13 is a vector map of a possible construction of 6 Pri-miRNAs and the order they are concatenated. There is also a red mark for where the mismatches are planned in the "shRNA" part for proper processing of the miRNA. Figure discloses the nucleotide sequence as SEQ ID NO: 146 and the amino acid sequences as SEQ ID NOS 147-151, respectively, in order of appearance.
Figure 14:
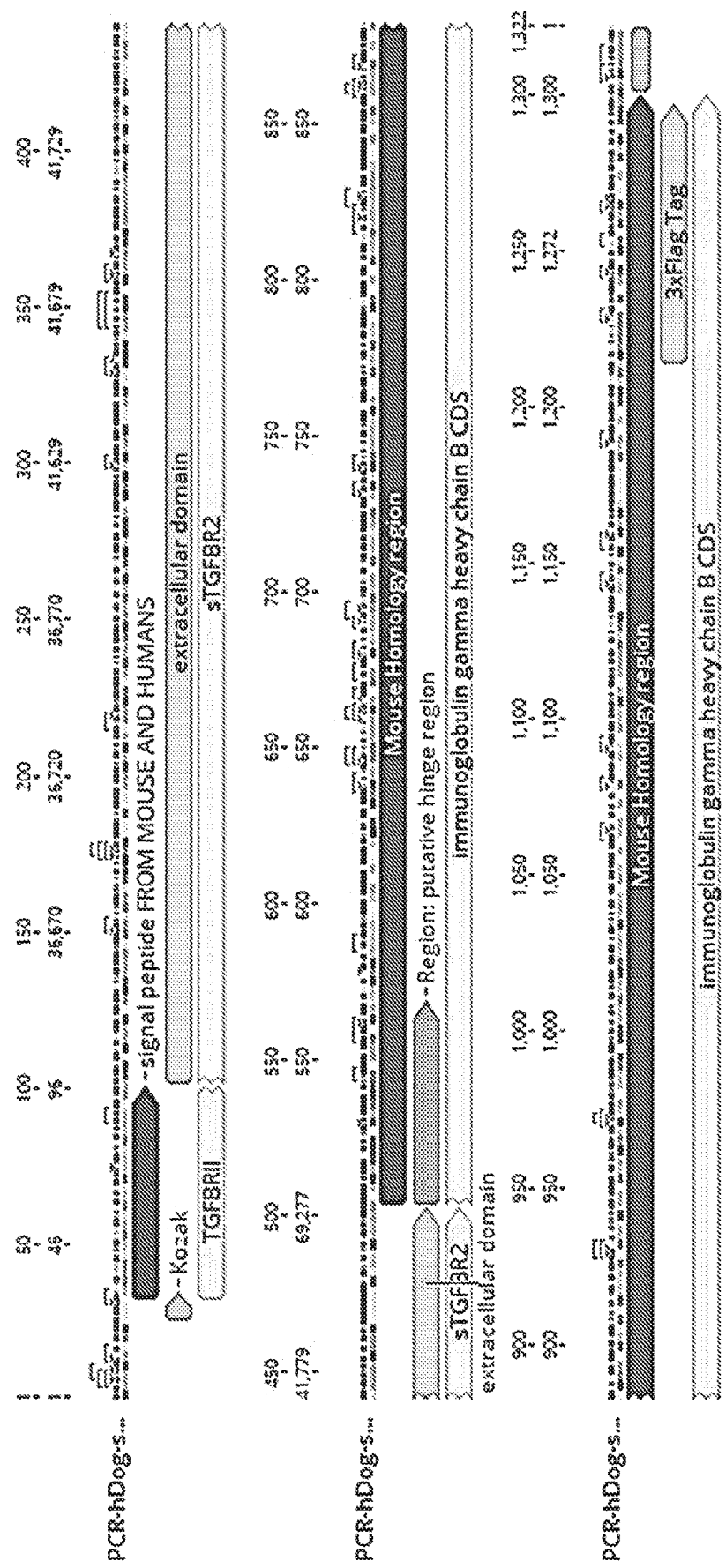
FIG. 14 depicts a vector map of sTGFbR2-Fc.

The disclosure provides for a gene therapy method for the delivery of a nucleic acid encoding Growth differentiation factor 15 (GDF15) and a nucleic acid encoding adiponectin, and a nucleic acid encoding ZAG and a nucleic acid encoding Nrf2. Combining delivery of an effective amount of all 4 of these nucleic acids has shown evidence of weight loss without toxicity (seen by body condition score and activity monitoring). These mice have lost up to 15% of their weight and continue in a downward trend as seen in FIG. 9.

Example 5: Expression Cassette

The disclosure provides an expression cassette contained within an AAV including 14 Pri-miRNA-shRNA sequences. The vector has a first cassette facing up stream and a second cassette facing downstream. The first cassette includes 7 miRNA-shRNA sequences. The second cassette include miRNA-shRNA sequences. The upstream facing cassette and the downstream facing cassette prevent read through between the two cassettes. A schematic of the two cassettes is as follows: ITR_3'UTR-1_7miRNAs_Promoter-1_Promoter-2_7miRNAs_3'UTR-2_ITR. The first cassette faces upstream 3'←5'. ← and the second cassette faces downstream 5'→3' ("normal") ← as indicated in the schematic ITR_____←_____→_____ITR. ITR-bGHpA-7miRNA-CMV-hEf1α-7miRNA-WPRE3-SV40 pA-ITR.

Example 6: Modification of Dog Protein Dog-stgfbr2-fc

The dog protein dog-stgfbr2-fc was modified to include the mouse/human secretion signal. The nucleic acid encoding dog-stgfbr2-fc was modified to replace the following innate secretion signal (SEQ ID NO: 120)
ATGCACAGTCAAGGGCGGGGTTGCAACAACACAAAACAAAACAAAACTTC

CGGACTTCGACCTGCAGCTGAGAAGAACATCTCGCAAAGCGGCGTT with the mouse/human secretion signal as follows:

(SEQ ID NO: 121)
ATGGGTCGGGGGCTGCTCCGGGGCCTGTGGCCGCTGCATATCGTCCTGTG

GACGCGCATCGCCAGCACG

The nucleic acid sequence encoding the final protein is as follows.

(SEQ ID NO: 122)
ATGGGTCGGGGGCTGCTCCGGGGCCTGTGGCCGCTGCATATCGTCCTGTG

GACGCGCATCGCCAGCACGAATAATGACATGATGGTCACTGACAGCAATG

GTGTCATCAAATTTCCACAATTGTGTAAATTTTGTGATGTGAGATCTTCC

ACCTGTGACAACCAGAAATCTTGCATGAGCAACTGCAGCATTACATCCAT

CTGTGAGAAGCCACATGAAGTCTGTCTGGCTGTCTGGAGAAAGAATGATG

AGAACATAACACTAGAGACTCTCTGCCATGACCCCAAGGATACCTACCAT

GGAATTGTTCTCGAAGATGCTGCCTCTTCGAAGTGCATTATGAAAGAAAA

GAAGGTGCTGGGGGAGACTTTCTTTATGTGTTCCTGTAGCTCCGACGAGT

GCAACGACTACATCATCTTCTCTGAAGAATATGCCACCAACAACCCTGAC

TTGTTGTTAGTCATATTCCAA*CCC*

*AAAAGAGAAAATGGAAGAGTTCCTCGCCCA*

*CCTGATTGTCCCAAATGCCCAGCCCCTGAAA*

*TGCTGGGAGGGCCTTCGGTCTTCATCTTTC*

*CCCCGAAACCCAAGGACACCCTCTTGATTGC*

*CCGAACACCTGAGGTCACATGTGTGGTGG*

*TGGATCTGGACCCAGAAGACCCTGAGGTGCA*

*GATCAGCTGGTTCGTGGACGGTAAGCAGA*

-continued

```
TGCAAACAGCCAAGACTCAGCCTCGTGAGGA

GCAGTTCAATGGCACCTACCGTGTGGTCAG

TGTCCTCCCCATTGGGCACCAGGACTGGCTC

AAGGGGAAGCAGTTCACGTGCAAAGTCAAC

AACAAAGCCCTCCCATCCCCGATCGAGAGG

ACCATCTCCAAGGCCAGAGGGCAAGCCCAT

CAGCCCAGTGTGTATGTCCTGCCGCCATCCC

GGGAGGAGTTGAGCAAGAACACAGTCAGCT

TGACATGCCTGATCAAAGACTTCTTCCCACC

TGACATTGATGTGGAGTGGCAGAGCAATGGA

CAGCAGGAGCCTGAGAGCAAGTACCGCAC

GACCCCGCCCCAGCTGGACGAGGACGGGTCC

TACTTCCTGTACAGCAAGCTCTCTGTGGAC

AAGAGCCGCTGGCAGCGGGGAGACACCTTCA

TATGTGCGGTGATGCATGAAGCTCTACAC

AACCACTACACACAGGAATCCCTCTCCCATTC

TCCGGGTAAAGGAGGGAGTGGTGGGTCCG

ATTACAAAGATCACGATGGGGACTATAAAGAT

CACGACATCGACTATAAGGATGACGATGA

TAAATGA.
```

Bold indicates the secretion signal. Bold and italics indicates the canine IGb heavy chain. Non-bolded indicates the canine TGFb receptor 2 extra cellular domain.

Figure 15:
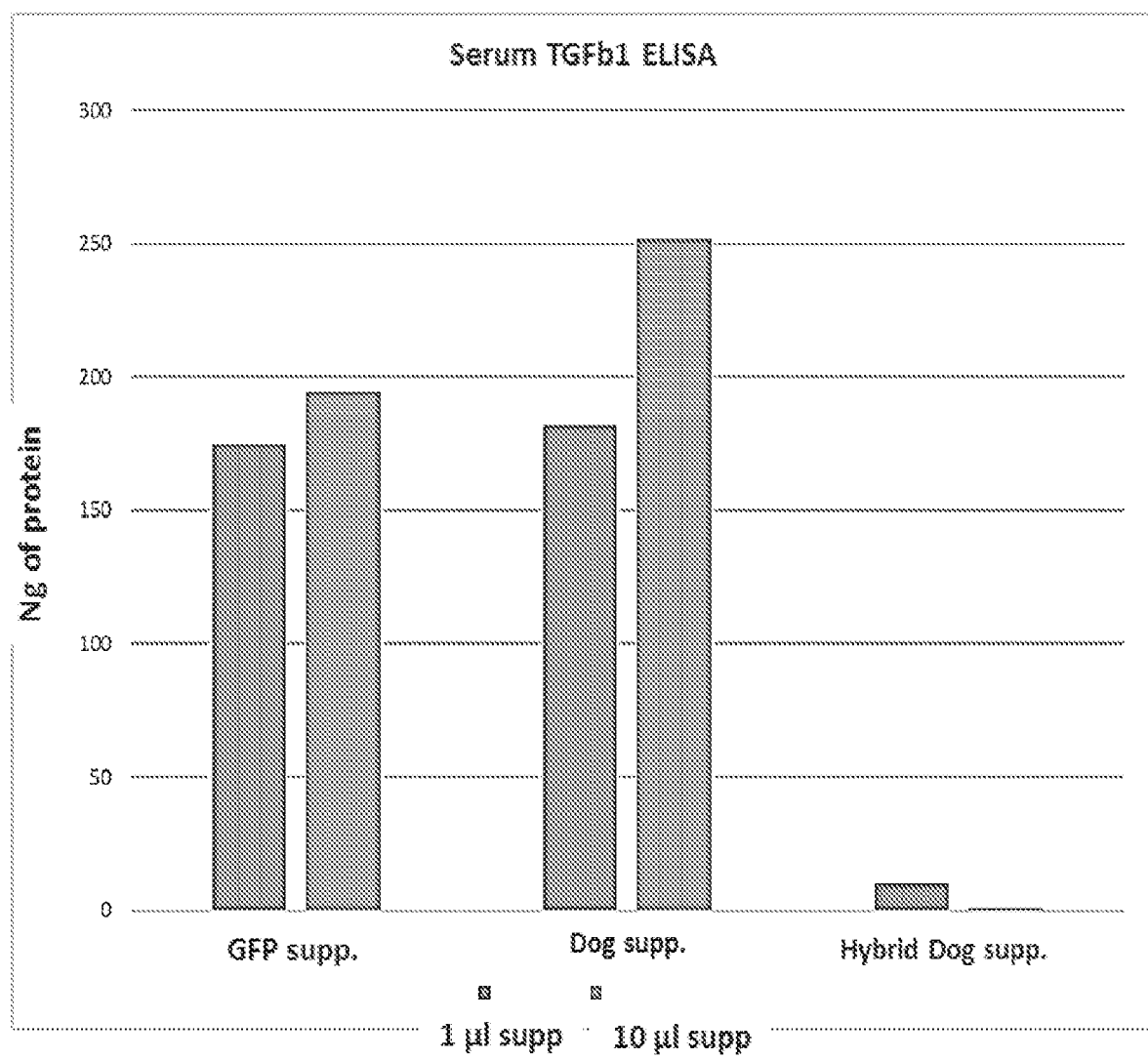
FIG. 15 depicts data of binding of soluble TGFb receptor 2 to TGFb1 in dog serum.

FIG. 15 indicates an in vitro ELISA assay in which it was demonstrated that the hybrid protein performs better than the original canine protein. The ELISA detects TGFb1, except when TGFb1 is bound by soluble TGF receptor 2 and is therefore prevented from binding in the ELISA assay. Briefly, supernatant from 293-Hek cells that were transfected with each construct or sHefla-EGFP as a control were mixed with dog serum containing natural dog TGFb1 and the cells were assayed for their ability to secrete soluble TGF receptor 2. As indicated in FIG. 15, the natural dog protein did not get produced or secreted as well as the hybrid dog protein including the mouse/human secretion signal. The 293-Hek cells were better able to secrete the hybrid dog protein including the mouse/human secretion signal.

The experiments include the following secretion factors in place of the natural TGFbR2 secretion signal. One of skill will be able to identify additional useful secretion signals in the publicly available information that modulate expression to the desired level based on the present disclosure. Also, a screening mutagenesis can be carried out to find the optimal secretion signal for the particular peptide sequence to be secreted. According to this aspect, the sequence that is being secreted can modulate the efficacy of the secretion signal and the secretion signal can be optimized for a particular gene of interest.

According to one aspect, a vector can include a synthetic intron to increase expression via enhanced transport of the RNA out of the nucleus. Synthetic or natural introns known to those of skill in the art can be used for this purpose.

Chymo Trypsinogen (world wide sebsite unitargeting.com/Resources/Trends07.pdf)

(SEQ ID NO: 123)
ATGGCTTTTCTTTGGTTGCTGAGCTGCTGGGCACTGCTGGGTACTACTTT

TGGA (SEQ ID NO: 124)
MAFLWLLSCWALLGTTFG

Trypsinogen
(SEQ ID NO: 125)
ATGAACTTGCTTCTCATCCTGACTTTTGTTGCAGCCGCCGTGGCT

HeavyChain
(SEQ ID NO: 126)
ATGGAGTTCGGGCTTTCTTGGGTGTTCTTGGTCGCTTTGTTTCGGGGGGT

CCAGTGT (SEQ ID NO: 127)
MEFGLSWVFLVALFRGVQC

IL2-ILco1 (PMID: 15619290)
(SEQ ID NO: 128)
ATGAGGATGCAACTTCTCCTCTTGATAGCCCTTTCCTTGGCTCTGGTCAC

CAACAGC (SEQ ID NO: 129)
MRMQLLLLIALSLALVTNS

IL2-ILco2 (PMID: 15619290)
(SEQ ID NO: 130)
MRRMQLLLLIALSLALVTNS

IL2 (PMID: 15619290)
(SEQ ID NO: 131)
MQLLSCIALILALV

Human serum albumin
(SEQ ID NO: 132)
MKWVTFISLLFLFSSAYS human azurocidin preprotein
(SEQ ID NO: 133)
MTRLTVLALLAGLLASSRA Gaussia luciferase
(SEQ ID NO: 134)
MGVKVLFALICIAVAEA Example 7: Methods of Preventing Heart Failure According to certain aspects, gene therapy methods are provided for treating or preventing heart failure. A first group of mice was treated with a 1E11vg/mouse for AAV8: sHefla-sTGFbR2-FC-WPRE3-SV40 pA and 1E11vg/mouse for AAV9: sHefla-Nrf2-WPRE3-SV40 pA (double therapy). A second group of mice was treated with 1E11vg/mouse for AAV8:sHefla-sTGFbR2-FC-WPRE3-SV40 pA (single therapy). Control AAC mice underwent surgery but did not receive the therapy. Mice receiving either the double therapy or the single therapy had higher fractional shortening, higher ejection fraction and lower heart mass compared to a control. According to certain aspects, mice are treated with sTGFbR2-FC, sTGFbR2-FC+FGF21, sTGFbR2-FC+ Klotho, or sTGFbR2-FC+FGF21+Klotho in a method of treating or preventing heart failure or renal failure.

Figure 19:
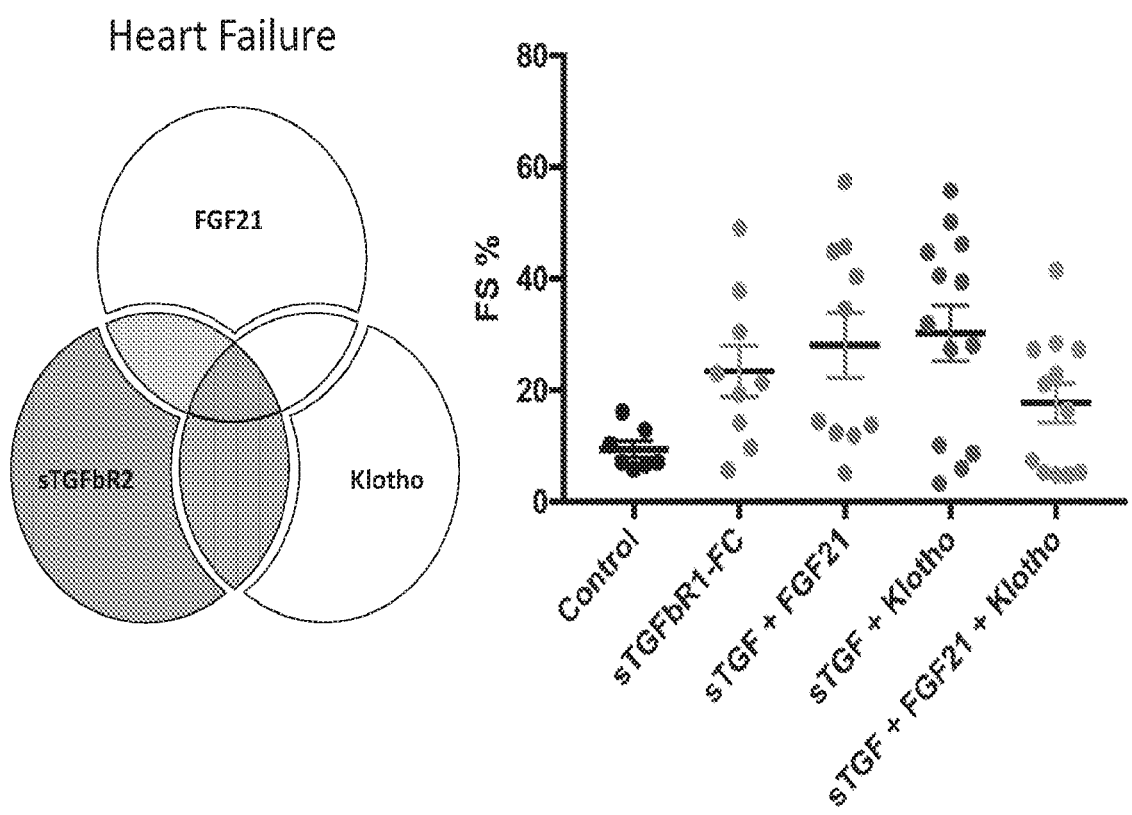
FIG. 19 depicts fractional shortening data.

The following combination of genes was assessed as a gene therapy method, such as by using one or more AAVs for treating or preventing heart failure: FGF21, Klotho, and sTGFbR2-FC. As indicated at FIG. 19, the Fractional shortening measurements (at 3 months post-surgery, surgery described previously for AAC) indicate that the combinations of genes treat ot prevent heart failure. More mice in the combination groups bifurcate into the compensated regime thereby overcoming the surgical banding placed 3 months prior. All the control mice become decompensated and will likely have died in the coming weeks. Whereas the mice in the other groups that ended up compensating showed no signs that they were going to die. The echocardiograms were all performed on conscience mice and were analyzed with native echo software.

Example 8: Methods of Promoting Weight Loss

According to certain aspects, gene therapy methods are provided for promoting weight loss, such as for promoting weight loss in obese individuals. Fat mice were obtained from Jackson labs that were on a high fat diet for 3 months. Post arrival from Jackson labs, the mice were maintained on a 45% high fat diet D12451 from research diets form about 1 week. The mice were then injected with different doses of AAV8:sHefla-FGF21-WPRE3-SV40 pA, as well as one combination of 1E9vg/mouse AAV8:sHefla-FGF21-WPRE3-SV40 pA, 1E11vg/mouse AAV8:sHefla-Klotho-WPRE3-SV40 pA, 1E11vg/mouse AAV8:sHefla-sTGFbR2-Fc-WPRE3-SV40 pA. All doses promoted weight loss while 1E11 and 1E10 promoted sustained weight loss.

Example 9: Methods of Increasing Life Span

Figure 20:
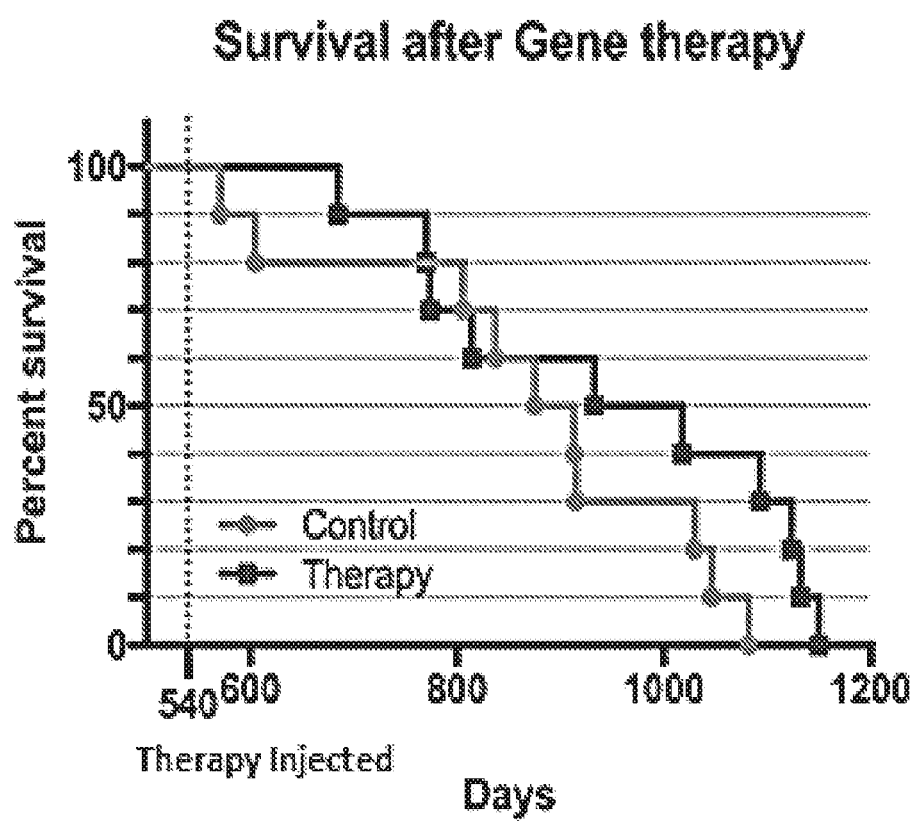
FIG. 20 depicts data of percent survival after gene therapy.

According to certain aspects, gene therapy methods as described herein are provided for increasing life span, health span or survival of an individual. An experiment was conducted using mice treated with sTGFbR2-FC in a gene therapy method described herein. Mice administered the sTGFbR2-FC gene provided an increase in life span as indicated in FIG. 20 with an approximate 10% increase in mean and maximum life span.

Figure 21:
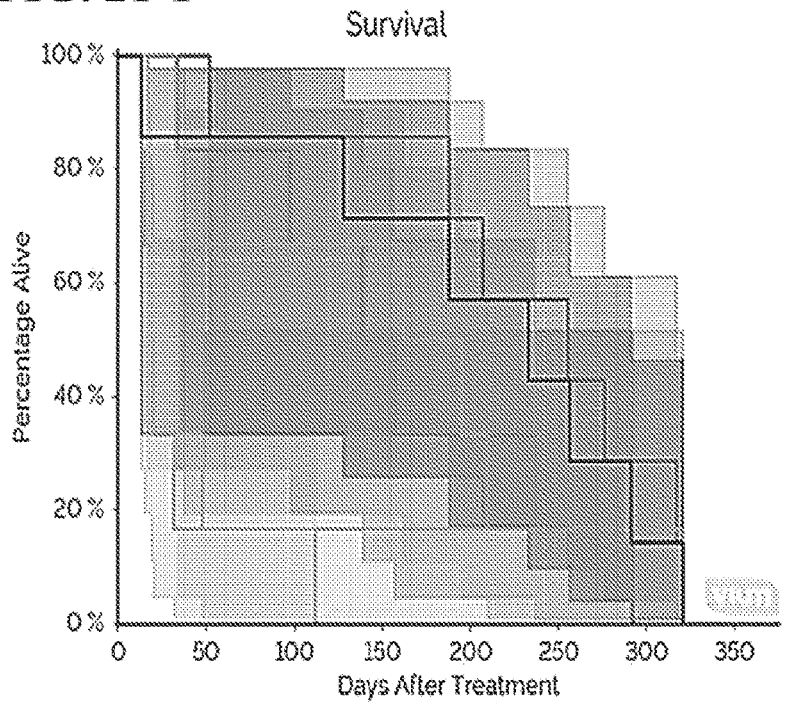
FIG. 21 depicts data directed to increased healthspan.
Figure 1:
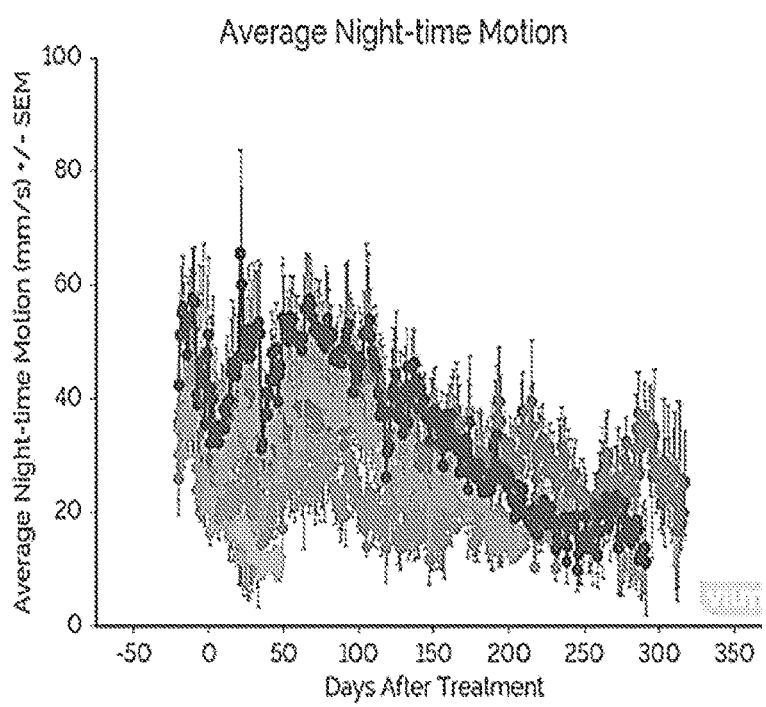
Figures 2, 21:
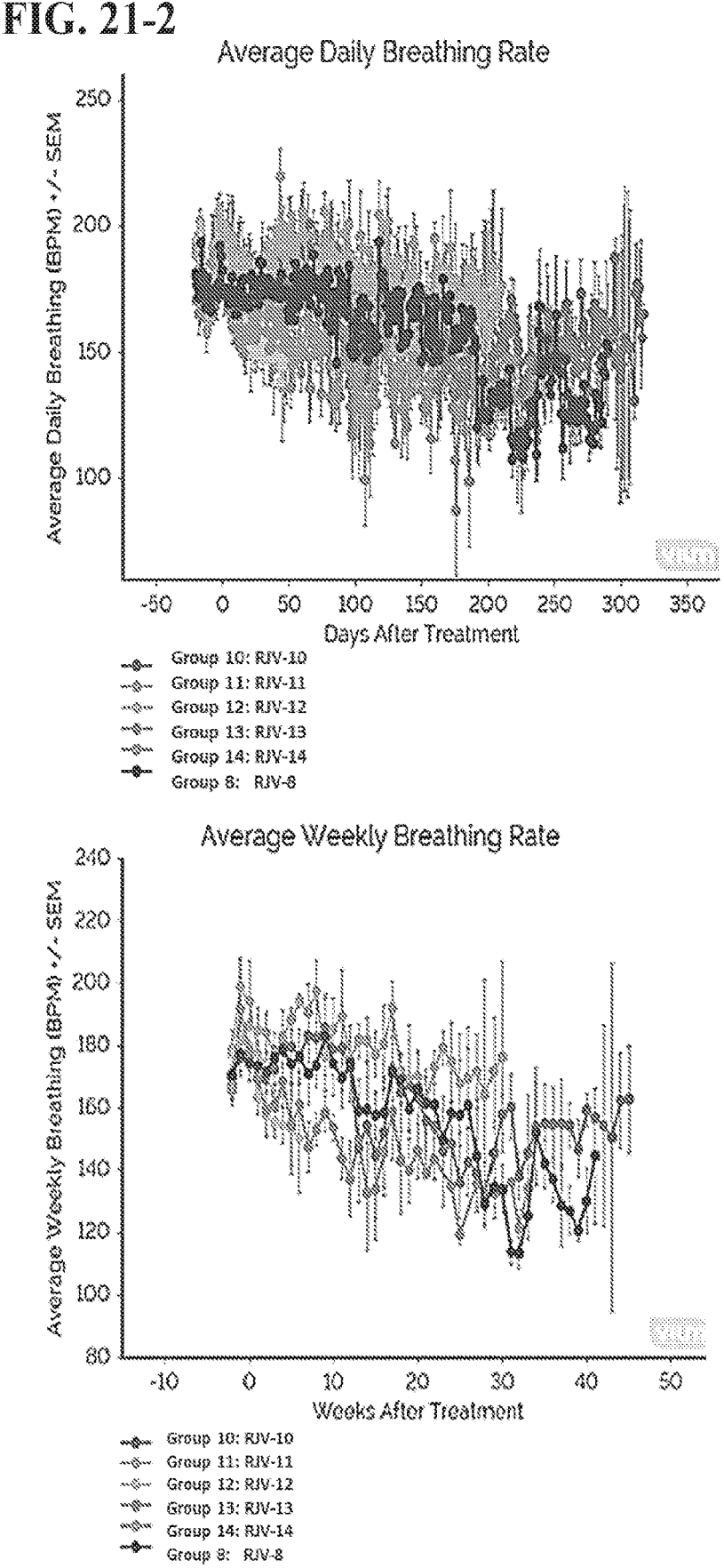
Figures 3, 21:
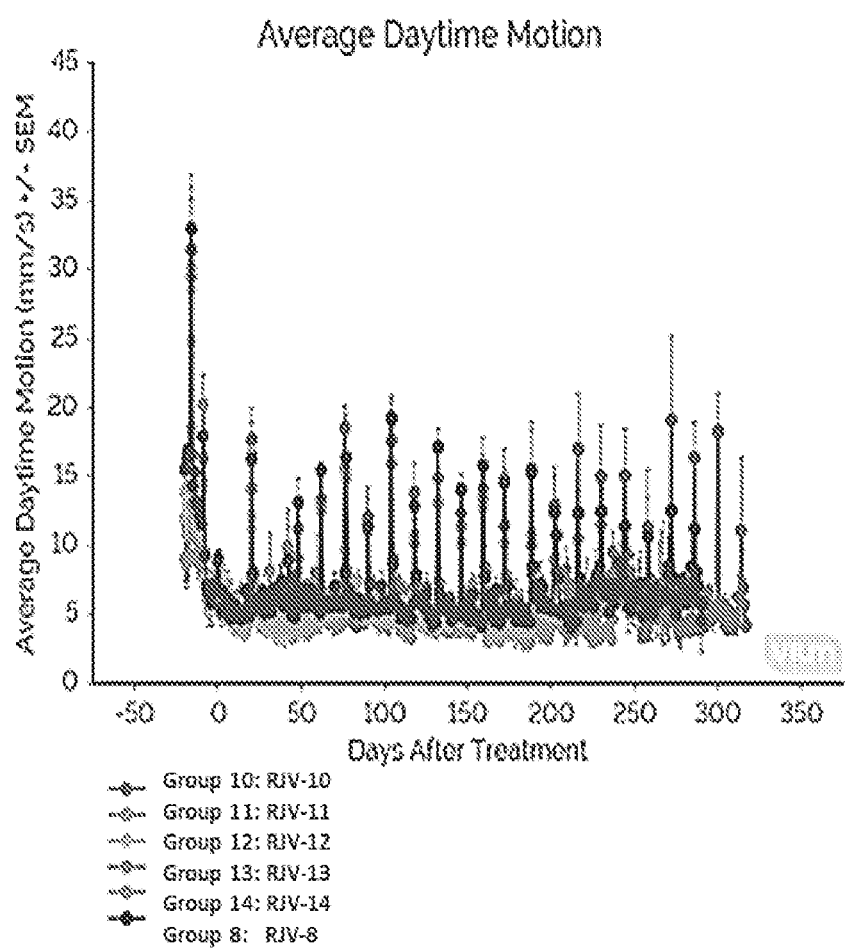
Figures 3, 21:
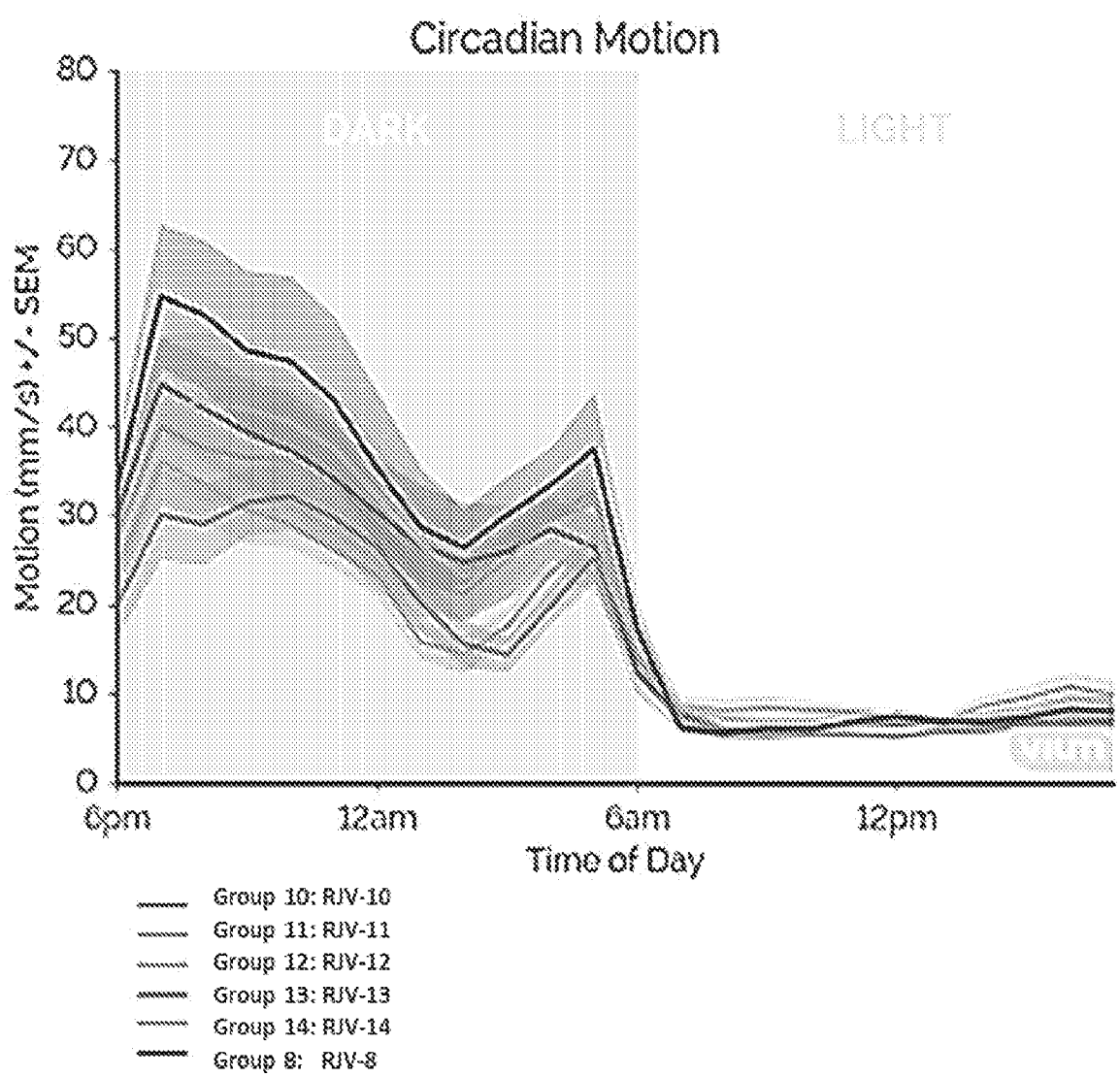
Figures 4, 21:
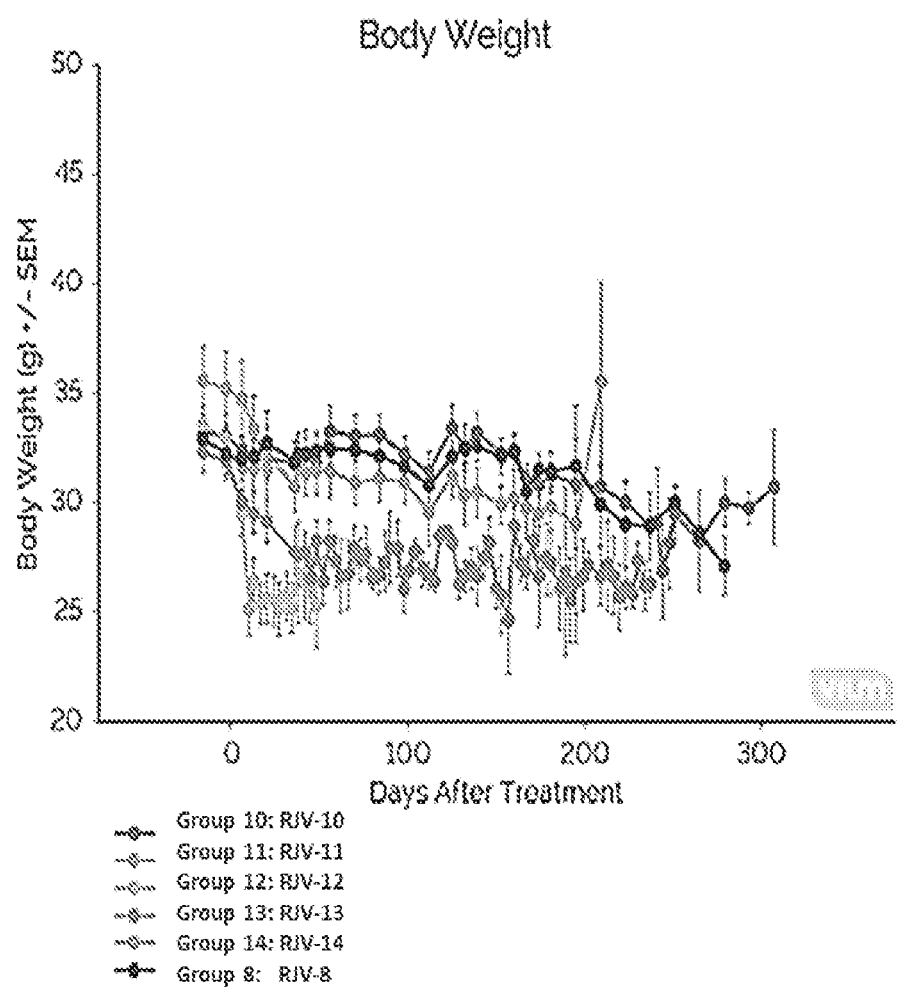

An additional experiment was carried out to determine increase in healthspan as measured by increased activity and respiration into old age using cameras and sensors 24 hours a day 7 days a week that provided image analysis to provide these metrics. The body weight of the mice was measured over time. The results are presented in FIG. 21. The experiment yielded numerous differences between the various therapy groups for circadian rhythms, breathing rates, lifespan, daily motions, and nighttime motion. The therapy groups and combination of gene therapies are identified in the Table 5 below.

| Group | RJV-1 | RJV-2 | RJV-3 | RJV-4 |
|---|---|---|---|---|
| Virus 1 | MT1 | sTGFbR2-FC | FGF21 | TERT |
| Virus 2 | Sirt6 | NRF2 | | |
| Virus 3 | sIGF1r-FC | | | |
| Virus 4 | Agtra1a-Adcy5-Coq7-(AAV-1) | | | |
| Virus 5 | Slc13a1-Ikbkb-(AAV-19) | | | |
| Virus 6 | Klotho | | | |
| Virus 7 | GDF15 | | | |
| Virus 8 | Ctf1-mTOR-Coq7-(AAV-16) | | | |
| Virus 9 | Slc13a5-Pappa-(AAV-22) | | | |
| Virus 10 | PCSK9-Rps6kb1-(AAV-17) | | | |

| Group | RJV-5 | RJV-6 | RJV-7 | RJV-8 |
|---|---|---|---|---|
| Virus 1 | FGF21 | FGF21 | FGF21 | AAV8:GFP |
| Virus 2 | TERT | TERT | TERT | AAV9:GFP |
| Virus 3 | | BubR1 | BubR1 | |
| Virus 4 | | Agtra1a-Adcy5-Coq7-(AAV-1) | Agtra1a-Adcy5-Coq7-(AAV-1) | |
| Virus 5 | | | Slc13a1-Ikbkb-(AAV-19) | |
| Virus 6 | | | | |
| Virus 7 | | | | |
| Virus 8 | | | | |
| Virus 9 | | | | |
| Virus 10 | | | | |

| Group | RJV-9 | RJV-10 | RJV-11 | RJV-12 |
|---|---|---|---|---|
| Virus 1 | Nrf2 | Txn1 | PCSK9-Rps6kb1-(AAV-17) | Ctf1-mTOR-Coq7-(AAV-16) |
| Virus 2 | Txn1 | Sirt6 | Klotho | Agtra1a-Adcy5-mTOR-(AAV-6) |
| Virus 3 | TFAM-p2A-Cisd2-P2A-Nudt1 | Mt1 | Nrf2 | Cisd2 |
| Virus 4 | Klotho | TFEB | Txn1 | MCAT |
| Virus 5 | Sirt6 | Pck1 | HAS2 | FGF21 |
| Virus 6 | Atg5 | Adiponectin | Nudt1 | GDF15 |
| Virus 7 | Agtra1a-Adcy5-Akt1-(AAV-4) | Cisd2 | BubR1 | Klotho |
| Virus 8 | MCAT | Nudt1 | Dgat1-Pappa-(AAV-14) | Slc13a1-Ikbkb-(AAV-19) |
| Virus 9 | Slc13a1-Ikbkb-(AAV-19) | Atg5 | Ctf1-mTOR-Coq7-Slc13a5-(AAV-11) | Txn1 |
| Virus 10 | Ctf1-mTOR-Coq7-Slc13a5-(AAV-11) | Ctf1-Ikbkb-Coq7-(AAV-9) | Agtra1a-Adcy5-Akt1-(AAV-4) | Sirt6 |

| Group | RJV-13 | RJV-14 |
|---|---|---|
| Virus 1 | MCAT | Txn1 |
| Virus 2 | Klotho | PCSK9-Rps6kb1-(AAV-17) |
| Virus 3 | GDF15 | Atg5 |
| Virus 4 | Neu1 | Ctf1-Akt1-(AAV-7) |
| Virus 5 | Mt1 | Pck1 |
| Virus 6 | hFoxP2 | klotho |
| Virus 7 | PCSK9-Rps6kb1-(AAV-17) | Nrf2 |
| Virus 8 | Ctf1-Ikbkb-Coq7-(AAV-9) | Cisd2 |

| | | |
|---|---|---|
| Virus 9 | Slc13a1-mTOR-(AAV-20) | Dgat1-Pappa-(AAV-14) |
| Virus 10 | TFAM-p2A-Cisd2-P2A-Nudt1 | Ctf1-mTOR-Coq7-Slc13a5-(AAV-11) |

Example 10: Methods of Treating or Preventing Renal Failure

Figure 22:
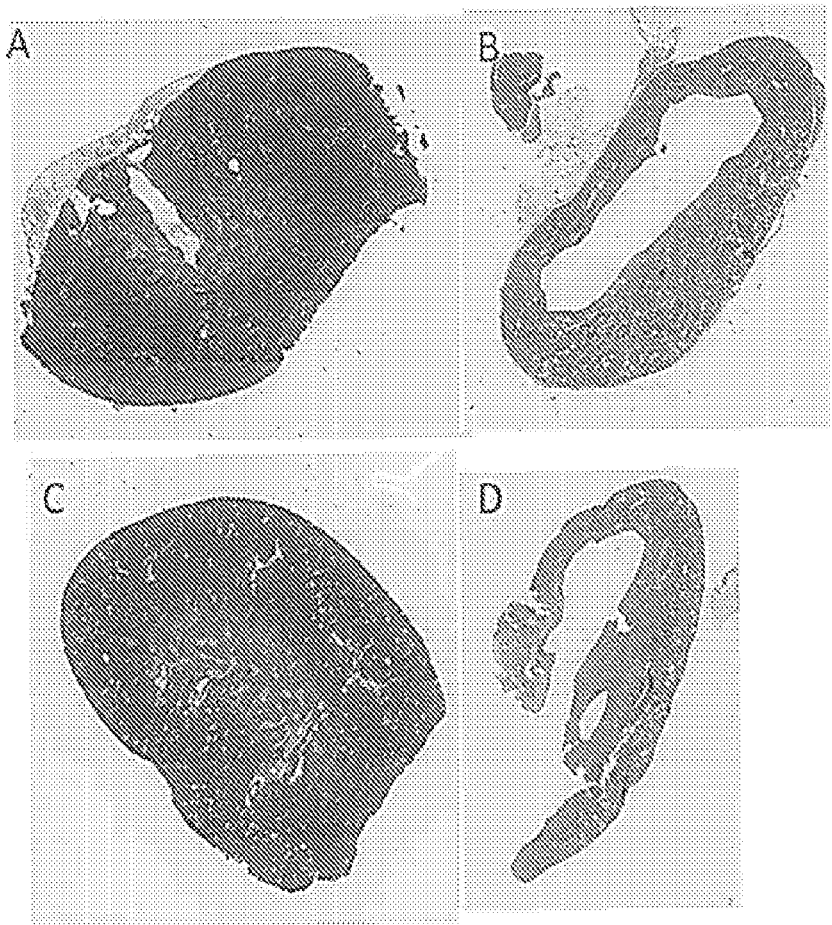
FIG. 22 depicts kidneys of control mice versus mice treated with gene therapy as described herein.

According to certain aspects, gene therapy methods are provided for treating or preventing renal failure. The following combination of genes is assessed as a gene therapy method, such as by using one or more AAV's for treating or preventing heart failure: FGF21, Klotho, and sTGFbR2-FC. FIG. 22 demonstrates a marked difference between the kidneys of control mice and mice treated with sTGFbR2-Fc gene therapy. A and C depict non-surgical contralateral control kidneys. B and D depict UUO kidneys with B depicting improved results compared to D.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

APPENDIX A

SEQUENCES: BOLD = secretion signal when indicated 1. (SEQ ID NO: 3) sTGFBr2 Human DNA
ATGGGTCGGGGGCTGCTCAGGGGCCTGTGGCCGCTGCACATCGTCCTGTGGACGC
GTATCGCCAGCACGATCCCACCGCACGTTCAGAAGTCGGATGTGGAAATGGAGGCCCA
GAAAGATGAAATCATCTGCCCCAGCTGTAATAGGACTGCCCATCCACTGAGACATATTA
ATAACGACATGATAGTCACTGACAACAACGGTGCAGTCAAGTTTCCACAACTGTGTAAA
TTTTGTGATGTGAGATTTTCCACCTGTGACAACCAGAAATCCTGCATGAGCAACTGCAGC
ATCACCTCCATCTGTGAGAAGCCACAGGAAGTCTGTGTGGCTGTATGGAGAAAGAATGA
CGAGAACATAACACTAGAGACAGTTTGCCATGACCCCAAGCTCCCCTACCATGACTTTAT
TCTGGAAGATGCTGCTTCTCCAAAGTGCATTATGAAGGAAAAAAAAAAGCCTGGTGAGA
CTTTCTTCATGTGTTCCTGTAGCTCTGATGAGTGCAATGACAACATCATCTTCTCAGAAGA
ATATAACACCAGCAATCCTGAC 2. (SEQ ID NO: 4) sTGFBr2 Dog DNA
ATGCACAGTCAAGGGCGGGGTTGCAACAACACAAAACAAAACAAAACTTCCGGACT
TCGACCTGCAGCTGAGAAGAACATCTCGCAAAGCGGCGTTAATAATGACATGATGGT
CACTGACAGCAATGGTGTCATCAAATTTCCACAATTGTGTAAATTTTGTGATGTGAGATC
TTCCACCTGTGACAACCAGAAATCTTGCATGAGCAACTGCAGCATTACATCCATCTGTGA
GAAGCCACATGAAGTCTGTCTGGCTGTCTGGAGAAAGAATGATGAGAACATAACACTAG
AGACTCTCTGCCATGACCCCAAGGATACCTACCATGGAATTGTTCTCGAAGATGCTGCCT
CTTCGAAGTGCATTATGAAAGAAAAGAAGGTGCTGGGGGAGACTTTCTTTATGTGTTCCT
GTAGCTCCGACGAGTGCAACGACTACATCATCTTCTCTGAAGAATATGCCACCAACAACC
CTGACTTGTTGTTAGTCATATTCCAA 3. (SEQ ID NO: 5) Another version of sTGFBr2 with mouse/human secretion signal
ATGGGTCGGGGGCTGCTCCGGGGCCTGTGGCCGCTGCATATCGTCCTGTGGACGC
GCATCGCCAGCACGAATAATGACATGATGGTCACTGACAGCAATGGTGTCATCAAATTT
CCACAATTGTGTAAATTTTGTGATGTGAGATCTTCCACCTGTGACAACCAGAAATCTTGC
ATGAGCAACTGCAGCATTACATCCATCTGTGAGAAGCCACATGAAGTCTGTCTGGCTGTC
TGGAGAAAGAATGATGAGAACATAACACTAGAGACTCTCTGCCATGACCCCAAGGATAC
CTACCATGGAATTGTTCTCGAAGATGCTGCCTCTTCGAAGTGCATTATGAAAGAAAAGAA
GGTGCTGGGGGAGACTTTCTTTATGTGTTCCTGTAGCTCCGACGAGTGCAACGACTACAT
CATCTTCTCTGAAGAATATGCCACCAACAACCCTGACTTGTTGTTAGTCATATTCCAA 4. sTGFBr2 Cat DNA 5. 04 sTGFBr2 Cow DNA 6. sTGFBr2 Sheep DNA 7. sTGFBr2 Horse DNA 8. sTGFBr2 Pig DNA 9. (SEQ ID NO: 6) sTGFBr2 Mouse DNA
ATGGGTCGGGGGCTGCTCCGGGGCCTGTGGCCGCTGCATATCGTCCTGTGGACGC
GCATCGCCAGCACGATCCCGCCGCACGTTCCCAAGTCGGATGTGGAAATGGAAGCCCA
GAAAGATGCATCCATCCACCTAAGCTGTAATAGGACCATCCATCCACTGAAACATTTTAA
CAGTGATGTCATGGCCAGCGACAATGGCGGTGCGGTCAAGCTTCCACAGCTGTGCAAGT
TTTGCGATGTGAGACTGTCCACTTGCGACAACCAGAAGTCCTGCATGAGCAACTGCAGCA
TCACGGCCATCTGTGAGAAGCCGCATGAAGTCTGCGTGGCCGTGTGGAGGAAGAACGAC
AAGAACATTACTCTGGAGACGGTTTGCCACGACCCCAAGCTCACCTACCACGGCTTCACT
CTGGAAGATGCCGCTTCTCCCAAGTGTGTCATGAAGGAAAAGAAAAGGGCGGGCGAGAC
TTTCTTCATGTGTGCCTGTAACATGGAAGAGTGCAACGATTACATCATCTTTTCGGAAGA
ATACACCACCAGCAGTCCCGAC APPENDIX A-continued SEQUENCES: BOLD = secretion signal when indicated 10. (SEQ ID NO: 7) sTGFBr2 Human AA
MGRGLLRGLWPLHIVLWTRIASTIPPHVQKSDVEMEAQKDEIICPSCNRTAHPLRHINND
MIVTDNNGAVKFPQLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNIIFSEEYNTSNPD 11. (SEQ ID NO: 8) sTGFBr2 Dog AA
MHSQGRGCNNTKQNKTSGLRPAAEKNISQSGVNNDMMVTDSNGVIKFPQLCKFCDVRSS
TCDNQKSCMSNCSITSICEKPHEVCLAVWRKNDENITLETLCHDPKDTYHGIVLEDAASSKCI
MKEKKVLGETFFMCSCSSDECNDYIIFSEEYATNNPD 12. sTGFBr2 Cat AA 13. sTGFBr2 Cow AA 14. sTGFBr2 Sheep AA 15. sTGFBr2 Horse AA 16. sTGFBr2 Pig AA 17. (SEQ ID NO: 9) sTGFBr2 Mouse AA
MGRGLLRGLWPLHIVLWTRIASTIPPHVPKSDVEMEAQKDASIHLSCNRTIHPLKHFNSDV
MASDNGGAVKLPQLCKFCDVRLSTCDNQKSCMSNCSITAICEKPHEVCVAVWRKNDKNITL
ETVCHDPKLTYHGFTLEDAASPKCVMKEKKRAGETFFMCACNMEECNDYIIFSEEYTTSSPD 18. Fc Human 19. (SEQ ID NO: 10) Fc Dog
CCCAAAAGAGAAAATGGAAGAGTTCCTCGCCCACCTGATTGTCCCAAATGCCCAGCCCC
TGAAATGCTGGGAGGGCCTTCGGTCTTCATCTTTCCCCCGAAACCCAAGGACACCCTCTT
GATTGCCCGAACACCTGAGGTCACATGTGTGGTGGTGGATCTGGACCCAGAAGACCCTG
AGGTGCAGATCAGCTGGTTCGTGGACGGTAAGCAGATGCAAACAGCCAAGACTCAGCCT
CGTGAGGAGCAGTTCAATGGCACCTACCGTGTGGTCAGTGTCCTCCCCATTGGGCACCAG
GACTGGCTCAAGGGGAAGCAGTTCACGTGCAAAGTCAACAACAAAGCCCTCCCATCCCC
GATCGAGAGGACCATCTCCAAGGCCAGAGGGCAAGCCCATCAGCCCAGTGTGTATGTCC
TGCCGCCATCCCGGGAGGAGTTGAGCAAGAACACAGTCAGCTTGACATGCCTGATCAAA
GACTTCTTCCCACCTGACATTGATGTGGAGTGGCAGAGCAATGGACAGCAGGAGCCTGA
GAGCAAGTACCGCACGACCCCGCCCCAGCTGGACGAGGACGGGTCCTACTTCCTGTACA
GCAAGCTCTCTGTGGACAAGAGCCGCTGGCAGCGGGGAGACACCTTCATATGTGCGGTG
ATGCATGAAGCTCTACACAACCACTACACACAGGAATCCCTCTCCCATTCTCCGGGTAAA
TGA 20. (SEQ ID NO: 11) Fc Dog AA version:
PKRENGRVPRPPDCPKCPAPEMLGGPSVFIFPPKPICDTLLIARTPEVTCVVVDLDPEDPEVQIS
WFVDGKQMQTAKTQPREEQFNGTYRVVSVLPIGHQDWLKGKQFTCKVNNKALPSPIERTIS
KARGQAHQPSVYVLPPSREELSKNTVSLTCLIKDFFPPDIDVEWQSNGQQEPESKYRTTPPQL
DEDGSYFLYSKLSVDKSRWQRGDTFICAVMHEALHNHYTQESLSHSPGK 21. Fc Cat 22. Fc Cow 23. Fc Sheep 24. Fc Horse 25. Fc Pig 26. (SEQ ID NO: 12) Fc Mouse
CCCAGAGGGCCCACAATCAAGCCCTGTCCTCCATGCAAATGCCCAGCACCTAACCTCGA
GGGTGGACCATCCGTCTTCATCTTCCCTCCAAAGATCAAGGATGTACTCATGATCTCCCT
GAGCCCCATAGTCACATGTGTGGTGGTGGATGTGAGCGAGGATGACCCAGATGTCCAGA
TCAGCTGGTTTGTGAACAACGTGGAAGTACACAGCTCAGACAAACCCATAGAGAG
GATTACAACAGTACTCTCCGGGTGGTCAGTGCCCTCCCCATCCAGCACCAGGACTGGATG
AGTGGCAAGGCGTTCGCATGCGCGGTCAACAACAAAGACCTCCCAGCGCCCATCGAGAG
AACCATCTCAAAACCCAAAGGGTCAGTAAGAGCTCCACAGGTATATGTCTTGCCTCCACC
AGAAGAAGAGATGACTAAGAAACAGGTCACTCTGACCTGCATGGTCACAGACTTCATGC
CTGAAGACATTTACGTGGAGTGGACCAACAACGGGAAAACAGAGCTAAACTACAAGAA
CACTGAACCAGTCCTGGACTCTGATGGTTCTTACTTCATGTACAGCAAGCTGAGAGTGGA
AAAGAAGAACTGGGTGGAAAGAAATAGCTACTCCTGTTCAGTGGTCCACGAGGGTCTGC
ACAATCACCACACGACTAAGAGCTTCTCCCGGACTCCGGGTAAATGA 27. (SEQ ID NO: 13) Fc Mouse AA version:
PRGPTIKPCPPCKCPAPNLEGGPSVFIFPPKIKDVLMISLSPIVTCVVVDVSEDDPDVQISWFVN
NVEVHTAQTQTHREDYNSTLRVVSALPIQHQDWMSGKAFACAVNNKDLPAPIERTISKPKGS
VRAPQVYVLPPPEEEMTKKQVTLTCMVTDFMPEDIYVEWTNNGKTELNYKNTEPVLDSDGS
YFMYSKLRVEKKNWVERNSYSCSVVHEGLHNHHTTKSFSRTPGK

APPENDIX A-continued

SEQUENCES: BOLD = secretion signal when indicated

28. UCP1

29. AMPK 30. humanizeFoxP2

31. NEU1

32. NGF

33. BubR1

34. NAMPT

35. Nmnat1

36. (SEQ ID NO: 14) mNrf2 (mXXX indicates Murine for mouse)
ATGATGGACTTGGAGTTGCCACCGCCAGGACTACAGTCCCAGCAGGACATGGATTTGATT
GACATCCTTTGGAGGCAAGACATAGATCTTGGAGTAAGTCGAGAAGTGTTTGACTTTAGT
CAGCGACAGAAGGACTATGAGTTGGAAAAACAGAAAAAACTCGAAAAGGAAAGACAAG
AGCAACTCCAGAAGGAACAGGAGAAGGCCTTTTTCGCTCAGTTTCAACTGGATGAAGAA
ACAGGAGAATTCCTCCCAATTCAGCCGGCCCAGCACATCCAGACAGACACTAGTGGATC
CGCCAGCTACTCCCAGGTTGCCCACATTCCCAAACAAGATGCCTTGTACTTTGAAGACTG
TATGCAGCTTTTGGCAGAGACATTCCCATTTGTTGATGACCATGAGTCGCTTGCCCTGGA
TATCCCCAGCCACGCTGAAAGTTCAGTCTTCACTGCCCCTCATCAGGCCCAGTCCCTCAA
TAGCTCTCTGGAGGCAGCCATGACTGATTTAAGCAGCATAGAGCAGGACATGGAGCAAG
TTTGGCAGGAGCTATTTTCCATTCCCGAATTACAGTGTCTTAATACCGAAAACAAGCAGC
TGGCTGATACTACCGCTGTTCCCAGCCCAGAAGCCACACTGACAGAAATGGACAGCAAT
TACCATTTTTACTCATCGATCTCCTCGCTGGAAAAAGAAGTGGGCAACTGTGGTCCACAT
TTCCTTCATGGTTTTGAGGATTCTTTCAGCAGCATCCTCTCCACTGATGATGCCAGCCAGC
TGACCTCCTTAGACTCAAATCCCACCTTAAACACAGATTTTGGCGATGAATTTTATTCTGC
TTTCATAGCAGAGCCCAGTGACGGTGGCAGCATGCCTTCCTCCGCTGCCATCAGTCAGTC
ACTCTCTGAACTCCTGGACGGGACTATTGAAGGCTGTGACCTGTCACTGTGTAAAGCTTT
CAACCCGAAGCACGCTGAAGGCACAATGGAATTCAATGACTCTGACTCTGGCATTTCACT
GAACACAAGTCCCAGCCGAGCGTCCCCAGAGCACTCCGTGGAGTCTTCCATTTACGGAG
ACCCACCGCCTGGGTTCAGTGACTCGGAAATGGAGGAGCTAGATAGTGCCCCTGGAAGT
GTCAAACAGAACGGCCCTAAAGCACAGCCAGCACATTCTCCTGGAGACACAGTACAGCC
TCTGTCACCAGCTCAAGGGCACAGTGCTCCTATGCGTGAATCCCAATGTGAAAATACAAC
AAAAAAAGAAGTTCCCGTGAGTCCTGGTCATCAAAAAGCCCCATTCACAAAAGACAAAC
ATTCAAGCCGCTTAGAGGCTCATCTCACACGAGATGAGCTTAGGGCAAAAGCTCTCCATA
TTCCATTCCCTGTCGAAAAAATCATTAACCTCCCTGTTGATGACTTCAATGAAATGATGTC
CAAGGAGCAATTCAATGAAGCTCAGCTCGCATTGATCCGAGATATACGCAGGAGAGGTA
AGAATAAAGTCGCCGCCCAGAACTGTAGGAAAAGGAAGCTGGAGAACATTGTCGAGCTG
GAGCAAGACTTGGGCCACTTAAAAGACGAGAGAGAAAAACTACTCAGAGAAAAGGGAG
AAAACGACAGAAACCTCCATCTACTGAAAAGGCGGCTCAGCACCTTGTATCTTGAAGTCT
TCAGCATGTTACGTGATGAGGATGGAAAGCCTTACTCTCCCAGTGAATACTCTCTGCAGC
AAACCAGAGATGGCAATGTGTTCCTTGTTCCCAAAAGCAAGAAGCCAGATACAAAGAAA
AACTAG 37. Sirt6

38. TERT 39. (SEQ ID NO: 15) mTFAM
ATGGCGCTGTTCCGGGGAATGTGGAGCGTGCTAAAAGCACTGGGGCGCACGGGGGTCGA
GATGTGCGCGGGCTGCGGGGGTCGCATCCCCTCGTCTATCAGTCTTGTCTGTATTCCGAA
GTGTTTTTCCAGCATGGGTAGCTATCCAAAGAAACCTATGAGTTCATACCTTCGATTTTCC
ACAGAACAGCTACCCAAATTTAAAGCTAAACACCCAGATGCAAACTTTCAGAATTGGT
TAGGAAAATTGCAGCCCTGTGGAGGGAGCTACCAGAAGCAGAAAAAAAGGTTTATGAA
GCTGATTTTAAAGCTGAGTGGAAAGCATACAAAGAAGCTGTGAGCAAGTATAAAGAGCA
GCTAACTCCAAGTCAGCTGATGGGTATGGAGAAGGAGGCCCGGCAGGACAGCGGTTAAAAA
AGAAAGCACTGGTAAAGAGAAGAGAATTAATTTTGCTTGGAAAACCAAAAAGACCTCGT
TCAGCATATAACATTTATGTATCTGAAAGCTTCCAGGAGGCAAAGGATGATTCGGCTCAG
GGAAAATTGAAGCTTGTAAATGAGGCTTGGAAAAATCTGTCTCCTGAGGAAAAGCAGGC
ATATATTCAGCTTGCTAAAGATGATAGGATTCGTTACGACAATGAAATGAAGTCTTGGGA
AGAGCAGATGGCTGAAGTTGGACGAAGTGATCTCATCCGTCGAAGTGTGAAACGATCCG
GAGACATCTCTGAGCATTAA

40. TFEB

41. Fat1

42. (SEQ ID NO: 16) Adiponectin
ATGCTACTGTTGCAAGCTCTCCTGTTCCTCTTAATCCTGCCCAGTCATGCCGAAGATGACG
TTACTACAACTGAAGAGCTAGCTCCTGCTTTGGTCCCTCCACCCAAGGGAACTTGTGCAG
GTTGGATGGCAGGCATCCCAGGACATCCTGGCCACAATGGCACACCAGGCCGTGATGGC
AGAGATGGCACTCCTGGAGAGAAGGGAGAGAAAGGAGATGCAGGTCTTCTTGGTCCTAA
GGGTGAGACAGGAGATGTTGGAATGACAGGAGCTGAAGGGCCACGGGGCTTCCCCGGA

APPENDIX A-continued

SEQUENCES: BOLD = secretion signal when indicated

```
ACCCCTGGCAGGAAAGGAGAGCCTGGAGAAGCCGCTTATGTGTATCGCTCAGCGTTCAG
TGTGGGGCTGGAGACCCGCGTCACTGTTCCCAATGTACCCATTCGCTTTACTAAGATCTT
CTACAACCAACAGAATCATTATGACGGCAGCACTGGCAAGTTCTACTGCAACATTCCGG
GACTCTACTACTTCTCTTACCACATCACGGTGTACATGAAAGATGTGAAGGTGAGCCTCT
TCAAGAAGGACAAGGCCGTTCTCTTCACCTACGACCAGTATCAGGAAAAGAATGTGGAC
CAGGCCTCTGGCTCTGTGCTCCTCCATCTGGAGGTGGGAGACCAAGTCTGGCTCCAGGTG
TATGGGGATGGGGACCACAATGGACTCTATGCAGATAACGTCAACGACTCTACATTTACT
GGCTTTCTTCTCTACCATGATACCAACTGATAA
```

42. Klotho (canine) (SEQ ID NO: 135)
```
ATGGCCACCTGCATTTTACAGATGAGATTCCTAAGGCTGGGGAAGATACTGTTCCACTCC
AGCCCACAAAGCACAGGTGGCAGTGGTGGGACCCGGGGACCTCGAGCTCCGGCACAGCT
GCGAACGCAGCGTGGCACAGATAAGTTAGTTGCTAAGTCAGAGCTCAAGGCTAAAACGG
CCCACCGCGCGCTGGCCGACCACTTCAGGGACTACGCCGAGCTCTGCTTCCGCCACTTCT
GCGGCCAGGTCAAGTACTGGATCACCATCGACAACCCCTACGTGGTGGCCTGGCACGGC
TACGCCACCGGTCGCCTGGCACCCGGAGTCAGAGGCAGCCCGCGGCTCGGGTACCTGGT
GGCGCACAACCTCCTCCTGGCTCACGCCAAAATCTGGCATCTCTACAATACTTCTTTCCG
CCCAACTCAGGGAGGCCAGGTATCCATTGCCCTAAGCTCCCACTGGATCAATCCTCGAAG
AATGACCGACCATAGCATCAAAGAATGTCAAAAATCTCTTGACTTTGTACTAGGCTGGTT
TGCCAAGCCCATATTTATTGATGGTGACTATCCTGAGAGCATGAAGAATAACCTGTCATC
TCTTCTGCCTGTTTTTACTGAATCTGAGAAAAAGTTCATCAAGGGAACAGCTGACTTTTT
GCTCTTTCTTTTGGACCAACTTTGAGTTTTCAACTCTTGACCCTCATATGAAGTTCCACC
AATTAGAATCTCCCAGCCTGAGGCAACTCCTTTCTTGGATTGATTGACCTTGAATATAACCACC
CTCAAATATTTATTGTGGAAAATGGCTGGTTTGTCTCAGGGACCACCAAGAGAGATGATG
CCAAATATATGTATTACCTCAAAAAATTCATAATGGAAACCTTAAAAGCCATCAGGCTGG
ATGGGGTGGATGTCATAGGATACACAGCGTGGTCCCTTATGGATGGCTTCGAGTGGCAC
AGAGGCTACAGCATCAGACGTGGACTCTTCTACGTGGACTTTCTAAGCCAGGATAAGAA
ACTGTTGCCAAAGTCTTCAGCCTTGTTCTACCAAAAGCTGATAGAGAAAAATGGCTTCCC
TCCTTTACCTGAAAATCAGCCCCTAGAAGGGACATTTCCCTGTGACTTTGCTTGGGGAAT
TGTTGACAACTACATTCAAGTGGACACCACTCTGTCTCAGTTTACCGACCCGAACGTTTA
CCTGTGGGACGTCCATCACAGCAAGAGGCTGATTAAGGTGGACGGCCTGCGGGCCAAGA
AGAGGAAGCCCTACTGCGTGGACTTTGCCGCCATCGGGCCCAGGTGGCCCTGCTGCAG
GAGATGCACGTCTCGCATTTTCACTTCTCGCTGGACTGGGCCTGCTCCTGCCGCTGGGC
AACCAGTCCCGGGTGAACCACGCGGCCCTGCACTACTACGGCTGCGTGGCCAGCGAGCT
CCTGCGCGCCAACATCACCCCGGTGGTGGCGCTCTGGAGACCAGCCGCTGCGCACCAGG
GTCTGCCTGGACCGCTGGCACAGCGCGGTGCCTGGGAGAACCCACGCACCAGCCCTGGCG
TTCGCCGAGTACGCGCGCCTGTGCTTCCGCGCCCTGGGCCGCCACGTCAAGGTGTGGATC
ACGCTGCGCGAGCCGCCCACGCGGAACCTGACGCTCCGCGCCGGGCACAACCTGCTGCG
GGCGCACGCGCTGGCCTGGCGCGTATACGACGAGCAGTTCCGGGGCTCGCAGCAGGGGA
AGGTGTCCATCGCCCTGCAGGCCGACTGGGTGGAGCCCGCCTGCCCCTTCCTCCCAGAAGG
ACCGCGAAGTGGCCGAGAGGGTTCTGGAGTTCGACGTCGGCTGGCCGAGCCCATC
TTCGGCTCCGGGGACTACCCGGCTGATGCGCGACTGGCTCACCCGGAGAGACCATTCC
CTCCTGCCCTATTTCACTGACGAAGAGAAGAGGCTAATCCGGGGTTCCTTTGACTTCCTG
GCCTTGAGCCATTACACCACCATCCTCGTGGACTGGAAAAGGAAGACCCAGTCAAATA
CAATGATTACCTGGAAGTGCAGGAGATGACCGACATCACCTGGCTCAACTCCCCCAGTC
AGGTGGCCGTAGTGCCCTGGGGCCTGCGCAAAGTGCTCAACTGGCTCAAGTTCAAGTAC
GGAGACCTCCCCATGTATATCGTATCCAACGGCATAGATGACGATCCGCGGGCAGCCCA
GGACTCGTTGAGGGTGTATTACATGCAGAACTATGTAAATGAAGCTCTGAAAGCCTACTG
ATTGGATGGTATCAATCTTTGTGGATACTTTGCCTACTCATTTAATGATCGCACAGCTCCG
AAGTTTGGCCTCTATCATTATGCTGCAAACCAGTTTGAGCCCAAACCGTCGGTGAAGCAT
TACAGGAAAATTATTGACAACAATGGCTTCCCAGGCCCTGAAACTTTGGGGCGGTTTTGT
CCAGAGGAATTCACCCTGTGCACCGAATGCAGCTTTTTTCACCACCGAAAGTCTTTACTG
GCTTTCATAGCTTTCCTACTTTTTGCTTTTATTATTTCTCTTTCTCTGATTTTCTACTACTCT
AGGAAAGGCAGAAGAAGTTATAAAGGAGGGAGTGGTGGGTCCGATTACAAAGATCACG
ATGGGGACTATAAAGATCACGACATCGACTATAAGGATGACGATGATAAATGA
```

43. FGF21 (canine) (SEQ ID NO: 136)
```
ATGGGCTGGGCCGAGGCCGGGTTCGAGCACCTGGGACTGTGGGTCCCTGTGCTGGCTGT
GCTTTTGCTGGAAGCCTGCCGGGCACATCCGATCCCTGACTCCAGCCCCCTCCTACAATT
TGGAGGTCAAGTTCGACAGCGGTACCTCTACACCGACGATGCCCAGGAGACAGAGGCCC
ACCTAGAGATCAGGGCCGATGGCACAGTGGTGGGGCTGCCCGCCAGAGCCCTGAAAGT
CTCCTGGAGCTGAAAGCCCTAAAGCCAGGGGTCATTCAAATCTTGGGAGTCAAAACATC
CAGGTTCCTGTGCCAGGGCCCAGATGGGACACTATATGGCTGCTCCATTTCGACCCTGT
GGCCTGCAGTTTCCGAGAACTGCTTCTTGAGGATGGGTACAACATCTACCACTCCGAGAC
CCTTGGTCTCCCGCTTGCCTGCGCCCCCACAACTCCGCATACCGGGACTTGGCACCCCG
CGGGCCTGCCCGCTTCCTGCCACTGCCAGGCCTGCTTCCAGCACCCCAGAGCCTCCAGG
GATCCTGGCCCCGGAGCCTCCTGACGTGGGCTCCTCGGACCCTCTGAGCATGGTGGGGCC
TTCACAGGGCCGGAGTCCCAGCTATGCTTCCTGATAG
```

44. GDF15 (hNAG)

45. IL4

46. ZAG

47. HAS2

48. Txn1

APPENDIX A-continued

SEQUENCES: BOLD = secretion signal when indicated

49. Cat
50. Plau
51. Ucp2
52. Atg5
53. NUDT1
54. Mt1
55. Adra1a (mut)
56. Pck1
57. Serpine1
58. GH
59. IFG1
60. TGFb1
61. PDE4b
62. mTOR
63. nf-kb
64. PCSK9
65. bCATm
66. ADcy5
67. Coq7
68. Eps8
69. Insr
70. Pappa
71. Shc1
72. Agtr1a
73. Slc13a1
74. Dgat1
75. Ikbkb
76. Kcna3
77. Myc
78. Surf1
79. Ubd
80. Rps6kb1
81. Ctf1
82. Htt
83. Irs1
84. Irs2
85. Mif
86. Trpv1
87. Prkar2b

APPENDIX A-continued

SEQUENCES: BOLD = secretion signal when indicated

88. Gsta4

89. Akt1

90. Gpx4

91. Bax

92. Cebpalpha

93. Cebpbeta 94. (SEQ ID NO: 17) heF1a Promoter
TTGGCTCCGGTGCCCGTCAGTGGGCAGAGCGCACATCGCCCACAGTCCCCGAGAAGTTGT
GGGGAGGGGTCGGCAATTGAACCGGTGCCTAGAGAAGGTGGCGCGGGGTAAACTGGGA
AAGTGATGTCGTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAACACAGGTAAG
TGCCGTGTGTGGTTCCCGCGGGCCTGGCCTCTTTACGGGTTATGGCCCTTGCGTGCCTTGA
ATTACTTCCACCTGGCTGCAGTACGTGATTCTTGATCCCGAGCTTCGGGTTGGAAGTGGG
TGGGAGAGTTCGAGGCCTTGCGCTTAAGGAGCCCCTTCGCCTCGTGCTTGAGTTGAGGCC
TGGCCTGGGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTTTTTTTCT
GGCAAGATAGTCTTGTAAATGCGGGCCAAGATCTGCACACTGGTATTTCGGTTTTTGGGG
CCGCGGGCGGCGACGGGGCCCGTGCGTCCCAGCGCACATGTTCGGCGAGGCGGGGCCTG
CGAGCGCGGCCACCGAGAATCGGACGGGGGTAGTCTCAAGCTGGCCGGCCTGCTCTGGT
GCCTGGCCTCGCGCCGCCGTGTATCGCCCCGCCCTGGGCGGCAAGGCTGGCCCGGTCGGC
ACCAGTTGCGTGAGCGGAAAGATGGCCGCTTCCCGGCCCTGCTGCAGGGAGCTCAAAAT
GGAGGACGCGGCGCTCGGGAGAGCGGGCGGGTGAGTCACCCACACAAAGGAAAAGGGC
CTTTCCGTCCTCAGCCGTCGCTTCATGTGACTCCACGGAGTACCGGGCGCCGTCCAGGCA
CCTCGATTAGTTCTCGAGCTTTTGGAGTACGTCGTCTTTAGGTTGGGGGGAGGGGTTTTAT
GCGATGGAGTTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATTCTCAAGCCT
CAGACAGTGGTTCAAAGTTTTTTTCTTCCATTTCAGGT 95. (SEQ ID NO: 18) sheF1a Promoter
AGGCTCCGGTGCCCGTCAGTGGGCAGAGCGCACATCGCCCACAGTCCCCGAGAAGTTGG
GGGGAGGGGTCGGCAATTGAACCGGTGCCTAGAGAAGGTGGCGCGGGGTAAACTGGGA
AAGTGATGTCGTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAACACA 96. (SEQ ID NO: 19) rheF1a Promoter
GGATCTGCGATCGCTCCGGTGCCCGTCAGTGGGCAGAGCGCACATCGCCCACAGTCCCC
GAGAAGTTGGGGGGAGGGGTCGGCAATTGAACGGGTGCCTAGAGAAGGTGGCGCGGGG
TAAACTGGGAAAGTGATGTCGTGTACTGGCTCCGCCTTTTTCCCGAGGGTGGGGGAGAAC
CGTATATAAGTGCAGTAGTCGCCGTGAACGTTCTTTTTCGCAACGGGTTTGCCGCCAGAA
CACAGCTGAAGCTTCGAGGGGCTCGCATCTCTCCTTCACGCGCCCGCCGCCCTACCTGAG
GCCGCCATCCACGCCGGTTGAGTCGCGTTCTGCCGCCTCCCGCCTGTGGTGCCTCCTGAA
CTGCGTCCGCCGTCTAGGTAAGTTTAAAGCTCAGGTCGAGACCGGGCCTTTGTCCGGCGC
TCCCTTGGAGCCTACCTAGACTCAGCCGGCTCTCCACGCTTTGCCTGACCCTGCTTGCTCA
ACTCTACGTCTTTGTTTCGTTTTCTGTTCTGCGCCGTTACAGATCCAAGCTGTGACCGGCG
CCTAC 97. AAT Promoter 98. thyroid hormone-binding globulin promoter 99. albumin promoter 100. thyroxin-binding globulin (TBG) promoter 101. Hepatic Control Region (HCR)-ApoCII hybrid promoter 102. HCR-hAAT hybrid promoter 103. AAT promoter combined with mouse albumin gene enhancer (Ealb) element and an apolipoprotein E promoter 104. (SEQ ID NO: 20) P2A
GGATCTGGCGCCACCAACTTCTCTCTGCTGAAGCAGGCCGGCGACGTGGAGGAGAACCC
AGGCCCA 105. (SEQ ID NO: 21) T2A
GAGGGCCGCGGCAGCCTGCTGACCTGCGGCGACGTGGAGGAAAACCCCGGCCCC

106. E2A 107. (SEQ ID NO: 22) 105 IRES

APPENDIX A-continued

SEQUENCES: BOLD = secretion signal when indicated

```
GCCCCTCTCCCTCCCCCCCCCTAACGTTACTGGCCGAAGCCGCTTGGAATAAGGCCGGT
GTGCGTTTGTCTATATGTTATTTTCCACCATATTGCCGTCTTTTGGCAATGTGAGGGCCCG
GAAACCTGGCCCTGTCTTCTTGACGAGCATTCCTAGGGGTCTTTCCCCTCTCGCCAAAGG
AATGCAAGGTCTGTTGAATGTCGTGAAGGAAGCAGTTCCTCTGGAAGCTTCTTGAAGACA
AACAACGTCTGTAGCGACCCTTTGCAGGCAGCGGAACCCCCCACCTGGCGACAGGTGCC
TCTGCGGCCAAAAGCCACGTGTATAAGATACACCTGCAAAGGCGGCACAACCCCAGTGC
CACGTTGTGAGTTGGATAGTTGTGGAAAGAGTCAAATGGCTCTCCTCAAGCGTATTCAAC
AAGGGGCTGAAGGATGCCCAGAAGGTACCCCATTGTATGGGATCTGATCTGGGGCCTCG
GTGCACATGCTTTACATGTGTTTAGTCGAGGTTAAAAAAACGTCTAGGCCCCCCGAACCA
CGGGGACGTGGTTTTCCTTTGAAAAACACGATGATAAGCCACC
```

108. AAV1 ITR 109. (SEQ ID NO: 23) AAV2 ITR 5' ITR
```
CCTGCAGGCAGCTGCGCGCTCGCTCGCTCACTGAGGCCGCCCGGGCGTCGGGCGACCTTT
GGTCGCCCGGCCTCAGTGAGCGAGCGAGCGCGCAGAGAGGGAGTGGCCAACTCCATCAC
TAGGGGTTCCT
```

110. (SEQ ID NO: 24) AAV2 ITR 3' ITR
```
CCTGCAGGCAGCTGCGCGCTCGCTCGCTCACTGAGGCCGCCCGGGCAAAGCCCGGGCGT
CGGGCGACCTTTGGTCGCCCGGCCTCAGTGAGCGAGCGAGCGCGCAGAGAGGGAGTGGC
CAACTCCATCACTAGGGGTTCCT
```

111. AAV5 ITR

112. AAV6 ITR

113. AAV7 ITR

114. AAV8 ITR

115. AAV9 ITR 116. (SEQ ID NO: 25) AAV-8 capsid
```
ATGGCTGCCGATGGTTATCTTCCAGATTGGCTCGAGGACAACCTCTCTGAGGGCATTCGC
GAGTGGTGGGCGCTGAAACCTGGAGCCCCGAAGCCCAAAGCCAACCAGCAAAAGCAGG
ACGACGGCCGGGGTCTGGTGCTTCCTGGCTACAAGTACCTCGGACCCTTCAACGGACTCG
ACAAGGGGGAGCCCGTCAACGCGGCGGACGCAGCGGCCCTCGAGCACGACAAGGCCTA
CGACCAGCAGCTGCAGGCGGGTGACAATCCGTACCTGCGGTATAACCACGCCGACGCCG
AGTTTCAGGAGCGTCTGCAAGAAGATACGTCTTTTGGGGGCAACCTCGGGCGAGCAGTC
TTCCAGGCCAAGAAGCGGGTTCTCGAACCTCTCGGTCTGGTTGAGGAAGGCGCTAAGAC
GGCTCCTGGAAAGAAGAGACCGGTAGAGCCATCACCCCAGCGTTCTCCAGACTCCTCTA
CGGGCATCGGCAAGAAGGCCAACAGCCCGCCAGAAAAGACTCAATTTTGGTCAGACT
GGCGACTCAGAGTCAGTTCCAGACCCTCAACCTCTCGGAGAACCTCCAGCAGCGCCCTCT
GGTGTGGGACCTAATACAATGGCTGCAGGCGGTGGCGCACCAATGGCAGACAATAACGA
AGGCGCCGACGGAGTGGGTAGTTCCTCGGGAAATTGGCATTGCGATTCCACATGGCTGG
GCGACAGAGTCATCACCACCAGCACCCGAACCTGGGCCCTGCCCACCTACAACAACCAC
CTCTACAAGCAAATCTCCAACGGGACATCGGGAGGAGCCACTCAACGACAACACCTACTT
CGGCTACAGCACCCCCTGGGGGTATTTTGACTTTAACAGATTCCACTGCCACTTTTCACC
ACGTGACTGGCAGCGACTCATCAACAACAACTGGGGATTCCGGCCCAAGAGACTCAGCT
TCAAGCTCTTCAACATCCAGGTCAAGGAGGTCACGCAGAATGAAGGCACCAAGACCATC
GCCAATAACCTCACCAGCACCATCCAGGTGTTTACGGACTCGGAGTACCAGCTGCCGTAC
GTTCTCGGCTCTGCCCACCAGGGCTGCCTGCCTCCGTTCCCGGCGGACGTGTTCATGATTC
CCCAGTACGGCTACCTAACACTCAACAACGGTAGTCAGGCCGTGGGACGCTCCTCCTTCT
ACTGCCTGGAATACTTTCCTTCGCAGATGCTGAGAACCGGCAACAACTTCCAGTTTACTT
ACACCTTCGAGGACGTGCCTTTCCACAGCAGCTACGCCCACAGCCAGAGCTTGGACCGG
CTGATGAATCCTCTGATTGACCAGTACCTGTACTACTTGTCTCGGACTCAAACAACAGGA
GGCACGGCAAATACGCAGACTCTGGGCTTCAGCCAAGGTGGGCCTAATACAATGGCCAA
TCAGGCAAAGAACTGGCTGCCAGGACCCTGTTACCGCCAACAACGCGTCTCAACGACAA
CCCGGGCAAAACAACAATAGCAACTTTGCCTGGACTGCTGGGACCAAATACCATCTGAAT
GGAAGAAATTCATTGGCTAATCCTGGCATCGCTATGGCAACACACAAAGACGACGAGGA
GCGTTTTTTTCCCAGTAACGGGATCCTGATTTTTGGCAAACAAAATGCTGCCAGAGACAA
TGCGGATTACAGCGATGTCATGCTCACCAGCGAGGAAGAAATCAAAACCACTAACCCTG
TGGCTACAGAGGAATACGGTATCGTGGCAGATAACTTGCAGCAGCAAAACACGGCTCCT
CAAATTGGAACTGTCAACAGCCAGGGGGCCTTACCCGGTATGGTCTGGCAGAACCGGGA
CGTGTACCTGCAGGGTCCCATCTGGGCCAAGATTCCTCACACGGACGGCAACTTCCACCC
GTCTCCGCTGATGGGCGGCTTTGGCCTGAACATCCTCCGCCTCAGATCCTGATCAAGAA
CACGCCTGTACCTGCGGATCCTCCGACCACCTTCAACCAGTCAAAGCTGAACTCTTTCAT
CACGCAATACAGCACCGGACAGGTCAGCGTGGAAATTGAATGGGAGCTGCAGAAGGAA
AACAGCAAGCGCTGGAACCCCGAGATCCAGTACACCTCCAACTACTACAAATCTACAAG
TGTGGACTTTGCTGTTAATACAGAAGGCGTGTACTCTGAACCCCGCCCCATTGGCACCCG
TTACCTCACCCGTAATCTG
```

117. AAV-9 capsid 118. (SEQ ID NO: 26) AAV-PHP.b capsid
```
ATGGCTGCCGATGGTTATCTTCCAGATTGGCTCGAGGACAACCTTAGTGAAGGAATTCGC
GAGTGGTGGGCTTTGAAACCTGGAGCCCCTCAACCCAAGGCAAATCAACAACATCAAGA
```

APPENDIX A-continued

SEQUENCES: BOLD = secretion signal when indicated

```
CAACGCTCGAGGTCTTGTGCTTCCGGGTTACAAATACCTTGGACCCGGCAACGGACTCGA
CAAGGGGGAGCCGGTCAACGCAGCAGACGCGGCGGCCCTCGAGCACGACAAGGCCTAC
GACCAGCAGCTCAAGGCCGGAGACAACCCGTACCTCAAGTACAACCACGCCGACGCCGA
GTTCCAGGAGCGGCTCAAAGAAGATACGTCTTTTGGGGGCAACCTCGGGCGAGCAGTCT
TCCAGGCCAAAAAGAGGCTTCTTGAACCTCTTGGTCTGGTTGAGGAAGCGGCTAAGACG
GCTCCTGGAAAGAAGAGGCCTGTAGAGCAGTCTCCTCAGGAACCGGACTCCTCCGCGGG
TATTGGCAAATCGGGTGCACAGCCCGCTAAAAAGAGACTCAATTTCGGTCAGACTGGCG
ACACAGAGTCAGTCCCAGACCCTCAACCAATCGGAGAACCTCCCGCAGCCCCCTCAGGT
GTGGGATCTCTTACAATGGCTTCAGGTGGTGGCGCACCAGTGGCAGACAATAACGAAGG
TGCCGATGGAGTGGGTAGTTCCTCGGGAAATTGGCATTGCGATTCCCAATGGCTGGGGG
ACAGAGTCATCACCACCAGCACCCGAACCTGGGCCCTGCCCACCTACAACAATCACCTCT
ACAAGCAAATCTCCAACAGCACATCTGGAGGATCTTCAAATGACAACGCCTACTTCGGCT
ACAGCACCCCTGGGGGTATTTTGACTTCAACAGATTCCACTGCCACTTCTCACCACGTG
ACTGGCAGCGACTCATCAACAACAACTGGGGATTCCGGCCTAAGCGACTCAACTTCAAG
CTCTTCAACATTCAGGTCAAAGAGGTTACGGACAACAATGGAGTCAAGACCATCGCCAA
TAACCTTACCAGCACGGTCCAGGTCTTCACGGACTCAGACTATCAGCTCCCGTACGTGCT
CGGGTCGGCTCACGAGGGCTGCCTCCCGCCGTTCCCAGCGGACGTTTTCATGATTCCTCA
GTACGGGTATCTGACGCTTAATGATGGAAGCCAGGCCGTGGGTCGTTCGTCCTTTTACTG
CCTGGAATATTTCCCGTCGCAAATGCTAAGAACGGGTAACAACTTCCAGTTCAGCTACGA
GTTTGAGAACGTACCTTTCCATAGCAGCTACGCTCACAGCCAAAGCCTGGACCGACTAAT
GAATCCACTCATCGACCAATACTTGTACTATCTCTCTAGAACTATTAACGGTTCTGGACA
GAATCAACAAACGCTAAATTCAGTGTGGCCGGACCCAGCAACATGGCTGTCCAGGGAA
GAAACTACATACCTGGACCCAGCTACCGACAACAACGTGTCTCAACCACTGTGACTCAA
AACAACAACAGCGAATTTGCTTGGCCTGGAGCTTCTTCTTGGGCTCTCAATGGACGTAAT
AGCTTGATGAATCCTGGACCTGCTATGGCCAGCCACAAAGAAGGAGAGGACCGTTTCTTT
CCTTTGTCTGGATCTTTAATTTTTGGCAAACAAGGTACCGGCAGAGACAACGTGGATGCG
GACAAAGTCATGATAACCAACGAAGAAGAAATTAAAACTACTAACCCGGTAGCAACGG
AGTCCTATGGACAAGTGGCCACAAACCACCAGAGTGCCCAAACTTTGGCGGTGCCTTTTA
AGGCACAGGCGCAGACCGGTTGGGTTCAAAACCAAGGAATACTTCCGGGTATGGTTTGG
CAGGACAGAGATGTGTACCTGCAAGGACCCATTTGGGCCAAAATTCCTCACACGGACGG
CAACTTTCACCCTTCTCCGCTGATGGGAGGGTTTGGAATGAAGCACCCGCCTCCTCAGAT
CCTCATCAAAAACACACCTGTACCTGCGGATCCTCCAACGGCCTTCAACAAGGACAAGCT
GAACTCTTTCATCACCCAGTATTCTACTGGCCAAGTCAGCGTGGAGATCGAGTGGGAGCT
GCAGAAGGAAAACAGCAAGCGCTGGAACCCGGAGATCCAGTACACTTCCAACTATTACA
AGTCTAATAATGTTGAATTTGCTGTTAATACTGAAGGTGTATATAGTGAACCCCGCCCCA
TTGGCACCAGATACCTGACTCGTAATCTG 119. (SEQ ID NO: 27) WPRE
AATCAACCTCTGGATTACAAAATTTGTGAAAGATTGACTGGTATTCTTAACTATGTTGCT
CCTTTTACGCTATGTGGATACGCTGCTTTAATGCCTTTGTATCATGCTATTGCTTCCCGTA
TGGCTTTCATTTTCTCCTCCTTGTATAAATCCTGGTTGCTGTCTCTTTATGAGGAGTTGTGG
CCCGTTGTCAGGCAACGTGGCGTGGTGTGCACTGTGTTTGCTGACGCAACCCCCACTGGT
TGGGGCATTGCCACCACCTGTCAGCTCCTTTCCGGGACTTTCGCTTTCCCCCTCCCTATTG
CCACGGCGGAACTCATCGCCGCCTGCCTTGCCCGCTGCTGGACAGGGGCTCGGCTGTTGG
GCACTGACAATTCCGTGGTGTTGTCGGGGAAGCTGACGTCCTTTCCATGGCTGCTCGCCT
GTGTTGCCACCTGGATTCTGCGCGGGACGTCCTTCTGCTACGTCCCTTCGGCCCTCAATCC
AGCGGACCTTCCTTCCCGCGGCCTGCTGCCGGCTCTGCGGCCTCTTCCGCGTCTTCGCCTT
CGCCCTCAGACGAGTCGGATCTCCCTTTGGGCCGCCTCCCCGCCTG 120. (SEQ ID NO: 28) WPRE3
AATCAACCTCTGGATTACAAAATTTGTGAAAGATTGACTGGTATTCTTAACTATGTTGCT
CCTTTTACGCTATGTGGATACGCTGCTTTAATGCCTTTGTATCATGCTATTGCTTCCCGTA
TGGCTTTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAATTCCGT
GGTGTT 121. (SEQ ID NO: 29) SV40pA
GCTTTATTTGTGAAATTTGTGATGCTATTGCTTTATTTGTAACCATTATAAGCTGCAATAA
ACAAGTTAACAACAACAATTGCATTCATTTTATGTTTCAGGTTCAGGGGGAGATGTGGGA
GGTTTTTTAAAGC 122. (SEQ ID NO: 30) bGHpA
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTC
CTTCTATAATATTATGGGGTGGAGGGGGGTGGTATGGAGCAAGGGGCAAGTTGGGAAGA
CAACCTGTAGGGCCTGCGGGGTCTATTGGGAACCAAGCTGGAGTGCAGTGGCACAATCT
TGGCTCACTGCAATCTCCGCCTCCTGGGTTCAAGCGATTCTCCTGCCTCAGCCTCCCGAGT
TGTTGGGATTCCAGGCATGCATGACCAGGCTCAGCTAATTTTGTTTTTTTGGTAGAGAC
GGGGTTTCACCATATTGGCCAGGCTGGTCTCCAACTCCTAATCTCAGGTGATCTACCCAC
CTTGGCCTCCCAAATTGCTGGGATTACAGGCGTGAACCACTGCTCCCTTCCCTGTCCTTCT
GATTTTGTAGGTAACCACGTGCGGACCGA 123. (SEQ ID NO: 31) rBGpA
TGGCTAATAAAGGAAATTTATTTTCATTGCAATAGTGTGTTGGAATTTTTTGTGTCTCTCA
CTCGGAAGGACATATGGGAGGGCAAATCATTTAAAACATCAGAATGAGTATTTGGTTTA
GAGTTTGGCAACATATGCCCATATGCTGGCTGCCATGAACAAAGGTTGGCTATAAAGAG
GTCATCAGTATATGAAACAGCCCCCTGCTGTCCATTCCTTATTCCATAGAAAAGCCTTGA
CTTGAGGTTAGATTTTTTTTATATTTTGTTTTGTGTTATTTTTTCTTTAACATCCCTAAAA
```

APPENDIX A-continued

SEQUENCES: BOLD = secretion signal when indicated

```
TTTTCCTTACATGTTTTACTAGCCAGATTTTTCCTCCTCTCCTGACTACTCCCAGTCATAGC
TGTCCCTCTTCTCTTATGGAGATC 124. (SEQ ID NO: 32) hGHpA
ACGGGTGGCATCCCTGTGACCCCTCCCCAGTGCCCTCTCCTGGCCCTGGAAGTTGCCACTC
CAGTGCCCACCAGCCTTGTCCTAATAAAATTAAGTTGCATCATTTTGTCTGACTAGGTGTC
CTTCTATAATATTATGGGGTGGAGGGGGGTGGTATGGAGCAAGGGGCAAGTTGGGAAGA
CAACCTGTAGGGCCTGCGGGGTCTATTGGGAACCAAGCTGGAGTGCAGTGGCACAATCT
TGGCTCACTGCAATCTCCGCCTCCTGGGTTCAAGCGATTCTCCTGCCTCAGCCTCCCGAGT
TGTTGGGATTCCAGGCATGCATGACCAGGCTCAGCTAATTTTTGTTTTTTTGGTAGAGAC
GGGGTTTCACCATATTGGCCAGGCTGGTCTCCAACTCCTAATCTCAGGTGATCTACCCAC
CTTGGCCTCCCAAATTGCTGGGATTACAGGCGTGAACCACTGCTCCCTTCCCTGTCCTT
```

APPENDIX B

| Name | SEQ ID | Molecule Type | Sequence |
|---|---|---|---|
| mAdipoQ | SEQ ID NO: 33 | DNA | ATGCTACTGTTGCAAGCTCTCCTGTTCCTCTTAATCCTGCCC<br>AGTCATGCCGAAGATGACGTTACTACAACTGAAGAGCTAGC<br>TCCTGCTTTGGTCCCTCCACCCAAGGGAACTTGTGCAGGTTG<br>GATGGCAGGCATCCCAGGACATCCTGGCCACAATGGCACAC<br>CAGGCCGTGATGGCAGAGATGGCACTCCTGGAGAGAAGGG<br>AGAGAAAGGAGATGCAGGTCTTCTTGGTCCTAAGGGTGAGA<br>CAGGAGATGTTGGAATGACAGGAGCTGAAGGGCCACGGGG<br>CTTCCCCGGAACCCCTGGCAGGAAAGGAGAGCCTGGAGAA<br>GCCGCTTATGTGTATCGCTCAGCGTTCAGTGTGGGGCTGGA<br>GACCCGCGTCACTGTTCCCAATGTACCCATTCGCTTTACTAA<br>GATCTTCTACAACCAACAGAATCATTATGACGGCAGCACTG<br>GCAAGTTCTACTGCAACATTCCGGGACTCTACTACTTCTCTT<br>ACCACATCACGGTGTACATGAAAGATGTGAAGGTGAGCCTC<br>TTCAAGAAGGACAAGGCCGTTCTCTTCACCTACGACCAGTA<br>TCAGGAAAAGAATGTGGACCAGGCCTCTGGCTCTGTGCTCC<br>TCCATCTGGAGGTGGGAGACCAAGTCTGGCTCCAGGTGTAT<br>GGGGATGGGGACCACAATGGACTCTATGCAGATAACGTCAA<br>CGACTCTACATTTACTGGCTTTCTTCTCTACCATGATACCAA<br>CTGA |
| mAdipoQ | SEQ ID NO: 34 | AA | MLLLQALLFLLILPSHAEDDVTTTEELAPALVPPPKGTCAGWM<br>AGIPGHPGHNGTPGRDGRDGTPGEKGEKGDAGLLGPKGETGD<br>VGMTGAEGPRGFPGTPGRKGEPGEAAYVYRSAFSVGLETRVT<br>VPNVPIRFTKIFYNQQNHYDGSTGKFYCNIPGLYYFSYHITVYM<br>KDVKVSLFKKDKAVLFTYDQYQEKNVDQASGSVLLHLEVGD<br>QVWLQVYGDGDHNGLYADNVNDSTFTGFLLYHDTN |
| mNrf2 | SEQ ID NO: 35 | DNA | ATGATGGACTTGGAGTTGCCACCGCCAGGACTACAGTCCCA<br>GCAGGACATGGATTTGATTGACATCCTTTGGAGGCAAGACA<br>TAGATCTTGGAGTAAGTCGAGAAGTGTTTGACTTTAGTCAG<br>CGACAGAAGGACTATGAGTTGGAAAAACAGAAAAAACTCG<br>AAAAAGGAAAGACAAGAGCAACTCCAGAAGGAACAGGAGA<br>AGGCCTTTTTCGCTCAGTTTCAACTGGATGAAGAAACAGGA<br>GAATTCCTCCCAATTCAGCCGGCCCAGCACATCCAGACAGA<br>CACTAGTGGATCCGCCAGCTACTCCCAGGTTGCCCACATTC<br>CCAAACAAGATGCCTTGTACTTTGAAGACTGTATGCAGCTTT<br>TGGCAGAGACATTCCCATTTGTTGATGACCATGAGTCGCTTG<br>CCCTGGATATCCCCAGCCACGCTGAAAGTTCAGTCTTCACT<br>GCCCCTCATCAGGCCCAGTCCCTCAATAGCTCTCTGGAGGC<br>AGCCATGACTGATTTAAGCAGCATAGAGCAGGACATGGAGC<br>AAGTTTGGCAGGAGCTATTTTCCATTCCCGAATTACAGTGTC<br>TTAATACCGAAAACAAGCAGCTGGCTGATACTACCGCTGTT<br>CCCAGCCCAGAAGCACACTGACAGAAATGGACAGCAATT<br>ACCATTTTTACTCATCGATCTCCTCGCTGGAAAAAGAAGT<br>GGCAACTGTGGTCCACATTTCCTTCATGGTTTTGAGGATTCT<br>TTCAGCAGCATCCTCTCCACTGATGATGCCAGCCAGCTGAC<br>CTCCTTAGACTCAAATCCCACCTTAAACACAGATTTTGGCGA<br>TGAATTTTATTCTGCTTTCATAGCAGAGCCCAGTGACGGTGG<br>CAGCATGCCTTCCTCCGCTGCCATCAGTCAGTCACTCTCTGA<br>ACTCCTGGACGGGACTATTGAAGGCTGTGACCTGTCACTGT<br>GTAAAGCTTTCAACCCGAAGCACGCTGAAGGCACAATGGAA<br>TTCAATGACTCTGACTCTGGCATTTCACTGAACACAAGTCCC<br>AGCCGAGCGTCCCAGAGCACTCCGTGGAGTCTTCCATTTA<br>CGGAGACCCACCGCCTGGGTTCAGTGACTCGGAAATGGAGG<br>AGCTAGATAGTGCCCCTGGAAGTGTCAAACAGAACGGCCCT<br>AAAGCACAGCCAGCACATTCTCCTGGAGACACAGTACAGCC<br>TCTGTCACCAGCTCAAGGGCACAGTGCTCCTATGCGTGAAT |

APPENDIX B-continued

| Name | SEQ ID | Molecule Type | Sequence |
|---|---|---|---|
| | | | CCCAATGTGAAAATACAACAAAAAAAGAAGTTCCCGTGAGT<br>CCTGGTCATCAAAAAGCCCCATTCACAAAAGACAAACATTC<br>AGCCCGCTTAGAGGCTCATCTCACACGAGATGAGCTTAGGG<br>CAAAAGCTCTCCATATTCCATTCCCTGTCGAAAAAATCATTA<br>ACCTCCCTGTTGATGACTTCAATGAAATGATGTCCAAGGAG<br>CAATTCAATGAAGCTCAGCTCGCATTGATCCGAGATATACG<br>CAGGAGAGGTAAGAATAAAGTCGCCGCCCAGAACTGTAGG<br>AAAAGGAAGCTGGAGAACATTGTCGAGCTGGAGCAAGACT<br>TGGGCCACTTAAAAGACGAGAGAGAAAAACTACTCAGAGA<br>AAAGGGAGAAAACGACAGAAACCTCCATCTACTGAAAAGG<br>CGGCTCAGCACCTTGTATCTTGAAGTCTTCAGCATGTTACGT<br>GATGAGGATGGAAAGCCTTACTCTCCCAGTGAATACTCTCT<br>GCAGCAAACCAGAGATGGCAATGTGTTCCTTGTTCCCAAAA<br>GCAAGAAGCCAGATACAAAGAAAAACTAG |
| mNrf2 | SEQ ID NO: 36 | AA | MMDLELPPPGLQSQQDMDLIDILWRQDIDLGVSREVEDFSQRQ<br>KDYELEKQKKLEKERQEQLQKEQEKAFFAQFQLDEETGEFLPI<br>QPAQHIQTDTSGSASYSQVAHIPKQDALYFEDCMQLLAETFPF<br>VDDHESLALDIPSHAESSVFTAPHQAQSLNSSLEAAMTDLSSIE<br>QDMEQVWQELFSIPELQCLNTENKQLADTTAVPSPEATLTEMD<br>SNYHFYSSISSLEKEVGNCGPHFLHGFEDSFSSILSTDDASQLTS<br>LDSNPTLNTDFGDEFYSAFIAEPSDGGSMPSSAAISQSLSELLDG<br>TIEGCDLSLCKAFNPKHAEGTMEFNDSDSGISLNTSPSRASPEH<br>SVESSIYGDPPPGFSDSEMEELDSAPGSVKQNGPKAQPAHSPGD<br>TVQPLSPAQGHSAPMRESQCENTTKKEVPVSPGHQKAPFTKD<br>KHSSRLEAHLTRDELRAKALHIPFPVEKIINLPVDDFNEMMSKE<br>QFNEAQLALIRDIRRRGKNKVAAQNCRKRKLENIVELEQDLGH<br>LKDEREKLLREKGENDRNLHLLKRRLSTLYLEVFSMLRDEDG<br>KPYSPSEYSLQQTRDGNVFLVPKSKKPDTKKN |
| sTGFBRII | SEQ ID NO: 37 | DNA | ATGGGTCGGGGGCTGCTCCGGGGCCTGTGGCCGCTGCATAT<br>CGTCCTGTGGACGCGCATCGCCAGCACGATCCCGCCGCACG<br>TTCCCAAGTCGGATGTGGAAATGGAAGCCCAGAAAGATGCA<br>TCCATCCACCTAAGCTGTAATAGGACCATCCATCCACTGAA<br>ACATTTTAACAGTGATGTCATGGCCAGCGACAATGGCGGTC<br>CGGTCAAGCTTCCACAGCTGTGCAAGTTTTGCGATGTGAGA<br>CTGTCCACTTGCGACAACCAGAAGTCCTGCATGAGCAACTG<br>CAGCATCACGGCCATCTGTGAGAAGCCGCATGAAGTCTGCG<br>TGGCCGTGTGGAGGAAGAACGACAAGAACATTACTCTGGA<br>GACGGTTTGCCACGACCCCAAGCTCACCTACCACGGCTTCA<br>CTCTGGAAGATGCCGCTTCTCCCAAGTGTGTCATGAAGGAA<br>AAGAAAAGGGCGGGCGAGACTTTCTTCATGTGTGCCTGTAA<br>CATGGAAGAGTGCAACGATTACATCATCTTTTCGGAAGAAT<br>ACACCACCAGCAGTCCCGACCCCAGAGGGCCCACAATCAA<br>GCCCTGTCCTCCATGCAAATGCCCAGCACCTAACCTCGAGG<br>GTGGACCATCCGTCTTCATCTTCCCTCCAAAGATCAAGGATG<br>TACTCATGATCTCCCTGAGCCCCATAGTCACATGTGTGGTGG<br>TGGATGTGAGCGAGGATGACCCAGATGTCCAGATCAGCTGG<br>TTTGTGAACAACGTGGAAGTACACACAGCTCAGACACAAAC<br>CCATAGAGAGGATTACAACAGTACTCTCCGGGTGGTCAGTG<br>CCCTCCCCATCCAGCACCAGGACTGGATGAGTGGCAAGGCG<br>TTCGCATGCGCGGTCAACAACAAAGACCTCCCAGCGCCCAT<br>CGAGAGAACCATCTCAAAACCCAAAGGGTCAGTAAGAGCT<br>CCACAGGTATATGTCTTGCCTCCACCAGAAGAAGAGATGAC<br>TAAGAAACAGGTCACTCTGACCTGCATGGTCACAGACTTCA<br>TGCCTGAAGACATTTACGTGGAGTGGACCAACAACGGGAAA<br>ACAGAGCTAAAACTACAAGAACACTGAACCAGTCCTGGACTC<br>TGATGGTTCTTACTTCATGTACAGCAAGCTGAGAGTGGAAA<br>AGAAGAACTGGGTGGAAAGAAATAGCTACTCCTGTTCAGTG<br>GTCCACGAGGGTCTGCACAATCACCACACGACTAAGAGCTT<br>CTCCCGGACTCCGGGTAAATGA |
| sTGFBRII | SEQ ID NO: 38 | AA | MGRGLLRGLWPLHIVLWTRIASTIPPHVPKSDVEMEAQKDASI<br>HLSCNRTIHPLKHFNSDVMASDNGGAVKLPQLCKFCDVRLST<br>CDNQKSCMSNCSITAICEKPHEVCVAVWRKNDKNITLETVCH<br>DPKLTYHGFTLEDAASPKCVMKEKKRAGETFFMCACNMEEC<br>NDYIIFSEEYTTSSPDPRGPTIKPCPPCKCPAPNLEGGPSVFIFPP<br>KIKDVLMISLSPIVTCVVVDVSEDDPDVQISWFVNNVEVHTAQ<br>TQTHREDYNSTLRVVSALPIQHQDWMSGKAFACAVNNKDLPA<br>PIERTISKPKGSVRAPQVYVLPPPEEEMTKKQVTLTCMVTDFM<br>PEDIYVEWTNNGKTELNYKNTEPVLDSDGSYFMYSKLRVEKK<br>NWVERNSYSCSVVHEGLHNHHTTKSFSRTPGK |
| GDF15 | SEQ ID NO: 39 | DNA | ATGGCCCCGCCCGCGCTCAGGCCCAGCCTCCAGGCGGCTC<br>TCAACTGAGGTTCCTGCTGTTCCTGCTGCTGTTGCTGCTGCT<br>GCTGTCATGGCCATCGCAGGGGACGCCCTGGCAATGCCTG<br>AACAGCGACCCTCCGGCCCTGAGTCCCAACTCAACGCCGAC |

APPENDIX B-continued

| Name | SEQ ID | Molecule Type | Sequence |
|---|---|---|---|
| | | | GAGCTACGGGGTCGCTTCCAGGACCTGCTGAGCCGGCTGCA
TGCCAACCAGAGCCGAGAGGACTCGAACTCAGAACCAAGT
CCTGACCCAGCTGTCCGGATACTCAGTCCAGAGGTGAGATT
GGGGTCCCACGGCCAGCTGCTACTCCGCGTCAACCGGGCGT
CGCTGAGTCAGGGTCTCCCCGAAGCCTACCGCGTGCACCGA
GCGCTGCTCCTGCTGACGCCGACGGCCCGCCCCTGGGACAT
CACTAGGCCCCTGAAGCGTGCGCTCAGCCTCCGGGGACCCC
GTGCTCCCGCATTACGCCTGCGCCTGACGCCGCCTCCGGAC
CTGGCTATGCTGCCCTCTGGCGGCACGCAGCTGGAACTGCG
CTTACGGGTAGCCGCCGGCAGGGGGCGCCGAAGCGCGCAT
GCGCACCCAAGAGACTCGTGCCCACTGGGTCCAGGGCGCTG
CTGTCACTTGGAGACTGTGCAGGCAACTCTTGAAGACTTGG
GCTGGAGCGACTGGGTGCTGTCCCCGCGCCAGCTGCAGCTG
AGCATGTGCGTGGGCGAGTGTCCCCACCTGTATCGCTCCGC
GAACACGCATGCGCAGATCAAAGCACGCCTGCATGGCCTGC
AGCCTGACAAGGTGCCTGCCCCGTGCTGTGTCCCCTCCAGC
TACACCCCGGTGGTTCTTATGCACAGGACAGACAGTGGTGT
GTCACTGCAGACTTATGATGACCTGGTGGCCCGGGGCTGCC
ACTGCGCTTGA |
| GDF15 | SEQ ID NO: 40 | AA | MAPPALQAQPPGGSQLRFLLFLLLLLLLLSWPSQGDALAMPEQ
RPSGPESQLNADELRGRFQDLLSRLHANQSREDSNSEPSPDPAV
RILSPEVRLGSHGQLLLRVNRASLSQGLPEAYRVHRALLLLTPT
ARPWDITRPLKRALSLRGPRAPALRLRLTPPPDLAMLPSGGTQ
LELRLRVAAGRGRRSAHAHPRDSCPLGPGRCCHLETVQATLE
DLGWSDWVLSPRQLQLSMCVGECPHLYRSANTHAQIKARLHG
LQPDKVPAPCCVPSSYTPVVLMHRTDSGVSLQTYDDLVARGC
HCA |
| hFoxp2 | SEQ ID NO: 41 | DNA | ATGATGCAGGAATCTGCGACAGAGACAATAAGCAACAGTTC
AATGAATCAAAATGGAATGAGCACTCTAAGCAGCCAATTAG
ATGCTGGCAGCAGAGATGGAAGATCAAGTGGTGACACCAG
CTCTGAAGTAAGCACAGTAGAACTGCTGCATCTGCAACAAC
AGCAGGCTCTCCAGGCAGCAAGACAACTTCTTTTACAGCAG
CAAACAAGTGGATTGAAATCTCCTAAGAGCAGTGATAAACA
GAGACCACTGCAGGTGCCTGTGTCAGTGGCCATGATGACTC
CCCAGGTGATCACCCCTCAGCAAATGCAGCAGATCCTTCAG
CAACAAGTCCTGTCTCCTCAGCAGCTACAAGCCCTTCTCCA
ACAACAGCAGGCTGTCATGCTGCAGCAGCAACAACTACAA
GAGTTTTACAAGAAACAGCAAGAGCAGTTACATCTTCAGCT
TTTGCAGCAGCAGCAACAGCAGCAGCAGCAACAACAG
CAGCAACAACAGCAGCAGCAACAACAACAACAGCAGC
AACAACAGCAGCAGCAGCAACAGCAGCAGCAGCAGCA
ACAGCATCCTGGAAAGCAAGCGAAAGAGCAGCAGCAGCAG
CAGCAGCAACAGCAATTGGCAGCCCAGCAGCTTGTCTTCCA
GCAGCAGCTTCTCCATATGCAACAACTCCAGCAGCAGCAGC
ATCTGCTCAGCCTTCAGCGTCAGGGACTCATCTCCATTCCAC
CTGGCCAGGCAGCACTTCCTGTCCAATCGCTGCCTCAAGCT
GGCTTAAGTCCTGCTGAGATTCAGCAGTTATGGAAAGAAGT
GACTGGAGTTCACAGTATGGAAGACAATGGCATTAAACATG
GAGGGCTAGACCTCACTACTAACAATTCCTCCTCGACTACC
TCCTCCAACACTTCCAAAGCATCACCACCAATAACTCATCA
TTCCATAGTGAATGGACAGTCTTCAGTTCTAAGTGCAAGAC
GAGACAGCTCGTCACATGAGGAGACTGGGGCCTCTCACACT
CTCTATGGCCATGGAGTTTGCAAATGGCCAGGCTGTGAAAG
CATTTGTGAAGATTTTGGACAGTTTTTAAAGCACCTTAACAA
TGAACACGCATTGGATGACCGAAGCACTGCTCAGTGTCGAG
TGCAAATGCAGGTGGTGCAACAGTTAGAAATACAGCTTTCT
AAAGAACGCGAACGTCTTCAAGCAATGATGACCCACTTGCA
CATGCGACCCTCAGAGCCCAAACCATCTCCCAAACCTCTAA
ATCTGGTGTCTAGTGTCACCATGTCGAAGAATATGTTGGAG
ACATCCCCACAGAGCTTACCTCAAACCCCTACCACACCAAC
GGCCCCAGTCACCCCGATTACCCAGGGACCCTCAGTAATCA
CCCCAGCCAGTGTGCCCAATGTGGGAGCCATACGAAGGCGA
CATTCAGACAAATACAACATTCCCATGTCATCAGAAATTGC
CCCAAACTATGAATTTTATAAAAATGCAGATGTCAGACCTC
CATTTACTTATGCAACTCTCATAAGGCAGGCTATCATGGAGT
CATCTGACAGGCAGTTAACACTTAATGAAATTTACAGCTGG
TTTACACGGACATTTGCTTACTTCAGGCGTAATGCAGCAACT
TGGAAGAATGCAGTACGTCATAATCTTAGCCTGCACAAGTG
TTTTGTTCGAGTAGAAAATGTTAAAGGAGCAGTATGGACTG
TGGATGAAGTAGAATACCAGAAGCGAAGGTCACAAAAGAT
AACAGGAAGTCCAACCTTAGTAAAAAATATACCTACCAGTT
TAGGCTATGGAGCAGCTCTTAATGCCAGTTTGCAGGCTGCC
TTGGCAGAGAGCAGTTTACCTTTGCTAAGTAATCCTGGACT
GATAAATAATGCATCCAGTGGCCTACTGCAGGCCGTCCACG
AAGACCTCAATGGTTCTCTGGATCACATTGACAGCAATGGA |

APPENDIX B-continued

| Name | SEQ ID | Molecule Type | Sequence |
|---|---|---|---|
| | | | AACAGTAGTCCGGGCTGCTCACCTCAGCCGCACATACATTC<br>AATCCACGTCAAGGAAGAGCCAGTGATTGCAGAGGATGAA<br>GACTGCCCAATGTCCTTAGTGACAACAGCTAATCACAGTCC<br>AGAATTAGAAGACGACAGAGAGATTGAAGAAGAGCCTTTA<br>TCTGAAGATCTGGAATGA |
| hFoxp2 | SEQ ID NO: 42 | AA | MMQESATETISNSSMNQNGMSTLSSQLDAGSRDGRSSGDTSSE<br>VSTVELLHLQQQQALQAARQLLLQQQTSGLKSPKSSDKQRPL<br>QVPVSVAMMTPQVITPQQMQQILQQQVLSPQQLQALLQQQQA<br>VMLQQQQLQEFYKKQQEQLHLQLLQQQQQQQQQQQQQQQ<br>QQQQQQQQQQQQQQQQQQQQQQQHPGKQAKEQQQQQQQ<br>QQLAAQQLVFQQQLLHMQQLQQQQHLLSLQRQGLISIPPGQA<br>ALPVQSLPQAGLSPAEIQQLWKEVTGVHSMEDNGIKHGGLDL<br>TTNNSSSTTSSNTSKASPPITHHSIVNGQSSVLSARRDSSSHEET<br>GASHTLYGHGVCKWPGCESICEDFGQFLKHLNNEHALDDRST<br>AQCRVQMQVVQQLEIQLSKERERLQAMMTHLHMRPSEPKPSP<br>KPLNLVSSVTMSKNMLETSPQSLPQTPTTPTAPVTPITQGPSVIT<br>PASVPNVGAIRRRHSDKYNIPMSSEIAPNYEFYKNADVRPPFTY<br>ATLIRQAIMESSDRQLTLNEIYSWFTRTFAYFRRNAATWKNAV<br>RHNLSLHKCFVRVENVKGAVWTVDEVEYQKRRSQKITGSPTL<br>VKNIPTSLGYGAALNASLQAALAESSLPLLSNPGLINNASSGLL<br>QAVHEDLNGSLDHIDSNGNSSPGCSPQPHIHSIHVKEEPVIAED<br>EDCPMSLVTTANHSPELEDDREIEEEPLSEDLE |
| mAtg5 | SEQ ID NO: 43 | DNA | ATGACAGATGACAAAGATGTGCTTCGAGATGTGTGGTTTGG<br>ACGAATTCCAACTTGCTTTACTCTCTATCAGGATGAGATAAC<br>TGAAAGAGAAGCAGAACCATACTATTTGCTTTTGCCAAGAG<br>TCAGCTATTTGACGTTGGTAACTGACAAAGTGAAAAAGCAC<br>TTTCAGAAGGTTATGAGACAAGAAGATGTTAGTGAGATATG<br>GTTTGAATATGAAGGCACACCCCTGAAATGGCATTATCCAA<br>TTGGTTTACTATTTGATCTTCTTGCATCAAGTTCAGCTCTTCC<br>TTGGAACATCACAGTACATTTCAAGAGTTTTCCAGAAAAGG<br>ACCTTCTACACTGTCCATCCAAGGATGCGGTTGAGGCTCACT<br>TTATGTCGTGTATGAAAGAAGCTGATGCTTTAAAGCATAAA<br>AGTCAAGTGATCAACGAAATGCAGAAAAAAGACCACAAGC<br>AGCTCTGGATGGGACTGCAGAATGACAGATTTGACCAGTTT<br>TGGGCCATCAACCGGAAACTCATGGAATATCCTCCAGAAGA<br>AAATGGATTTCGTTATATCCCCTTTAGAATATATCAGACCAC<br>GACGGAGCGGCCTTTCATCCAGAAGCTGTTCCGGCCTGTGG<br>CCGCAGATGGACAGCTGCACACACTTGGAGATCTCCTCAGA<br>GAAGTCTGTCCTTCCGCAGTCGCCCCTGAAGATGGAGAGAA<br>GAGGAGCCAGGTGATGATTCACGGGATAGAGCCAATGCTG<br>GAAACCCCTCTGCAGTGGCTGAGCGAGCATCTGAGCTACCC<br>AGATAACTTTCTTCATATTAGCATTGTCCCCCAGCCAACAGA<br>TTAA |
| mAtg5 | SEQ ID NO: 44 | AA | MTDDKDVLRDVWFGRIPTCFTLYQDEITEREAEPYYLLLPRVS<br>YLTLVTDKVKKHFQKVMRQEDVSEIWFEYEGTPLKWHYPIGL<br>LFDLLASSSALPWNITVHFKSFPEKDLLHCPSKDAVEAHFMSC<br>MKEADALKHKSQVINEMQKKDHKQLWMGLQNDRFDQFWAI<br>NRKLMEYPPEENGFRYIPFRIYQTTTERPFIQKLFRPVAADGQL<br>HTLGDLLREVCPSAVAPEDGEKRSQVMIHGIEPMLETPLQWLS<br>EHLSYPDNFLHISIVPQPTD |
| mBub1b | SEQ ID NO: 45 | DNA | ATGGCGGAGGCGAGTGAAGCCATGTGCCTGGAGGGAGCAG<br>AGTGGGAGCTGAGTAAAGAAAACATACAGCCCTTACGGCA<br>CGGGCGGGTCATGTCCACACTTCAGGGAGCTTTGGCAAAGC<br>AAGAGTCAGCTGGCCACACTGCTCTGCAGCAGCAGAAACG<br>GGCATTTGAATCTGAAATCCGCTTTTACTCTGGAGATGACCC<br>TCTGGATGTGTGGGACAGATATATTAATTGGACAGAACAGA<br>ACTACCCTCAAGGGGGAAGGAGAGTAACATGTCAGCGTTA<br>GTGGAGAGAGCGATAGAAGCACTCCAAGGAGAGACGCGCT<br>ATTATAATGACCCCCGCTTTCTCAGTCTCTGGATCAAATTGG<br>GACATTTGTGCAATGAACCTTTGGATATGTACAGCTATTTAC<br>AAAGCCAAGGAATTGGCGTTTCCCTTGCCCAGTTCTATATTT<br>CATGGGCTGAAGAATACGAAGCTAGAGAAAATTTCAAGAA<br>AGCGGACATAATATTTCAGGAAGGGATTGAACGCAAGGCTG<br>AGCCCCTGGACAGACTGCAGTCCCAGCACAGACAGTTCCAG<br>TCTCGAGTGTCGCGACAAGCTTTCTTGGCCCTTGGGAATGA<br>AGAGGAGGAGGCTTTGGAGCCTTCTGAACCACAGAGAAGCT<br>CGCTAGCTGAGCTGAAGAGCAGAGGGAAGAAGATGGCCAG<br>AGCGCCCATCAGCCGTCGGAAGTGCTCTGAAAGCTCCAG<br>GTCAGAGCAGAGGATTCCTAAATGCAGTTCCCCAGCCAGTA<br>CACGGTAATCGCAGGATCACCGTTTTTGATGAAAATGCCGA<br>TACCGCGTCTAGACCGGAGTTATCTAAGCCTGTAGCCCAGC<br>CATGGATGGCACCCCCTGTGCCCAGGGCCAAAGAGAACGA<br>ACTTCAGCCAGGCCCATGGAGCACAGACAGGCCGGTGGGA |

APPENDIX B-continued

| Name | SEQ ID | Molecule Type | Sequence |
|---|---|---|---|
| | | | CGCAGGCCTCATGACAATCCAGCCTCTGTGACGTCGATACC CAGCGTGCTTCCCAGCTTTACGCCGTACGTGGAAGAGAGCG CCCAGCAGACAGTCATGACACCATGCAAGATTGAGCCTAGT ATCAACCATGTTCTCAGCACCAGGAAGCCAGGAAGAGAAG AAGGAGACCCCTTGCAGAGAGTTCAGAGTCATCAGCAAGGC TGTGAGGAGAAGAAGGAGAAGATGATGTACTGTAAGGAGA AGATCTATGCCGGAGTTGGGGAGTTCTCCTTTGAGGAGATC CGAGCTGAAGTGTTCCGAAAGAAGCTGAAAGAACGAAGGG AAGCCGAGCTGTTGACCAGTGCAAAGAAGAGGGAGGAGAT GCAGAAGCAGATCGAAGAGATGGAGAGGAGGCTGAAGGCA ATGCAGGCTGTTCAGCAAGAAGGAGCTGGTGGCCAGCAAG AAGAGAAGATGCCTACAGAGGACCCAGCCAGATTGCAGAT TGCTTCGGGGCCTCAGGAAATGTCGGGAGTTCCTCTGTCCTG TTCCATCTGTCCACTAAGCTCGAATCCTAGGGAAATTTCACC TGCTGAGAACATTTTGCAAGAACAGCCTGATTCTAAAGGTT CCAGTATGCCTTTCTCCATTTTTGATGAGTCTCTTTCAGACA AAAAAGACAAAAGTCCTGCTACAGGTGGTCCACAGGTTCTC AATGCCCAGAGAAGACCCCTTTCAGTTCTCAAAACTACAGA AGTGGGCACCACAAATGAGGATGTGTCTCCCGATATTTGTG ATGAACTCACAGAACTTGAGCCTCTGAGTGAAGACGCCATC ATCACTGGTTTCAGGAACGTCACTCTCTGTCCCAACCCTGAG GACACTTGTGACTTTGCTAGAGCAGCTCGTTTGGCATCTACT CCTTTCCATGAGATACTGTCCTCGAAGGGCATCGCTGCTGAT CCCGAGGGACTGTTGCAGGAAGAGGATCTGGATGGGAAGG CCGCCGAGGCTCATCACACTGTTCATCACCAGGCCCTCATC ATAAAGAAACTGAGCCCAATTATTGAAGACAGCCGTGAGGC CACCCACTCATCTGGCTTCTCCAGGTCTTCTTCCTCAGCTCC CAGTACATCCTCCATCAAAGGCTTTCAGCTTCTGGAAAAGC TGGAGCTGACTAATGACGGGGCAGAAAATGCTATTCAGTCA CCCTGGTGTTCACAGTATCGCCTACAACTGTTAAAATCCCTA CTAGAGATAAGTGCTTTTGCGGAGTTTTCTGTGGAAGACCG ACCGATGCCTGTGCTGGAAATAGGGAAGGAGATTGAGTTAG GTCCTGAGGATTACGTCATCAAGCAAGAGCACCTAACATGT GACGATTACAGGTTATTCTGGGTGGCACCAAGAAGCTCTGC AGAGCTAACCATGATAAAGGCATCATCTCAGCCTATCCGT GGGATTTTTATATCAACCTCAAGTTGAAGGAGCGTCTGAAT GAGGACTATGACCAGCTTTGCAGCTGCTGTCAGTACCAAGA TGGCCATGTTGTTTGGTACCAGTATATAAACTGCTCCACCCT TCAGAATCTTCTCCAACACAGCGAATTTGTTACTCATGAAAT AATAGTGTTGATTATTTACAACCTCTTGACAATCGTGGAGA AGCTACACAGAGCTGAAATAGTGCACGGAGACTTGAGTCCA CGGAGTCTGATCCTACGAAACAGAATCCACGACCCCTATGA CTATGTAAATAAGGACGATCACGCTGTGAGGATCATGGACT TCTCCTACAGTGTTGACCTGAGGGTGCAGCTGGATGCGTTTG CCTATAGTGGCTTTCGGACTGCACAGATCCTGGAAGGACAA AAGATCCTGGCTAACTGTTCTTCTCCCTACCATGTAGATCTG TTGGGTATAGCAGACCTAGCGCACTTACTCCTGTTCAAGGA GCACCTCCATGTCTTCTGGGATGGACTCCTCTGGAAACTTAG CCAGAGCACCTCTGAGCTAAAAGACAGTGAATTGTGGAATA AATTCTTTGTGCGGATTCTGAATGCCAGTGACAAGTCCACA GTGTCTGTTCTGGGGGAGCTGGCAGCAGAAATGGGTGGGGC TTTTGATGCCACATTCCATAGCCACCTGAACAGAGCCCTGTG GAAGCTGGGGAAGACAATCAGCCCGGAAGCTTTGCTCACTC AGCAAGACAAGCAGCCAGGCGGCTCCCAGAGCCCTGCCTA A |
| mBub1b | SEQ ID NO: 46 | AA | MAEASEAMCLEGAEWELSKENIQPLRHGRVMSTLQGALAKQE SAGHTALQQQKRAFESEIRFYSGDDPLDVWDRYINWTEQNYP QGGKESNMSALVERATEALQGETRYYNDPRFLSLWIKLGHLCN EPLDMYSYLQSQGIGVSLAQFYISWAEEYEARENFKKADIIFQE GIERKAEPLDRLQSQHRQFQSRVSRQAFLALGNEEEEALEPSEP QRSSLAELKSRGKKMARAPISRVGSALKAPGQSRGFLNAVPQP VHGNRRITVFDENADTASRPELSKPVAQPWMAPPVPRAKENE LQPGPWSTDRPVGRRPHDNPASVTSIPSVLPSFTPYVEESAQQT VMTPCKIEPSINHVLSTRKPGREEGDPLQRVQSHQQGCEEKKE KMMYCKEKIYAGVGEFSFEEIRAEVFRKKLKERREAELLTSAK KREEMQKQIEEMERRLKAMQAVQQEGAGGQQEEKMPTEDPA RLQIASGPQEMSGVPLSCSICPLSSNPREISPAENILQEQPDSKGS SMPFSIFDESLSDKKDKSPATGGPQVLNAQRRPLSVLKTTEVGT TNEDVSPDICDELTELEPLSEDAIITGFRNVTLCPNPEDTCDFAR AARLASTPFHEILSSKGIAADPEGLLQEEDLDGKAAEAHHTVH HQALIIKKLSPIIEDSREATHSSGFSRSSSSAPSTSSIKGFQLLEKL ELTNDGAENAIQSPWCSQYRLQLLKSLLEISAFAEFSVEDRPMP VLEIGKEIELGPEDYVIKQEHLTCDDYRLFWVAPRSSAELTMIK ASSQPIPWDFYINLKLKERLNEDYDQLCSCCQYQDGHVVWYQ YINCSTLQNLLQHSEFVTHEIIVLIIYNLLTIVEKLHRAEIVHGDL SPRSLILRNRIHDPYDYVNKDDHAVRIMDFSYSVDLRVQLDAF |

APPENDIX B-continued

| Name | SEQ ID | Molecule Type | Sequence |
|---|---|---|---|
| | | | AYSGFRTAQILEGQKILANCSSPYHVDLLGIADLAHLLLFKEHL HVFWDGLLWKLSQSTSELKDSELWNKFFVRILNASDKSTVSVL GELAAEMGGAFDATFHSHLNRALWKLGKTISPEALLTQQDKQ PGGSQSPA |
| MCat | SEQ ID NO: 47 | DNA | ATGTCCGTCCTGACGCCGCTGCTGCTGCGGGGCTTGACAGG CTCGGCCCGGCGGCTCCCAGTGCCGCGCGCCAAGATCCATT CGTTGGGGGATCCACCGGTCGCCACCATGTCGGACAGTCGG GACCCAGCCAGCGACCAGATGAAGCAGTGGAAGGAGCAGC GGGCCTCGCAGAGACCTGATGTCCTGACCACCGGAGGCGGG AACCCAATAGGAGATAAACTTAATATCATGACCGCGGGGTC CCGAGGGCCCCTCCTCGTTCAGGATGTGGTTTTCACTGACGA GATGGCACACTTTGACAGAGAGCGGATTCCTGAGAGAGTGG TACACGCAAAAGGAGCAGGTGCTTTTGGATACTTTGAGGTC ACCCACGATATCACCAGATACTCCAAGGCAAAGGTGTTTGA GCATATTGGAAAGAGGACCCCTATTGCCGTTCGATTCTCCA CAGTCGCTGGAGAGTCAGGCTCAGCTGACACAGTTCGTGAC CCTCGGGGGTTTGCAGTGAAATTTTACACTGAAGATGGTAA CTGGGATCTTGTGGGAAACAACACCCCTATTTTCTTCATCAG GGATGCCATATTGTTTCCATCCTTTATCCATAGCCAGAAGAG AAACCCACAGACTCACCTGAAGGATCCTGACATGGTCTGGG ACTTCTGGAGTCTTCGTCCCGAGTCTCTCCATCAGGTTTCTT TCTTGTTCAGTGACCGAGGGATTCCCGATGGTCACCGGCAC ATGAATGGCTATGGATCACACACCTTCAAGTTGGTTAATGC AGATGGAGAGGCAGTCTATTGCAAGTTCCATTACAAGACCG ACCAGGGCATCAAAAACTTGCCTGTTGGAGAGGCAGGAAG GCTTGCTCAGGAAGATCCGGATTATGGCCTCCGAGATCTTTT CAATGCCATCGCCAATGGCAATTACCCGTCCTGGACGTTTTA CATCCAGGTCATGACTTTTAAGGAGGCAGAAACTTTCCCAT TTAATCCATTTGATCTGACCAAGGTTTGGCCTCACAAGGACT ACCCTCTTATACCAGTTGGCAAACTGGTTTTAAACAAAAAT CCAGTTAATTACTTTGCTGAAGTTGAACAGATGGCTTTTGAC CCAAGCAATATGCCCCCTGGCATCGAGCCCAGCCCTGACAA AATGCTTCAGGGCCGCCTTTTTTGCCTACCCGGACACTCACCG CCACCGCCTGGGACCCAACTATCTGCAGATACCTGTGAACT GTCCCTACCGCGCTCGAGTGGCCAACTACCAGCGTGATGGC CCCATGTGCATGCATGACAACAGGGTGGTGCCCCCAACTA TTACCCCAACAGCTTCAGCGCACCAGAGCAGCAGCGCTCAG CCCTGGAGCACAGCGTCCAGTGCGCTGTAGATGTGAAACGC TTCAACAGTGCTAATGAAGACAATGTCACTCAGGTGCGGAC ATTCTACACAAAGGTGTTGAACGAGGAGGAGAGGAAACGC CTGTGTGAGAACATTGCCGGCCACCTGAAGGACGCTCAGCT TTTTCATTCAGAAGAAAGCGGTCAAGAATTTCACTGACGTCC ACCCTGACTATGGGGCCCGCATCCAGGCTCTTCTGGACAAG TACAACGCTGAGAAGCCTAAGAACGCAATTCACACCTACAC GCAGGCCGGCTCTCACATGGCTGCGAAGGGAAAAGCTAAC CTGTAA |
| MCat | SEQ ID NO: 48 | AA | MSVLTPLLLRGLTGSARRLPVPRAKIHSLGDPPVATMSDSRDP ASDQMKQWKEQRASQRPDVLTTGGGNPIGDKLNIMTAGSRGP LLVQDVVFTDEMAHFDRERIPERVVHAKGAGAFGYFEVTHDI TRYSKAKVFEHIGKRTPIAVRFSTVAGESGSADTVRDPRGFAV KFYTEDGNWDLVGNNTPIFFIRDAILFPSFIHSQKRNPQTHLKD PDMVWDFWSLRPESLHQVSFLFSDRGIPDGHRHMNGYGSHTF KLVNADGEAVYCKFHYKTDQGIKNLPVGEAGRLAQEDPDYG LRDLFNAIANGNYPSWTFYIQVMTFKEAETFPFNPFDLTKVWP HKDYPLIPVGKLVLNKNPVNYFAEVEQMAFDPSNMPPGIEPSP DKMLQGRLFAYPDTHRHRLGPNYLQIPVNCPYRARVANYQRD GPMCMHDNQGGAPNYYPNSFSAPEQQRSALEHSVQCAVDVK RFNSANEDNVTQVRTFYTKVLNEEERKRLCENIAGHLKDAQLF IQKKAVKNFTDVHPDYGARIQALLDKYNAEKPKNAIHTYTQA GSHMAAKGKANL |
| mCisd2 | SEQ ID NO: 49 | DNA | ATGGTCCTGGACAGCGTGGCCCGCATCGTGAAGGTGCAGCT GCCCGCCTACCTCAAGCAGCTCCCGGTCCCGACAGCATCA CCGGGTTCGCCCGCCTCACAGTTTCAGACTGGCTCCGCCTAC TGCCCTTCCTGGGGTACTTGCGCTTCTGGGCTACCTCGCAG TGCGCCCATTCTTCCCAAAGAAGAAGCAACAGAAGGATAGC TTGATCAATCTTAAGATACAAAAGGAAAATCCCAAGGTGGT GAATGAGATAAACATTGAAGATCTGTGTCTCACCAAAGCAG CTTATTGTAGGTGCTGGCGGTCCAAGACGTTTCCTGCCTGTG ATGGATCCCATAATAAGCATAATGAATTGACAGGCGATAAC GTGGGTCCTCTCATCCTGAAGAAGAAAGAAGTATAA |

APPENDIX B-continued

| Name | SEQ ID | Molecule Type | Sequence |
|---|---|---|---|
| mCisd2 | SEQ ID NO: 50 | AA | MVLDSVARIVKVQLPAYLKQLPVPDSITGFARLTVSDWLRLLP<br>FLGVLALLGYLAVRPFFPKKKQQKDSLINLKIQKENPKVVNEIN<br>IEDLCLTKAAYCRCWRSKTFPACDGSHNKHNELTGDNVGPLIL<br>KKKEV |
| mFgf21 | SEQ ID NO: 51 | DNA | ATGGAATGGATGAGATCTAGAGTTGGGACCCTGGGACTGTG<br>GGTCCGACTGCTGCTGGCTGTCTTCCTGCTGGGGGTCTACCA<br>AGCATACCCCATCCCTGACTCCAGCCCCTCCTCCAGTTTGG<br>GGGTCAAGTCCGGCAGAGGTACCTCTACACAGATGACGACC<br>AAGACACTGAAGCCCACCTGGAGATCAGGGAGGATGGAAC<br>AGTGGTAGGCGCAGCACACCGCAGTCCAGAAAGTCTCCTGG<br>AGCTCAAAGCCTTGAAGCCAGGGGTCATTCAAATCCTGGGT<br>GTCAAAGCCTCTAGGTTTCTTTGCCAACAGCCAGATGGAGC<br>TCTCTATGGATCGCCTCACTTTGATCCTGAGGCCTGCAGCTT<br>CAGAGAACTGCTGCTGGAGGACGGTTACAATGTGTACCAGT<br>CTGAAGCCCATGGCCTGCCCCTGCGTCTGCCTCAGAAGGAC<br>TCCCCAAACCAGGATGCAACATCCTGGGGACCTGTGCGCTT<br>CCTGCCCATGCCAGGCCTGCTCCACGAGCCCCAAGACCAAG<br>CAGGATTCCTGCCCCAGAGCCCCCAGATGTGGGCTCCTCT<br>GACCCCCTGAGCATGGTAGAGCCTTTACAGGGCCGAAGCCC<br>CAGCTATGCGTCCTGA |
| mFgf21 | SEQ ID NO: 52 | AA | MEWMRSRVGTLGLWVRLLLAVFLLGVYQAYPIPDSSPLLQFG<br>GQVRQRYLYTDDDQDTEAHLEIREDGTVVGAAHRSPESLLEL<br>KALKPGVIQILGVKASRFLCQQPDGALYGSPHFDPEACSFRELL<br>LEDGYNVYQSEAHGLPLRLPQKDSPNQDATSWGPVRFLPMPG<br>LLHEPQDQAGFLPPEPPDVGSSDPLSMVEPLQGRSPSYAS |
| mKlotho | SEQ ID NO: 53 | DNA | ATGCTAGCCCGCGCCCTCCTCGCCGCCCGCCGCGGCTGGT<br>GCTGCTCCGTTTGCTGTTGCTGCATCTGCTGCTGCTCGCCCT<br>GCGCGCCCGCTGCCTGAGCGCTGAGCGGGTCAGGGCGCGC<br>AGACCTGGGCTCGCTTCGCGCGCGCTCCTGCCCCAGAGGCC<br>GCTGGCCTCCTCCACGACACCTTCCCCGACGGTTTCCTCTGG<br>GCGGTAGGCAGCGCCGCCGCCTATCAGACCGAGGGCGGCTGGC<br>GACAGCACGGCAAAGGCGCGTCCATCTGGGACACTTTCACC<br>CATCACTCTGGGGCGGCCCCGTCCGACTCCCCGATCGTCGT<br>GGCGCCGTCGGGTGCCCCGTCGCCTCCCCTGTCCTCCACTGG<br>AGATGTGGCCAGCGATAGTTACAACAACGTCTACCGCGACA<br>CAGAGGGGCTGCGCGAACTGGGGGTCACCCACTACCGCTTC<br>TCCATATCGTGGGCGCGGGTGCTCCCCAATGGCACCGCGGG<br>CACTCCCAACCGCGAGGGGCTGCGCTACTACCGGCGGCTGC<br>TGGAGCGGCTGCGGGAGCTGGGCGTGCAGCCGGTGGTTACC<br>CTGTACCATTGGGACCTGCCACAGCGCCTGCAGGACACCTA<br>TGGCGGATGGGCCAATCGCGCCCTGGCCGACCATTTCAGGG<br>ATTATGCCGAGCTCTGCTTCCGCCACTTCGGTGGTCAGGTCA<br>AGTACTGGATCACCATTGACAACCCCTACGTGGTGGCCTGG<br>CACGGGTATGCCACCGGGCGCCTGGCCCCGGGCGTGAGGG<br>GCAGCTCCAGGCTCGGGTACCTGGTTGCCCACAACCTACTT<br>TTGGCTCATGCCAAAGTCTGGCATCTCTACAACACCTCTTTC<br>CGCCCCACACAGGGAGGCCGGGTGTCTATCGCCTTAAGCTC<br>CCATTGGATCAATCCTCGAAGAATGACTGACTATAATATCA<br>GAGAATGCCAGAAGTCTCTTGACTTTGTGCTAGGCTGGTTTG<br>CCAAACCCATATTTATTGATGGCGACTACCCAGAGAGTATG<br>AAGAACAACCTCTCGTCTCTTCTGCCTGATTTTACTGAATCT<br>GAGAAGAGGCTCATCAGAGGAACTGCTGACTTTTTTGCTCT<br>CTCCTTCGGACCAACCTTGAGCTTTCAGCTATTGGACCCTAA<br>CATGAAGTTCCGCCAATTGGAGTCTCCAACCTGAGGCAGC<br>TTCTGTCTTGGATAGATCTGGAATATAACCACCCTCCAATAT<br>TTATTGTGGAAAATGGCTGGTTTGTCTCGGGAACCACCAAA<br>AGGGATGATGCCAAATATATGTATTATCTCAAGAAGTTCAT<br>AATGGAAACCTTAAAAGCAATCAGACTGGATGGGGTCGAC<br>GTCATTGGGTACACCGCGTGGTCGCTCATGGACGGTTTCGA<br>GTGGCATAGGGGCTACAGCATCCGGCGAGGACTCTTCTACG<br>TTGACTTTCTGAGTCAGGACAAGGAGCTGTTGCCAAAGTCT<br>TCGGCCTTGTTCTACCAAAAGCTGATAGAGGACAATGGCTT<br>TCCTCCTTTACCTGAAAACCAGCCCCTTGAAGGGACATTTCC<br>CTGTGACTTTGCTTGGGGAGTTGTTGACAACTACGTTCAAGT<br>GGACACTACTCTCTCAGTTTACTGACCCGAATGTCTATCT<br>GTGGGATGTGCATCACAGTAAGAGGCTTATTAAAGTAGACG<br>GGGTTGTAGCCAAGAAGAGAAAACCTTACTGTGTTGATTTC<br>TCTGCCATCCGGCCTCAGATAACCTTACTTGAGAAATGCG<br>GGTCACCCACTTTCGCTTCTCCCTGGACTGGGCCCTGATCTT<br>GCCTCTGGGTAACCAGACCCAAGTGAACCACACGGTTCTGC<br>ACTTCTACCGCTGCATGATCAGCGAGCTGGTGCACGCCAAC<br>ATCACTCCAGTGGTGGCCCTGTGGCAGCCAGCAGCCCCGCA<br>CCAAGGCCTGCCACATGCCCTTGCAAAACATGGGGCCTGGG<br>AGAACCCGCACACTGCTCTGGCGTTTGCAGACTACGCAAAC |

APPENDIX B-continued

| Name | SEQ ID | Molecule Type | Sequence |
|---|---|---|---|
| | | | CTGTGTTTTAAAGAGTTGGGTCACTGGGTCAATCTCTGGATC<br>ACCATGAACGAGCCAAACACACGGAACATGACCTATCGTGC<br>CGGGCACCACCTCCTGAGAGCCCATGCCTTGGCTTGGCATC<br>TGTACGATGACAAGTTTAGGGCGGCTCAGAAAGGCAAAATA<br>TCCATCGCCTTGCAGGCTGACTGGATAGAACCGGCCTGCCC<br>TTTCTCTCAAAATGACAAAGAAGTGGCCGAGAGAGTTTTGG<br>AATTTGATATAGGCTGGCTGGCAGAGCCTATTTTTGGTTCCG<br>GAGATTATCCACGTGTGATGAGGGACTGGCTGAACCAAAAA<br>ACAATTTTCTTTTGCCCTATTTCACCGAAGATGAAAAAAA<br>GCTAGTCCGGGGTTCCTTTGACTTCCTGGCCGGTGAGTCATTA<br>CACCACCATTCTGGTAGACTGGGAAAAGGAGGATCCGATGA<br>AATACAACGATTACTTGGAGGTACAGGAGATGACTGACATC<br>ACATGGCTCAACTCTCCCAGTCAGGTGGCAGTGGTGCCTTG<br>GGGGCTGCGCAAAGTGCTCAACTGGCTAAGGTTCAAGTACG<br>GAGACCTCCCGATGTATGTGACAGCCAATGGAATCGATGAT<br>GACCCCCACGCCGAGCAAGACTCACTGAGGATCTATTATAT<br>TAAGAATTATGTGAATGAGGCTCTGAAAGCCTACGTGTTGG<br>ACGACATCAACCTTTGTGGCTACTTTGCGTATTCACTTAGTG<br>ATCGCTCAGCTCCCAAGTCTGGCTTTTATCGATATGCTGCGA<br>ATCAGTTTGAGCCCAAACCATCTATGAAACATTACAGGAAA<br>ATTATTGACAGCAATGGCTTCCTGGGTTCTGGAACACTGGG<br>AAGGTTTTGTCCAGAAGAATACACTGTGTGCACCGAATGTG<br>GATTTTTTCAAACCCGGAAGTCTTTGCTGGTCTTCATCTCGT<br>TTCTTGTTTTTACTTTTATTATTTCTCTTGCTCTCATTTTTCAC<br>TACTCCAAGAAAGGCCAGAGAAGTTATAAGTAA |
| mKlotho | SEQ ID NO: 54 | AA | MLARAPPRRPPRLVLLRLLLLHLLLLALRARCLSAEPGQGAQT<br>WARFARAPAPEAAGLLHDTFPDGFLWAVGSAAYQTEGGWRQ<br>HGKGASIWDTFTHHSGAAPSDSPIVVAPSGAPSPPLSSTGDVAS<br>DSYNNVYRDTEGLRELGVTHYRFSISWARVLPNGTAGTPNRE<br>GLRYYRRLLERLRELGVQPVVTLYHWDLPQRLQDTYGGWAN<br>RALADHFRDYAELCFRHFGGQVKYWITIDNPYVVAWHGYAT<br>GRLAPGVRGSSRLGYLVAHNLLLAHAKVWHLYNTSFRPTQGG<br>RVSIALSSHWINPRRMTDYNIRECQKSLDFVLGWFAKPIFIDGD<br>YPESMKNNLSSLLPDFTESEKRLIRGTADFFALSFGPTLSFQLLD<br>PNMKFRQLESPNLRQLLSWIDLEYNHPPIFIVENGWFVSGTTKR<br>DDAKYMYYLKKFIMETLKAIRLDGVDVIGYTAWSLMDGFEW<br>HRGYSIRRGLFYVDFLSQDKELLPKSSALFYQKLIEDNGFPPLP<br>ENQPLEGTFPCDFAWGVVDNYVQVDTTLSQFTDPNVYLWDV<br>HHSKRLIKVDGVVAKKRKPYCVDFSAIRPQITLLREMRVTHFR<br>FSLDWALILPLGNQTQVNHTVLHFYRCMISELVHANITPVVAL<br>WQPAAPHQGLPHALAKHGAWENPHTALAFADYANLCFKELG<br>HWVNLWITMNEPNTRNMTYRAGHHLLRAHALAWHLYDDKF<br>RAAQKGKISIALQADWIEPACPFSQNDKEVAERVLEFDIGWLA<br>EPIFGSGDYPRVMRDWLNQKNNFLLPYFTEDEKKLVRGSFDFL<br>AVSHYTTILVDWEKEDPMKYNDYLEVQEMTDITWLNSPSQVA<br>VVPWGLRKVLNWLRFKYGDLPMYVTANGIDDDPHAEQDSLRI<br>YYIKNYVNEALKAYVLDDINLCGYFAYSLSDRSAPKSGFYRY<br>AANQFEPKPSMKHYRKIIDSNGFLGSGTLGRFCPEEYTVCTEC<br>GFFFQTRKSLLVFISFLVFTFIISLALIFHYSKKGQRSYK |
| mMt1 | SEQ ID NO: 55 | DNA | ATGGACCCCAACTGCTCCTGCTCCACCGGCGGCTCCTGCAC<br>TTGCACCAGCTCCTGCGCCTGCAAGAACTGCAAGTGCACCT<br>CCTGCAAGAAGAGTGAGTTGGGACACCTTGGGTGGCGGCTA<br>AGGCTAGGGGCGGGGAACTCCTACAAAACTGGCTCTGAGA<br>AATGTCCTTTGCTTCCCGGAGGCCATTGTATTGTCTCGGGGA<br>CAGAACTATACAGAGAACTATTTAAAAAAACCGAGGTCTTC<br>TCTGTTGGGACAGGAAGCAGAGGTCTTCAGCCAGGCTGAC<br>CTCTTCCTCCTCCTTTCTAGGCTGCTGCTCCTGCTGTCCCGTG<br>GGCTGCTCCAAATGTGCCCAGGGCTGTGTCTGCAAAGGCGC<br>CGCGGACAAGTGCACGTGCTGTGCCT |
| mMt1 | SEQ ID NO: 56 | AA | MDPNCSCSTGGSCTCTSSCACKCNCKCTSCKKSELGHLGWRLR<br>LGAGNSYKTGSEKCPLLPGGHCIVSGTELYRELFKKTEVFSVG<br>DRKQRSSARLTSSSSFLGCCSCCPVGCSKCAQGCVCKGAADK<br>CTCCA |
| mNeu1 | SEQ ID NO: 57 | DNA | ATGGTGGGGCAGACCCGACCAGACCCCGGGGACCGCTGA<br>GCTATTGGGCGGGCCGTCGGGGTCAGGGGCTCGCAGCGATC<br>TTCCTGCTCCTGGTGTCCGCGGCGGAATCCGAGGCCAGGGC<br>AGAGGATGACTTCAGCCTGGTGCAGCCGCTGGTGACCATGG<br>AGCAGCTGCTGTGGGTGAGCGGGAAGCAGATCGGCTCTGTA<br>GACACTTTCCGCATCCCGCTCATCACAGCCACCCCTCGGGG<br>CACGCTCCTGGCCTTCGCTGAGGCCAGGAAAAAATCTGCAT<br>CCGATGAGGGGGCCAAGTTCATCGCCATGAGGAGGTCCACG<br>GACCAGGGTAGCACGTGGTCCTCTACAGCCTTCATCGTAGA<br>CGATGGGGAGGCCTCCGATGGCCTGAACCTGGGCGCTGTGG |

| Name | SEQ ID | Molecule Type | Sequence |
|---|---|---|---|
| | | | TGAACGATGTAGACACAGGGATAGTGTTCCTTATCTATACC<br>CTCTGTGCTCACAAGGTCAACTGCCAGGTGGCCTCTACCAT<br>GTTGGTTTGGAGTAAGGACGACGGCATTTCCTGGAGCCCAC<br>CCCGGAATCTCTCTGTGGATATTGGCACAGAGATGTTTGCCC<br>CTGGACCTGGCTCAGGCATTCAGAAACAGCGGGAGCCTGGG<br>AAGGGCCGGCTCATTGTGTGTGGACACGGGACGCTGGAGCG<br>AGATGGGGTCTTCTGTCTCCTCAGTGATGACCACGGTGCCTC<br>CTGGCACTACGGCACTGGAGTGAGCGGCATTCCCTTTGGCC<br>AGCCCAAACACGATCACGATTTCAACCCCGACGAGTGCCAG<br>CCCTACGAGCTTCCAGATGGCTCGGTCATCATCAACGCCCG<br>GAACCAGAATAACTACCATTGCCGCTGCAGGATCGTCCTCC<br>GCAGCTATGACGCCTGTGACACCCTCAGGCCCCGGGATGTG<br>ACCTTCGACCCTGAGCTCGTGGACCCTGTGGTAGCTGCAGG<br>AGCACTAGCCACCAGCTCCGGCATTGTCTTCTTCTCCAATCC<br>AGCCCACCCTGAGTTCCGAGTGAACCTGACCCTGCGCTGGA<br>GTTTCAGCAATGGTACATCCTGGCTGAAGGAGAGGGTCCAG<br>GTGTGGCCGGGACCCAGCGGCTACTCGTCCCTGACAGCCCT<br>GGAAAACAGCACGGATGGAAAGAAGCAGCCCCCGCAGCTG<br>TTCGTTCTGTACGAGAAAGGCCTGAACCGGTACACCGAGAG<br>CATCTCCATGGTCAAAATCAGCGTCTACGGCACGCTCTGA |
| mNeu1 | SEQ ID NO: 58 | AA | MVGADPTRPRGPLSYWAGRRGQGLAAIFLLLVSAAESEARAE<br>DDFSLVQPLVTMEQLLWVSGKQIGSVDTFRIPLITATPRGTLLA<br>FAEARKKSASDEGAKFTAMRRSTDQGSTWSSTAFIVDDGEASD<br>GLNLGAVVNDVDTGIVFLIYTLCAHKVNCQVASTMLVWSKD<br>DGISWSPPRNLSVDIGTEMFAPGPGSSGIQKQREPGKGRLIVCGH<br>GTLERDGVFCLLSDDHGASWHYGTGVSGIPFGQPKHDHDFNP<br>DECQPYELPDGSVIINARNQNNYHCRCRIVLRSYDACDTLRPR<br>DVTFDPELVDPVVAAGALATSSGIVFFSNPAHPEFRVNLTLRW<br>SFSNGTSWLKERVQVWPGPSGYSSLTALENSTDGKKQPPQLFV<br>LYEKGLNRYTESISMVKISVYGTL |
| mNudt1 | SEQ ID NO: 59 | DNA | ATGAGCACCTCCAGGCTTTATACCCTTGTGCTAGTGCTACAG<br>CCTCAGCGAGTTCTCCTGGGCATGAAGAAGAGGGGCTTTGG<br>TGCTGGCCGCTGGAATGGCTTCGGGGGCAAGGTGCAGGAAG<br>GAGAGACCATTGAGGATGGGGCTAAGAGAGAGCTGCTGGA<br>AGAAAGTGGTCTGAGCGTGGATACACTGCACAAGGTAGGCC<br>ACATCTCGTTTGAATTTGTGGGCTCCCCTGAGCTGATGGACG<br>TGCATATCTTCTCGGCTGACCATGTGCACGGGACGCCCACA<br>GAGAGTGAAGAAATGCGCCCTCAGTGGTTCCAACTGGACCA<br>GATCCCCTTTGCCGACATGGGCCGGATGACAGCTACTGGT<br>TCCCACTCCTGCTTCAGAAGAAGAAGTTCTGTGGGCACTTC<br>AAGTTCCAGGATCAGGACACGATCCTCAGTTACTCGCTGCG<br>AGAGGTGGACTCATTCTAA |
| mNudt1 | SEQ ID NO: 60 | AA | MSTSRLYTLVLVLQPQRVLLGMKKRGFGAGRWNGFGGKVQE<br>GETIEDGAKRELLEESGLSVDTLHKVGHISFEFVGSPELMDVHI<br>FSADHVHGTPTESEEMRPQWFQLDQIPFADMVVPDDSYWFPLL<br>LQKKKFCGHFKFQDQDTILSYSLREVDSF |
| mPck1 | SEQ ID NO: 61 | DNA | ATGCCTCCTCAGCTGCATAACGGTCTGGACTTCTCTGCCAAG<br>GTCATCCAGGGCAGCCTCGACAGCCTGCCCCAGGCAGTGAG<br>GAAGTTCGTGGAAGGCAATGCTCAGCTGTGCCAGCCGGAGT<br>ATATCCACATCTGCGATGGCTCCGAGGAGGAGTACGGGCAG<br>TTGCTGACCCACATGCAGGAGGAGGGTGTCATCCGCAAGCT<br>GAAGAAATATGACAACTGTTGGCTGGCTCTCACTGACCCTC<br>GAGATGTGGCCAGGATCGAAAGCAAGACAGTCATCATCACC<br>CAAGAGCAGAGAGACACAGTGCCCATCCCCAAAACTGGCC<br>TCAGCCAGCTGGGCCGCTGGATGTCGGAAGAGGACTTTGAG<br>AAAGCATTCAACGCCAGGTTCCCAGGGTGCATGAAAGGCCG<br>CACCATGTATGTCATCCCATTCAGCATGGGGCCACTGGGCT<br>CGCCGCTGGCCAAGATTGGTATTGAACTGACAGACTCGCCC<br>TATGTGGTGGCCAGCATGCGGATCATGACTCGGATGGGCAT<br>ATCTGTGCTGGAGGCCCTGGGAGATGGGGAGTTCATCAAGT<br>GCCTGCACTCTGTGGGGTGCCCTCTCCCCTTAAAAAAGCCTT<br>TGGTCAACAACTGGGCCTGCAACCCTGAGCTGACCCTGATC<br>GCCCACCTCCCGGACCGCAGAGAGATCATCTCCTTTGGAAG<br>CGGATATGGTGGAACTCACTACTCGGGAAGAAATGCTTTG<br>CGTTGCGGATCGCCAGCCGTCTGGCTAAGGAGGAAGGGTGG<br>CTGGCGGAGCATATGCTGATCCTGGGCATAACTAACCCCGA<br>AGGCAAGAAGAATACCTGGCCGCAGCCTTCCCTAGTGCCT<br>GTGGGAAGACCAACTTGGCCATGATGAACCCCAGCCTGCCC<br>GGGTGGAAGGTCGAATGTGTGGGCGATGACATCGCCTGGAT<br>GAAGTTTGATGCCCAAGGCAACTTAAGGGCTATCAACCCAG<br>AAAACGGGTTTTTTGGAGTTGCTCCTGGCACCTCAGTGAAG<br>ACAAATCCAAATGCCATTAAAACCATCCAGAAAAACACCAT<br>CTTCACCAACGTGGCTGAGACTAGCGATGGGGGTGTTTACT |

APPENDIX B-continued

| Name | SEQ ID | Molecule Type | Sequence |
|---|---|---|---|
| | | | GGGAAGGCATCGATGAGCCGCTGGCCCCGGGAGTCACCATC<br>ACCTCCTGGAAGAACAAGGAGTGGAGACCGCAGGACGCGG<br>AACCATGTGCCCATCCCAACTCGAGATTCTGCACCCCTGCC<br>AGCCAGTGCCCCATTATTGACCCTGCCTGGAATCTCCAGA<br>AGGAGTACCCATTGAGGGTATCATCTTTGGTGGCCGTAGAC<br>CTGAAGGTGTCCCCCTTGTCTATGAAGCCCTCAGCTGGCAG<br>CATGGGGTGTTTGTAGGAGCAGCCATGAGATCTGAGGCCAC<br>AGCTGCTGCAGAACACAAGGGCAAGATCATCATGCACGAC<br>CCCTTTGCCATGCGACCCTTCTTCGGCTACAACTTCGGCAAA<br>TACCTGGCCCACTGGCTGAGCATGGCCCACCGCCCAGCAGC<br>CAAGTTGCCCAAGATCTTCCATGTCAACTGGTTCCGGAAGG<br>ACAAAGATGGCAAGTTCCTCTGGCCAGGCTTTGGCGAGAAC<br>TCCCGGGTGCTGGAGTGGATGTTCGGCGGATTGAAGGGGA<br>AGACAGCGCCAAGCTCACGCCCATCGGCTACATCCCTAAGG<br>AAAACGCCTTGAACCTGAAAGGCCTGGGGGGCGTCAACGTG<br>GAGGAGCTGTTTGGGATCTCTAAGGAGTTCTGGGAGAAGGA<br>GGTGGAGGAGATCGACAGGTATCTGGAGGACCAGGTCAAC<br>ACCGACCTCCCTTACGAAATTGAGAGGGAGCTCCGAGCCCT<br>GAAACAGAGAATCAGCCAGATGTAA |
| mPck1 | SEQ ID NO: 62 | AA | MPPQLHNGLDFSAKVIQGSLDSLPQAVRKFVEGNAQLCQPEYI<br>HICDGSEEEYGQLLTHMQEEGVIRKLKKYDNCWLALTDPRDV<br>ARIESKTVIITQEQRDTVPIPKTGLSQLGRWMSEEDFEKAFNAR<br>FPGCMKGRTMYVIPFSMGPLGSPLAKIGIELTDSPYVVASMRI<br>MTRMGISVLEALGDGEFIKCLHSVGCPLPLKKPLVNNWACNPE<br>LTLIAHLPDRREIISFGSGYYGGNSLLGKKCFALRIASRLAKEEG<br>WLAEHMLILGITNPEGKKKYLAAAFPSACGKTNLAMMNPSLP<br>GWKVECVGDDIAWMKFDAQGNLRAINPENGFFGVAPGTSVK<br>TNPNAIKTIQKNTIFTNVAETSDGGVYWEGIDEPLAPGVTITSW<br>KNKEWRPQDAEPCAHPNSRFCTPASQCPIIDPAWESPEGVPIEG<br>IIFGGRRPEGVPLVYEALSWQHGVFVGAAMRSEATAAAEHKG<br>KIIMHDPFAMRPFFGYNFGKYLAHWLSMAHRPAAKLPKIFHV<br>NWFRKDKDGKFLWPGFGENSRVLEWMFGRIEGEDSAKLTPIG<br>YIPKENALNLKGLGGVNVEELFGISKEFWEKEVEEIDRYLEDQ<br>VNTDLPYEIERELRALKQRISQM |
| mSirt6 | SEQ ID NO: 63 | DNA | ATGTGGCAGTCCTCCAGCGTGGTTTTCCACACGGGCGCCGG<br>CATCAGCACCGCCTCTGGCATCCCCGACTTCAGAGGCCCCC<br>ATGGCGTGTGGACCATGGAGGAACGCGGCCTGGCCCCCAA<br>GTTTGACACCACCTTCGAGAATGCTCGGCCCTCGAAGACCC<br>ACATGGCCCTGGTTCAGCTAGAACGCATGGGCTTCCTCAGC<br>TTCCTGGTCAGCCAGAACGTAGACGGGCTGCACGTGCGCTC<br>GGGCTTCCCCAGGGACAAGCTGGCAGAGCTGCACGGGAAAC<br>ATGTTTGTAGAGGAATGTCCCAAGTGTAAGACGCAGTACGT<br>CAGAGAGACACGGTTGTGGGCACCATGGGCCTCAAGGCCACA<br>GGCCGGCTCTGCACCGTGGCCAAGACCAGGGGACTTCGGGC<br>CTGTAGAGGGGAGCTGAGAGACACCATTCTGGACTGGGAG<br>GACTCGTTGCCTGACCGGGACCTGATGCTCGCTGATGAGGC<br>CAGCAGGACCGCAGACCTGTCTGTCACCCTGGGTACCTCGC<br>TGCAGATCCGCCCCAGTGGGAACCTGCCCCTTGCCACTAAG<br>CGCCGAGGAGGCCGTCTGGTCATTGTCAACCTGCAACCCAC<br>AAAAACATGACCGCCAGGCTGACCTGCGCATCCACGGCTACG<br>TGGATGAGGTGATGTGCAGACTCATGAAGCATCTGGGGCTG<br>GAGATTCCAGCCTGGGATGGACCCTGCGTGCTAGACAAAGC<br>CCTGCCACCTCTGCCTCGCCCAGTAGCACTCAAGGCTGAGC<br>CCCCCGTGCATCTCAATGGTGCAGTGCATGTTTCGTATAAGT<br>CCAAGCCCAACAGCCCTATACTCCACAGGCCCCCCAAAAGA<br>GTGAAGACCGAGGCTGCCCCCAGCTGA |
| mSirt6 | SEQ ID NO: 64 | AA | MWQSSSVVFHTGAGISTASGIPDFRGPHGVWTMEERGLAPKF<br>DTTFENARPSKTHMALVQLERMGFLSFLVSQNVDGLHVRSGF<br>PRDKLAELHGNMFVEECPKCKTQYVRDTVVGTMGLKATGRL<br>CTVAKTRGLRACRGELRDTILDWEDSLPDRDLMLADEASRTA<br>DLSVTLGTSLQIRPSGNLPLATKRRGGRLVIVNLQPTKHDRQA<br>DLRIHGYVDEVMCRLMKHLGLEIPAWDGPCVLDKALPPLPRP<br>VALKAEPPVHLNGAVHVSYKSKPNSPILHRPPKRVKTEAAPS |
| mTERT | SEQ ID NO: 65 | DNA | ATGACCCGCGCTCCTCGTTGCCCCGCGGTGCGCTCTCTGCTG<br>CGCAGCCGATACCGGGAGGTGTGGCCGCTGGCAACCTTTGT<br>GCGGCGCCTGGGGCCCGAGGGCAGGCGGCTTGTGCAACCC<br>GGGGACCCGAAGATCTACCGCACTTTGGTTGCCCAATGCCT<br>AGTGTGCATGCACTGGGGCTCACAGCCTCCACCTGCCGACC<br>TTTCCTTCCACCAGGTGTCATCCCTGAAAGAGCTGGTGGCCA<br>GGGTTGTGCAGAGACTCTGCGAGCGCAACGAGAGAAACGT<br>GCTGGCTTTTGGCTTTGAGCTGCTTAACGAGGCCAGAGGCG<br>GGCCTCCCATGGCCTTCACTAGTAGCGTGCGTAGCTACTTGC<br>CCAACACTGTTATTGAGACCCTGCGTGTCAGTGGTGCATGG |

APPENDIX B-continued

| Name | SEQ ID | Molecule Type | Sequence |
|---|---|---|---|
| | | | ATGCTACTGTTGAGCCGAGTGGGCGACGACCTGCTGGTCTA
CCTGCTGGCACACTGTGCTCTTTATCTTCTGGTGCCCCCCAG
CTGTGCCTACCAGGTGTGTGGGTCTCCCCTGTACCAAATTTG
TGCCACCACGGATATCTGGCCCTCTGTGTCCGCTAGTTACAG
GCCCACCCCGACCCGTGGGCAGGAATTTCACTAACCTTAGGT
TCTTACAACAGATCAAGAGCAGTAGTCGCCAGGAAGCACCG
AAACCCCTGGCCTTGCCATCTCGAGGTACAAAGAGGCATCT
GAGTCTCACCAGTACAAGTGTGCCTTCAGCTAAGAAGGCCA
GATGCTATCCTGTCCCGAGAGTGGAGGAGGGACCCCACAGG
CAGGTGCTACCAACCCCATCAGGCAAATCATGGGTGCCAAG
TCCTGCTCGGTCCCCCGAGGTGCCTACTGCAGAGAAAGATT
TGTCTTCTAAAGGAAAGGTGTCTGACCTGAGTCTCTCTGGGT
CGGTGTGCTGTAAACACAAGCCCAGCTCCACATCTCTGCTG
TCACCACCCCGCCAAAATGCCTTTCAGCTCAGGCCATTTATT
GAGACCAGACATTTCCTTTACTCCAGGGGAGATGGCCAAGA
GCGTCTAAACCCCTCATTCCTACTCAGCAACCTCCAGCCTAA
CTTGACTGGGGCCAGGAGACTGGTGGAGATCATCTTTCTGG
GCTCAAGGCCTAGGACATCAGGACCACTCTGCAGGACACAC
CGTCTATCGCGTCGATACTGGCAGATGCGGCCCCTGTTCCA
ACAGCTGCTGGTGAACCATGCAGAGTGCCAATATGTCAGAC
TCCTCAGGTCACATTGCAGGTTTCGAACAGCAAACCAACAG
GTGACAGATGCCTTGAACACCAGCCCACCGCACCTCATGGA
TTTGCTCCGCCTGCACAGCAGTCCCTGGCAGGTATATGGTTT
TCTTCGGGCCTGTCTCTGCAAGGTGGTGTCTGCTAGTCTCTG
GGGTACCAGGCACAATGAGCGCCGCTTCTTTAAGAACTTAA
AGAAGTTCATCTCGTTGGGGAAATACGGCAAGCTATCACTG
CAGGAACTGATGTGGAAGATGAAAGTAGAGGATTGCCACT
GGCTCCGCAGCAGCCCGGGGAAGGACCGTGTCCCCGCTGCA
GAGCACCGTCTGAGGGAGAGGATCCTGGCTACGTTCCTGTT
CTGGCTGATGGACACATACGTGGTACAGCTGCTTAGGTCAT
TCTTTTACATCACAGAGAGCACATTCCAGAAGAACAGGCTC
TTCTTCTACCGTAAGAGTGTGTGGAGCAAGCTGCAGAGCAT
TGGAGTCAGGCAACACCTTGAGAGAGTGCGGCTACGGGAG
CTGTCACAAGAGGAGGTCAGGCATCACCAGGACACCTGGCT
AGCCATGCCCATCTGCAGACTGCGCTTCATCCCCAAGCCCA
ACGGCCTGCGGCCCATTGTGAACATGAGTTATAGCATGGGT
ACCAGAGCTTTGGGCAGAAGGAAGCAGGCCCAGCATTTCAC
CCAGCGTCTCAAGACTCTCTTCAGCATGCTCAACTATGAGC
GGACAAAACATCCTCACCTTATGGGGTCTTCTGTACTGGGT
ATGAATGACATCTACAGGACCTGGCGGGCCTTTGTGCTGCG
TGTGCGTGCTCTGGACCAGACACCCAGGATGTACTTTGTTA
AGGCAGATGTGACCGGGGCCTATGATGCCATCCCCCAGGGT
AAGCTGGTGGAGGTTGTTGCCAATATGATCAGGCACTCGGA
GAGCACGTACTGTATCCGCCAGTATGCAGTGGTCCGGAGAG
ATAGCCAAGGCCAAGTCCACAAGTCCTTTAGGAGACAGGTC
ACCACCCTCTCTGACCTCCAGCCATACATGGGCCAGTTCCTT
AAGCATCTGCAGGATTCAGATGCCAGTGCACTGAGGAACTC
CGTTGTCATCGAGCAGAGCATCTCTATGAATGAGAGCAGCA
GCAGCCTGTTTGACTTCTTCCTGCACTTCCTGCGTCACAGTG
TCGTAAAGATTGGTGACAGGTGCTATACGCAGTGCCAGGGC
ATCCCCCAGGGCTCCAGCCTATCCACCCTGCTCTGCAGTCTG
TGTTTCGGAGACATGGAGAACAAGCTGTTTGCTGAGGTGCA
GCGGGATGGGTTGCTTTTACGTTTTGTTGATGACTTTCTGTT
GGTGACGCCTCACTTGGACCAAGCAAAAACCTTCCTCAGCA
CCCTGGTCCATGGCGTTCCTGAGTATGGGTGCATGATAAAC
TTGCAGAAGACAGTGGTGAACTTCCCTGTGGAGCCTGGTAC
CCTGGGTGGTGCAGCTCCATACCAGCTGCCTGCTCACTGCCT
GTTTCCCTGGTGTGGCTTGCTGCTGGACACTCAGACTTTGGA
GGTGTTCTGTGACTACTCAGGTTATGCCCAGACCTCAATTAA
GACGAGCCTCACCTTCCAGAGTGTCTTCAAAGCTGGGAAGA
CCATGCGGAACAAGCTCCTGTCGGTCTTGCGGTTGAAGTGT
CACGGTCTATTTCTAGACTTGCAGGTGAACAGCCTCCAGAC
AGTCTGCATCAATATACAAGATCTTCCTGCTTCAGGCCTA
CAGGTTCCATGCATGTGTGATTCAGCTTCCCTTTGACCAGCG
TGTTAGGAAGAACCTCACATTCTTTCTGGGCATCATCTCCAG
CCAAGCATCCTGCTGCTATGCTATCCTGAAGGTCAAGAATC
CAGGAATGACACTAAAGGCCTCTGGCTCCTTTCCTCCTGAA
GCCGCACATTGGCTCTGCTACCAGGCCTTCCTGCTCAAGCTG
GCTGCTCATTCTGTCATCTACAAATGTCTCCTGGGACCTCTG
AGGACAGCCCAAAAACTGCTGTGCCGGAAGCTCCCAGAGG
CGACAATGACCATCCTTAAAGCTGCAGCTGACCCAGCCCTA
AGCACAGACTTTCAGACCATTTTGGACTAA |
| mTERT | SEQ ID NO: 66 | AA | MTRAPRCPAVRSLLRSRYREVWPLATFVRRLGPEGRRLVQPG
DPKIYRTLVAQCLVCMHWGSQPPPADLSFHQVSSLKELVARV
VQRLCERNERNVLAFGFELLNEARGGPPMAFTSSVRSYLPNTV
IETLRVSGAWMLLLSRVGDDLLVYLLAHCALYLLVPPSCAYQ |

APPENDIX B-continued

| Name | SEQ ID | Molecule Type | Sequence |
|---|---|---|---|
| | | | VCGSPLYQICATTDIWPSVSASYRPTRPVGRNFTNLRFLQQIKS SSRQEAPKPLALPSRGTKRHLSLTSTSVPSAKKARCYPVPRVEE GPHRQVLPTPSGKSWVPSPARSPEVPTAEKDLSSKGKVSDLSLS GSVCCKHKPSSTSLLSPPRQNAFQLRPFIETRHFLYSRGDGQER LNPSFLLSNLQPNLTGARRLVEIIFLGSRPRTSGPLCRTHRLSRR YWQMRPLFQQLLVNHAECQYVRLLRSHCRFRTANQQVTDAL NTSPPHLMDLLRLHSSPWQVYGFLRACLCKVVSASLWGTRHN ERRFFKNLKKFISLGKYGKLSLQELMWKMKVEDCHWLRSSPG KDRVPAAEHRLRERILATFLFWLMDTYVVQLLRSFFYITESTFQ KNRLFFYRKSVWSKLQSIGVRQHLERVRLRELSQEEVRHHQD TWLAMPICRLRFTPKPNGLRPIVNMSYSMGTRALGRRKQAHF TQRLKTLFSMLNYERTKHPHLMGSSVLGMNDIYRTWRAFVLR VRALDQTPRMYFVKADVTGAYDAIPQGKLVEVVANMIRHSES TYCIRQYAVVRRDSQGQVHKSFRRQVTTLSDLQPYMGQFLKH LQDSDASALRNSVVIEQSISMNESSSSLFDFFLHFLRHSVVKIGD RCYTQCQGIPQGSSLSTLLCSLCFGDMENKLFAEVQRDGLLLR FVDDFLLVTPHLDQAKTFLSTLVHGVPEYGCMINLQKTVVNFP VEPGTLGGAAPYQLPAHCLFPWCGLLLDTQTLEVFCDYSGYA QTSIKTSLTFQSVFKAGKTMRNKLLSVRLKCHGLFLDLQVNS LQTVCINIYKIFLLQAYRFHACVIQLPFDQRVRKNLTFFLGIISS QASCCYAILKVKNPGMTLKASGSFPPEAAHWLCYQAFLLKLA AHSVIYKCLLGPLRTAQKLLCRKLPEATMTILKAAADPALSTD FQTILD |
| mTfeb | SEQ ID NO: 67 | DNA | ATGGCGTCACGCATCGGGCTGCGCATGCAGCTCATGCGGGA GCAGGCCCAGCAGGAGGAGCAGCGAGAGCGCATGCAGCAG CAGGCTGTCATGCATTATATGCAACAGCAGCAGCAGCAGCA GCAGCAGCTGGGTGGGCCCCCCACCCCAGCCATCAACACCC CTGTCCACTTCCAGTCGCCCCCGCCTGTGCCCGGGGAGGTG CTGAAGGTGCAGTCCTACCTGGAGAACCCCACCTCCTACCA CCTGCAACAGTCCCAGCATCAGAAGGTTCGGAAGTATCTGT CTGAGACCTATGGGAACAAGTTTGCTGCCCACGTGAGCCCA GCCCAAGGTTCCCCGAAGCCTGCCCCAGCAGCATCCCCAGG GGTGCGGGCTGGACACGTACTGTCCACCTCGGCCGGCAACA GTGCTCCCAACAGTCCCATGGCCATGCTACATATCAGCTCC AACCCCGAGAAAGAGTTTGATGATGTCATTGACAACATTAT GCGCCTGGACAGCGTGCTGGGCTACATCAACCCTGAGATGC AGATGCCTAACACGCTGCCCCTGTCTAGCAGCCACCTGAAC GTGTACAGCGGTGACCCCCAGGTCACAGCCTCCATGGTGGG TGTCACCAGCAGCTCCTGCCCTGCCGACCTGACTCAGAAGC GAGAGCTAACAGATGCTGAGAGCAGAGCCCTGGCCAAGGA GCGGCAGAAGAAAGACAATCACAACCTAATTGAGAGAAGA CGCAGGTTCAACATCAATGACCGGATCAAGGAGCTGGGAAT GCTGATCCCCAAGGCCAACGACCTGGACGTGCGCTGGAACA AAGGCACCATCCTCAAGGCCTCTGTGGATTACATCCGGAGG ATGCAGAAGGACCTGCAGAAGTCCCGGGAGCTGGAGAACC ACTCCCGGCGCCTGGAGATGACTAACAAGCAGCTCTGGCTC CGCATCCAGGAGCTGGAGATGCAGGCACGCGTGCACGGCCT CCCCACCACCTCGCCGTCGGGTGTGAATATGGCCGAGCTGG CCCAGCAGGTGGTGAAGCAAGAGTTGCCCAGTGAGGATGG CCCAGGGGAGGCGCTGATGCTGGGGCCTGAGGTCCCTGAGC CTGAGCAAATGCCGGCTCTTCCTCCCCAGGCTCCGCTGCCCT CGGCCGCCCAGCCACAGTCTCCGTTCCATCACCTGGACTTC AGCCATGGCCTGAGCTTTGGGGGTGGGGCGACGAGGGGC CCACAGGTTACCCCGATACCCTGGGGACAGAGCACGGCTCC CCATTCCCCAACCTGTCCAAGAAGGATCTGGACTTAATGCT CCTAGATGACTCCCTGCTCCCCCTGGCCTCTGACCCCCTCTT TTCTACCATGTCTCCTGAGGCCTCCAAGGCCAGCAGCCGCC GGAGCAGCTTCAGCATGGAGGAGGGTGATGTTCTGTGA |
| mTfeb | SEQ ID NO: 68 | AA | MASRIGLRMQLMREQAQQEEQRERMQQQAVMHYMQQQQQQ QQQLGGPPTPAINTPVHFQSPPPVPGEVLKVQSYLENPTSYHLQ QSQHQKVRKYLSETYGNKFAAHVSPAQGSPKPAPAASPGVRA GHVLSTSAGNSAPNSPMAMLHISSNPEKEFDDVIDNIMRLDSV LGYINPEMQMPNTLPLSSSHLNVYSGDPQVTASMVGVTSSSCP ADLTQKRELTDAESRALAKERQKKDNHNLIERRRRFNINDRIK ELGMLIPKANDLDVRWNKGTILKASVDYIRRMQKDLQKSREL ENHSRRLEMTNKQLWLRIQELEMQARVHGLPTTSPSGVNMAE LAQQVVKQELPSEDGPGEALMLGPEVPEPEQMPALPPQAPLPS AAQPQSPFHHLDFSHGLSFGGGGDEGPTGYPDTLGTEHGSPFP NLSKKDLDLMLLDDSLLPLASDPLFSTMSPEASKASSRRSSFSM EEGDVL |
| mTxn1 | SEQ ID NO: 69 | DNA | ATGGTGAAGCTGATCGAGAGCAAGGAAGCTTTTCAGGAGGC CCTGGCCGCCGCGGGAGACAAGCTTGTCGTGGTGGACTTCT CTGCTACGTGGTGTGGACCTTGCAAAATGATCAAGCCCTTCT TCCATTCCCTCTGTGACAAGTATTCCAATGTGGTGTTCCTTG |

APPENDIX B-continued

| Name | SEQ ID | Molecule Type | Sequence |
|---|---|---|---|
| | | | AAGTGGATGTGGATGACTGCCAGGATGTTGCTGCAGACTGT<br>GAAGTCAAATGCATGCCGACCTTCCAGTTTTATAAAAAGGG<br>TCAAAAGGTGGGGGAGTTCTCCGGTGCTAACAAGGAAAAG<br>CTTGAAGCCTCTATTACTGAATATGCCTAA |
| mTxn1 | SEQ ID NO: 70 | AA | MVKLIESKEAFQEALAAAGDKLVVVDFSATWCGPCKMIKPFF<br>HSLCDKYSNVVFLEVDVDDCQDVAADCEVKCMPTFQFYKKG<br>QKVGEFSGANKEKLEASITEYA |
| mUcp1 | SEQ ID NO: 71 | DNA | ATGGTGAACCCGACAACTTCCGAAGTGCAACCCACCATGGG<br>GGTCAAGATCTTCTCAGCCGGAGTTTCAGCTTGCCTGGCAG<br>ATATCATCACCTTCCCGCTGGACACTGCCAAAGTCCGCCTTC<br>AGATCCAAGGTGAAGGCCAGGCTTCCAGTACCATTAGGTAT<br>AAAGGTGTCCTAGGGACCATCACCACCCTGGCAAAAACAG<br>AAGGATTGCCGAAACTGTACAGCGGTCTGCCTGCGGGCATT<br>CAGAGGCAAATCAGCTTTGCCTCACTCAGGATTGGCCTCTA<br>CGACTCAGTCCAAGAGTACTTCTCTTCAGGGAGAGAAACAC<br>CTGCCTCTCTCGGAAACAAGATCTCAGCCGGCTTAATGACT<br>GGAGGTGTGGCAGTGTTCATTGGGCAGCCTACAGAGGTCGT<br>GAAGGTCAGAATGCAAGCCCAGAGCCATCTGCATGGGATCA<br>AACCCCGCTACACGGGGACCTACAATGCTTACAGAGTTATA<br>GCCACCACAGAAAGCTTGTCAACACTTTGGAAAGGGACGAC<br>CCCTAATCTAATGAGAAATGTCATCATCAATTGTACAGAGC<br>TGGTAACATATGACCTCATGAAGGGGGCCCTTGTAAACAAC<br>AAAATACTGGCAGATGACGTCCCCTGCCATTTACTGTCAGC<br>TCTTGTTGCCGGGTTTTGCACCACACTCCTGGCCTCTCCAGT<br>GGATGTGGTAAAAACAAGATTCATCAACTCTCTGCCAGGAC<br>AGTACCCAAGCGTACCAAGCTGTGCGATGTCCATGTACACC<br>AAGGAAGGACCGACGGCCTTTTTCAAAGGGTTTGTGGCTTC<br>TTTTCTGCGACTCGGGTCCTGGAACGTCATCATGTTTGTGTG<br>CTTTGAACAGCTGAAAAAGAGCTGATGAAGTCCAGACAG<br>ACAGTGGATTGTACCACATAA |
| mUcp1 | SEQ ID NO: 72 | AA | MVNPTTSEVQPTMGVKIFSAGVSACLADIITFPLDTAKVRLQIQ<br>GEGQASSTIRYKGVLGTITTLAKTEGLPKLYSGLPAGIQRQISFA<br>SLRIGLYDSVQEYFSSGRETPASLGNKISAGLMTGGVAVFIGQP<br>TEVVKVRMQAQSHLHGIKPRYTGTYNAYRVIATTESLSTLWK<br>GTTPNLMRNVIINCTELVTYDLMKGALVNNKILADDVPCHLLS<br>ALVAGFCTLLLASPVDVVKTRFINSLPGQYPSVPSCAMSMYTK<br>EGPTAFFKGFVASFLRLGSWNVIMFVCFEQLKKELMKSRQTV<br>DCTT |
| nmr Has2 | SEQ ID NO: 73 | DNA | ATGCATTGTGAGAGGTTTCTATGTGTCCTGAGAATAATTGG<br>AACTACACTTTTTGGAGTGTCTCTCCTCCTCGGAATCACAGC<br>TGCTTATATTGTTGGCTACCAGTTTATCCAAACAGATAATTA<br>CTACTTCTCATTTGGACTGTACGGTGCCTTTTTAGCCTCGCA<br>TCTCATCATCCAAAGCCTCTTTGCCTTTTTGGAACACCGGAA<br>AATGAAGAAGTCCCTTGAAACCCCGATTAAATTGAACAAAA<br>CGGTAGCACTCTGCATCGCTGCGTACCAAGAGGACCCTGAC<br>TACTTACGGAAATGTTTGCAATCTGTGAAAAGGCTGACCTA<br>CCCTGGGATTAAAGTCGTGATGGTCATCGATGGGAACTCAG<br>ACGACGACCTTTACATGATGGACATATTCAGCGAAGTTATG<br>GGCAGGGACAAATCGGCCACGTACATCTGGAAGAACAACTT<br>TCATGAAAAGGGACCTGGTGAGACAGAAGAGTCCCATAAA<br>GAAAGTTCACAACATGTCACCCAATTGGTCTTGTCTAGCAA<br>AAGTGTTTGCATCATGCAAAAATGGGGTGGAAAGAGAGAA<br>GTCATGTACACAGCCTTCAGAGCACTGGGGCGAAGCGTGGA<br>TTATGTACAGGTGTGTGACTCAGATACTATGCTTGACCCTGC<br>CTCATCTGTGGAGATGGTGAAGGTCTTAGAGGAAGACCCTA<br>TGGTTGGAGGTGTTGGAGGAGATGTCCAGATTTTAAACAAG<br>TATGATTCCTGGATCTCCTTCCTCAGCAGCGTGAGATACTGG<br>ATGGCTTTTAATATAGAAAGGGCCTGCCAGTCTTATTTTGGC<br>TGTGTCCAGTGCATAAGCGGTCCTCTGGGAATGTACAGAAA<br>CTCCTTGCTGCATGAATTTGTGGAAGACTGGTACAGTCAGG<br>AATTCATGGGTAACCAATGCAGTTTTGGTGACGACAGGCAC<br>CTTACCAACAGGGTGTTGAGTCTGGGCTATGCAACTAAATA<br>CACGGCTCGGTCCAAGTGCCTTACTGAAACTCCCATAGAAT<br>ATCTGAGATGGCTGAACCAGCAGACCCGTTGGAGCAAGTCC<br>TACTTCCGAGAGTGGCTGTACAATGCCATGTGGTTTCACAA<br>GCATCACTTGTGGATGACCTATGAAGCTGTTATCACTGGATT<br>CTTTCCTTTCTTTCATTGCCACAGTCATCCAGCTCTTCTAC<br>AGGGGTAAAATCTGGAACATCCTCCTCTTCCTGTTAACTGTC<br>CAGCTAGTGGGTCTCATCAAGTCATCTTTTGCCAGCTGCCTT<br>AGAGGAAATATCGTCATGGTATTCATGTCTCTGATTCAGTG<br>TTATACATGTCAAGTCTACTTCCTGCCAAGATGTTTGCAATT<br>GCAACCATAAACAAAGCTGGGTGGGGCACATCTGGAAGGA<br>AGACCATTGTTGTTAATTTCATAGGACTTATTCCAGTGTCCG |

APPENDIX B-continued

| Name | SEQ ID | Molecule Type | Sequence |
|---|---|---|---|
| | | | TGTGGTTTACAATCCTTCTAGGTGGTGTAATTTTCACCATTT ATAAGGAATCTAAAAAGCCATTTTCCGAATCCAAACAGACT GTTCTCATCGTGGGAACTTTGATCTATGCATGCTACTGGGTC ATGCTTTTGACTCTCTATGTGGTTCTCATCAATAAGTGTGGC AGGCGGAAGAAGGGACAACAGTATGACATGGTGCTTGATG TATGA |
| nmr Has2 | SEQ ID NO: 74 | AA | MHCERFLCVLRIIGTTLFGVSLLLGITAAYIVGYQFIQTDNYYFS FGLYGAFLASHLIIQSLFAFLEHRKMKKSLETPIKLNKTVALCIA AYQEDPDYLRKCLQSVKRLTYPGIKVVMVIDGNSDDDLYMM DIFSEVMGRDKSATYIWKNNFHEKGPGETEESHKESSQHVTQL VLSSKSVCIMQKWGGKREVMYTAFRALGRSVDYVQVCDSDT MLDPASSVEMVKVLEEDPMVGGVGGDVQILNKYDSWISFLSS VRYWMAFNIERACQSYFGCVQCISGPLGMYRNSLLHEFVEDW YSQEFMGNQCSFGDDRHLTNRVLSLGYATKYTARSKCLTETPI EYLRWLNQQTRWSKSYFREWLYNAMWFHKHHLWMTYEAVI TGFFPPFFLIATVIQLFYRGKIWNILLFLLTVQLVGLIKSSFASCLR GNIVMVFMSLYSVLYMSSLLPAKMFAIATINKAGWGTSGRKTI VVNFIGLIPVSVWFTILLGGVIFTIYKESKKPFSESKQTVLIVGTL IYACYWVMLLTLYVVLINKCGRRKKGQQYDMVLDV |
| Adcy5-Coq7 | SEQ ID NO: 75 | DNA | CCAAGGTATATTGCTGTTGACAGTGAGCGACGCTGCAGATA TTCCGCTCTAAGTGAAGCCACAGATGTTAGAGCGGAAAATC TGCAGAGCTGCCTACTGCCTCGGACTTCAAGGGGCTTGCGG CCGCCATCTCCATGGCTGTACCACCTTGTCGGCCAGGTTACT ACAGATATGTATGTTGAATCTCATTACATATCTGTTGTAACC TGCTCTGACATTTTGGTATCTTTCATCTGACCACGTACTACC TTCTATCTGATGTGACAGCTTCTGTAGCACCAGATGAAGATT GGGCTCAATGTTTAGTTATTTGAGCCCAAGCTTCATCTGTGT ACTGCTAGCTGTAGAACTCCAGCTTCGGCCTGTAACTTATGA TAGCAATGTCAGCAGTGCCTGGCAGCCGTGGATCGAATAAT TTAAGATTCTAAAATTATAGTATTCGATCAACGGCTGCAAA GTAAGGTTGACCATACTCTACAGTTGTTGATTTCGTGGCTAC AGAGTTTCCTTAGCAGAGCTGGATGCAGTGCAGCCATATAT TTGTCTAAACTATAATATATGGCTGCACTGCATATAGCTACT GCTAGGCAATCCTTCCCTCGATAAGATGCAGCGGCGGCTCC TCTCCCCATGGCCCTGGCCTTGTTGAAGAGGATTATCCTGGG CTCAGAGATAATCCTCTACAACAAGGGCAGGGACCTGGGGA CCCCGGCACCGGCAGGCTAGC |
| Agtr1a-Adcy5-alct1-ikbkb | SEQ ID NO: 76 | DNA | GGCCAAGGTATATTGCTGTTGACAGTGAGCGACGCTGCAGA TATTCCGCTCTAAGTGAAGCCACAGATGTTAGAGCGGAAAA TCTGCAGAGCTGCCTACTGCCTCGGACTTCAAGGGGCTTGC GGCCGCCATCTCCATGGCTGTACCACCTTGTCGGCCAGGTT ACTACAGATATGTATGTTGAATCTCATTACATATCTGTTGTA ACCTGCTCTGACATTTTGGTATCTTTCATCTGACCACGTACT ACCTTCTATCTGATGTGACAGCTTCTGTAGCACCCTGTTACT ACACATACTTTTGTTTAGTTATAAAGTATGTGGAGTAACAG GTGTACTGCTAGCTGTAGAACTCCAGCTTCGGCCTGTAACTT ATGATAGCAATGTCAGCAGTGCCTCCTGTTCCCTTTCCTAAT CATTTAAGATTCTAAAATTATAGGATTAGGAATGGGAACAG TAAGTAAGGTTGACCATACTCTACAGTTGTTGATTTCGTGGC TACAGAGTTTCCTTAGCAGAGCTGTGGCACCTTTATTGGCTA CAATGTCTAAACTATTTGTAGCCAATAAAGGTGCCCTAGCT ACTGCTAGGCAATCCTTCCCTCGATAAGTATGGGGCCTGGC TCGAGCAGGGGGCGAGGGATGCATCTAGTAGAGCGGATGA TTGGTCCCCTCCCTTAACAAGTCGAACTGTCTTGTCCTTCCC TCCCAATGACCGCGTCTTCGTCACAGTCAGCGGCGGCTCCT CTCCCCATGGCCCTGATGCTGTCCCTGGTCCTTATGCTGGGC TCAGAATACCTGGTGTGAGTCTCAGTCAGGGACCTGGGGAC CCCGGCACCGGCAGGCTA |
| Agtr1a-Adcy5-Coq7 | SEQ ID NO: 77 | DNA | CCAAGGTATATTGCTGTTGACAGTGAGCGACGCTGCAGATA TTCCGCTCTAAGTGAAGCCACAGATGTTAGAGCGGAAAATC TGCAGAGCTGCCTACTGCCTCGGACTTCAAGGGGCTTGCGG CCGCCATCTCCATGGCTGTACCACCTTGTCGGCCAGGTTACT ACAGATATGTATGTTGAATCTCATTACATATCTGTTGTAACC TGCTCTGACATTTTGGTATCTTTCATCTGACCACGTACTACC TTCTATCTGATGTGACAGCTTCTGTAGCACCCTGTTACTACA CATACTTTTGTTTAGTTATAAAGTATGTGGAGTAACAGGTGT ACTGCTAGCTGTAGAACTCCAGCTTCGGCCTGTAACTTATGA TAGCAATGTCAGCAGTGCCTCCTGTTCCCTTTCCTAATCATT TAAGATTCTAAAATTATAGGATTAGGAATGGGAACAGTAAG TAAGGTTGACCATACTCTACAGTTGTTGATTTCGTGGCTACA GAGTTTCCTTAGCAGAGCTGGATGCAGTGCAGCCATATATT TGTCTAAACTATAATATATGGCTGCACTGCATATAGCTACTG CTAGGCAATCCTTCCCTCGATAAGATGCAGCGGCGGCTCCT |

APPENDIX B-continued

| Name | SEQ ID | Molecule Type | Sequence |
|---|---|---|---|
| | | | CTCCCCATGGCCCTGGCCTTGTTGAAGAGGATTATCCTGGGC TCAGAGATAATCCTCTACAACAAGGGCAGGGACCTGGGGAC CCCGGCACCGGCAGGCTAGC |
| Agtr1a-Adcy5-mTOR | SEQ ID NO: 78 | DNA | GGCCAAGGTATATTGCTGTTGACAGTGAGCGACGCTGCAGA TATTCCGCTCTAAGTGAAGCCACAGATGTTAGAGCGGAAAA TCTGCAGAGCTGCCTACTGCCTCGGACTTCAAGGGGCTTGC GGCCGCCATCTCCATGGCTGTACCACCTTGTCGGCCAGGTT ACTACAGATATGTATGTTGAATCTCATTACATATCTGTTGTA ACCTGCTCTGACATTTTGGTATCTTTCATCTGACCACGTACT ACCTTCTATCTGATGTGACAGCTTCTGTAGCACCCTGTTACT ACACATACTTTTGTTTAGTTATAAAGTATGTGGAGTAACAG GTGTACTGCTAGCTGTAGAACTCCAGCTTCGGCCTGTAACTT ATGATAGCAATGTCAGCAGTGCCTCCTGTTCCCTTTCCTAAT CATTTAAGATTCTAAAATTATAGGATTAGGAATGGGAACAG TAAGTAAGGTTGACCATACTCTACAGTTGTTGATTTCGTGGC TACAGAGTTTCCTTAGCAGAGCTGCTGGATGCAGTGGCGAC ATTTTGTCTAAACTATAAATGTCGCCACTGCATCCATTAGCT ACTGCTAGGCAATCCTTCCCTCGATAAGTATGGGGCCTGGC TCGAGCAGGGGCGAGGGATCAGACAGTTGGACTTGTTAAA TGGTCCCCTCCCTCTTGTCTGAATCAGGTAATGTCCTTCCCT CCCAATGACCGCGTCTTCGTCACAGTCAGCGGCGGCTCCTC TCCCCATGGCCCTGATGCTGTCCCTGGTCCTTATGCTGGGCT CAGACATAAGGACCACGGACAGCAACAGGGACCTGGGGAC CCCGGCACCGGCAGGCTA |
| Agtr1a-Ikbkb-mTOR | SEQ ID NO: 79 | DNA | GGCCAAGGTATATTGCTGTTGACAGTGAGCGACCTTACCTG AATCAGACAAGAAGTGAAGCCACAGATGTTCTTGTCTGAAT CAGGTAATGCTGCCTACTGCCTCGGACTTCAAGGGGCTTGC GGCCGCCATCTCCATGGCTGTACCACCTTGTCGGGCATCTA GTAGAGCGGATGATTGTTGAATCTCATTTCATCCGCTCAACT AGATGGTCTGACATTTTGGTATCTTTCATCTGACCACGTACT ACCTTCTATCTGATGTGACAGCTTCTGTAGCACCCTGTTACT ACACATACTTTTGTTTAGTTATAAAGTATGTGGAGTAACAG GTGTACTGCTAGCTGTAGAACTCCAGCTTCGGCCTGTAACTT ATGATAGCAATGTCAGCAGTGCCTCCTGTTCCCTTTCCTAAT CATTTAAGATTCTAAAATTATAGGATTAGGAATGGGAACAG TAAGTAAGGTTGACCATACTCTACAGTTGTTGATTTCGTGGC TACAGAGTTTCCTTAGCAGAGCTGCTGGATGCAGTGGCGAC ATTTTGTCTAAACTATAAATGTCGCCACTGCATCCATTAGCT ACTGCTAGGCAATCCTTCCCTCGATAAGTATGGGGCCTGGC TCGAGCAGGGGCGAGGGATCAGACAGTTGGACTTGTTAAA TGGTCCCCTCCCTATGAACGGTCTTTCCCTCTGTCCTTCCCTC CCAATGACCGCGTCTTCGTCACAGTCAGCGGCGGCTCCTCT CCCCATGGCCCTGGCCTTGTTGAAGAGGATTATCCTGGGCTC AGACATAAGGACCACGGACAGCAACAGTGACCTGGGGACC CCGGCACCGGCAGGCTA |
| Agtr1a-Ikbkb | SEQ ID NO: 80 | DNA | CCAAGGTATATTGCTGTTGACAGTGAGCGACCTTACCTGAA TCAGACAAGAAGTGAAGCCACAGATGTTCTTGTCTGAATCA GGTAATGCTGCCTACTGCCTCGGACTTCAAGGGGCTTGCGG CCGCCATCTCCATGGCTGTACCACCTTGTCGGGCATCTAGTA GAGCGGATGATTGTTGAATCTCATTTCATCCGCTCAACTAGA TGGTCTGACATTTTGGTATCTTTCATCTGACCACGTACTACC TTCTATCTGATGTGACAGCTTCTGTAGCACCCTGTTACTACA CATACTTTTGTTTAGTTATAAAGTATGTGGAGTAACAGGTGT ACTGCTAGCTGTAGAACTCCAGCTTCGGCCTGTAACTTATGA TAGCAATGTCAGCAGTGCCTCCTGTTCCCTTTCCTAATCATT TAAGATTCTAAAATTATAGGATTAGGAATGGGAACAGTAAG TAAGGTTGACCATACTCTACAGTTGTTGATTTCGTGGCTACA GAGTTTCCTTAGCAGAGCTGGCTCTAAAGAAGGCTTATGAA TGTCTAAACTATTTCATAAGCCTACTTTAGAGATAGCTACTG CTAGGCAATCCTTCCCTCGATAAGTATGGGGCCTGGCTCGA GCAGGGGGCGAGGGATGCATCTAGTAGAGCGGATGATTGG TCCCCTCCCTCATCCGCTCAACTAGATGAGTCCTTCCCTCCC AATGACCGCGTCTTGGCTAGC |
| Ctf1-Akt1 | SEQ ID NO: 81 | DNA | CCAAGGTATATTGCTGTTGACAGTGAGCGACTCTGAGACTG ACACCAGGTATGTGAAGCCACAGATGATACCTGGTGTGAGT CTCAGCGCTGCCTACTGCCTCGGACTTCAAGGGGCTTGCGG CCGCCATCTCCATGGCTGTACCACCTTGTCGGTGGCACCTTT ATTGGCTACAATGTTCATTTGTAGCCAATTAAGGTG CCTTCTGACATTTTGGTATCTTTCATCTGACCACGTACTACC TTCTATCTGATGTGACAGCTTCTGTAGCACGCCACCCTCTTC ACGGCCAATGTTTAGTTATTTGGCCGTGACGAGGGTGGCTG TACTGCTAGCTGTAGAACTCCAGCTTCGGCCTGTAACTTATG ATAGCAATGTCAGCAGTGCCTCGCCACCCTCTTCACGGCCA |

APPENDIX B-continued

| Name | SEQ ID | Molecule Type | Sequence |
|---|---|---|---|
| | | | ATTAAGATTCTAAAATTATTGGGCCGTGAACAGGGTGGCTA<br>AGTAAGGTTGACCATACTCTACAGTTGTTGATTTCGTGGCTA<br>CAGAGTTTCCTTAGCAGAGCTGTGGCACCTTTATTGGCTACA<br>ATGTCTAAACTATTTGTAGCCAATAAAGGTGCCCTAGCTACT<br>GCTAGGCAATCCTTCCCTCGATAAGATGCAGCGGCGGCTCC<br>TCTCCCCATGGCCCTGCTTGGGCTGTCCCTATCTTTCCTGGG<br>CTCAGAGAAAGATAGGGTCAGCCCAACCAGGGACCTGGGG<br>ACCCCGGCACCGGCAGGCTAGC |
| Ctf1-Coq7 | SEQ ID NO: 82 | DNA | CCAAGGTATATTGCTGTTGACAGTGAGCGACCTTGGGCTGT<br>CCCTATCTTTCGTGAAGCCACAGATGGAAAGATAGGGTCAG<br>CCCAATGCTGCCTACTGCCTCGGACTTCAAGGGGCTTGCGG<br>CCGCCATCTCCATGGCTGTACCACCTTGTCGGGGCAGCCGT<br>GGATCGAATAATTGTTGAATCTCATTATATTCGATCAACGGC<br>TGCGTCTGACATTTTGGTATCTTTCATCTGACCACGTACTAC<br>CTTCTATCTGATGTGACAGCTTCTGTAGCACGCCACCCTCTT<br>CACGGCCAATGTTTAGTTATTTGGCCGTGACGAGGGTGGCT<br>GTACTGCTAGCTGTAGAACTCCAGCTTCGGCCTGTAACTTAT<br>GATAGCAATGTCAGCAGTGCCTCGCCACCCTCTTCACGGCC<br>AATTAAGATTCTAAAATTATTGGGCCGTGAACAGGGTGGCT<br>AAGTAAGGTTGACCATACTCTACAGTTGTTGATTTCGTGGCT<br>ACAGAGTTTCCTTAGCAGAGCTGGATGCAGTGCAGCCATAT<br>ATTTGTCTAAACTATAATATATGGCTGCACTGCATATAGCTA<br>CTGCTAGGCAATCCTTCCCTCGATAAGATGCAGCGGCGGCT<br>CCTCTCCCCATGGCCCTGGCCTTGTTGAAGAGGATTATCCTG<br>GGCTCAGAGATAATCCTCTACAACAAGGGCAGGGACCTGGG<br>GACCCCGGCACCGGCAGGCTAGC |
| Ctf1-ikbkb-Coq7 | SEQ ID NO: 83 | DNA | GGCCAAGGTATATTGCTGTTGACAGTGAGCGACCTTACCTG<br>AATCAGACAAGAAGTGAAGCCACAGATGTTCTTGTCTGAAT<br>CAGGTAATGCTGCCTACTGCCTCGGACTTCAAGGGGCTTGC<br>GGCCGCCATCTCCATGGCTGTACCACCTTGTCGGGCATCTA<br>GTAGAGCGGATGATTGTTGAATCTCATTTCATCCGCTCAACT<br>AGATGGTCTGACATTTTGGTATCTTTCATCTGACCACGTACT<br>ACCTTCTATCTGATGTGACAGCTTCTGTAGCACGCCACCCTC<br>TTCACGGCCAATGTTTAGTTATTTGGCCGTGACGAGGGTGG<br>CTGTACTGCTAGCTGTAGAACTCCAGCTTCGGCCTGTAACTT<br>ATGATAGCAATGTCAGCAGTGCCTCGCCACCCTCTTCACGG<br>CCAATTAAGATTCTAAAATTATTGGGCCGTGAACAGGGTGG<br>CTAAGTAAGGTTGACCATACTCTACAGTTGTTGATTTCGTGG<br>CTACAGAGTTTCCTTAGCAGAGCTGGATGCAGTGCAGCCAT<br>ATATTTGTCTAAACTATAATATATGGCTGCACTGCATATAGC<br>TACTGCTAGGCAATCCTTCCCTCGATAAGTATGGGCCTGG<br>CTCGAGCAGGGGCGAGGGATGCATCTAGTAGAGCGGATG<br>ATTGGTCCCCTCCCAACTGCCACTGTTGATGTTTGTCCTTCC<br>CTCCCAATGACCGCGTCTTCGTCACAGTCAGCGGCGGCTCC<br>TCTCCCCATGGCCCTGCGATGCAGAGTCCAGGATAATCTGG<br>GCTCAGAGATAATCCTCTACAACAAGGGCAGGGACCTGGGG<br>ACCCCGGCACCGGCAGGCTA |
| Ctf1-mTOR-Coq7-Slc13a5 | SEQ ID NO: 84 | DNA | GGCCAAGGTATATTGCTGTTGACAGTGAGCGACATGCTGTC<br>CCTGGTCCTT'TGGTGAAGCCACAGATGCATAAGGACCACG<br>GACAGCAGGCTGCCTACTGCCTCGGACTTCAAGGGGCTTGC<br>GGCCGCCATCTCCATGGCTGTACCACCTTGTCGGCTGGATG<br>CAGTGGCGACATTTTGTTGAATCTCATTAATGTCGCCAGTGC<br>ATCCACTCTGACATTTTGGTATCTTTCATCTGACCACGTACT<br>ACCTTCTATCTGATGTGACAGCTTCTGTAGCACGCCACCCTC<br>TTCACGGCCAATGTTTAGTTATTTGGCCGTGACGAGGGTGG<br>CTGTACTGCTAGCTGTAGAACTCCAGCTTCGGCCTGTAACTT<br>ATGATAGCAATGTCAGCAGTGCCTCGCCACCCTCTTCACGG<br>CCAATTAAGATTCTAAAATTATTGGGCCGTGAACAGGGTGG<br>CTAAGTAAGGTTGACCATACTCTACAGTTGTTGATTTCGTGG<br>CTACAGAGTTTCCTTAGCAGAGCTGGATGCAGTGCAGCCAT<br>ATATTTGTCTAAACTATAATATATGGCTGCACTGCATATAGC<br>TACTGCTAGGCAATCCTTCCCTCGATAAGTATGGGCCTGG<br>CTCGAGCAGGGGCGAGGGATCGAGGGAAACACCGTTCAT<br>ATTGGTCCCCTCCCTTAACAAGTCGAACTGTCTTGTCCTTCC<br>CTCCCAATGACCGCGTCTTCGTCACAGTCAGCGGCGGCTCC<br>TCTCCCCATGGCCCTGGCCTTGTTGAAGAGGATTATCCTGGG<br>CTCAGAGATAATCCTCTACAACAAGGGCAGGGACCTGGGGA<br>CCCCGGCACCGGCAGGCTA |
| Ctf1-mTOR-Coq7 | SEQ ID NO: 85 | DNA | GGCCAAGGTATATTGCTGTTGACAGTGAGCGACATGCTGTC<br>CCTGGTCCTTATGGTGAAGCCACAGATGCATAAGGACCACG<br>GACAGCAGGCTGCCTACTGCCTCGGACTTCAAGGGGCTTGC<br>GGCCGCCATCTCCATGGCTGTACCACCTTGTCGGCTGGATG<br>CAGTGGCGACATTTTGTTGAATCTCATTAATGTCGCCAGTGC |

APPENDIX B-continued

| Name | SEQ ID | Molecule Type | Sequence |
|---|---|---|---|
| | | | ATCCACTCTGACATTTTGGTATCTTTCATCTGACCACGTACT<br>ACCTTCTATCTGATGTGACAGCTTCTGTAGCACGCCACCCTC<br>TTCACGGCCAATGTTTAGTTATTTGGCCGTGACGAGGGTGG<br>CTGTACTGCTAGCTGTAGAACTCCAGCTTCGGCCTGTAACTT<br>ATGATAGCAATGTCAGCAGTGCCTCGCCACCCTCTTCACGG<br>CCAATTAAGATTCTAAAATTATTGGGCCGTGAACAGGGTGG<br>CTAAGTAAGGTTGACCATACTCTACAGTTGTTGATTTCGTGG<br>CTACAGAGTTTCCTTAGCAGAGCTGGATGCAGTGCAGCCAT<br>ATATTTGTCTAAACTATAATATATGGCTGCACTGCATATAGC<br>TACTGCTAGGCAATCCTTCCCTCGATAAGTATGGGGCCTGG<br>CTCGAGCAGGGGCGAGGGATCAGACAGTTGGACTTGTTAA<br>ATGGTCCCCTCCCTATGAACGGTCTTTCCCTCTGTCCTTCCC<br>TCCCAATGACCGCGTCTTCGTCACAGTCAGCGGCGGCTCCT<br>CTCCCCATGGCCCTGGCCTTGTTGAAGAGGATTATCCTGGGC<br>TCAGAGATAATCCTCTACAACAAGGGCAGGGACCTGGGGAC<br>CCCGGCACCGGCAGGCTA |
| Ctf1-<br>Slc13a1-<br>pappa | SEQ ID NO: 86 | DNA | CCAAGGTATATTGCTGTTGACAGTGAGCGACCCTGGGCTTC<br>TAACTTTGTTAGTGAAGCCACAGATGTAACAAAGTTACAAG<br>CCCAGTGCTGCCTACTGCCTCGGACTTCAAGGGGCTTGCGG<br>CCGCCATCTCCATGGCTGTACCACCTTGTCGGCCGCATCTTA<br>AACTTGGAGTTTGTTGAATCTCATTACTCCAAGTTAAAGATG<br>CGCTCTGACATTTTGGTATCTTTCATCTGACCACGTACTACC<br>TTCTATCTGATGTGACAGCTTCTGTAGCACGCCACCCTCTTC<br>ACGGCCAATGTTTAGTTATTTGGCCGTGACGAGGGTGGCTG<br>TACTGCTAGCTGTAGAACTCCAGCTTCGGCCTGTAACTTATG<br>ATAGCAATGTCAGCAGTGCCTCGCCACCCTCTTCACGGCCA<br>ATTAAGATTCTAAAATTATTGGGCCGTGAACAGGGTGGCTA<br>AGTAAGGTTGACCATACTCTACAGTTGTTGATTTCGTGGCTA<br>CAGAGTTTCCTTAGCAGAGCTGCCTGGAGATTGATGCAGCA<br>ATTGTCTAAACTATATTGCTGCATCAATCTCCAGTTAGCTAC<br>TGCTAGGCAATCCTTCCCTCGATAAGATGCAGCGGCGGCTC<br>CTCTCCCCATGGCCCTGGCGGCTGATGAAGCTCTATATCTGG<br>GCTCAGAATATAGAGCTTGATCAGCCGGCAGGGACCTGGGG<br>ACCCCGGCACCGGCAGGCTAGC |
| Ctf1-<br>Slc13a5 | SEQ ID NO: 87 | DNA | CCAAGGTATATTGCTGTTGACAGTGAGCGACGCAGGTATGT<br>ATCCAATACATGTGAAGCCACAGATGATGTATTGGATTCAT<br>ACCTGAGCTGCCTACTGCCTCGGACTTCAAGGGGCTTGCGG<br>CCGCCATCTCCATGGCTGTACCACCTTGTCGGCGAGGGAAA<br>CACCGTTCATATTGTTGAATCTCATTTATGAACGGTCTTTCC<br>CTCCTCTGACATTTTGGTATCTTTCATCTGACCACGTACTAC<br>CTTCTATCTGATGTGACAGCTTCTGTAGCACGCCACCCTCTT<br>CACGGCCAATGTTTAGTTATTTGGCCGTGACGAGGGTGGCT<br>GTACTGCTAGCTGTAGAACTCCAGCTTCGGCCTGTAACTTAT<br>GATAGCAATGTCAGCAGTGCCTCGCCACCCTCTTCACGGCC<br>AATTAAGATTCTAAAATTATTGGGCCGTGAACAGGGTGGCT<br>AAGTAAGGTTGACCATACTCTACAGTTGTTGAGACTACGCC<br>TGGCTCGAGCAGGGGCGAGGGATCGAGGGAAACACCGTT<br>CATATTGGTCCCCTCCCTATGAACGGTCTTTCCCTCTGTCCTT<br>CCCTCCCAATGACCGCGTCTTCGTCACAGTCAGCGGCGGCT<br>CCTCTCCCCATGGCCCTGCTTGGGCTGTCCCTATCTTTCCTG<br>GGCTCAGAGAAAGATAGGGTCAGCCCAACCAGGGACCTGG<br>GGACCCCGGCACCGGCAGGCTAGC |
| Dgat1-<br>Pappa | SEQ ID NO: 88 | DNA | CCAAGGTATATTGCTGTTGACAGTGAGCGACGCGGCTGATG<br>AAGCTCTATATGTGAAGCCACAGATGATATAGAGCTTGATC<br>AGCCGAGCTGCCTACTGCCTCGGACTTCAAGGGGCTTGCGG<br>CCGCCATCTCCATGGCTGTACCACCTTGTCGGCCTGGAGATT<br>GATGCAGCAATTGTTGAATCTCATTTTGCTGCATCTATCTCC<br>AGCTCTGACATTTTGGTATCTTTCATCTGACCACGTACTACC<br>TTCTATCTGATGTGACAGCTTCTGTAGCAGCCCTTCAAGGAT<br>ATGGACTATGTTTAGTTATTAGTCCATATACTTGAAGGGAGT<br>ACTGCTAGCTGTAGAACTCCAGCTTCGGCCTGTAACTTATGA<br>TAGCAATGTCAGCAGTGCCTCGGATCATTGAGCGTCTCTTAT<br>TAAGATTCTAAAATTATTGAGAGACGCTGAATGATCCTAAG<br>TAAGGTTGACCATACTCTACAGTTGTTGATTTCGTGGCTACA<br>GAGTTTCCTTAGCAGAGCTGCCTGGAGATTGATGCAGCAAT<br>TGTCTAAACTATATTGCTGCATCAATCTCCAGTTAGCTACTG<br>CTAGGCAATCCTTCCCTCGATAAGATGCAGCGGCGGCTCCT<br>CTCCCCATGGCCCTGCCTGAGTAATGCAAGGTTATTCTGGGC<br>TCAGAAATAACCTTGCTTTTACTCAGCCAGGGACCTGGGGAC<br>CCCGGCACCGGCAGCTAGC |
| Pcsk9-<br>Rps6kb1 | SEQ ID NO: 89 | DNA | CCAAGGTATATTGCTGTTGACAGTGAGCGACCAGAGGCTAC<br>AGATTGAACAAGTGAAGCCACAGATGTTGTTCAATCTCTAG<br>CCTCTTGCTGCCTACTGCCTCGGACTTCAAGGGGCTTGCGGC |

APPENDIX B-continued

| Name | SEQ ID | Molecule Type | Sequence |
|---|---|---|---|
| | | | CGCCATCTCCATGGCTGTACCACCTTGTCGGCCCTTTCATTG TGGACCTGATTGTTAATCTCATTACAGGTCCACCATGAAA GGCTCTGACATTTTGGTATCTTTCATCTGACCACGTACTACC TTCTATCTGATGTGACAGCTTCTGTAGCACCACTCGAACAGC TACAGCTATGTTTAGTTATTAGCTGTAGCGGTTCGAGTGTGT ACTGCTAGCTGTAGAACTCCAGCTTCGGCCTGTAACTTATGA TAGCAATGTCAGCAGTGCCTGCTGATCCACTTCTCTACCAAT TAAGATTCTAAAATTATTGGGTAGAGAACTGGATCAGAAAG TAAGGTTGACCATACTCTACAGTTGTTGATTTCGTGGCTACA GAGTTTCCTTAGCAGAGCTGACATTGTTACACAGCCAGTATT GTCTAAACTATATACTGGCTGTGTAACAATGGTAGCTACTG CTAGGCAATCCTTCCCTCGATAAGATGCAGCGGCGGCTCCT CTCCCCATGGCCCTGGCATGGAACATTGTGAGAAATCTGGG CTCAGAATTTCTCACAAAGTTCCATGGCAGGGACCTGGGGA CCCCGGCACCGGCAGGCTAGC |
| Slc13a1-ikbkb | SEQ ID NO: 90 | DNA | CCAAGGTATATTGCTGTTGACAGTGAGCGACCTTACCTGAA TCAGACAAGAAGTGAAGCCACAGATGTTCTTGTCTGAATCA GGTAATGCTGCCTACTGCCTCGGACTTCAAGGGGCTTGCGG CCGCCATCTCCATGGCTGTACCACCTTGTCGGGCATCTAGTA GAGCGGATGATTGTTAATCTCATTTCATCCGCTCAACTAGA TGGTCTGACATTTTGGTATCTTTCATCTGACCACGTACTACC TTCTATCTGATGTGACAGCTTCTGTAGCACCTGGGCTTCTAA CTTTGTTATGTTTAGTTATTAACAAAGTTCGAAGCCCAGTGT ACTGCTAGCTGTAGAACTCCAGCTTCGGCCTGTAACTTATGA TAGCAATGTCAGCAGTGCCTCCGCATCTTTAAACTTGGAGTTT TAAGATTCTAAAATTATACCTCCAAGTTAAAGATGCGAAAG TAAGGTTGACCATACTCTACAGTTGTTGATTTCGTGGCTACA GAGTTTCCTTAGCAGAGCTGGCCTACATCCTCTTTGTTATTT GTCTAAACTATAATAACAAAGACGATGTAGGATAGCTACTG CTAGGCAATCCTTCCCTCGATAAGTATGGGGCCTGGCTCGA GCAGGGGGCGAGGGATGCATCTAGTAGAGCGGATGATTGG TCCCCTCCCTCATCCGCTCAACTAGATGAGTCCTTCCCTCCC AATGACCGCGTCTTGGCTAGC |
| Slc13a1-mTOR | SEQ ID NO: 91 | DNA | CCAAGGTATATTGCTGTTGACAGTGAGCGACCCTGGGCTTC TAACTTTGTTAGTGAAGCCACAGATGTAACAAAGTTACAAG CCCAGTGCTGCCTACTGCCTCGGACTTCAAGGGGCTTGCGG CCGCCATCTCCATGGCTGTACCACCTTGTCGGCCGCATCTTA AACTTGGAGTTTGTTGAATCTCATTACTCCAAGTTAAAGATG CGCTCTGACATTTTGGTATCTTTCATCTGACCACGTACTACC TTCTATCTGATGTGACAGCTTCTGTAGCACCTGGGCTTCTAA CTTTGTTATGTTTAGTTATTAACAAAGTTCGAAGCCCAGTGT ACTGCTAGCTGTAGAACTCCAGCTTCGGCCTTCACGTGGCTA CAGAGTTTCCTTAGCAGAGCTGCTGGATGCAGTGGCGACAT TTGTCTAAACTATAAATGTCGCCACTGCATCCATTAGCTACT GCTAGGCAATCCTTCCCTCGATAAATGGATGGCCTGGCTCG AGCAGGGGGCGAGGGATCAGACAGTTGGACTTGTTAAATG GTCCCCTCCCTTAACAAGTCGAACTGTCTTGTCCTTCCCTCC CAATGACCGCGTCTTCGTCACAGTCAGCGGCGGCTCCTCTC CCCATGGCCCTGATGCTGTCCCTGGTCCTTATGCTGGGCTCA GACATAAGGACCACGGACAGCAACAGGGACCTGGGGACCC CGGCACCGGCAGGCTAGC |
| Slc13a5-Pappa | SEQ ID NO: 92 | DNA | CCGGCCAAGGTATATTGCTGTTGACAGTGAGCGACGCGGCT GATGAAGCTCTATATGTGAAGCCACAGATGATATAGAGCTT GATCAGCCGAGCTGCCTACTGCCTCGGACTTCAAGGGGCTT GCGGCCGCCATCTCCATGGCTGTACCACCTTGTCGGCCTGG AGATTGATGCAGCAATTGTTGAATCTCATTTTGCTGCATCTA TCTCCAGCTCTGACATTTTGGTATCTTTCATCTGACCACGTA CTACCTTCTATCTGATGTGACAGCTTCTGTAGCAGCAGGTAT GTATCCAATACATTGTTTAGTTATATGTATTGGAGACATACC TGAGTACTGCTAGCTGTAGAACTCCAGCTTCGGCCTGTAACT TATGATAGCAATGTCAGCAGTGCCTCGAGGGAAACACCGTT CATATTTAAGATTCTAAAATTATAGATGAACGGTCTTTCCCT CAAAGTAAGGTTGACCATACTCTACAGTTGTTGATTTCGTGG CTACAGAGTTTCCTTAGCAGAGCTGCCTGGAGATTGATGCA GCAATTGTCTAAACTATATTGCTGCATCAATCTCCAGTTAGC TACTGCTAGGCAATCCTTCCCTCGATAAGTATGGGGCCTGG CTCGAGCAGGGGCGAGGGATCGAGGGAAACACCGTTCAT ATTGGTCCCCTCCCTATGAACGGTCTTTCCCTCTGTCCTTCC CTCCCAATGACCGCGTCTTGGCTAGC |
| Slc13a5-PDE4b-mTOR | SEQ ID NO: 93 | DNA | GGCCAAGGTATATTGCTGTTGACAGTGAGCGACGCCGTGAA GCAAATAGCAGTTGTGAAGCCACAGATGAACTGCTATTTCC TTCACGGAGCTGCCTACTGCCTCGGACTTCAAGGGGCTTGC GGCCGCCATCTCCATGGCTGTACCACCTTGTCGGCAACCGG |

APPENDIX B-continued

| Name | SEQ ID | Molecule Type | Sequence |
|---|---|---|---|
| | | | ATGCTCAAGATATTTGTTGAATCTCATTATATCTTGAGGATC
CGGTTCTCTGACATTTTGGTATCTTTCATCTGACCACGTACT
ACCTTCTATCTGATGTGACAGCTTCTGTAGCAGCAGGTATGT
ATCCAATACATTGTTTAGTTATATGTATTGGAGACATACCTG
AGTACTGCTAGCTGTAGAACTCCAGCTTCGGCCTGTAACTTA
TGATAGCAATGTCAGCAGTGCCTCGAGGGAAACACCGTTCA
TATTTAAGATTCTAAAATATAGATGAACGGTCTTTCCCTCA
AAGTAAGGTTGACCATACTCTACAGTTGTTGATTTCGTGGCT
ACAGAGTTTCCTTAGCAGAGCTGCTGGATGCAGTGGCACA
TTTTGTCTAAACTATAAATGTCGCCACTGCATCCATTAGCTA
CTGCTAGGCAATCCTTCCCTCGATAAGTATGGGGCCTGGCTC
GAGCAGGGGGCGAGGGATCAGACAGTTGGACTTGTTAAAT
GGTCCCCTCCCTCATCCGCTCAACTAGATGAGTCCTTCCCTC
CCAATGACCGCGTCTTCGTCGTTTCAGCGGCGGCTCCTCTCC
CCATGGCCCTGTCTGAGACTGACACCAGGTATCTGGGCTCA
GACATAAGGACCACGGACAGCAACAGGGACCTGGGGACCC
CGGCACCGGCAGGCTAG |
| miR16-1-5 | SEQ ID NO: 94 | DNA | TGTCAGCAGTGCCT |
| miR16-1-3' | SEQ ID NO: 95 | DNA | AGTAAGGTTGACCA |
| mir16-1-stem-loop | SEQ ID NO: 96 | DNA | TTAAGATTCTAAAATTAT |
| miR30a-5' | SEQ ID NO: 97 | DNA | TGTTGACAGTGAGCGAC |
| miR20a-3' | SEQ ID NO: 98 | DNA | GTACTGCTAGCTGTAG |
| mir20a-5' | SEQ ID NO: 99 | DNA | GACAGCTTCTGTAGCA |
| mir20a-stem-loop | SEQ ID NO: 100 | DNA | TGTTTAGTTAT |
| mir21-3' | SEQ ID NO: 101 | DNA | CTGACATTTTGGTATCT |
| miR21-5' | SEQ ID NO: 102 | DNA | TGTACCACCTTGTCGG |
| mir21-stem-loop | SEQ ID NO: 103 | DNA | TGTTGAATCTCATT |
| mir30a-stem-loop | SEQ ID NO: 104 | DNA | GTGAAGCCACAGATG |
| mir122-stem-loop | SEQ ID NO: 105 | DNA | TGTCTAAACTAT |
| mir150-3' | SEQ ID NO: 106 | DNA | CAGGGACCTGGGGAC |
| mir150-stem-loop | SEQ ID NO: 107 | DNA | CTGGGCTCAGA |
| miR-30a | SEQ ID NO: 108 | DNA | GCTGCCTACTGCCTCGG |
| miR-122 | SEQ ID NO: 109 | DNA | TTCCTTCAGCAGAGCTG |
| miR-122 | SEQ ID NO: 110 | DNA | TAGCTACTGCTAGGCA |
| miR-150 | SEQ ID NO: 111 | DNA | CTCCCCATGGCCCTG |
| miR16-1-5' | SEQ ID NO: 112 | DNA | TGTCAGCAGTGCCT |
| shEf1a | SEQ ID NO: 117 | DNA | AGGCTCCGGTGCCCGTCAGTGGGCAGAGCGCACATCGCCCA
CAGTCCCCGAGAAGTTGGGGGGAGGGGTCGGCAATTGAAC
CGGTGCCTAGAGAAGGTGGCGCGGGGTAAACTGGGAAAGT
GATGTCGTGTACTGGCTCCGCCTTTTTCCCGAGGGTGGGGG
AGAACCGTATATAAGTGCAGTAGTCGCCGTGAACGTTCTTT
TTCGCAACGGGTTTGCCGCCAGAACACA |
| WPRE3 | SEQ ID NO: 113 | DNA | AATCAACCTCTGGATTACAAAATTTGTGAAAGATTGACTGG
TATTCTTAACTATGTTGCTCCTTTTACGCTATGTGGATACGC
TGCTTTAATGCCTTTGTATCATGCTATTGCTTCCCGTATGGCT
TTCATTTTCTCCTCCTTGTATAAATCCTGGTTAGTTCTTGCCA
CGGCGGAACTCATCGCCGCCTGCCTTGCCCGCTGCTGGACA
GGGGCTCGGCTGTTGGGCACTGACAATTCCGTGGTGTT |

APPENDIX B-continued

| Name | SEQ ID | Molecule Type | Sequence |
|---|---|---|---|
| SV40 late Poly Adenylation | SEQ ID NO: 114 | DNA | GCTTTATTTGTGAAATTTGTGATGCTATTGCTTTATTTGTAAC CATTATAAGCTGCAATAAACAAGTTAACAACAACAATTGCA TTCATTTTATGTTTCAGGTTCAGGGGGAGATGTGGGAGGTTT TTTAAAGC |
| full ITR-ITR sTgfbR2-Fc | SEQ ID NO: 115 | DNA | CCTTAATTAGGCTGCGCGCTCGCTCGCTCACTGAGGCCGCC CGGGCAAAGCCCGGGCGTCGGGCGACCTTTGGTCGCCCGGC CTCAGTGAGCGAGCGAGCGCGCAGAGAGGGAGTGGCCAAC TCCATCACTAGGGGTTCCTTGTAGTTAATGATTAACCCGCCA TGCTACTTATCTACGTAGCCATGCTCTAGGAAGATCGGAATT CCTTGGCTCCGGTGCCCGTCAGTGGGCAGAGCGCACATCGC CCACAGTCCCCGAGAAGTTGTGGGGAGGGGTCGGCAATTGA ACCGGTGCCTAGAGAAGGTGGCGCGGGGTAAACTGGGAAA GTGATGTCGTGTACTGGCTCCGCCTTTTTCCCGAGGGTGGG GAGAACCGTATATAAGTGCAGTAGTCGCCGTGAACGTTCTT TTTCGCAACGGGTTTGCCGCCAGAACACAGGTAAGTGCCGT GTGTGGTTCCCGCGGGCCTGGCCTCTTTACGGGTTATGGCCC TTGCGTGCCTTGAATTACTTCCACCTGGCTGCAGTACGTGAT TCTTGATCCCGAGCTTCGGGTTGGAAGTGGGTGGGAGAGTT CGAGGCCTTGCGCTTAAGGAGCCCCTTCGCCTCGTGCTTGA GTTGAGGCCTGGCCTGGGCGCTGGGGCCGCCGCGTGCGAAT CTGGTGGCACCTTCGCGCCTGTCTCGCTGCTTTCGATAAGTC TCTAGCCATTTAAAATTTTTGATGACCTGCTGCGACGCTTTT TTTCTGGCAAGATAGTCTTGTAAATGCGGGCCAAGATCTGC ACACTGGTATTTCGGTTTTTGGGGCCGCGGGCGGCGACGGG GCCCGTGCGTCCCAGCGCACATGTTCGGCGAGGCGGGGCCT GCGAGCGCGGCCACCGAGAATCGGACGGGGGTAGTCTCAA GCTGGCCGGCCTGCTCTGGTGCCTGGCCTCGCGCCGCCGTG TATCGCCCCGCCCTGGGCGGCAAGGCTGGCCCGGTCGGCAC CAGTTGCGTGAGCGGAAAGATGGCCGCTTCCCGGCCCTGCT GCAGGGAGCTCAAAATGGAGGACGCGGCGCTCGGGAGAGC GGGCGGGTGAGTCACCCACACAAAGGAAAAGGGCCTTTCC GTCCTCAGCCGTCGCTTCATGTGACTCCACGGAGTACCGGG CGCCGTCCAGGCACCTCGATTAGTTCTCGAGCTTTTGGAGTA CGTCGTCTTTAGGTTGGGGGGAGGGGTTTTATGCGATGGAG TTTCCCCACACTGAGTGGGTGGAGACTGAAGTTAGGCCAGC TTGGCACTTGATGTAATTCTCCTTGGAATTTGCCCTTTTTGA GTTTGGATCTTGGTTCATTCTCAAGCCTCAGACAGTGGTTCA AAGTTTTTTTCTTCCATTTCAGGTGCGGCCTGCCACCATGGG TCGGGGGCTGCTCCGGGGCCTGTGGCCGCTGCATATCGTCC TGTGGACGCGCATCGCCAGCACGATCCCGCCGCACGTTCCC AAGTCGGATGTGGAAATGGAAGCCCAGAAAGATGCATCCA TCCACCTAAGCTGTAATAGGACCATCCATCCACTGAAACAT TTTAACAGTGATGTCATGGCCAGCGACAATGGCGGTGCGGT CAAGCTTCCACAGCTGTGCAAGTTTTGCGATGTGAGACTGT CCACTTGCGACAACCAGAAGTCCTGCATGAGCAACTGCAGC ATCACGGCCATCTGTGAGAAGCCGCATGAAGTCTGCGTGGC CGTGTGGAGGAAGAACGACAAGAACATTACTCTGGAGACG GTTTGCCACGACCCCAAGCTCACCTACCACGGCTTCACTCTG GAAGATGCCGCTTCTCCCAAGTGTGTCATGAAGGAAAAGAA AAGGGCGGGCGAGACTTTCTTCATGTGTGCCTGTAACATGG AAGAGTGCAACGATTACATCATCTTTTCGGAAGAATACACC ACCAGCAGTCCCGACCCCAGAGGGCCCACAATCAAGCCCTG TCCTCCATGCAAATGCCCAGCACCTAACCTCGAGGGTGGAC CATCCGTCTTCATCTTCCCTCCAAAGATCAAGGATGTACTCA TGATCTCCCTGAGCCCCATAGTCACATGTGTGGTGGTGGAT GTGAGCGAGGATGACCCAGATGTCCAGATCAGCTGGTTTGT GAACAACGTGGAAGTACACAGCTCAGACACAAACCCAT AGAGAGGATTACAACAGTACTCTCCGGGTGGTCAGTGCCCT CCCCATCCAGCACCAGGACTGGATGAGTGGCAAGGCGTTCG CATGCGCGGTCAACAACAAAGACCTCCCAGCGCCCATCGAG AGAACCATCTCAAAACCCAAAGGGTCAGTAAGAGCTCCAC AGGTATATGTCTTGCCTCCACCAGAAGAAGAGATGACTAAG AAACAGGTCACTCTGACCTGCATGGTCACAGACTTCATGCC TGAAGACATTTACGTGGAGTGGACCAACAACGGGAAAACA GAGCTAAACTACAAGAACACTGAACCAGTCCTGGACTCTGA TGGTTCTTACTTCATGTACAGCAAGCTGAGAGTGGAAAAGA AGAACTGGGTGGAAAGAAATAGCTACTCCTGTTCAGTGGTC CACGAGGGTCTGCACAATCACCACACGACTAAGAGCTTCTC CCGGACTCCGGGTAAATGAGCTAGCAATCAACCTCTGGATT ACAAAATTTGTGAAAGATTGACTGGTATTCTTAACTATGTTG CTCCTTTTACGCTATGTGGATACGCTGCTTTAATGCCTTTGT ATCATGCTATTGCTTCCCGTATGGCTTTCATTTTCTCCTCCTT GTATAAATCCTGGTTAGTTCTTGCCACGGCGGAACTCATCGC CGCCTGCCTTGCCCGCTGCTGGACAGGGGCTCGGCTGTTGG GCACTGACAATTCCGTGGTGTTTATTTGTGAAATTTGTGATG CTATTGCTTTATTTGTAACCATTCTAGCTTTATTTGTGAAATT |

APPENDIX B-continued

| Name | SEQ ID | Molecule Type | Sequence |
|---|---|---|---|
| | | | TGTGATGCTATTGCTTTATTTGTAACCATTATAAGCTGCAAT AAACAAGTTAACAACAACAATTGCATTCATTTTATGTTTCAG GTTCAGGGGGAGATGTGGGAGGTTTTTTAAAGCGGGGGATC CAAATTCCCGATAAGGATCTTCCTAGAGCATGGCTACGTAG ATAAGTAGCATGGCGGGTTAATCATTAACTACAAGGAACCC CTAGTGATGGAGTTGGCCACTCCCTCTCTGCGCGCTCGCTCG CTCACTGAGGCCGGGCGACCAAAGGTCGCCCGACGCCCGG GCTTTGCCCGGGCGGCCTCAGTGAGCGAGCGAGCGCGCAGC CTTAATTAA |
| full ITR-ITR Nrf2 | SEQ ID NO: 116 | DNA | CCTTAATTAGGCTGCGCGCTCGCTCGCTCACTGAGGCCGCC CGGGCAAAGCCCGGGCGTCGGGCGACCTTTGGTCGCCCGGC CTCAGTGAGCGAGCGAGCGCGCAGAGAGGGAGTGGCCAAC TCCATCACTAGGGGTTCCTTGTAGTTAATGATTAACCCGCCA TGCTACTTATCTACGTAGCCATGCTCTAGGAAGATCGGAATT CCTTGGCTCCGGTGCCCGTCAGTGGGCAGAGCGCACATCGC CCACAGTCCCCGAGAAGTTGTGGGGAGGGGTCGGCAATTGA ACCGGTGCCTAGAGAAGGTGGCGCGGGGTAAACTGGGAAA GTGATGTCGTGTACTGGCTCCGCCTTTTTCCCGAGGGTGGGG GAGAACCGTATATAAGTGCAGTAGTCGCCGTGAACGTTCTT TTTCGCAACGGGTTTGCCGCCAGAACACAGGTAAGTGCCGT GTGTGGTTCCCGCGGGCCTGGCCTCTTTACGGGTTATGGCCT TGCGTGCCTTGAATTACTTCCACCTGGCTGCAGTACGTGAT TCTTGATCCCGAGCTTCGGGTTGGAAGTGGGTGGGAGAGTT CGAGGCCTTGCGCTTAAGGAGCCCCTTCGCCTCGTGCTTGA GTTGAGGCCTGGCCTGGGCGCTGGGGCCGCCGCGTGCGAAT CTGGTGGCACCTTCGCGCCTGTCTCGCTGCTTTCGATAAGTC TCTAGCCATTTAAAATTTTTGATGACCTGCTGCGACGCTTTT TTTCTGGCAAGATAGTCTTGTAAATGCGGGCCAAGATCTGC ACACTGGTATTTCGGTTTTTGGGGCCGCGGGCGGCGACGGG GCCCGTGCGTCCCAGCGCACATGTTCGGCGAGGCGGGGCCT GCGAGCGCGGCCACCGAGAATCGGACGGGGGTAGTCTCAA GCTGGCCGGCCTGCTCTGGTGCCTGGCCTCGCGCCGCCGTG TATCGCCCCGCCCTGGGCGGCAAGGCTGGCCCGGTCGGCAC CAGTTGCGTGAGCGGAAAGATGGCCGCTTCCCGGCCCTGCT GCAGGGAGCTCAAAATGGAGGACGCGGCGCTCGGGAGAGC GGGCGGGTGAGTCACCCACACAAAGGAAAAGGGCCTTTCC GTCCTCAGCCGTCGCTTCATGTGACTCCACGGAGTACCGGG CGCCGTCCAGGCACCTCGATTAGTTCTCGAGCTTTTGGAGTA CGTCGTCTTTAGGTTGGGGGGAGGGGTTTTATGCGATGGAG TTTCCCCACACTGAGTGGGTGGAGACTGAAGTTAGGCCAGC TTGGCACTTGATGTAATTCTCCTTGGAATTTGCCCTTTTTGA GTTTGGATCTTGGTTCATTCTCAAGCCTCAGACAGTGGTTCA AAGTTTTTTTCTTCCATTTCAGGTGCGGCCGCTCCGCCACCA TGATGGACTTGGAGTTGCCACCGCCAGGACTACAGTCCCAG CAGGACATGGATTTGATTGACATCCTTTGGAGGCAAGACAT AGATCTTGGAGTAAGTCGAGAAGTGTTTGACTTTAGTCAGC GACAGAAGGACTATGAGTTGGAAAAACAGAAAAAACTCGA AAAGGAAAGACAAGAGCAACTCCAGAAGGAACAGGAGAA GGCCTTTTTCGCTCAGTTTCAACTGGATGAAGAAACAGGAG AATTCCTCCCAATTCAGCCGGCCCAGCACATCCAGACAGAC ACTAGTGGATCCGCCAGCTACTCCCAGGTTGCCCACATTCC CAAACAAGATGCCTTGTACTTTGAAGACTGTATGCAGCTTTT GGCAGAGACATTCCCATTTGTTGATGACCATGAGTCGCTTG CCCTGGATATCCCCAGCCACGCTGAAAGTTCAGTCTTCACT GCCCCTCATCAGGCCCAGTCCCTCAATAGCTCTCTGGAGGC AGCCATGACTGATTTAAGCAGCATAGAGCAGGACATGGAGC AAGTTTGGCAGGAGCTATTTTCCATTCCCGAATTACAGTGTC TTAATACCGAAAACAAGCAGCTGGCTGATACTACCGCTGTT CCCAGCCCAGAAGCCACACTGACAGAAATGGACAGCAATT ACCATTTTTACTCATCGATCTCCTCGCTGGAAAAAGAAGTG GGCAACTGTGGTCCACATTTCCTTCATGGTTTTGAGGATTCT TTCAGCAGCATCCTCTCCACTGATGATGCCAGCCAGCTGAC CTCCTTAGACTCAAATCCCACCTTAAACACAGATTTTGGCGA TGAATTTTATTCTGCTTTCATAGCAGAGCCCAGTGACGGTGG CAGCATGCCTTCCTCCGCTGCCATCAGTCAGTCACTCTCTGA ACTCCTGGACGGGACTATTGAAGGCTGTGACCTGTCACTGT GTAAAGCTTTCAACCCGAAGCACGCTGAAGGCACAATGGAA TTCAATGACTCTGACTCTGGCATTTCACTGAACACAAGTCCC AGCCGAGCGTCCCAGAGCACTCCGTGGAGTCTTCCATTTA CGGAGACCCACCGCCTGGGTTCAGTGACTCGGAAATGGAGG AGCTAGATAGTGCCCCTGGAAGTGTCAAACAGAACGGCCCT AAAGCACAGCCAGCACATTCTCCTGGAGACACAGTACAGCC TCTGTCACCAGCTCAAGGGCACAGTGCTCCTATGCGTGAAT CCCAATGTGAAAATACAACAAAAAAAGAAGTTCCCGTGAGT CCTGGTCATCAAAAAGCCCCATTCACAAAAGACAAACATTC AAGCCGCTTAGAGGCTCATCTCACACGAGATGAGCTTAGGG |

APPENDIX B-continued

| Name | SEQ ID | Molecule Type | Sequence |
|---|---|---|---|
| | | | CAAAAGCTCTCCATATTCCATTCCCTGTCGAAAAAATCATTA<br>ACCTCCCTGTTGATGACTTCAATGAAATGATGTCCAAGGAG<br>CAATTCAATGAAGCTCAGCTCGCATTGATCCGAGATATACG<br>CAGGAGAGGTAAGAATAAAGTCGCCGCCCAGAACTGTAGG<br>AAAAGGAAGCTGGAGAACATTGTCGAGCTGGAGCAAGACT<br>TGGGCCACTTAAAAGACGAGAGAGAAAAACTACTCAGAGA<br>AAAGGGAGAAAACGACAGAAACCTCCATCTACTGAAAAGG<br>CGGCTCAGCACCTTGTATCTTGAAGTCTTCAGCATGTTACGT<br>GATGAGGATGGAAAGCCTTACTCTCCCAGTGAATACTCTCT<br>GCAGCAAACCAGAGATGGCAATGTGTTCCTTGTTCCCAAAA<br>GCAAGAAGCCAGATACAAAGAAAAACTAGAGCGGGCTAGC<br>AATCAACCTCTGGATTACAAAATTTGTGAAAGATTGACTGG<br>TATTCTTAACTATGTTGCTCCTTTTACGCTATGTGGATACGC<br>TGCTTTAATGCCTTTGTATCATGCTATTGCTTCCCGTATGGCT<br>TTCATTTTCTCCTCCTTGTATAAATCCTGGTTAGTTCTTGCCA<br>CGGCGGAACTCATCGCCGCCTGCCTTGCCCGCTGCTGGACA<br>GGGGCTCGGCTGTTGGGCACTGACAATTCCGTGGTGTTTATT<br>TGTGAAATTTGTGATGCTATTGCTTTATTTGTAACCATTCTA<br>GCTTTATTTGTGAAATTTGTGATGCTATTGCTTTATTTGTAAC<br>CATTATAAGCTGCAATAAACAAGTTAACAACAACAATTGCA<br>TTCATTTTATGTTTCAGGTTCAGGGGGAGATGTGGGAGGTTT<br>TTTAAAGCGGGGGATCCAAATTCCCGATAAGGATCTTCCTA<br>GAGCATGGCTACGTAGATAAGTAGCATGGCGGGTTAATCAT<br>TAACTACAAGGAACCCCTAGTGATGGAGTTGGCCACTCCCT<br>CTCTGCGCGCTCGCTCGCTCACTGAGGCCGGGCGACCAAAG<br>GTCGCCCGACGCCCGGGCTTTGCCCGGGCGGCCTCAGTGAG<br>CGAGCGAGCGCGCAGCCTTAATTAA |

What is claimed is:

1. A method of treating a subject having obesity, diabetes, heart failure, or renal failure, comprising:
administering to the subject a viral vector comprising a first nucleic acid sequence encoding an sTGFβR2 polypeptide and a second nucleic acid sequence encoding an FGF21 polypeptide; or
administering to the subject a first viral vector comprising a first nucleic acid sequence encoding an sTGFβR2 polypeptide and a second viral vector comprising a second nucleic acid sequence encoding an FGF21 polypeptide, and
wherein the first and/or second nucleic acid sequence is operably linked to a regulatory sequence for expression of the sTGFβR2 polypeptide and FGF21 polypeptide.

2. The method of claim 1, wherein the regulatory sequence comprises a promoter.

3. The method of claim 1, wherein the regulatory sequence comprises a promoter selected from the group consisting of a heF1a promoter, CAGGS (cytomegalovirus, chicken beta-actin intron, splice acceptor of the rabbit beta-globin gene), CMV, shEf1a (truncated hEf1a), an AAT promoter, a thyroid hormone-binding globulin promoter, an albumin promoter, a thyroxin-binding globulin (TBG) promoter, a hepatic control region (HCR)-ApoCII hybrid promoter, CASI, a HCR-hAAT hybrid promoter, and an AAT promoter combined with mouse albumin gene enhancer (Ealb) element and an apolipoprotein E promoter.

4. The method of claim 1, wherein the regulatory sequence comprises a liver tissue specific promoter for expression of the sTGFβR2 polypeptide or the FGF21 polypeptide in liver cells.

5. The method of claim 1, wherein the regulatory sequence comprises a constitutive promoter or an inducible promoter.

6. The method of claim 1, wherein the first nucleic acid sequence is operably linked to a 3' untranslated region for RNA stability and expression in mammalian cells.

7. The method of claim 6, wherein the 3' untranslated region comprises a WPRE, a WPRE3, an SV40 late poly adenylation signal, an HBG poly adenylation signal, a Rabbit beta globin poly A, Bovine bgpA, an ETC poly adenylation signal, or a hybrid thereof.

8. The method of claim 7, wherein the SV40 late poly adenylation signal comprises a truncated SEQ ID NO:114.

9. The method of claim 1, wherein the first nucleic acid sequence and second nucleic acid sequence is operably linked via a polycistronic element, optionally wherein the polycistronic element is an IRES or a 2A sequence for expression of sTGFβR2 and FGF21 from a polycistronic transcript.

10. The method of claim 1, wherein the viral vector is an adeno-associated virus (AAV) vector.

11. The method of claim 10, wherein the AAV vector is derived from an AAV serotype selected from the group consisting of AAV1, AAV2, AAV3, AAV4, AAV5, AAV6, AAV7, AAV8, AAV9, AAV10, AAV11, AAV12, AAV2.5, and AAVrh10.XX viral vectors, where XX represents a variant.

12. The method of claim 1, wherein the sTGFβR2 polypeptide has at least 95% sequence identity to amino acids 33-159 of the amino acid sequence set forth in SEQ ID NO: 8.

13. The method of claim 1, wherein the sTGFβR2 polypeptide comprises amino acids 33-159 of the amino acid sequence set forth in SEQ ID NO: 8.

14. The method of claim 1, wherein the sTGFβR2 polypeptide is encoded by a nucleic acid sequence that has at least 85% sequence identity to the nucleic acid sequence set forth in SEQ ID NO: 5.

15. The method of claim 1, wherein the sTGFβR2 polypeptide is encoded by a nucleic acid sequence that has at least 90% sequence identity to nucleotides 70 to 471 of the nucleic acid sequence set forth in SEQ ID NO: 5.

16. The method of claim 1, wherein the sTGFβR2 polypeptide or the FGF21 polypeptide is a fusion polypeptide comprising an Ig Fc domain, wherein the Ig Fc domain is selected from the group consisting of a human, a canine, a feline, a bovine, an ovine, a caprine, an equine, a murine, and a porcine Fc or a subtype thereof, including IgG1, IgG2a, IgG2b, IgG3 and IgG4.

17. The method of claim 16, wherein the Ig Fc domain has at least 90% sequence identity to the amino acid sequence set forth in SEQ ID NO: 11 or 13.

18. The method of claim 1, wherein the method treats heart failure in the subject.

19. The method of claim 1, wherein the method treats renal failure in the subject.

20. The method of claim 1, wherein the method treats heart failure and renal failure in the subject.

21. The method of claim 1, wherein the method comprises administering to the subject a viral vector comprising:
an apolipoprotein E promoter;
the first nucleic acid sequence and the second nucleic acid sequence;
a woodchuck hepatitis posttranscriptional regulatory element (WPRE); and
an SV40 late polyadenylation signal.

22. The method of claim 21, wherein the WPRE comprises a truncated version of the WPRE, optionally WPRE3.

* * * * *

SEQUENCE LISTING

<160> NUMBER OF SEQ ID NOS: 151

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggaagaata caccaccagc agtcccgacc ccagagggcc cacaatcaag ccctgtcc      58

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcatttaccc ggagtccggg agaagctc      28

<210> SEQ ID NO 3
<211> LENGTH: 552
<212> TYPE: DNA
<213> ORGANISM: Homo sapiens

<400> SEQUENCE: 3
atgggtcggg ggctgctcag gggcctgtgg ccgctgcaca tcgtcctgtg gacgcgtatc      60
gccagcacga tcccaccgca cgttcagaag tcggatgtgg aaatggaggc ccagaaagat     120
gaaatcatct gccccagctg taataggact gccatccac tgagacatat taataacgac     180
atgatagtca ctgacaacaa cggtgcagtc aagtttccac aactgtgtaa attttgtgat     240

```
gtgagatttt ccacctgtga caaccagaaa tcctgcatga gcaactgcag catcacctcc    300
atctgtgaga agccacagga agtctgtgtg gctgtatgga gaaagaatga cgagaacata    360
acactagaga cagtttgcca tgaccccaag ctcccctacc atgactttat tctggaagat    420
gctgcttctc caaagtgcat tatgaaggaa aaaaaaaagc ctggtgagac tttcttcatg    480
tgttcctgta gctctgatga gtgcaatgac aacatcatct tctcagaaga atataacacc    540
agcaatcctg ac                                                        552

<210> SEQ ID NO 4
<211> LENGTH: 498
<212> TYPE: DNA
<213> ORGANISM: Canis sp.

<400> SEQUENCE: 4
atgcacagtc aagggcgggg ttgcaacaac acaaaacaaa acaaaacttc cggacttcga    60
cctgcagctg agaagaacat ctcgcaaagc ggcgttaata atgacatgat ggtcactgac    120
agcaatggtg tcatcaaatt ccacaattg tgtaaatttt gtgatgtgag atcttccacc    180
tgtgacaacc agaaatcttg catgagcaac tgcagcatta catccatctg tgagaagcca    240
catgaagtct gtctggctgt ctggagaaag aatgatgaga acataacact agagactctc    300
tgccatgacc caaggatac ctaccatgga attgttctcg aagatgctgc ctcttcgaag    360
tgcattatga agaaaagaa ggtgctgggg gagactttct ttatgtgttc ctgtagctcc    420
gacgagtgca acgactacat catcttctct gaagaatatg ccaccaacaa ccctgacttg    480
ttgttagtca tattccaa                                                  498

<210> SEQ ID NO 5
<211> LENGTH: 471
<212> TYPE: DNA
<213> ORGANISM: Unknown
<220> FEATURE:
<223> OTHER INFORMATION: Description of Unknown:
      sTGFBr2 with mouse/human secretion signal sequence

<400> SEQUENCE: 5
atgggtcggg ggctgctccg gggcctgtgg ccgctgcata tcgtcctgtg gacgcgcatc    60
gccagcacga taatgacat gatggtcact gacagcaatg gtgtcatcaa atttccacaa    120
ttgtgtaaat tttgtgatgt gagatcttcc acctgtgaca accagaaatc ttgcatgagc    180
aactgcagca ttcatccat ctgtgagaag ccacatgaag tctgtctggc tgtctggaga    240
aagaatgatg agaacataac actagagact ctctgccatg accccaagga tacctaccat    300
ggaattgttc tcgaagatgc tgcctcttcg aagtgcatta tgaaagaaaa gaaggtgctg    360
ggggagactt tctttatgtg ttcctgtagc tccgacgagt gcaacgacta catcatcttc    420
tctgaagaat atgccaccaa caaccctgac ttgttgttag tcatattcca a             471

<210> SEQ ID NO 6
<211> LENGTH: 552
<212> TYPE: DNA
<213> ORGANISM: Mus musculus

<400> SEQUENCE: 6
atgggtcggg ggctgctccg gggcctgtgg ccgctgcata tcgtcctgtg gacgcgcatc    60
gccagcacga tcccgccgca cgttcccaag tcggatgtgg aaatggaagc cagaaagat     120 gcatccatcc acctaagctg taataggacc atccatccac tgaaacattt aacagtgat    180
```

-continued

```
gtcatggcca gcgacaatgg cggtgcggtc aagcttccac agctgtgcaa gttttgcgat      240
gtgagactgt ccacttgcga caaccagaag tcctgcatga gcaactgcag catcacggcc      300
atctgtgaga gccgcatga agtctgcgtg ccgtgtgga ggaagaacga caagaacatt        360
actctggaga cggtttgcca cgaccccaag ctcacctacc acggcttcac tctggaagat      420
gccgcttctc ccaagtgtgt catgaaggaa aagaaaaggg cgggcgagac tttcttcatg      480
tgtgcctgta acatggaaga gtgcaacgat tacatcatct tttcggaaga atacaccacc      540
agcagtcccg ac                                                          552
```

<210> SEQ ID NO 7
<211> LENGTH: 184
<212> TYPE: PRT
<213> ORGANISM: Homo sapiens

<400> SEQUENCE: 7

```
Met Gly Arg Gly Leu Leu Arg Gly Leu Trp Pro Leu His Ile Val Leu
1               5                  10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp
            180
```

<210> SEQ ID NO 8
<211> LENGTH: 159
<212> TYPE: PRT
<213> ORGANISM: Canis sp.

<400> SEQUENCE: 8

```
Met His Ser Gln Gly Arg Gly Cys Asn Asn Thr Lys Gln Asn Lys Thr
1               5                   10                  15

Ser Gly Leu Arg Pro Ala Ala Glu Lys Asn Ile Ser Gln Ser Gly Val
            20                  25                  30

Asn Asn Asp Met Met Val Thr Asp Ser Asn Gly Val Ile Lys Phe Pro
        35                  40                  45

Gln Leu Cys Lys Phe Cys Asp Val Arg Ser Ser Thr Cys Asp Asn Gln
    50                  55                  60
```

```
Lys Ser Cys Met Ser Asn Cys Ser Ile Thr Ser Ile Cys Glu Lys Pro
 65                  70                  75                  80

His Glu Val Cys Leu Ala Val Trp Arg Lys Asn Asp Glu Asn Ile Thr
                 85                  90                  95

Leu Glu Thr Leu Cys His Asp Pro Lys Asp Thr Tyr His Gly Ile Val
            100                 105                 110

Leu Glu Asp Ala Ala Ser Ser Lys Cys Ile Met Lys Glu Lys Lys Val
        115                 120                 125

Leu Gly Glu Thr Phe Phe Met Cys Ser Cys Ser Ser Asp Glu Cys Asn
    130                 135                 140

Asp Tyr Ile Ile Phe Ser Glu Glu Tyr Ala Thr Asn Asn Pro Asp
145                 150                 155
```

<210> SEQ ID NO 9
<211> LENGTH: 184
<212> TYPE: PRT
<213> ORGANISM: Mus musculus

<400> SEQUENCE: 9

```
Met Gly Arg Gly Leu Leu Arg Gly Leu Trp Pro Leu His Ile Val Leu
  1               5                  10                  15

Trp Thr Arg Ile Ala Ser Thr Ile Pro Pro His Val Pro Lys Ser Asp
                 20                  25                  30

Val Glu Met Glu Ala Gln Lys Asp Ala Ser Ile His Leu Ser Cys Asn
            35                  40                  45

Arg Thr Ile His Pro Leu Lys His Phe Asn Ser Asp Val Met Ala Ser
 50                  55                  60

Asp Asn Gly Gly Ala Val Lys Leu Pro Gln Leu Cys Lys Phe Cys Asp
 65                  70                  75                  80

Val Arg Leu Ser Thr Cys Asp Asn Gln Lys Ser Cys Met Ser Asn Cys
                 85                  90                  95

Ser Ile Thr Ala Ile Cys Glu Lys Pro His Glu Val Cys Val Ala Val
            100                 105                 110

Trp Arg Lys Asn Asp Lys Asn Ile Thr Leu Glu Thr Val Cys His Asp
        115                 120                 125

Pro Lys Leu Thr Tyr His Gly Phe Thr Leu Glu Asp Ala Ala Ser Pro
    130                 135                 140

Lys Cys Val Met Lys Glu Lys Lys Arg Ala Gly Glu Thr Phe Phe Met
145                 150                 155                 160

Cys Ala Cys Asn Met Glu Glu Cys Asn Asp Tyr Ile Ile Phe Ser Glu
                165                 170                 175

Glu Tyr Thr Thr Ser Ser Pro Asp
            180
```

<210> SEQ ID NO 10
<211> LENGTH: 714
<212> TYPE: DNA
<213> ORGANISM: Canis sp.

<400> SEQUENCE: 10

```
cccaaaagag aaaatggaag agttcctcgc ccacctgatt gtcccaaatg cccagcccct    60
gaaatgctgg gagggccttc ggtcttcatc tttcccccga aacccaagga caccctcttg   120
attgcccgaa cacctgaggt cacatgtgtg gtggtggatc tggacccaga agaccctgag   180
gtgcagatca gctggttcgt ggacggtaag cagatgcaaa cagccaagac tcagcctcgt   240
gaggagcagt tcaatggcac ctaccgtgtg gtcagtgtcc tccccattgg gcaccaggac   300
```

```
tggctcaagg ggaagcagtt cacgtgcaaa gtcaacaaca aagccctccc atccccgatc      360
gagaggacca tctccaaggc cagagggcaa gcccatcagc ccagtgtgta tgtcctgccg      420
ccatcccggg aggagttgag caagaacaca gtcagcttga catgcctgat caaagacttc      480
ttcccacctg acattgatgt ggagtggcag agcaatggac agcaggagcc tgagagcaag      540
taccgcacga ccccgcccca gctggacgag gacgggtcct acttcctgta cagcaagctc      600
tctgtggaca gagccgctg gcagcgggga gacaccttca tatgtgcggt gatgcatgaa      660
gctctacaca accactacac acaggaatcc ctctcccatt ctccgggtaa atga          714
```

<210> SEQ ID NO 11
<211> LENGTH: 237
<212> TYPE: PRT
<213> ORGANISM: Canis sp.

<400> SEQUENCE: 11

```
Pro Lys Arg Glu Asn Gly Arg Val Pro Arg Pro Asp Cys Pro Lys
1               5                   10                  15

Cys Pro Ala Pro Glu Met Leu Gly Gly Pro Ser Val Phe Ile Phe Pro
            20                  25                  30

Pro Lys Pro Lys Asp Thr Leu Leu Ile Ala Arg Thr Pro Glu Val Thr
        35                  40                  45

Cys Val Val Asp Leu Asp Pro Glu Asp Pro Glu Val Gln Ile Ser
    50                  55                  60

Trp Phe Val Asp Gly Lys Gln Met Gln Thr Ala Lys Thr Gln Pro Arg
65                  70                  75                  80

Glu Glu Gln Phe Asn Gly Thr Tyr Arg Val Val Ser Val Leu Pro Ile
                85                  90                  95

Gly His Gln Asp Trp Leu Lys Gly Lys Gln Phe Thr Cys Lys Val Asn
            100                 105                 110

Asn Lys Ala Leu Pro Ser Pro Ile Glu Arg Thr Ile Ser Lys Ala Arg
        115                 120                 125

Gly Gln Ala His Gln Pro Ser Val Tyr Val Leu Pro Pro Ser Arg Glu
    130                 135                 140

Glu Leu Ser Lys Asn Thr Val Ser Leu Thr Cys Leu Ile Lys Asp Phe
145                 150                 155                 160

Phe Pro Pro Asp Ile Asp Val Glu Trp Gln Ser Asn Gly Gln Gln Glu
                165                 170                 175

Pro Glu Ser Lys Tyr Arg Thr Thr Pro Pro Gln Leu Asp Glu Asp Gly
            180                 185                 190

Ser Tyr Phe Leu Tyr Ser Lys Leu Ser Val Asp Lys Ser Arg Trp Gln
        195                 200                 205

Arg Gly Asp Thr Phe Ile Cys Ala Val Met His Glu Ala Leu His Asn
    210                 215                 220

His Tyr Thr Gln Glu Ser Leu Ser His Ser Pro Gly Lys
225                 230                 235
```

<210> SEQ ID NO 12
<211> LENGTH: 699
<212> TYPE: DNA
<213> ORGANISM: Mus musculus

<400> SEQUENCE: 12

```
cccagagggc ccacaatcaa gccctgtcct ccatgcaaat gcccagcacc taacctcgag       60
ggtggaccat ccgtcttcat cttccctcca aagatcaagg atgtactcat gatctccctg      120
```

```
agccccatag tcacatgtgt ggtggtggat gtgagcgagg atgacccaga tgtccagatc    180
agctggtttg tgaacaacgt ggaagtacac acagctcaga cacaaaccca tagagaggat    240
tacaacagta ctctccgggt ggtcagtgcc ctccccatcc agcaccagga ctggatgagt    300
ggcaaggcgt tcgcatgcgc ggtcaacaac aaagacctcc cagcgcccat cgagagaacc    360
atctcaaaac ccaaagggtc agtaagagct ccacaggtat atgtcttgcc tccaccagaa    420
gaagagatga ctaagaaaca ggtcactctg acctgcatgg tcacagactt catgcctgaa    480
gacatttacg tggagtggac caacaacggg aaaacagagc taaactacaa gaacactgaa    540
ccagtcctgg actctgatgg ttcttacttc atgtacagca agctgagagt ggaaaagaag    600
aactgggtgg aaagaaatag ctactcctgt tcagtggtcc acgagggtct gcacaatcac    660
cacacgacta agagcttctc ccggactccg ggtaaatga                           699
```

<210> SEQ ID NO 13
<211> LENGTH: 232
<212> TYPE: PRT
<213> ORGANISM: Mus musculus

<400> SEQUENCE: 13

```
Pro Arg Gly Pro Thr Ile Lys Pro Cys Pro Pro Cys Lys Cys Pro Ala
1               5                   10                  15

Pro Asn Leu Glu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Ala Phe Ala Cys Ala Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Glu Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His Thr Thr Lys
    210                 215                 220

Ser Phe Ser Arg Thr Pro Gly Lys
225                 230
```

<210> SEQ ID NO 14
<211> LENGTH: 1794
<212> TYPE: DNA
<213> ORGANISM: Mus musculus

<400> SEQUENCE: 14

```
atgatggact tggagttgcc accgccagga ctacagtccc agcaggacat ggatttgatt        60
gacatccttt ggaggcaaga catagatctt ggagtaagtc gagaagtgtt tgactttagt       120
cagcgacaga aggactatga gttggaaaaa cagaaaaaac tcgaaaagga agacaagag        180
caactccaga aggaacagga gaaggccttt ttcgctcagt ttcaactgga tgaagaaaca       240
ggagaattcc tcccaattca gccggcccag cacatccaga cagacactag tggatccgcc       300
agctactccc aggttgccca cattcccaaa caagatgcct tgtactttga agactgtatg       360
cagcttttgg cagagacatt cccatttgtt gatgaccatg agtcgcttgc cctggatatc       420
cccagccacg ctgaaagttc agtcttcact gcccctcatc aggcccagtc cctcaatagc       480
tctctggagg cagccatgac tgatttaagc agcatagagc aggacatgga gcaagtttgg       540
caggagctat tttccattcc cgaattacag tgtcttaata ccgaaaacaa gcagctggct       600
gatactaccg ctgttcccag cccagaagcc acactgacag aaatggacag caattaccat       660
ttttactcat cgatctcctc gctggaaaaa gaagtgggca actgtggtcc acatttcctt       720
catggttttg aggattcttt cagcagcatc ctctccactg atgatgccag ccagctgacc       780
tccttagact caaatcccac cttaaacaca gattttggcg atgaattta ttctgctttc        840
atagcagagc ccagtgacgg tggcagcatg ccttcctccg ctgccatcag tcagtcactc       900
tctgaactcc tggacgggac tattgaaggc tgtgacctgt cactgtgtaa agcttttcaac      960
ccgaagcacg ctgaaggcac aatggaattc aatgactctg actctggcat ttcactgaac      1020
acaagtccca gccgagcgtc cccagagcac tccgtggagt cttccattta cggagaccca      1080
ccgcctgggt tcagtgactc ggaaatggag gagctagata gtgcccctgg aagtgtcaaa      1140
cagaacggcc ctaaagcaca gccagcacat tctcctggag acacagtaca gcctctgtca      1200
ccagctcaag ggcacagtgc tcctatgcgt gaatcccaat gtgaaaatac aacaaaaaaa      1260
gaagttcccg tgagtcctgg tcatcaaaaa gccccattca caaaagacaa acattcaagc      1320
cgcttagagg ctcatctcac acgagatgag cttagggcaa aagctctcca tattccattc      1380
cctgtcgaaa aaatcattaa cctccctgtt gatgacttca tgaaatgat gtccaaggag       1440
caattcaatg aagctcagct cgcattgatc cgagatatac gcaggagagg taagaataaa      1500
gtcgccgccc agaactgtag gaaaaggaag ctggagaaca ttgtcgagct ggagcaagac      1560
ttgggccact aaaagacga gagagaaaaa ctactcagag aaaagggaga aaacgacaga       1620
aacctccatc tactgaaaag gcggctcagc accttgtatc ttgaagtctt cagcatgtta      1680
cgtgatgagg atggaaagcc ttactctccc agtgaatact ctctgcagca aaccagagat      1740
ggcaatgtgt tccttgttcc caaaagcaag aagccagata caaagaaaaa ctag             1794
```

<210> SEQ ID NO 15
<211> LENGTH: 732
<212> TYPE: DNA
<213> ORGANISM: Mus musculus

<400> SEQUENCE: 15

```
atggcgctgt tccggggaat gtggagcgtg ctaaaagcac tggggcgcac ggggggtcgag       60
atgtgcgcgg gctgcggggg tcgcatcccc tcgtctatca gtcttgtctg tattccgaag      120
tgttttttcca gcatgggtag ctatccaaag aaacctatga gttcatacct tcgattttcc       180
acagaacagc tacccaaatt taaagctaaa cacccagatg caaaactttc agaattggtt      240
```

| | |
|---|---|
| aggaaaattg cagccctgtg gagggagcta ccagaagcag aaaaaaaggt ttatgaagct | 300 |
| gattttaaag ctgagtggaa agcatacaaa gaagctgtga gcaagtataa agagcagcta | 360 |
| actccaagtc agctgatggg tatggagaag gaggcccggc agagacggtt aaaaaagaaa | 420 |
| gcactggtaa agagaagaga attaatttg cttggaaaac caaaaagacc tcgttcagca | 480 |
| tataacattt atgtatctga aagcttccag gaggcaaagg atgattcggc tcagggaaaa | 540 |
| ttgaagcttg taaatgaggc ttggaaaaat ctgtctcctg aggaaaagca ggcatatatt | 600 |
| cagcttgcta aagatgatag gattcgttac gacaatgaaa tgaagtcttg ggaagagcag | 660 |
| atggctgaag ttggacgaag tgatctcatc cgtcgaagtg tgaaacgatc cggagacatc | 720 |
| tctgagcatt aa | 732 |

<210> SEQ ID NO 16
<211> LENGTH: 747
<212> TYPE: DNA
<213> ORGANISM: Unknown
<220> FEATURE:
<223> OTHER INFORMATION: Description of Unknown:
    Adiponectin sequence

<400> SEQUENCE: 16

| | |
|---|---|
| atgctactgt tgcaagctct cctgttcctc ttaatcctgc ccagtcatgc cgaagatgac | 60 |
| gttactacaa ctgaagagct agctcctgct ttggtccctc cacccaaggg aacttgtgca | 120 |
| ggttggatgg caggcatccc aggacatcct ggccacaatg gcacaccagg ccgtgatggc | 180 |
| agagatggca ctcctggaga gaagggagag aaaggagatg caggtcttct tggtcctaag | 240 |
| ggtgagacag gagatgttgg aatgacagga gctgaagggc cacggggctt ccccggaacc | 300 |
| cctggcagga aggagagcc tggagaagcc gcttatgtgt atcgctcagc gttcagtgtg | 360 |
| gggctggaga cccgcgtcac tgttcccaat gtacccattc gctttactaa gatcttctac | 420 |
| aaccaacaga atcattatga cggcagcact ggcaagttct actgcaacat tccgggactc | 480 |
| tactacttct cttaccacat cacggtgtac atgaaagatg tgaaggtgag cctcttcaag | 540 |
| aaggacaagg ccgttctctt cacctacgac cagtatcagg aaaagaatgt ggaccaggcc | 600 |
| tctggctctg tgctcctcca tctggaggtg ggagaccaag tctggctcca ggtgtatggg | 660 |
| gatgggacc acaatggact ctatgcagat aacgtcaacg actctacatt tactggcttt | 720 |
| cttctctacc atgataccaa ctgataa | 747 |

<210> SEQ ID NO 17
<211> LENGTH: 1174
<212> TYPE: DNA
<213> ORGANISM: Homo sapiens

<400> SEQUENCE: 17

| | |
|---|---|
| ttggctccgg tgcccgtcag tgggcagagc gcacatcgcc cacagtcccc gagaagttgt | 60 |
| ggggagggt cggcaattga accggtgcct agagaaggtg gcgcgggta aactgggaaa | 120 |
| gtgatgtcgt gtactggctc cgccttttc ccgagggtgg gggagaaccg tatataagtg | 180 |
| cagtagtcgc cgtgaacgtt cttttttcgca acgggtttgc cgccagaaca caggtaagtg | 240 |
| ccgtgtgtgg ttcccgcggg cctggcctct ttacggggtta tggcccttgc gtgccttgaa | 300 |
| ttacttccac ctggctgcag tacgtgattc ttgatcccga gcttcgggtt ggaagtgggt | 360 |
| gggagagttc gaggccttgc gcttaaggag cccttcgcc tcgtgcttga gttgaggcct | 420 |
| ggcctgggcg ctggggccgc cgcgtgcgaa tctggtggca ccttcgcgcc tgtctcgctg | 480 |

```
ctttcgataa gtctctagcc atttaaaatt tttgatgacc tgctgcgacg cttttttttct    540 ggcaagatag tcttgtaaat gcgggccaag atctgcacac tggtatttcg gttttttgggg    600 ccgcgggcgg cgacggggcc cgtgcgtccc agcgcacatg ttcggcgagg cggggcctgc     660
gagcgcggcc accgagaatc ggacgggggt agtctcaagc tggccggcct gctctggtgc    720
ctggcctcgc gccgccgtgt atcgccccgc cctgggcggc aaggctggcc cggtcggcac    780
cagttgcgtg agcggaaaga tggccgcttc ccggccctgc tgcagggagc tcaaaatgga    840
ggacgcggcg ctcgggagag cgggcgggtg agtcacccac acaaaggaaa agggccttc    900 cgtcctcagc cgtcgcttca tgtgactcca cggagtaccg ggcgccgtcc aggcacctcg    960
attagttctc gagcttttgg agtacgtcgt ctttaggttg gggggagggg ttttatgcga   1020
tggagtttcc ccacactgag tgggtggaga ctgaagttag gccagcttgg cacttgatgt   1080
aattctcctt ggaatttgcc cttttttgagt ttggatcttg gttcattctc aagcctcaga   1140
cagtggttca agtttttttt cttccatttc aggt                              1174
```

<210> SEQ ID NO 18
<211> LENGTH: 231
<212> TYPE: DNA
<213> ORGANISM: Homo sapiens

<400> SEQUENCE: 18

```
aggctccggt gcccgtcagt gggcagagcg cacatcgccc acagtccccg agaagttggg    60
gggaggggtc ggcaattgaa ccggtgccta gagaaggtgg cgcggggtaa actgggaaag   120
tgatgtcgtg tactggctcc gccttttttcc cgagggtggg ggagaaccgt atataagtgc   180
agtagtcgcc gtgaacgttc ttttttcgcaa cgggtttgcc gccagaacac a           231
```

<210> SEQ ID NO 19
<211> LENGTH: 544
<212> TYPE: DNA
<213> ORGANISM: Unknown
<220> FEATURE:
<223> OTHER INFORMATION: Description of Unknown:
      rhEF1a promoter sequence

<400> SEQUENCE: 19

```
ggatctgcga tcgctccggt gcccgtcagt gggcagagcg cacatcgccc acagtccccg    60
agaagttggg gggaggggtc ggcaattgaa cgggtgccta gagaaggtgg cgcggggtaa   120
actgggaaag tgatgtcgtg tactggctcc gccttttttcc cgagggtggg ggagaaccgt   180
atataagtgc agtagtcgcc gtgaacgttc ttttttcgcaa cgggtttgcc gccagaacac   240
agctgaagct tcgagggggct cgcatctctc cttcacgcgc ccgccgccct acctgaggcc   300
gccatccacg ccggttgagt cgcgttctgc gcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                              544
```

<210> SEQ ID NO 20
<211> LENGTH: 66
<212> TYPE: DNA
<213> ORGANISM: Porcine teschovirus-1

<400> SEQUENCE: 20

<210> SEQ ID NO 21
<211> LENGTH: 54
<212> TYPE: DNA
<213> ORGANISM: Thosea asigna virus

<400> SEQUENCE: 21
gagggccgcg gcagcctgct gacctgcggc gacgtggagg aaaacccgg cccc      54

<210> SEQ ID NO 22
<211> LENGTH: 581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gcccctctcc ctcccccccc cctaacgtta ctggccgaag ccgcttggaa taaggccggt      60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag     180
gaatgcaagg tctgttgaat gtcgtgaagg aagcagttcc tctggaagct tcttgaagac     240
aaacaacgtc tgtagcgacc ctttgcaggc agcggaaccc cccacctggc gacaggtgcc     300
tctgcggcca aaagccacgt gtataagata cacctgcaaa ggcggcacaa ccccagtgcc     360
acgttgtgag ttggatagtt gtggaaagag tcaaatggct ctcctcaagc gtattcaaca     420
aggggctgaa ggatgcccag aaggtacccc attgtatggg atctgatctg ggcctcggt      480
gcacatgctt tacatgtgtt tagtcgaggt taaaaaaacg tctaggcccc ccgaaccacg     540
gggacgtggt tttcctttga aaaacacgat gataagccac c                          581

<210> SEQ ID NO 23
<211> LENGTH: 130
<212> TYPE: DNA
<213> ORGANISM: Adeno-associated virus 2

<400> SEQUENCE: 23
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 24
<211> LENGTH: 141
<212> TYPE: DNA
<213> ORGANISM: Adeno-associated virus 2

<400> SEQUENCE: 24
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc t                                               141

<210> SEQ ID NO 25
<211> LENGTH: 2214
<212> TYPE: DNA
<213> ORGANISM: Adeno-associated virus 8

<400> SEQUENCE: 25

```
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg acccttcaa cggactcgac     180
aaggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag ccaacagcc cgccagaaaa agactcaatt ttggtcagac tggcgactca     540
gagtcagttc cagaccctca acctctcgga gaacctccag cagcgccctc tggtgtggga     600
cctaatacaa tggctgcagg cggtggcgca ccaatggcag acaataacga aggcgccgac     660
ggagtgggta gttcctcggg aaattggcat tgcgattcca catggctggg cgacagagtc     720
atcaccacca gcacccgaac ctgggccctg cccacctaca caaccaccct ctacaagcaa     780
atctccaacg ggacatcggg aggagccacc aacgacaaca cctacttcgg ctacagcacc     840
ccctgggggt attttgactt taacagattc cactgccact tttcaccacg tgactggcag     900
cgactcatca caacaactg gggattccgg cccaagagac tcagcttcaa gctcttcaac     960
atccaggtca aggaggtcac gcagaatgaa ggcaccaaga ccatcgccaa taacctcacc    1020
agcaccatcc aggtgtttac ggactcggag taccagctgc cgtacgttct cggctctgcc    1080
caccagggct gcctgcctcc gttcccggcg gacgtgttca tgattcccca gtacggctac    1140
ctaacactca caacggtag tcaggccgtg gacgctcct ccttctactg cctggaatac    1200
tttccttcgc agatgctgag aaccggcaac aacttccagt ttacttacac cttcgaggac    1260
gtgcctttcc acagcagcta cgcccacagc cagagcttgg accggctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga ttttggcaa acaaaatgct gccagagaca tgcggatta cagcgatgtc    1680
atgctcacca gcgaggaaga aatcaaaacc actaaccctg tggctacaga ggaatacggt    1740
atcgtggcag ataacttgca gcagcaaaac acggctcctc aaattggaac tgtcaacagc    1800
cagggggcct acccggtat ggtctggcag aaccgggacg tgtacctgca gggtcccatc    1860
tgggccaaga ttcctcacac ggacggcaac ttccacccgt ctcgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctg          2214
```

<210> SEQ ID NO 26
<211> LENGTH: 2229

```
<212> TYPE: DNA
<213> ORGANISM: Adeno-associated virus

<400> SEQUENCE: 26
atggctgccg atggttatct tccagattgg ctcgaggaca accttagtga aggaattcgc      60
gagtggtggg cttttgaaacc tggagcccct caacccaagg caaatcaaca acatcaagac     120
aacgctcgag gtcttgtgct tccgggttac aaataccttg acccggcaa cggactcgac       180
aaggggggagc cggtcaacgc agcagacgcg gcggccctcg agcacgacaa ggcctacgac     240
cagcagctca aggccggaga caacccgtac ctcaagtaca ccacgccga cgccgagttc      300
caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct       600
cttacaatgg cttcaggtgg tggcgcacca gtggcagaca taacgaagg tgccgatgga     660
gtgggtagtt cctcgggaaa ttggcattgc gattcccaat ggctgggga cagagtcatc     720
accaccagca cccgaacctg ggccctgccc acctacaaca atcacctcta caagcaaatc     780
tccaacagca catctggagg atcttcaaat gacaacgcct acttcggcta cagcaccccc     840
tgggggtatt ttgacttcaa cagattccac tgccacttct caccacgtga ctggcagcga     900
ctcatcaaca caactggggg attccggcct aagcgactca acttcaagct cttcaacatt     960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gtttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctctagaact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttcctt gtctggatct      1620
ttaattttg gcaaacaagg taccggcaga gacaacgtgg atgcggacaa agtcatgata    1680
accaacgaag aagaaattaa aactactaac ccggtagcaa cggagtccta tggacaagtg    1740
gccacaaacc accagagtgc ccaaactttg cggtgcctt taaggcaca ggcgcagacc     1800
ggttgggttc aaaaccaagg aatacttccg ggtatggttt gcaggacag agatgtgtac    1860
ctgcaaggac ccatttgggc caaaattcct cacacggacg gcaactttca cccttctccg    1920
ctgatgggag ggtttggaat gaagcacccg cctcctcaga tcctcatcaa aaacacacct    1980
gtacctgcgg atcctccaac ggccttcaac aaggacaagc tgaactcttt catcacccag    2040
tattctactg gccaagtcag cgtggagatc gagtgggagc tgcagaagga aaacagcaag    2100
cgctggaacc cggagatcca gtacacttcc aactattaca agtctaataa tgttgaattt    2160
gctgttaata ctgaaggtgt atatagtgaa ccccgcccca ttggcaccag ataccctgact    2220
```

```
cgtaatctg                                                             2229

<210> SEQ ID NO 27
<211> LENGTH: 592
<212> TYPE: DNA
<213> ORGANISM: Woodchuck hepatitis virus

<400> SEQUENCE: 27
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttgc tgtctcttta tgaggagttg       180
tggcccgttg tcaggcaacg tggcgtggtg tgcactgtgt ttgctgacgc aaccccact        240 ggttggggca ttgccaccac ctgtcagctc ctttccggga cttcgctttt ccccctccct       300
attgccacgg cggaactcat cgccgcctgc cttgcccgct gctggacagg ggctcggctg       360
ttgggcactg acaattccgt ggtgttgtcg gggaagctga cgtcctttcc atggctgctc       420
gcctgtgttg ccacctggat tctgcgcggg acgtccttct gctacgtccc ttcggccctc       480
aatccagcgg accttccttc ccgcggcctg ctgccggctc tgcggcctct tccgcgtctt       540
cgccttcgcc ctcagacgag tcggatctcc ctttgggccg cctccccgcc tg              592

<210> SEQ ID NO 28
<211> LENGTH: 248
<212> TYPE: DNA
<213> ORGANISM: Woodchuck hepatitis virus

<400> SEQUENCE: 28
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttag ttcttgccac ggcggaactc       180
atcgccgcct gccttgcccg ctgctggaca ggggctcggc tgttgggcac tgacaattcc       240
gtggtgtt                                                              248

<210> SEQ ID NO 29
<211> LENGTH: 134
<212> TYPE: DNA
<213> ORGANISM: Simian virus 40

<400> SEQUENCE: 29
gctttatttg tgaaatttgt gatgctattg ctttatttgt aaccattata agctgcaata        60
aacaagttaa caacaacaat tgcattcatt ttatgtttca ggttcagggg gagatgtggg       120
aggtttttta aagc                                                       134

<210> SEQ ID NO 30
<211> LENGTH: 510
<212> TYPE: DNA
<213> ORGANISM: Bos sp.

<400> SEQUENCE: 30
acgggtggca tccctgtgac ccctccccag tgcctctcct ggccctggaa gttgccactc        60
cagtgcccac cagccttgtc ctaataaaat taagttgcat cattttgtct gactaggtgt       120
ccttctataa tattatgggg tggaggggggg tggtatggag caaggggcaa gttgggaaga       180
caacctgtag ggcctgcggg gtctattggg aaccaagctg gagtgcagtg gcacaatctt       240
ggctcactgc aatctccgcc tcctgggttc aagcgattct cctgcctcag cctcccgagt       300
```

| | |
|---|---|
| tgttgggatt ccaggcatgc atgaccaggc tcagctaatt tttgtttttt tggtagagac | 360 |
| ggggtttcac catattggcc aggctggtct ccaactccta atctcaggtg atctacccac | 420 |
| cttggcctcc caaattgctg ggattacagg cgtgaaccac tgctcccttc cctgtccttc | 480 |
| tgattttgta ggtaaccacg tgcggaccga | 510 |

<210> SEQ ID NO 31
<211> LENGTH: 387
<212> TYPE: DNA
<213> ORGANISM: Oryctolagus sp.

<400> SEQUENCE: 31

| | |
|---|---|
| tggctaataa aggaaattta ttttcattgc aatagtgtgt tggaattttt tgtgtctctc | 60 |
| actcggaagg acatatggga gggcaaatca tttaaaacat cagaatgagt atttggttta | 120 |
| gagtttggca acatatgccc atatgctggc tgccatgaac aaaggttggc tataaagagg | 180 |
| tcatcagtat atgaaacagc cccctgctgt ccattcctta ttccatagaa aagccttgac | 240 |
| ttgaggttag atttttttta tattttgttt tgtgttattt ttttctttaa catccctaaa | 300 |
| attttcctta catgttttac tagccagatt tttcctcctc cctgactac tcccagtcat | 360 |
| agctgtccct cttctcttat ggagatc | 387 |

<210> SEQ ID NO 32
<211> LENGTH: 479
<212> TYPE: DNA
<213> ORGANISM: Homo sapiens

<400> SEQUENCE: 32

| | |
|---|---|
| acgggtggca tccctgtgac ccctccccag tgcctctcct ggccctggaa gttgccactc | 60 |
| cagtgcccac cagccttgtc ctaataaaat taagttgcat cattttgtct gactaggtgt | 120 |
| ccttctataa tattatgggg tggagggggg tggtatggag caaggggcaa gttgggaaga | 180 |
| caacctgtag ggcctgcggg gtctattggg aaccaagctg gagtgcagtg gcacaatctt | 240 |
| ggctcactgc aatctccgcc tcctgggttc aagcgattct cctgcctcag cctcccgagt | 300 |
| tgttgggatt ccaggcatgc atgaccaggc tcagctaatt tttgtttttt tggtagagac | 360 |
| ggggtttcac catattggcc aggctggtct ccaactccta atctcaggtg atctacccac | 420 |
| cttggcctcc caaattgctg ggattacagg cgtgaaccac tgctcccttc cctgtcctt | 479 |

<210> SEQ ID NO 33
<211> LENGTH: 744
<212> TYPE: DNA
<213> ORGANISM: Mus musculus

<400> SEQUENCE: 33

| | |
|---|---|
| atgctactgt tgcaagctct cctgttcctc ttaatcctgc ccagtcatgc cgaagatgac | 60 |
| gttactacaa ctgaagagct agctcctgct ttggtccctc acccaaggg aacttgtgca | 120 |
| ggttggatgg caggcatccc aggacatcct ggccacaatg gcacaccagg ccgtgatggc | 180 |
| agagatggca ctcctggaga gaagggagag aaaggagatg caggtcttct tggtcctaag | 240 |
| ggtgagacag gagatgttgg aatgacagga gctgaagggc cacggggctt ccccggaacc | 300 |
| cctggcagga aaggagagcc tggagaagcc gcttatgtgt atcgctcagc gttcagtgtg | 360 |
| gggctggaga cccgcgtcac tgttcccaat gtacccattc gctttactaa gatcttctac | 420 |
| aaccaacaga tcattatga cggcagcact ggcaagttct actgcaacat tccgggactc | 480 |

```
tactacttct cttaccacat cacggtgtac atgaaagatg tgaaggtgag cctcttcaag    540
aaggacaagg ccgttctctt cacctacgac cagtatcagg aaaagaatgt ggaccaggcc    600
tctggctctg tgctcctcca tctggaggtg ggagaccaag tctggctcca ggtgtatggg    660
gatggggacc acaatggact ctatgcagat aacgtcaacg actctacatt tactggcttt    720
cttctctacc atgataccaa ctga                                           744
```

```
<210> SEQ ID NO 34
<211> LENGTH: 247
<212> TYPE: PRT
<213> ORGANISM: Mus musculus

<400> SEQUENCE: 34
```

```
Met Leu Leu Leu Gln Ala Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
        50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Val Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
                145                 150                 155             160

Tyr Tyr Phe Ser Tyr His Ile Thr Val Tyr Met Lys Asp Val Lys Val
            165                 170                 175

Ser Leu Phe Lys Lys Asp Lys Ala Val Leu Phe Thr Tyr Asp Gln Tyr
        180                 185                 190

Gln Glu Lys Asn Val Asp Gln Ala Ser Gly Ser Val Leu Leu His Leu
    195                 200                 205

Glu Val Gly Asp Gln Val Trp Leu Gln Val Tyr Gly Asp Gly Asp His
210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245
```

```
<210> SEQ ID NO 35
<211> LENGTH: 1794
<212> TYPE: DNA
<213> ORGANISM: Mus musculus

<400> SEQUENCE: 35
```

```
atgatggact tggagttgcc accgccagga ctacagtccc agcaggacat ggatttgatt     60
gacatccttt ggaggcaaga catagatctt ggagtaagtc gagaagtgtt tgactttagt    120
cagcgacaga aggactatga gttggaaaaa cagaaaaaac tcgaaaagga aagacaagag    180
```

```
caactccaga aggaacagga gaaggccttt ttcgctcagt ttcaactgga tgaagaaaca      240
ggagaattcc tcccaattca gccggcccag cacatccaga cagacactag tggatccgcc      300
agctactccc aggttgccca cattcccaaa caagatgcct tgtactttga agactgtatg      360
cagcttttgg cagagacatt cccatttgtt gatgaccatg agtcgcttgc cctggatatc      420
cccagccacg ctgaaagttc agtcttcact gcccctcatc aggcccagtc cctcaatagc      480
tctctggagg cagccatgac tgatttaagc agcatagagc aggacatgga gcaagtttgg      540
caggagctat tttccattcc cgaattacag tgtcttaata ccgaaaacaa gcagctggct      600
gatactaccg ctgttcccag cccagaagcc acactgacag aaatggacag caattaccat      660
ttttactcat cgatctcctc gctggaaaaa gaagtgggca actgtggtcc acatttcctt      720
catggttttg aggattcttt cagcagcatc ctctccactg atgatgccag ccagctgacc      780
tccttagact caaatcccac cttaaacaca gattttggcg atgaatttta ttctgctttc      840
atagcagagc ccagtgacgg tggcagcatg ccttcctccg ctgccatcag tcagtcactc      900
tctgaactcc tggacgggac tattgaaggc tgtgacctgt cactgtgtaa agctttcaac      960
ccgaagcacg ctgaaggcac aatggaattc aatgactctg actctggcat ttcactgaac     1020
acaagtccca gccgagcgtc cccagagcac tccgtggagt cttccattta cggagaccca     1080
ccgcctgggt tcagtgactc ggaaatggag gagctagata gtgcccctgg aagtgtcaaa     1140
cagaacggcc ctaaagcaca gccagcacat tctcctggag acacagtaca gcctctgtca     1200
ccagctcaag ggcacagtgc tcctatgcgt gaatcccaat gtgaaaatac aacaaaaaaa     1260
gaagttcccg tgagtcctgg tcatcaaaaa gccccattca caaaagacaa acattcaagc     1320
cgcttagagg ctcatctcac acgagatgag cttagggcaa aagctctcca tattccattc     1380
cctgtcgaaa aaatcattaa cctccctgtt gatgacttca atgaaatgat gtccaaggag     1440
caattcaatg aagctcagct cgcattgatc cgagatatac gcaggagagg taagaataaa     1500
gtcgccgccc agaactgtag gaaaaggaag ctggagaaca ttgtcgagct ggagcaagac     1560
ttgggccact aaaagacga gagagaaaaa ctactcagag aaaagggaga aaacgacaga     1620
aacctccatc tactgaaaag gcggctcagc accttgtatc ttgaagtctt cagcatgtta     1680
cgtgatgagg atggaaagcc ttactctccc agtgaatact ctctgcagca aaccagagat     1740
ggcaatgtgt tccttgttcc caaaagcaag aagccagata caaagaaaaa ctag            1794
```

<210> SEQ ID NO 36
<211> LENGTH: 597
<212> TYPE: PRT
<213> ORGANISM: Mus musculus

<400> SEQUENCE: 36

```
Met Met Asp Leu Glu Leu Pro Pro Gly Leu Gln Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Gln Lys Asp Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Phe Gln Leu Asp Glu Glu Thr
65                  70                  75                  80

Gly Glu Phe Leu Pro Ile Gln Pro Ala Gln His Ile Gln Thr Asp Thr
```

```
                    85                  90                  95
Ser Gly Ser Ala Ser Tyr Ser Gln Val Ala His Ile Pro Lys Gln Asp
            100                 105                 110

Ala Leu Tyr Phe Glu Asp Cys Met Gln Leu Ala Glu Thr Phe Pro
            115                 120                 125

Phe Val Asp Asp His Glu Ser Leu Ala Leu Asp Ile Pro Ser His Ala
            130                 135                 140

Glu Ser Ser Val Phe Thr Ala Pro His Gln Ala Gln Ser Leu Asn Ser
145                 150                 155                 160

Ser Leu Glu Ala Ala Met Thr Asp Leu Ser Ser Ile Glu Gln Asp Met
                    165                 170                 175

Glu Gln Val Trp Gln Glu Leu Phe Ser Ile Pro Glu Leu Gln Cys Leu
            180                 185                 190

Asn Thr Glu Asn Lys Gln Leu Ala Asp Thr Thr Ala Val Pro Ser Pro
            195                 200                 205

Glu Ala Thr Leu Thr Glu Met Asp Ser Asn Tyr His Phe Tyr Ser Ser
            210                 215                 220

Ile Ser Ser Leu Glu Lys Glu Val Gly Asn Cys Gly Pro His Phe Leu
225                 230                 235                 240

His Gly Phe Glu Asp Ser Phe Ser Ser Ile Leu Ser Thr Asp Asp Ala
                    245                 250                 255

Ser Gln Leu Thr Ser Leu Asp Ser Asn Pro Thr Leu Asn Thr Asp Phe
            260                 265                 270

Gly Asp Glu Phe Tyr Ser Ala Phe Ile Ala Glu Pro Ser Asp Gly Gly
            275                 280                 285

Ser Met Pro Ser Ser Ala Ala Ile Ser Gln Ser Leu Ser Glu Leu Leu
            290                 295                 300

Asp Gly Thr Ile Glu Gly Cys Asp Leu Ser Leu Cys Lys Ala Phe Asn
305                 310                 315                 320

Pro Lys His Ala Glu Gly Thr Met Glu Phe Asn Asp Ser Asp Ser Gly
                    325                 330                 335

Ile Ser Leu Asn Thr Ser Pro Ser Arg Ala Ser Pro Glu His Ser Val
            340                 345                 350

Glu Ser Ser Ile Tyr Gly Asp Pro Pro Gly Phe Ser Asp Ser Glu
            355                 360                 365

Met Glu Glu Leu Asp Ser Ala Pro Gly Ser Val Lys Gln Asn Gly Pro
            370                 375                 380

Lys Ala Gln Pro Ala His Ser Pro Gly Asp Thr Val Gln Pro Leu Ser
385                 390                 395                 400

Pro Ala Gln Gly His Ser Ala Pro Met Arg Glu Ser Gln Cys Glu Asn
                    405                 410                 415

Thr Thr Lys Lys Glu Val Pro Val Ser Pro Gly His Gln Lys Ala Pro
            420                 425                 430

Phe Thr Lys Asp Lys His Ser Ser Arg Leu Glu Ala His Leu Thr Arg
            435                 440                 445

Asp Glu Leu Arg Ala Lys Ala Leu His Ile Pro Phe Pro Val Glu Lys
            450                 455                 460

Ile Ile Asn Leu Pro Val Asp Asp Phe Asn Glu Met Met Ser Lys Glu
465                 470                 475                 480

Gln Phe Asn Glu Ala Gln Leu Ala Leu Ile Arg Asp Ile Arg Arg Arg
                    485                 490                 495

Gly Lys Asn Lys Val Ala Ala Gln Asn Cys Arg Lys Arg Lys Leu Glu
            500                 505                 510
```

Asn Ile Val Glu Leu Glu Gln Asp Leu Gly His Leu Lys Asp Glu Arg
            515                 520                 525

Glu Lys Leu Leu Arg Glu Lys Gly Glu Asn Asp Arg Asn Leu His Leu
        530                 535                 540

Leu Lys Arg Arg Leu Ser Thr Leu Tyr Leu Glu Val Phe Ser Met Leu
545                 550                 555                 560

Arg Asp Glu Asp Gly Lys Pro Tyr Ser Pro Ser Glu Tyr Ser Leu Gln
                565                 570                 575

Gln Thr Arg Asp Gly Asn Val Phe Leu Val Pro Lys Ser Lys Lys Pro
            580                 585                 590

Asp Thr Lys Lys Asn
            595

<210> SEQ ID NO 37
<211> LENGTH: 1251
<212> TYPE: DNA
<213> ORGANISM: Unknown
<220> FEATURE:
<223> OTHER INFORMATION: Description of Unknown:
      sTGFBRII sequence

<400> SEQUENCE: 37
atgggtcggg ggctgctccg gggcctgtgg ccgctgcata tcgtcctgtg gacgcgcatc      60
gccagcacga tcccgccgca cgttcccaag tcggatgtgg aaatggaagc ccagaaagat    120
gcatccatcc acctaagctg taataggacc atccatccac tgaaacattt taacagtgat    180
gtcatggcca cgacaatgg cggtgcggtc aagcttccac agctgtgcaa gttttgcgat    240
gtgagactgt ccacttgcga caaccagaag tcctgcatga gcaactgcag catcacggcc    300
atctgtgaga agccgcatga agtctgcgtg gccgtgtgga ggaagaacga caagaacatt    360
actctggaga cggtttgcca cgaccccaag ctcacctacc acggcttcac tctggaagat    420
gccgcttctc ccaagtgtgt catgaaggaa aagaaaaggg cgggcgagac tttcttcatg    480
tgtgcctgta acatggaaga gtgcaacgat tacatcatct tttcggaaga atacaccacc    540
agcagtcccg accccagagg gcccacaatc aagccctgtc ctccatgcaa atgcccagca    600
cctaacctcg agggtggacc atccgtcttc atcttccctc caaagatcaa ggatgtactc    660
atgatctccc tgagcccat agtcacatgt gtggtggtgg atgtgagcga ggatgaccca    720
gatgtccaga tcagctggtt tgtgaacaac gtggaagtac acacagctca gacacaaacc    780
catagagagg attacaacag tactctccgg gtggtcagtg ccctccccat ccagcaccag    840
gactggatga gtggcaaggc gttcgcatgc gcggtcaaca caaagacct cccagcgccc    900 atcgagagaa ccatctcaaa acccaaaggg tcagtaagag ctccacaggt atatgtcttg    960
cctccaccag aagaagagat gactaagaaa caggtcactc tgacctgcat ggtcacagac   1020
ttcatgcctg aagacattta cgtggagtgg accaacaacg gaaaacaga gctaaactac   1080 aagaacactg aaccagtcct ggactctgat ggttcttact tcatgtacag caagctgaga   1140
gtggaaaaga gaactgggt ggaaagaaat agctactcct gttcagtggt ccacgagggt   1200
ctgcacaatc accacgac taagagcttc tcccggactc cgggtaaatg a              1251

<210> SEQ ID NO 38
<211> LENGTH: 416
<212> TYPE: PRT
<213> ORGANISM: Unknown
<220> FEATURE:
<223> OTHER INFORMATION: Description of Unknown:

-continued sTGFBRII sequence

<400> SEQUENCE: 38

```
Met Gly Arg Gly Leu Arg Gly Leu Trp Pro Leu His Ile Val Leu
1               5                   10                  15

Trp Thr Arg Ile Ala Ser Thr Ile Pro Pro His Val Pro Lys Ser Asp
            20                  25                  30

Val Glu Met Glu Ala Gln Lys Asp Ala Ser Ile His Leu Ser Cys Asn
        35                  40                  45

Arg Thr Ile His Pro Leu Lys His Phe Asn Ser Asp Val Met Ala Ser
    50                  55                  60

Asp Asn Gly Gly Ala Val Lys Leu Pro Gln Leu Cys Lys Phe Cys Asp
65                  70                  75                  80

Val Arg Leu Ser Thr Cys Asp Asn Gln Lys Ser Cys Met Ser Asn Cys
                85                  90                  95

Ser Ile Thr Ala Ile Cys Glu Lys Pro His Glu Val Cys Val Ala Val
                100                 105                 110

Trp Arg Lys Asn Asp Lys Asn Ile Thr Leu Glu Thr Val Cys His Asp
            115                 120                 125

Pro Lys Leu Thr Tyr His Gly Phe Thr Leu Glu Asp Ala Ala Ser Pro
        130                 135                 140

Lys Cys Val Met Lys Glu Lys Lys Arg Ala Gly Glu Thr Phe Phe Met
145                 150                 155                 160

Cys Ala Cys Asn Met Glu Glu Cys Asn Asp Tyr Ile Ile Phe Ser Glu
                165                 170                 175

Glu Tyr Thr Thr Ser Ser Pro Asp Pro Arg Gly Pro Thr Ile Lys Pro
                180                 185                 190

Cys Pro Pro Cys Lys Cys Pro Ala Pro Asn Leu Glu Gly Gly Pro Ser
            195                 200                 205

Val Phe Ile Phe Pro Pro Lys Ile Lys Asp Val Leu Met Ile Ser Leu
        210                 215                 220

Ser Pro Ile Val Thr Cys Val Val Val Asp Val Ser Glu Asp Asp Pro
225                 230                 235                 240

Asp Val Gln Ile Ser Trp Phe Val Asn Asn Val Glu Val His Thr Ala
                245                 250                 255

Gln Thr Gln Thr His Arg Glu Asp Tyr Asn Ser Thr Leu Arg Val Val
                260                 265                 270

Ser Ala Leu Pro Ile Gln His Gln Asp Trp Met Ser Gly Lys Ala Phe
            275                 280                 285

Ala Cys Ala Val Asn Asn Lys Asp Leu Pro Ala Pro Ile Glu Arg Thr
        290                 295                 300

Ile Ser Lys Pro Lys Gly Ser Val Arg Ala Pro Gln Val Tyr Val Leu
305                 310                 315                 320

Pro Pro Pro Glu Glu Glu Met Thr Lys Lys Gln Val Thr Leu Thr Cys
                325                 330                 335

Met Val Thr Asp Phe Met Pro Glu Asp Ile Tyr Val Glu Trp Thr Asn
                340                 345                 350

Asn Gly Lys Thr Glu Leu Asn Tyr Lys Asn Thr Glu Pro Val Leu Asp
            355                 360                 365

Ser Asp Gly Ser Tyr Phe Met Tyr Ser Lys Leu Arg Val Glu Lys Lys
        370                 375                 380

Asn Trp Val Glu Arg Asn Ser Tyr Ser Cys Ser Val Val His Glu Gly
385                 390                 395                 400
```

Leu His Asn His His Thr Thr Lys Ser Phe Ser Arg Thr Pro Gly Lys
            405                 410                 415

<210> SEQ ID NO 39
<211> LENGTH: 912
<212> TYPE: DNA
<213> ORGANISM: Unknown
<220> FEATURE:
<223> OTHER INFORMATION: Description of Unknown:
      GDF15 sequence

<400> SEQUENCE: 39

```
atggccccgc cgcgctcca ggcccagcct ccaggcggct ctcaactgag gttcctgctg      60
ttcctgctgc tgttgctgct gctgctgtca tggccatcgc aggggacgc cctggcaatg    120
cctgaacagc gaccctccgg ccctgagtcc caactcaacg ccgacgagct acggggtcgc    180
ttccaggacc tgctgagccg gctgcatgcc aaccagagcc gagaggactc gaactcagaa    240
ccaagtcctg acccagctgt ccggatactc agtccagagg tgagattggg gtcccacggc    300
cagctgctac tccgcgtcaa ccgggcgtcg ctgagtcagg gtctccccga agcctaccgc    360
gtgcaccgag cgctgctcct gctgacgccg acggcccgcc cctgggacat cactaggccc    420
ctgaagcgtg cgctcagcct ccggggaccc cgtgctcccg cattacgcct gcgcctgacg    480
ccgcctccgg acctggctat gctgccctct ggcggcacgc agctggaact gcgcttacgg    540
gtagccgccg gcagggggcg ccgaagcgcg catgcgcacc aagagactc gtgcccactg    600
ggtccagggc gctgctgtca cttggagact gtgcaggcaa ctcttgaaga cttgggctgg    660
agcgactggg tgctgtcccc gcgccagctg cagctgagca tgtgcgtggg cgagtgtccc    720
cacctgtatc gctccgcgaa cacgcatgcg cagatcaaag cacgcctgca tggcctgcag    780
cctgacaagg tgcctgcccc gtgctgtgtc ccctccagct acaccccggt ggttcttatg    840
cacaggacag acagtggtgt gtcactgcag acttatgatg acctggtggc ccggggctgc    900
cactgcgctt ga                                                        912
```

<210> SEQ ID NO 40
<211> LENGTH: 303
<212> TYPE: PRT
<213> ORGANISM: Unknown
<220> FEATURE:
<223> OTHER INFORMATION: Description of Unknown:
      GDF15 sequence

<400> SEQUENCE: 40

Met Ala Pro Pro Ala Leu Gln Ala Gln Pro Gly Gly Ser Gln Leu
1               5                   10                  15

Arg Phe Leu Leu Phe Leu Leu Leu Leu Leu Leu Ser Trp Pro
            20                  25                  30

Ser Gln Gly Asp Ala Leu Ala Met Pro Glu Gln Arg Pro Ser Gly Pro
        35                  40                  45

Glu Ser Gln Leu Asn Ala Asp Glu Leu Arg Gly Arg Phe Gln Asp Leu
    50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu

```
            115                 120                 125
Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300

<210> SEQ ID NO 41
<211> LENGTH: 2145
<212> TYPE: DNA
<213> ORGANISM: Homo sapiens

<400> SEQUENCE: 41
atgatgcagg aatctgcgac agagacaata agcaacagtt caatgaatca aaatggaatg      60
agcactctaa gcagccaatt agatgctggc agcagagatg gaagatcaag tggtgacacc     120
agctctgaag taagcacagt agaactgctg catctgcaac aacagcaggc tctccaggca     180
gcaagacaac ttcttttaca gcagcaaaca agtggattga aatctcctaa gagcagtgat     240
aaacagagac cactgcaggt gcctgtgtca gtggccatga tgactcccca ggtgatcacc     300
cctcagcaaa tgcagcagat ccttcagcaa caagtcctgt ctcctcagca gctacaagcc     360
cttctccaac aacagcaggc tgtcatgctg cagcagcaac aactacaaga gttttacaag     420
aaacagcaag agcagttaca tcttcagctt ttgcagcagc agcagcaaca gcagcagcag     480
caacaacagc agcaacaaca gcagcagcaa caacaacaac aacagcagca acaacagcag     540
cagcagcagc aacagcagca gcagcagcaa cagcatcctg aaagcaagc gaaagagcag     600 cagcagcagc agcagcaaca gcaattggca gcccagcagc ttgtcttcca gcagcagctt     660
ctccatatgc aacaactcca gcagcagcag catctgctca gccttcagcg tcagggactc     720
atctccattc cacctggcca ggcagcactt cctgtccaat cgctgcctca agctggctta     780
agtcctgctg agattcagca gttatggaaa gaagtgactg gagttcacag tatggaagac     840
aatggcatta acatggagg ctagacctc actactaaca attcctcctc gactacctcc     900
tccaacactt ccaaagcatc accaccaata actcatcatt ccatagtgaa tggacagtct     960
tcagttctaa gtgcaagacg agacagctcg tcacatgagg agactggggc ctctcacact    1020
ctctatggcc atggagtttg caaatggcca ggctgtgaaa gcatttgtga agattttgga    1080
```

| | | |
|---|---|---|
| cagtttttaa agcaccttaa caatgaacac gcattggatg accgaagcac tgctcagtgt | 1140 | |
| cgagtgcaaa tgcaggtggt gcaacagtta gaaatacagc tttctaaaga acgcgaacgt | 1200 | |
| cttcaagcaa tgatgaccca cttgcacatg cgaccctcag agcccaaacc atctcccaaa | 1260 | |
| cctctaaatc tggtgtctag tgtcaccatg tcgaagaata tgttggagac atccccacag | 1320 | |
| agcttacctc aaacccctac cacaccaacg gccccagtca ccccgattac ccagggaccc | 1380 | |
| tcagtaatca ccccagccag tgtgcccaat gtgggagcca tacgaaggcg acattcagac | 1440 | |
| aaatacaaca ttcccatgtc atcagaaatt gccccaaact atgaattta taaaaatgca | 1500 | |
| gatgtcagac ctccatttac ttatgcaact ctcataaggc aggctatcat ggagtcatct | 1560 | |
| gacaggcagt taacacttaa tgaaatttac agctggttta cacggacatt tgcttacttc | 1620 | |
| aggcgtaatg cagcaacttg gaagaatgca gtacgtcata atcttagcct gcacaagtgt | 1680 | |
| tttgttcgag tagaaaatgt taaaggagca gtatggactg tggatgaagt agaataccag | 1740 | |
| aagcgaaggt cacaaaagat aacaggaagt ccaaccttag taaaaaatat acctaccagt | 1800 | |
| ttaggctatg gagcagctct taatgccagt ttgcaggctg ccttggcaga gagcagttta | 1860 | |
| cctttgctaa gtaatcctgg actgataaat aatgcatcca gtggcctact gcaggccgtc | 1920 | |
| cacgaagacc tcaatggttc tctggatcac attgacagca atggaaacag tagtccgggc | 1980 | |
| tgctcacctc agccgcacat acattcaatc cacgtcaagg aagagccagt gattgcagag | 2040 | |
| gatgaagact gcccaatgtc cttagtgaca acagctaatc acagtccaga attagaagac | 2100 | |
| gacagagaga ttgaagaaga gcctttatct gaagatctgg aatga | 2145 | |

<210> SEQ ID NO 42
<211> LENGTH: 714
<212> TYPE: PRT
<213> ORGANISM: Homo sapiens

<400> SEQUENCE: 42

```
Met Met Gln Glu Ser Ala Thr Glu Thr Ile Ser Asn Ser Ser Met Asn
1               5                   10                  15

Gln Asn Gly Met Ser Thr Leu Ser Ser Gln Leu Asp Ala Gly Ser Arg
            20                  25                  30

Asp Gly Arg Ser Ser Gly Asp Thr Ser Ser Glu Val Ser Thr Val Glu
        35                  40                  45

Leu Leu His Leu Gln Gln Gln Ala Leu Gln Ala Ala Arg Gln Leu
    50                  55                  60

Leu Leu Gln Gln Gln Thr Ser Gly Leu Lys Ser Pro Lys Ser Ser Asp
65                  70                  75                  80

Lys Gln Arg Pro Leu Gln Val Pro Val Ser Val Ala Met Met Thr Pro
                85                  90                  95

Gln Val Ile Thr Pro Gln Gln Met Gln Gln Ile Leu Gln Gln Gln Val
            100                 105                 110

Leu Ser Pro Gln Gln Leu Gln Ala Leu Leu Gln Gln Gln Gln Ala Val
        115                 120                 125

Met Leu Gln Gln Gln Leu Gln Glu Phe Tyr Lys Lys Gln Gln Glu
    130                 135                 140

Gln Leu His Leu Gln Leu Leu Gln Gln Gln Gln Gln Gln Gln Gln Gln
145                 150                 155                 160

Gln Gln Gln Gln Gln Gln Gln Gln Gln Gln Gln Gln Gln Gln Gln
                165                 170                 175

Gln Gln Gln Gln Gln Gln Gln Gln Gln Gln Gln Gln Gln Gln His
            180                 185                 190
```

```
Pro Gly Lys Gln Ala Lys Glu Gln Gln Gln Gln Gln Gln Gln
        195                 200                 205
Leu Ala Ala Gln Gln Leu Val Phe Gln Gln Leu Leu His Met Gln
        210                 215                 220
Gln Leu Gln Gln Gln Gln His Leu Leu Ser Leu Gln Arg Gln Gly Leu
225                 230                 235                 240
Ile Ser Ile Pro Pro Gly Gln Ala Ala Leu Pro Val Gln Ser Leu Pro
                245                 250                 255
Gln Ala Gly Leu Ser Pro Ala Glu Ile Gln Gln Leu Trp Lys Glu Val
                260                 265                 270
Thr Gly Val His Ser Met Glu Asp Asn Gly Ile Lys His Gly Gly Leu
                275                 280                 285
Asp Leu Thr Thr Asn Asn Ser Ser Ser Thr Thr Ser Ser Asn Thr Ser
                290                 295                 300
Lys Ala Ser Pro Pro Ile Thr His His Ser Ile Val Asn Gly Gln Ser
305                 310                 315                 320
Ser Val Leu Ser Ala Arg Arg Asp Ser Ser His Glu Glu Thr Gly
                325                 330                 335
Ala Ser His Thr Leu Tyr Gly His Gly Val Cys Lys Trp Pro Gly Cys
                340                 345                 350
Glu Ser Ile Cys Glu Asp Phe Gly Gln Phe Leu Lys His Leu Asn Asn
                355                 360                 365
Glu His Ala Leu Asp Asp Arg Ser Thr Ala Gln Cys Arg Val Gln Met
                370                 375                 380
Gln Val Val Gln Gln Leu Glu Ile Gln Leu Ser Lys Glu Arg Glu Arg
385                 390                 395                 400
Leu Gln Ala Met Met Thr His Leu His Met Arg Pro Ser Glu Pro Lys
                405                 410                 415
Pro Ser Pro Lys Pro Leu Asn Leu Val Ser Ser Val Thr Met Ser Lys
                420                 425                 430
Asn Met Leu Glu Thr Ser Pro Gln Ser Leu Pro Gln Thr Pro Thr Thr
                435                 440                 445
Pro Thr Ala Pro Val Thr Pro Ile Thr Gln Gly Pro Ser Val Ile Thr
                450                 455                 460
Pro Ala Ser Val Pro Asn Val Gly Ala Ile Arg Arg Arg His Ser Asp
465                 470                 475                 480
Lys Tyr Asn Ile Pro Met Ser Ser Glu Ile Ala Pro Asn Tyr Glu Phe
                485                 490                 495
Tyr Lys Asn Ala Asp Val Arg Pro Pro Phe Thr Tyr Ala Thr Leu Ile
                500                 505                 510
Arg Gln Ala Ile Met Glu Ser Ser Asp Arg Gln Leu Thr Leu Asn Glu
                515                 520                 525
Ile Tyr Ser Trp Phe Thr Arg Thr Phe Ala Tyr Phe Arg Arg Asn Ala
                530                 535                 540
Ala Thr Trp Lys Asn Ala Val Arg His Asn Leu Ser Leu His Lys Cys
545                 550                 555                 560
Phe Val Arg Val Glu Asn Val Lys Gly Ala Val Trp Thr Val Asp Glu
                565                 570                 575
Val Glu Tyr Gln Lys Arg Arg Ser Gln Lys Ile Thr Gly Ser Pro Thr
                580                 585                 590
Leu Val Lys Asn Ile Pro Thr Ser Leu Gly Tyr Gly Ala Ala Leu Asn
                595                 600                 605
```

Ala Ser Leu Gln Ala Ala Leu Ala Glu Ser Ser Leu Pro Leu Leu Ser
        610                 615                 620

Asn Pro Gly Leu Ile Asn Asn Ala Ser Ser Gly Leu Leu Gln Ala Val
625                 630                 635                 640

His Glu Asp Leu Asn Gly Ser Leu Asp His Ile Asp Ser Asn Gly Asn
                645                 650                 655

Ser Ser Pro Gly Cys Ser Pro Gln Pro His Ile His Ser Ile His Val
            660                 665                 670

Lys Glu Glu Pro Val Ile Ala Glu Asp Glu Asp Cys Pro Met Ser Leu
            675                 680                 685

Val Thr Thr Ala Asn His Ser Pro Glu Leu Glu Asp Asp Arg Glu Ile
    690                 695                 700

Glu Glu Glu Pro Leu Ser Glu Asp Leu Glu
705                 710

<210> SEQ ID NO 43
<211> LENGTH: 828
<212> TYPE: DNA
<213> ORGANISM: Mus musculus

<400> SEQUENCE: 43
atgacagatg acaaagatgt gcttcgagat gtgtggtttg gacgaattcc aacttgcttt      60
actctctatc aggatgagat aactgaaaga gaagcagaac catactattt gcttttgcca     120
agagtcagct atttgacgtt ggtaactgac aaagtgaaaa agcactttca gaaggttatg     180
agacaagaag atgttagtga gatatggttt gaatatgaag gcacacccct gaaatggcat     240
tatccaattg gtttactatt tgatcttctt gcatcaagtt cagctcttcc ttggaacatc     300
acagtacatt tcaagagttt tccagaaaag gaccttctac actgtccatc caaggatgcg     360
gttgaggctc actttatgtc gtgtatgaaa gaagctgatg ctttaaagca taaaagtcaa     420
gtgatcaacg aaatgcagaa aaagaccac aagcagctct ggatgggact gcagaatgac     480
agatttgacc agttttgggc catcaaccgg aaactcatgg aatatcctcc agaagaaaat     540
ggatttcgtt atatcccctt tagaatatat cagaccacga cggagcggcc tttcatccag     600
aagctgttcc ggcctgtggc cgcagatgga cagctgcaca cacttggaga tctcctcaga     660
gaagtctgtc cttccgcagt cgcccctgaa gatggagaga agaggagcca ggtgatgatt     720
cacgggatag agccaatgct ggaaacccct ctgcagtggc tgagcgagca tctgagctac     780
ccagataact tcttcatat tagcattgtc ccccagccaa cagattaa                  828

<210> SEQ ID NO 44
<211> LENGTH: 275
<212> TYPE: PRT
<213> ORGANISM: Mus musculus

<400> SEQUENCE: 44

Met Thr Asp Asp Lys Asp Val Leu Arg Asp Val Trp Phe Gly Arg Ile
1               5                   10                  15

Pro Thr Cys Phe Thr Leu Tyr Gln Asp Glu Ile Thr Glu Arg Glu Ala
                20                  25                  30

Glu Pro Tyr Tyr Leu Leu Leu Pro Arg Val Ser Tyr Leu Thr Leu Val
            35                  40                  45

Thr Asp Lys Val Lys Lys His Phe Gln Lys Val Met Arg Gln Glu Asp
        50                  55                  60

Val Ser Glu Ile Trp Phe Glu Tyr Glu Gly Thr Pro Leu Lys Trp His
65                  70                  75                  80

```
Tyr Pro Ile Gly Leu Leu Phe Asp Leu Leu Ala Ser Ser Ala Leu
                85                  90                  95

Pro Trp Asn Ile Thr Val His Phe Lys Ser Phe Pro Glu Lys Asp Leu
            100                 105                 110

Leu His Cys Pro Ser Lys Asp Ala Val Glu Ala His Phe Met Ser Cys
        115                 120                 125

Met Lys Glu Ala Asp Ala Leu Lys His Lys Ser Gln Val Ile Asn Glu
    130                 135                 140

Met Gln Lys Lys Asp His Lys Gln Leu Trp Met Gly Leu Gln Asn Asp
145                 150                 155                 160

Arg Phe Asp Gln Phe Trp Ala Ile Asn Arg Lys Leu Met Glu Tyr Pro
                165                 170                 175

Pro Glu Glu Asn Gly Phe Arg Tyr Ile Pro Phe Arg Ile Tyr Gln Thr
            180                 185                 190

Thr Thr Glu Arg Pro Phe Ile Gln Lys Leu Phe Arg Pro Val Ala Ala
        195                 200                 205

Asp Gly Gln Leu His Thr Leu Gly Asp Leu Leu Arg Glu Val Cys Pro
    210                 215                 220

Ser Ala Val Ala Pro Glu Asp Gly Glu Lys Arg Ser Gln Val Met Ile
225                 230                 235                 240

His Gly Ile Glu Pro Met Leu Glu Thr Pro Leu Gln Trp Leu Ser Glu
                245                 250                 255

His Leu Ser Tyr Pro Asp Asn Phe Leu His Ile Ser Ile Val Pro Gln
            260                 265                 270

Pro Thr Asp
        275

<210> SEQ ID NO 45
<211> LENGTH: 3159
<212> TYPE: DNA
<213> ORGANISM: Mus musculus

<400> SEQUENCE: 45
atggcggagg cgagtgaagc catgtgcctg gagggagcag agtgggagct gagtaaagaa      60
aacatacagc ccttacggca cgggcgggtc atgtccacac ttcagggagc tttggcaaag     120
caagagtcag ctggccacac tgctctgcag cagcagaaac gggcatttga atctgaaatc     180
cgcttttact ctggagatga ccctctggat gtgtgggaca gatatattaa ttggacagaa     240
cagaactacc ctcaagggg gaaggagagt aacatgtcag cgttagtgga gagagcgata     300
gaagcactcc aaggagagac gcgctattat aatgaccccc gctttctcag tctctggatc     360
aaattgggac atttgtgcaa tgaaccttg gatatgtaca gctatttaca agccaagga     420 attggcgttt cccttgccca gttctatatt tcatgggctg aagaatacga agctagagaa     480
aatttcaaga agcggacat aatatttcag gaagggattg aacgcaaggc tgagccctg     540 gacagactgc agtcccagca cagacagttc cagtctcgag tgtcgcgaca agctttcttg     600
gcccttggga tgaagagga ggaggctttg gagccttctg aaccacagag aagctcgcta     660
gctgagctga gagcagagg gaagaagatg gccagagcgc ccatcagccg tgtcggaagt     720
gctctgaaag ctccaggtca gagcagagga ttcctaaatg cagttcccca gccagtacac     780
ggtaatcgca ggatcaccgt ttttgatgaa aatgccgata ccgcgtctag accggagtta     840
tctaagccta tagcccagcc atggatggca ccccctgtgc ccagggccaa agagaacgaa     900
cttcagccag gcccatggag cacagacagg ccggtgggac gcaggcctca tgacaatcca     960
```

```
gcctctgtga cgtcgatacc cagcgtgctt cccagcttta cgccgtacgt ggaagagagc   1020
gcccagcaga cagtcatgac accatgcaag attgagccta gtatcaacca tgttctcagc   1080
accaggaagc caggaagaga agaaggagac cccttgcaga gagttcgagt catcagcaa    1140 ggctgtgagg agaagaagga gaagatgatg tactgtaagg agaagatcta tgccggagtt   1200
ggggagttct cctttgagga gatccgagct gaagtgttcc gaaagaagct gaaagaacga   1260
agggaagccg agctgttgac cagtgcaaag aagagggagg agatgcagaa gcagatcgaa   1320
gagatggaga ggaggctgaa ggcaatgcag gctgttcagc aagaaggagc tggtggccag   1380
caagaagaga agatgcctac agaggaccca gccagattgc agattgcttc ggggcctcag   1440
gaaatgtcgg gagttcctct gtcctgttcc atctgtccac taagctcgaa tcctagggaa   1500
atttcacctg ctgagaacat tttgcaagaa cagcctgatt ctaaaggttc agtatgcct    1560 ttctccattt ttgatgagtc tctttcagac aaaaaagaca aaagtcctgc tacaggtggt   1620
ccacaggttc tcaatgccca gagaagaccc ctttcagttc tcaaaactac agaagtgggc   1680
accacaaatg aggatgtgtc tcccgatatt tgtgatgaac tcacagaact tgagcctctg   1740
agtgaagacg ccatcatcac tggtttcagg aacgtcactc tctgtcccaa ccctgaggac   1800
acttgtgact ttgctagagc agctcgtttg gcatctactc cttttcatga gatactgtcc   1860
tcgaagggca tcgctgctga tcccgaggga ctgttgcagg aagaggatct ggatgggaag   1920
gccgccgagg ctcatcacac tgttcatcac caggccctca tcataaagaa actgagccca   1980
attattgaag acagccgtga ggccacccac tcatctggct tctccaggtc ttcttcctca   2040
gctcccagta catcctccat caaaggcttt cagcttctgg aaaagctgga gctgactaat   2100
gacggggcag aaaatgctat tcagtcaccc tggtgttcac agtatcgcct acaactgtta   2160
aaatccctac tagagataag tgcttttgcg gagttttctg tggaagaccg accgatgcct   2220
gtgctggaaa tagggaagga gattgagtta ggtcctgagg attacgtcat caagcaagag   2280
cacctaacat gtgacgatta caggttattc tgggtggcac aagaagctc tgcagagcta   2340 accatgataa aggcatcatc tcagcctatc ccgtgggatt tttatatcaa cctcaagttg   2400
aaggagcgtc tgaatgagga ctatgaccag cttttgcagct gctgtcagta ccaagatggc   2460
catgttgttt ggtaccagta tataaactgc tccaccctcc agaatcttct ccaacacagc   2520
gaatttgtta ctcatgaaat aatagtgttg attatttaca acctcttgac aatcgtggag   2580
aagctacaca gagctgaaat agtgcacgga gacttgagtc cacggagtct gatcctacga   2640
aacagaatcc acgacccccta tgactatgta aataaggacg atcacgctgt gaggatcatg   2700
gacttctcct acagtgttga cctgagggtg cagctggatg cgtttgccta gtggcttt    2760 cggactgcac agatcctgga aggacaaaag atcctgcta actgttcttc tccctaccat   2820
gtagatctgt tgggtatagc agacctagcg cacttactcc tgttcaagga gcacctccat   2880
gtcttctggg atggactcct ctggaaactt agccagagca cctctgagct aaaagacagt   2940
gaattgtgga ataaattctt tgtgcggatt ctgaatgcca gtgacaagtc cacagtgtct   3000
gttctggggg agctggcagc agaaatgggt ggggcttttg atgccacatt ccatagccac   3060
ctgaacagag ccctgtggaa gctggggaag acaatcagcc cggaagcttt gctcactcag   3120
caagacaagc agccaggcgg ctcccagagc cctgcctaa                          3159
```

<210> SEQ ID NO 46
<211> LENGTH: 1052
<212> TYPE: PRT

<213> ORGANISM: Mus musculus

<400> SEQUENCE: 46

```
Met Ala Glu Ala Ser Glu Ala Met Cys Leu Glu Gly Ala Glu Trp Glu
1               5                   10                  15
Leu Ser Lys Glu Asn Ile Gln Pro Leu Arg His Gly Arg Val Met Ser
                20                  25                  30
Thr Leu Gln Gly Ala Leu Ala Lys Gln Glu Ser Ala Gly His Thr Ala
            35                  40                  45
Leu Gln Gln Gln Lys Arg Ala Phe Glu Ser Glu Ile Arg Phe Tyr Ser
        50                  55                  60
Gly Asp Asp Pro Leu Asp Val Trp Asp Arg Tyr Ile Asn Trp Thr Glu
65                  70                  75                  80
Gln Asn Tyr Pro Gln Gly Gly Lys Glu Ser Asn Met Ser Ala Leu Val
                85                  90                  95
Glu Arg Ala Ile Glu Ala Leu Gln Gly Glu Thr Arg Tyr Tyr Asn Asp
            100                 105                 110
Pro Arg Phe Leu Ser Leu Trp Ile Lys Leu Gly His Leu Cys Asn Glu
        115                 120                 125
Pro Leu Asp Met Tyr Ser Tyr Leu Gln Ser Gln Gly Ile Gly Val Ser
130                 135                 140
Leu Ala Gln Phe Tyr Ile Ser Trp Ala Glu Tyr Glu Ala Arg Glu
145                 150                 155                 160
Asn Phe Lys Lys Ala Asp Ile Ile Phe Gln Glu Gly Ile Glu Arg Lys
                165                 170                 175
Ala Glu Pro Leu Asp Arg Leu Gln Ser Gln His Arg Gln Phe Gln Ser
            180                 185                 190
Arg Val Ser Arg Gln Ala Phe Leu Ala Leu Gly Asn Glu Glu Glu
                195                 200                 205
Ala Leu Glu Pro Ser Glu Pro Gln Arg Ser Ser Leu Ala Glu Leu Lys
        210                 215                 220
Ser Arg Gly Lys Lys Met Ala Arg Ala Pro Ile Ser Arg Val Gly Ser
225                 230                 235                 240
Ala Leu Lys Ala Pro Gly Gln Ser Arg Gly Phe Leu Asn Ala Val Pro
                245                 250                 255
Gln Pro Val His Gly Asn Arg Arg Ile Thr Val Phe Asp Glu Asn Ala
            260                 265                 270
Asp Thr Ala Ser Arg Pro Glu Leu Ser Lys Pro Val Ala Gln Pro Trp
        275                 280                 285
Met Ala Pro Pro Val Pro Arg Ala Lys Glu Asn Glu Leu Gln Pro Gly
        290                 295                 300
Pro Trp Ser Thr Asp Arg Pro Val Gly Arg Arg Pro His Asp Asn Pro
305                 310                 315                 320
Ala Ser Val Thr Ser Ile Pro Ser Val Leu Pro Ser Phe Thr Pro Tyr
                325                 330                 335
Val Glu Glu Ser Ala Gln Gln Thr Val Met Thr Pro Cys Lys Ile Glu
            340                 345                 350
Pro Ser Ile Asn His Val Leu Ser Thr Arg Lys Pro Gly Arg Glu Glu
        355                 360                 365
Gly Asp Pro Leu Gln Arg Val Gln Ser His Gln Gln Gly Cys Glu Glu
    370                 375                 380
Lys Lys Glu Lys Met Met Tyr Cys Lys Glu Lys Ile Tyr Ala Gly Val
385                 390                 395                 400
```

```
Gly Glu Phe Ser Phe Glu Glu Ile Arg Ala Glu Val Phe Arg Lys Lys
                405                 410                 415

Leu Lys Glu Arg Arg Glu Ala Glu Leu Leu Thr Ser Ala Lys Lys Arg
        420                 425                 430

Glu Glu Met Gln Lys Gln Ile Glu Glu Met Glu Arg Arg Leu Lys Ala
            435                 440                 445

Met Gln Ala Val Gln Glu Gly Ala Gly Gln Gln Glu Glu Lys
        450                 455                 460         Lys

Met Pro Thr Glu Asp Pro Ala Arg Leu Gln Ile Ala Ser Gly Pro Gln
465                 470                 475                 480

Glu Met Ser Gly Val Pro Leu Ser Cys Ser Ile Cys Pro Leu Ser Ser
                485                 490                 495

Asn Pro Arg Glu Ile Ser Pro Ala Glu Asn Ile Leu Gln Glu Gln Pro
            500                 505                 510

Asp Ser Lys Gly Ser Ser Met Pro Phe Ser Ile Phe Asp Glu Ser Leu
        515                 520                 525

Ser Asp Lys Lys Asp Lys Ser Pro Ala Thr Gly Gly Pro Gln Val Leu
    530                 535                 540

Asn Ala Gln Arg Arg Pro Leu Ser Val Leu Lys Thr Thr Glu Val Gly
545                 550                 555                 560

Thr Thr Asn Glu Asp Val Ser Pro Asp Ile Cys Asp Glu Leu Thr Glu
                565                 570                 575

Leu Glu Pro Leu Ser Glu Asp Ala Ile Ile Thr Gly Phe Arg Asn Val
            580                 585                 590

Thr Leu Cys Pro Asn Pro Glu Asp Thr Cys Asp Phe Ala Arg Ala Ala
        595                 600                 605

Arg Leu Ala Ser Thr Pro Phe His Glu Ile Leu Ser Ser Lys Gly Ile
    610                 615                 620

Ala Ala Asp Pro Glu Gly Leu Leu Gln Glu Glu Asp Leu Asp Gly Lys
625                 630                 635                 640

Ala Ala Glu Ala His His Thr Val His His Gln Ala Leu Ile Ile Lys
                645                 650                 655

Lys Leu Ser Pro Ile Ile Glu Asp Ser Arg Glu Ala Thr His Ser Ser
            660                 665                 670

Gly Phe Ser Arg Ser Ser Ser Ala Pro Ser Thr Ser Ser Ile Lys
        675                 680                 685         Lys

Gly Phe Gln Leu Leu Glu Lys Leu Glu Leu Thr Asn Asp Gly Ala Glu
    690                 695                 700

Asn Ala Ile Gln Ser Pro Trp Cys Ser Gln Tyr Arg Leu Gln Leu Leu
705                 710                 715                 720

Lys Ser Leu Leu Glu Ile Ser Ala Phe Ala Glu Phe Ser Val Glu Asp
                725                 730                 735

Arg Pro Met Pro Val Leu Glu Ile Gly Lys Glu Ile Glu Leu Gly Pro
            740                 745                 750

Glu Asp Tyr Val Ile Lys Gln Glu His Leu Thr Cys Asp Asp Tyr Arg
        755                 760                 765

Leu Phe Trp Val Ala Pro Arg Ser Ser Ala Glu Leu Thr Met Ile Lys
    770                 775                 780

Ala Ser Ser Gln Pro Ile Pro Trp Asp Phe Tyr Ile Asn Leu Lys Leu
785                 790                 795                 800

Lys Glu Arg Leu Asn Glu Asp Tyr Asp Gln Leu Cys Ser Cys Cys Gln
                805                 810                 815

Tyr Gln Asp Gly His Val Val Trp Tyr Gln Tyr Ile Asn Cys Ser Thr
```

```
                     820                 825                 830
Leu Gln Asn Leu Leu Gln His Ser Glu Phe Val Thr His Glu Ile Ile
            835                 840                 845

Val Leu Ile Ile Tyr Asn Leu Leu Thr Ile Val Glu Lys Leu His Arg
    850                 855                 860

Ala Glu Ile Val His Gly Asp Leu Ser Pro Arg Ser Leu Ile Leu Arg
865                 870                 875                 880

Asn Arg Ile His Asp Pro Tyr Asp Tyr Val Asn Lys Asp Asp His Ala
            885                 890                 895

Val Arg Ile Met Asp Phe Ser Tyr Ser Val Asp Leu Arg Val Gln Leu
                900                 905                 910

Asp Ala Phe Ala Tyr Ser Gly Phe Arg Thr Ala Gln Ile Leu Glu Gly
            915                 920                 925

Gln Lys Ile Leu Ala Asn Cys Ser Ser Pro Tyr His Val Asp Leu Leu
        930                 935                 940

Gly Ile Ala Asp Leu Ala His Leu Leu Leu Phe Lys Glu His Leu His
945                 950                 955                 960

Val Phe Trp Asp Gly Leu Leu Trp Lys Leu Ser Gln Ser Thr Ser Glu
                965                 970                 975

Leu Lys Asp Ser Glu Leu Trp Asn Lys Phe Phe Val Arg Ile Leu Asn
            980                 985                 990

Ala Ser Asp Lys Ser Thr Val Ser  Val Leu Gly Glu Leu  Ala Ala Glu
        995                 1000                 1005

Met Gly  Gly Ala Phe Asp Ala  Thr Phe His Ser His  Leu Asn Arg
   1010                  1015                 1020

Ala Leu  Trp Lys Leu Gly Lys  Thr Ile Ser Pro Glu  Ala Leu Leu
   1025                  1030                 1035

Thr Gln  Gln Asp Lys Gln Pro  Gly Gly Ser Gln Ser  Pro Ala
   1040                  1045                 1050

<210> SEQ ID NO 47
<211> LENGTH: 1692
<212> TYPE: DNA
<213> ORGANISM: Unknown
<220> FEATURE:
<223> OTHER INFORMATION: Description of Unknown:
      MCat sequence

<400> SEQUENCE: 47
atgtccgtcc tgacgccgct gctgctgcgg ggcttgacag gctcggcccg gcggctccca      60
gtgccgcgcg ccaagatcca ttcgttgggg gatccaccgg tcgccaccat gtcggacagt     120
cgggacccag ccagcgacca gatgaagcag tggaaggagc agcgggcctc gcagagacct     180
gatgtcctga ccaccggagg cgggaaccca ataggagata aacttaatat catgaccgcg     240
gggtcccgag ggcccctcct cgttcaggat gtggttttca ctgacgagat ggcacacttt     300
gacagagagc ggattcctga gagtggta cacgcaaaag gagcaggtgc ttttggatac       360
tttgaggtca cccacgatat caccagatac tccaaggcaa aggtgtttga gcatattgga     420
aagaggaccc ctattgccgt tcgattctcc acagtcgctg gagagtcagg ctcagctgac     480
acagttcgtg accctcgggg gtttgcagtg aaattttaca ctgaagatgg taactgggat     540
cttgtgggaa acaacacccc tattttcttc atcagggatg ccatattgtt tccatccttt     600
atccatagcc agaagagaaa cccacagact cacctgaagg atcctgacat ggtctgggac     660
ttctggagtc ttcgtcccga gtctctccat caggtttctt cttgttcag tgaccgaggg     720
```

```
attcccgatg gtcaccggca catgaatggc tatggatcac acaccttcaa gttggttaat    780
gcagatggag aggcagtcta ttgcaagttc cattacaaga ccgaccaggg catcaaaaac    840
ttgcctgttg gagaggcagg aaggcttgct caggaagatc cggattatgg cctccgagat    900
cttttcaatg ccatcgccaa tggcaattac ccgtcctgga cgttttacat ccaggtcatg    960
acttttaagg aggcagaaac tttcccattt aatccatttg atctgaccaa ggtttggcct   1020
cacaaggact accctcttat accagttggc aaactggttt taaacaaaaa tccagttaat   1080
tactttgctg aagttgaaca gatggctttt gacccaagca atatgccccc tggcatcgag   1140
cccagccctg acaaaatgct tcagggccgc cttttttgcct acccggacac tcaccgccac   1200
cgcctgggac ccaactatct gcagatacct gtgaactgtc cctaccgcgc tcgagtggcc   1260
aactaccagc gtgatggccc catgtgcatg catgacaacc agggtggtgc ccccaactat   1320
taccccaaca gcttcagcgc accagagcag cagcgctcag ccctggagca cagcgtccag   1380
tgcgctgtag atgtgaaacg cttcaacagt gctaatgaag acaatgtcac tcaggtgcgg   1440
acattctaca caaggtgtt gaacgaggag gagaggaaac gcctgtgtga aacattgcc   1500
ggccacctga aggacgctca gcttttcatt cagaagaaag cggtcaagaa tttcactgac   1560
gtccaccctg actatggggc ccgcatccag gctcttctgg acaagtacaa cgctgagaag   1620
cctaagaacg caattcacac ctacacgcag gccggctctc acatggctgc gaagggaaaa   1680
gctaacctgt aa                                                       1692
```

<210> SEQ ID NO 48
<211> LENGTH: 563
<212> TYPE: PRT
<213> ORGANISM: Unknown
<220> FEATURE:
<223> OTHER INFORMATION: Description of Unknown:
      MCat sequence

<400> SEQUENCE: 48

```
Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Asp Pro
            20                  25                  30

Pro Val Ala Thr Met Ser Asp Ser Arg Asp Pro Ala Ser Asp Gln Met
        35                  40                  45

Lys Gln Trp Lys Glu Gln Arg Ala Ser Gln Arg Pro Asp Val Leu Thr
    50                  55                  60

Thr Gly Gly Gly Asn Pro Ile Gly Asp Lys Leu Asn Ile Met Thr Ala
65                  70                  75                  80

Gly Ser Arg Gly Pro Leu Leu Val Gln Asp Val Val Phe Thr Asp Glu
                85                  90                  95

Met Ala His Phe Asp Arg Glu Arg Ile Pro Glu Arg Val Val His Ala
            100                 105                 110

Lys Gly Ala Gly Ala Phe Gly Tyr Phe Glu Val Thr His Asp Ile Thr
        115                 120                 125

Arg Tyr Ser Lys Ala Lys Val Phe Glu His Ile Gly Lys Arg Thr Pro
    130                 135                 140

Ile Ala Val Arg Phe Ser Thr Val Ala Gly Glu Ser Gly Ser Ala Asp
145                 150                 155                 160

Thr Val Arg Asp Pro Arg Gly Phe Ala Val Lys Phe Tyr Thr Glu Asp
                165                 170                 175

Gly Asn Trp Asp Leu Val Gly Asn Asn Thr Pro Ile Phe Phe Ile Arg
```

```
                  180             185             190
Asp Ala Ile Leu Phe Pro Ser Phe Ile His Ser Gln Lys Arg Asn Pro
            195                 200                 205
Gln Thr His Leu Lys Asp Pro Asp Met Val Trp Asp Phe Trp Ser Leu
            210                 215                 220
Arg Pro Glu Ser Leu His Gln Val Ser Phe Leu Phe Ser Asp Arg Gly
225                 230                 235                 240
Ile Pro Asp Gly His Arg His Met Asn Gly Tyr Gly Ser His Thr Phe
                245                 250                 255
Lys Leu Val Asn Ala Asp Gly Glu Ala Val Tyr Cys Lys Phe His Tyr
            260                 265                 270
Lys Thr Asp Gln Gly Ile Lys Asn Leu Pro Val Gly Glu Ala Gly Arg
            275                 280                 285
Leu Ala Gln Glu Asp Pro Asp Tyr Gly Leu Arg Asp Leu Phe Asn Ala
            290                 295                 300
Ile Ala Asn Gly Asn Tyr Pro Ser Trp Thr Phe Tyr Ile Gln Val Met
305                 310                 315                 320
Thr Phe Lys Glu Ala Glu Thr Phe Pro Phe Asn Pro Phe Asp Leu Thr
                325                 330                 335
Lys Val Trp Pro His Lys Asp Tyr Pro Leu Ile Pro Val Gly Lys Leu
            340                 345                 350
Val Leu Asn Lys Asn Pro Val Asn Tyr Phe Ala Glu Val Glu Gln Met
            355                 360                 365
Ala Phe Asp Pro Ser Asn Met Pro Pro Gly Ile Glu Pro Ser Pro Asp
            370                 375                 380
Lys Met Leu Gln Gly Arg Leu Phe Ala Tyr Pro Asp Thr His Arg His
385                 390                 395                 400
Arg Leu Gly Pro Asn Tyr Leu Gln Ile Pro Val Asn Cys Pro Tyr Arg
                405                 410                 415
Ala Arg Val Ala Asn Tyr Gln Arg Asp Gly Pro Met Cys Met His Asp
            420                 425                 430
Asn Gln Gly Gly Ala Pro Asn Tyr Tyr Pro Asn Ser Phe Ser Ala Pro
            435                 440                 445
Glu Gln Gln Arg Ser Ala Leu Glu His Ser Val Gln Cys Ala Val Asp
            450                 455                 460
Val Lys Arg Phe Asn Ser Ala Asn Glu Asp Asn Val Thr Gln Val Arg
465                 470                 475                 480
Thr Phe Tyr Thr Lys Val Leu Asn Glu Glu Arg Lys Arg Leu Cys
                485                 490                 495
Glu Asn Ile Ala Gly His Leu Lys Asp Ala Gln Leu Phe Ile Gln Lys
            500                 505                 510
Lys Ala Val Lys Asn Phe Thr Asp Val His Pro Asp Tyr Gly Ala Arg
            515                 520                 525
Ile Gln Ala Leu Leu Asp Lys Tyr Asn Ala Glu Lys Pro Lys Asn Ala
            530                 535                 540
Ile His Thr Tyr Thr Gln Ala Gly Ser His Met Ala Ala Lys Gly Lys
545                 550                 555                 560
Ala Asn Leu

<210> SEQ ID NO 49
<211> LENGTH: 408
<212> TYPE: DNA
<213> ORGANISM: Mus musculus
```

<400> SEQUENCE: 49

```
atggtcctgg acagcgtggc ccgcatcgtg aaggtgcagc tgcccgccta cctcaagcag      60
ctcccggtcc ccgacagcat caccgggttc gcccgcctca cagtttcaga ctggctccgc     120
ctactgccct cctcgggggt acttgcgctt ctgggctacc tcgcagtgcg cccattcttc     180
ccaaagaaga agcaacagaa ggatagcttg atcaatctta agatacaaaa ggaaaatccc     240
aaggtggtga atgagataaa cattgaagat ctgtgtctca ccaaagcagc ttattgtagg     300
tgctggcggt ccaagacgtt tcctgcctgt gatggatccc ataataagca taatgaattg     360
acaggcgata acgtgggtcc tctcatcctg aagaagaaag aagtataa                  408
```

<210> SEQ ID NO 50
<211> LENGTH: 135
<212> TYPE: PRT
<213> ORGANISM: Mus musculus

<400> SEQUENCE: 50

```
Met Val Leu Asp Ser Val Ala Arg Ile Val Lys Val Gln Leu Pro Ala
1               5                   10                  15

Tyr Leu Lys Gln Leu Pro Val Pro Asp Ser Ile Thr Gly Phe Ala Arg
            20                  25                  30

Leu Thr Val Ser Asp Trp Leu Arg Leu Leu Pro Phe Leu Gly Val Leu
        35                  40                  45

Ala Leu Leu Gly Tyr Leu Ala Val Arg Pro Phe Phe Pro Lys Lys Lys
    50                  55                  60

Gln Gln Lys Asp Ser Leu Ile Asn Leu Lys Ile Gln Lys Glu Asn Pro
65                  70                  75                  80

Lys Val Val Asn Glu Ile Asn Ile Glu Asp Leu Cys Leu Thr Lys Ala
                85                  90                  95

Ala Tyr Cys Arg Cys Trp Arg Ser Lys Thr Phe Pro Ala Cys Asp Gly
            100                 105                 110

Ser His Asn Lys His Asn Glu Leu Thr Gly Asp Asn Val Gly Pro Leu
        115                 120                 125

Ile Leu Lys Lys Lys Glu Val
    130                 135
```

<210> SEQ ID NO 51
<211> LENGTH: 633
<212> TYPE: DNA
<213> ORGANISM: Mus musculus

<400> SEQUENCE: 51

```
atggaatgga tgagatctag agttgggacc ctgggactgt gggtccgact gctgctggct      60
gtcttcctgc tggggtcta ccaagcatac cccatccctg actccagccc cctcctccag     120
tttggggtc aagtccggca gaggtacctc tacacagatg acgaccaaga cactgaagcc     180
cacctggaga tcaggagga tggaacagtg gtaggcgcag cacccgcag tccagaaagt     240
ctcctggagc tcaaagcctt gaagccaggg gtcattcaaa tcctgggtgt caaagcctct     300
aggtttcttt gccaacagcc agatggagct ctctatggat cgcctcactt tgatcctgag     360
gcctgcagct tcagagaact gctgctggag gacggttaca atgtgtacca gtctgaagcc     420
catggcctgc ccctgcgtct gcctcagaag gactccccaa accaggatgc aacatcctgg     480
ggacctgtgc gcttcctgcc catgccaggc ctgctccacg agcccaagac caagcagga     540
ttcctgcccc cagagccccc agatgtgggc tcctctgacc ccctgagcat ggtagagcct     600
```

```
ttacagggcc gaagcccag ctatgcgtcc tga                                    633
```

<210> SEQ ID NO 52
<211> LENGTH: 210
<212> TYPE: PRT
<213> ORGANISM: Mus musculus

<400> SEQUENCE: 52

```
Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
                20                  25                  30

Pro Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
        50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210
```

<210> SEQ ID NO 53
<211> LENGTH: 3045
<212> TYPE: DNA
<213> ORGANISM: Mus musculus

<400> SEQUENCE: 53

```
atgctagccc gcgccctcc tcgccgcccg ccgcggctgg tgctgctccg tttgctgttg    60
ctgcatctgc tgctgctcgc cctgcgcgcc cgctgcctga gcgctgagcc gggtcagggc   120
gcgcagacct gggctcgctt cgcgcgcgct cctgccccag aggccgctgg cctcctccac   180
gacaccttcc ccgacggttt cctctgggcg gtaggcagcg ccgcctatca gaccgagggc   240
ggctggcgac agcacggcaa aggcgcgtcc atctgggaca ctttcaccca tcactctggg   300
gcggccccgt ccgactcccc gatcgtcgtg gcgccgtcgg gtgccccgtc gcctcccctg   360
tcctccactg gagatgtggc cagcgatagt tacaacaacg tctaccgcga cacagagggg   420
ctgcgcgaac tggggggtcac ccactaccgc ttctccatat cgtgggcgcg ggtgctcccc   480
aatggcaccg cgggcactcc caaccgcgag gggctgcgct actaccggcg gctgctggag   540
cggctgcggg agctgggcgt gcagccggtg gttaccctgt accattggga cctgccacag   600
```

```
cgcctgcagg acacctatgg cggatgggcc aatcgcgccc tggccgacca tttcagggat    660
tatgccgagc tctgcttccg ccacttcggt ggtcaggtca agtactggat caccattgac    720
aaccccctacg tggtggcctg cacgggtat gccaccgggc gcctggcccc gggcgtgagg    780
ggcagctcca ggctcgggta cctggttgcc cacaacctac ttttggctca tgccaaagtc    840
tggcatctct acaacacctc tttccgcccc acacagggag gccgggtgtc tatcgcctta    900
agctcccatt ggatcaatcc tcgaagaatg actgactata atatcagaga atgccagaag    960
tctcttgact ttgtgctagg ctggtttgcc aaacccatat ttattgatgg cgactaccca    1020
gagagtatga agaacaacct ctcgtctctt ctgcctgatt ttactgaatc tgagaagagg    1080
ctcatcagag gaactgctga cttttttgct ctctccttcg gaccaacctt gagctttcag    1140
ctattggacc ctaacatgaa gttccgccaa ttggagtctc ccaacctgag gcagcttctg    1200
tcttggatag atctggaata taaccaccct ccaatattta ttgtggaaaa tggctggttt    1260
gtctcgggaa ccaccaaaag ggatgatgcc aaatatatgt attatctcaa gaagttcata    1320
atggaaacct taaaagcaat cagactggat ggggtcgacg tcattgggta caccgcgtgg    1380
tcgctcatgg acggtttcga gtggcatagg ggctacagca tccggcgagg actcttctac    1440
gttgactttc tgagtcagga caaggagctg ttgccaaagt cttcggcctt gttctaccaa    1500
aagctgatag aggacaatgg ctttcctcct ttacctgaaa accagcccct tgaagggaca    1560
tttccctgtg actttgcttg gggagttgtt gacaactacg ttcaagtgga cactactctc    1620
tctcagtttta ctgacccgaa tgtctatctg tgggatgtgc atcacagtaa gaggcttatt    1680
aaagtagacg gggttgtagc caagaagaga aaaccttact gtgttgattt ctctgccatc    1740
cggcctcaga taaccttact tcgagaaatg cgggtcaccc actttcgctt ctccctggac    1800
tgggccctga tcttgcctct gggtaaccag acccaagtga accacacggt tctgcacttc    1860
taccgctgca tgatcagcga gctggtgcac gccaacatca ctccagtggt ggccctgtgg    1920
cagccagcag ccccgcacca aggcctgcca catgcccttg caaaacatgg ggcctgggag    1980
aacccgcaca ctgctctggc gtttgcagac tacgcaaacc tgtgttttaa agagttgggt    2040
cactgggtca atctctggat caccatgaac gagccaaaca cacggaacat gacctatcgt    2100
gccgggcacc acctcctgag agcccatgcc ttggcttggc atctgtacga tgacaagttt    2160
agggcggctc agaaaggcaa aatatccatc gccttgcagg ctgactggat agaaccggcc    2220
tgcccttttct ctcaaaatga caaagaagtg gccgagagag ttttggaatt tgatataggc    2280
tggctggcag agcctatttt tggttccgga gattatccac gtgtgatgag ggactggctg    2340
aaccaaaaaa acaatttttct tttgccctat ttcaccgaag atgaaaaaaa gctagtccgg    2400
ggttccttttg acttcctggc ggtgagtcat tacaccacca ttctggtaga ctgggaaaag    2460
gaggatccga tgaaatacaa cgattacttg gaggtacagg agatgactga catcacatgg    2520
ctcaactctc ccagtcaggt ggcagtggtg ccttgggggc tgcgcaaagt gctcaactgg    2580
ctaaggttca agtacggaga cctcccgatg tatgtgacag ccaatggaat cgatgatgac    2640
ccccacgccg agcaagactc actgaggatc tattatatta agaattatgt gaatgaggct    2700
ctgaaagcct acgtgttgga cgacatcaac ctttgtggct actttgcgta ttcacttagt    2760
gatcgctcag ctcccaagtc tggcttttat cgatatgctg cgaatcagtt tgagcccaaa    2820
ccatctatga acattacag gaaaattatt gacagcaatg gcttcctggg ttctggaaca    2880
ctgggaaggt tttgtccaga agaatacact gtgtgcaccg aatgtggatt ttttcaaacc    2940
```

```
cggaagtctt tgctggtctt catctcgttt cttgtttta  cttttattat ttctcttgct   3000
ctcatttttc actactccaa gaaaggccag agaagttata agtaa                   3045
```

<210> SEQ ID NO 54
<211> LENGTH: 1014
<212> TYPE: PRT
<213> ORGANISM: Mus musculus

<400> SEQUENCE: 54

```
Met Leu Ala Arg Ala Pro Pro Arg Arg Pro Pro Arg Leu Val Leu Leu
1               5                   10                  15

Arg Leu Leu Leu Leu His Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Leu Ser Ser Thr Gly Asp Val Ala Ser
        115                 120                 125

Asp Ser Tyr Asn Asn Val Tyr Arg Asp Thr Glu Gly Leu Arg Glu Leu
130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
    210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
    290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
```

-continued

```
              355                 360                 365
Phe Ala Leu Ser Phe Gly Pro Thr Leu Ser Phe Gln Leu Leu Asp Pro
370                 375                 380
Asn Met Lys Phe Arg Gln Leu Glu Ser Pro Asn Leu Arg Gln Leu Leu
385                 390                 395                 400
Ser Trp Ile Asp Leu Glu Tyr Asn His Pro Ile Phe Ile Val Glu
                405                 410                 415
Asn Gly Trp Phe Val Ser Gly Thr Thr Lys Arg Asp Asp Ala Lys Tyr
                420                 425                 430
Met Tyr Tyr Leu Lys Lys Phe Ile Met Glu Thr Leu Lys Ala Ile Arg
                435                 440                 445
Leu Asp Gly Val Asp Val Ile Gly Tyr Thr Ala Trp Ser Leu Met Asp
450                 455                 460
Gly Phe Glu Trp His Arg Gly Tyr Ser Ile Arg Arg Gly Leu Phe Tyr
465                 470                 475                 480
Val Asp Phe Leu Ser Gln Asp Lys Glu Leu Leu Pro Lys Ser Ser Ala
                485                 490                 495
Leu Phe Tyr Gln Lys Leu Ile Glu Asp Asn Gly Phe Pro Pro Leu Pro
                500                 505                 510
Glu Asn Gln Pro Leu Glu Gly Thr Phe Pro Cys Asp Phe Ala Trp Gly
                515                 520                 525
Val Val Asp Asn Tyr Val Gln Val Asp Thr Thr Leu Ser Gln Phe Thr
530                 535                 540
Asp Pro Asn Val Tyr Leu Trp Asp Val His His Ser Lys Arg Leu Ile
545                 550                 555                 560
Lys Val Asp Gly Val Val Ala Lys Lys Arg Lys Pro Tyr Cys Val Asp
                565                 570                 575
Phe Ser Ala Ile Arg Pro Gln Ile Thr Leu Leu Arg Glu Met Arg Val
                580                 585                 590
Thr His Phe Arg Phe Ser Leu Asp Trp Ala Leu Ile Leu Pro Leu Gly
                595                 600                 605
Asn Gln Thr Gln Val Asn His Thr Val Leu His Phe Tyr Arg Cys Met
                610                 615                 620
Ile Ser Glu Leu Val His Ala Asn Ile Thr Pro Val Val Ala Leu Trp
625                 630                 635                 640
Gln Pro Ala Ala Pro His Gln Gly Leu Pro His Ala Leu Ala Lys His
                645                 650                 655
Gly Ala Trp Glu Asn Pro His Thr Ala Leu Ala Phe Ala Asp Tyr Ala
                660                 665                 670
Asn Leu Cys Phe Lys Glu Leu Gly His Trp Val Asn Leu Trp Ile Thr
                675                 680                 685
Met Asn Glu Pro Asn Thr Arg Asn Met Thr Tyr Arg Ala Gly His His
                690                 695                 700
Leu Leu Arg Ala His Ala Leu Ala Trp His Leu Tyr Asp Asp Lys Phe
705                 710                 715                 720
Arg Ala Ala Gln Lys Gly Lys Ile Ser Ile Ala Leu Gln Ala Asp Trp
                725                 730                 735
Ile Glu Pro Ala Cys Pro Phe Ser Gln Asn Asp Lys Glu Val Ala Glu
                740                 745                 750
Arg Val Leu Glu Phe Asp Ile Gly Trp Leu Ala Glu Pro Ile Phe Gly
                755                 760                 765
Ser Gly Asp Tyr Pro Arg Val Met Arg Asp Trp Leu Asn Gln Lys Asn
                770                 775                 780
```

```
Asn Phe Leu Leu Pro Tyr Phe Thr Glu Asp Glu Lys Leu Val Arg
785                 790                 795                 800

Gly Ser Phe Asp Phe Leu Ala Val Ser His Tyr Thr Thr Ile Leu Val
            805                 810                 815

Asp Trp Glu Lys Glu Asp Pro Met Lys Tyr Asn Asp Tyr Leu Glu Val
                820                 825                 830

Gln Glu Met Thr Asp Ile Thr Trp Leu Asn Ser Pro Ser Gln Val Ala
            835                 840                 845

Val Val Pro Trp Gly Leu Arg Lys Val Leu Asn Trp Leu Arg Phe Lys
850                 855                 860

Tyr Gly Asp Leu Pro Met Tyr Val Thr Ala Asn Gly Ile Asp Asp
865                 870                 875                 880

Pro His Ala Glu Gln Asp Ser Leu Arg Ile Tyr Tyr Ile Lys Asn Tyr
                885                 890                 895

Val Asn Glu Ala Leu Lys Ala Tyr Val Leu Asp Asp Ile Asn Leu Cys
            900                 905                 910

Gly Tyr Phe Ala Tyr Ser Leu Ser Asp Arg Ser Ala Pro Lys Ser Gly
            915                 920                 925

Phe Tyr Arg Tyr Ala Ala Asn Gln Phe Glu Pro Lys Pro Ser Met Lys
            930                 935                 940

His Tyr Arg Lys Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
            980                 985                 990

Phe Thr Phe Ile Ile Ser Leu Ala  Leu Ile Phe His Tyr  Ser Lys Lys
            995                 1000                1005

Gly Gln  Arg Ser Tyr Lys
    1010

<210> SEQ ID NO 55
<211> LENGTH: 397
<212> TYPE: DNA
<213> ORGANISM: Mus musculus

<400> SEQUENCE: 55
atggacccca actgctcctg ctccaccggc ggctcctgca cttgcaccag ctcctgcgcc    60
tgcaagaact gcaagtgcac ctcctgcaag aagagtgagt gggacaccct tgggtggcgg   120
ctaaggctag gggcggggaa ctcctacaaa actggctctg agaaatgtcc tttgcttccc   180
ggaggccatt gtattgtctc ggggacagaa ctatacagag aactatttaa aaaaaccgag   240
gtcttctctg ttggggacag aagcagagg tcttcagcca ggctgacctc ttcctcctcc   300
tttctaggct gctgctcctg ctgtcccgtg ggctgctcca aatgtgccca gggctgtgtc   360
tgcaaaggcg ccgcggacaa gtgcacgtgc tgtgcct                            397

<210> SEQ ID NO 56
<211> LENGTH: 132
<212> TYPE: PRT
<213> ORGANISM: Mus musculus

<400> SEQUENCE: 56

Met Asp Pro Asn Cys Ser Cys Ser Thr Gly Gly Ser Cys Thr Cys Thr
1               5                   10                  15
```

Ser Ser Cys Ala Cys Lys Asn Cys Lys Cys Thr Cys Lys Lys Ser
            20                  25                  30

Glu Leu Gly His Leu Gly Trp Arg Leu Arg Leu Gly Ala Gly Asn Ser
        35                  40                  45

Tyr Lys Thr Gly Ser Glu Lys Cys Pro Leu Leu Pro Gly Gly His Cys
    50                  55                  60

Ile Val Ser Gly Thr Glu Leu Tyr Arg Glu Leu Phe Lys Lys Thr Glu
65                  70                  75                  80

Val Phe Ser Val Gly Asp Arg Lys Gln Arg Ser Ser Ala Arg Leu Thr
                85                  90                  95

Ser Ser Ser Ser Phe Leu Gly Cys Cys Ser Cys Cys Pro Val Gly Cys
            100                 105                 110

Ser Lys Cys Ala Gln Gly Cys Val Cys Lys Gly Ala Ala Asp Lys Cys
            115                 120                 125

Thr Cys Cys Ala
        130

<210> SEQ ID NO 57
<211> LENGTH: 1230
<212> TYPE: DNA
<213> ORGANISM: Mus musculus

<400> SEQUENCE: 57
atggtggggg cagacccgac cagaccccgg ggaccgctga gctattgggc gggccgtcgg      60
ggtcaggggc tcgcagcgat cttcctgctc ctggtgtccg cggcggaatc cgaggccagg     120
gcagaggatg acttcagcct ggtgcagccg ctggtgacca tggagcagct gctgtgggtg     180
agcgggaagc agatcggctc tgtagacact ttccgcatcc cgctcatcac agccacccct     240
cggggcacgc tcctggcctt cgctgaggcc aggaaaaaat ctgcatccga tgaggggcc      300 aagttcatcg ccatgaggag gtccacggac cagggtagca cgtggtcctc tacagccttc     360
atcgtagacg atgggggagc ctccgatggc ctgaacctgg cgctgtggt gaacgatgta      420 gacacaggga tagtgttcct tatctatacc ctctgtgctc acaaggtcaa ctgccaggtg     480
gcctctacca tgttggtttg gagtaaggac gacggcattt cctggagccc accccggaat     540
ctctctgtgg atattggcac agagatgttt gcccctggac ctggctcagg cattcagaaa     600
cagcgggagc tgggaagggcc cggctcatt gtgtgtggac acgggacgct ggagcgagat     660
ggggtcttct gtctcctcag tgatgaccac ggtgcctcct ggcactacgg cactggagtg     720
agcggcattc cctttggcca gcccaaacac gatcacgatt caaccccga cgagtgccag      780 ccctacgagc ttccagatgg ctcggtcatc atcaacgccc ggaaccagaa taactaccat     840
tgccgctgca ggatcgtcct ccgcagctat gacgcctgtg cacccctcag gccccgggat     900
gtgaccttcg accctgagct cgtggaccct gtggtagctg caggagcact agccaccagc     960
tccggcattg tcttcttctc caatccagcc cacctgagt tccgagtgaa cctgaccctg    1020
cgctggagtt tcagcaatgg tacatcctgg ctgaaggaga gggtccaggt gtggccggga    1080
cccagcggct actcgtccct gacagccctg gaaaacagca cggatggaaa gaagcagccc    1140
ccgcagctgt tcgttctgta cgagaaaggc ctgaaccggt acaccgagag catctccatg    1200
gtcaaaatca gcgtctacgg cacgctctga                                     1230

<210> SEQ ID NO 58
<211> LENGTH: 409
<212> TYPE: PRT
<213> ORGANISM: Mus musculus

<400> SEQUENCE: 58

```
Met Val Gly Ala Asp Pro Thr Arg Pro Arg Gly Pro Leu Ser Tyr Trp
1               5                   10                  15

Ala Gly Arg Arg Gly Gln Gly Leu Ala Ala Ile Phe Leu Leu Leu Val
            20                  25                  30

Ser Ala Ala Glu Ser Glu Ala Arg Ala Glu Asp Asp Phe Ser Leu Val
        35                  40                  45

Gln Pro Leu Val Thr Met Glu Gln Leu Leu Trp Val Ser Gly Lys Gln
    50                  55                  60

Ile Gly Ser Val Asp Thr Phe Arg Ile Pro Leu Ile Thr Ala Thr Pro
65                  70                  75                  80

Arg Gly Thr Leu Leu Ala Phe Ala Glu Ala Arg Lys Lys Ser Ala Ser
                85                  90                  95

Asp Glu Gly Ala Lys Phe Ile Ala Met Arg Arg Ser Thr Asp Gln Gly
            100                 105                 110

Ser Thr Trp Ser Ser Thr Ala Phe Ile Val Asp Gly Glu Ala Ser
        115                 120                 125

Asp Gly Leu Asn Leu Gly Ala Val Val Asn Asp Val Asp Thr Gly Ile
    130                 135                 140

Val Phe Leu Ile Tyr Thr Leu Cys Ala His Lys Val Asn Cys Gln Val
145                 150                 155                 160

Ala Ser Thr Met Leu Val Trp Ser Lys Asp Gly Ile Ser Trp Ser
            165                 170                 175

Pro Pro Arg Asn Leu Ser Val Asp Ile Gly Thr Glu Met Phe Ala Pro
            180                 185                 190

Gly Pro Gly Ser Gly Ile Gln Lys Gln Arg Glu Pro Gly Lys Gly Arg
        195                 200                 205

Leu Ile Val Cys Gly His Gly Thr Leu Glu Arg Asp Gly Val Phe Cys
    210                 215                 220

Leu Leu Ser Asp Asp His Gly Ala Ser Trp His Tyr Gly Thr Gly Val
225                 230                 235                 240

Ser Gly Ile Pro Phe Gly Gln Pro Lys His Asp His Asp Phe Asn Pro
            245                 250                 255

Asp Glu Cys Gln Pro Tyr Glu Leu Pro Asp Gly Ser Val Ile Ile Asn
            260                 265                 270

Ala Arg Asn Gln Asn Asn Tyr His Cys Arg Cys Arg Ile Val Leu Arg
        275                 280                 285

Ser Tyr Asp Ala Cys Asp Thr Leu Arg Pro Arg Asp Val Thr Phe Asp
    290                 295                 300

Pro Glu Leu Val Asp Pro Val Val Ala Ala Gly Ala Leu Ala Thr Ser
305                 310                 315                 320

Ser Gly Ile Val Phe Phe Ser Asn Pro Ala His Pro Glu Phe Arg Val
            325                 330                 335

Asn Leu Thr Leu Arg Trp Ser Phe Ser Asn Gly Thr Ser Trp Leu Lys
            340                 345                 350

Glu Arg Val Gln Val Trp Pro Gly Pro Ser Gly Tyr Ser Ser Leu Thr
        355                 360                 365

Ala Leu Glu Asn Ser Thr Asp Gly Lys Lys Gln Pro Pro Gln Leu Phe
    370                 375                 380

Val Leu Tyr Glu Lys Gly Leu Asn Arg Tyr Thr Glu Ser Ile Ser Met
385                 390                 395                 400

Val Lys Ile Ser Val Tyr Gly Thr Leu
```

<210> SEQ ID NO 59
<211> LENGTH: 471
<212> TYPE: DNA
<213> ORGANISM: Mus musculus

<400> SEQUENCE: 59

```
atgagcacct ccaggcttta taccctgtg ctagtgctac agcctcagcg agttctcctg      60
ggcatgaaga agaggggctt tggtgctggc cgctggaatg gcttcggggg caaggtgcag    120
gaaggagaga ccattgagga tggggctaag agagagctgc tggaagaaag tggtctgagc    180
gtggatacac tgcacaaggt aggccacatc tcgtttgaat ttgtgggctc ccctgagctg    240
atggacgtgc atatcttctc ggctgaccat gtgcacggga cgcccacaga gagtgaagaa    300
atgcgccctc agtggttcca actggaccag atccccttg ccgacatgtg gccggatgac    360
agctactggt tcccactcct gcttcagaag aagaagttct gtgggcactt caagttccag    420
gatcaggaca cgatcctcag ttactcgctg cgagaggtgg actcattcta a             471
```

<210> SEQ ID NO 60
<211> LENGTH: 156
<212> TYPE: PRT
<213> ORGANISM: Mus musculus

<400> SEQUENCE: 60

```
Met Ser Thr Ser Arg Leu Tyr Thr Leu Val Leu Val Leu Gln Pro Gln
 1               5                  10                  15
Arg Val Leu Leu Gly Met Lys Lys Arg Gly Phe Gly Ala Gly Arg Trp
             20                  25                  30
Asn Gly Phe Gly Gly Lys Val Gln Glu Gly Glu Thr Ile Glu Asp Gly
         35                  40                  45
Ala Lys Arg Glu Leu Leu Glu Glu Ser Gly Leu Ser Val Asp Thr Leu
     50                  55                  60
His Lys Val Gly His Ile Ser Phe Glu Phe Val Gly Ser Pro Glu Leu
 65                  70                  75                  80
Met Asp Val His Ile Phe Ser Ala Asp His Val His Gly Thr Pro Thr
                 85                  90                  95
Glu Ser Glu Glu Met Arg Pro Gln Trp Phe Gln Leu Asp Gln Ile Pro
            100                 105                 110
Phe Ala Asp Met Trp Pro Asp Asp Ser Tyr Trp Phe Pro Leu Leu Leu
        115                 120                 125
Gln Lys Lys Lys Phe Cys Gly His Phe Lys Phe Gln Asp Gln Asp Thr
    130                 135                 140
Ile Leu Ser Tyr Ser Leu Arg Glu Val Asp Ser Phe
145                 150                 155
```

<210> SEQ ID NO 61
<211> LENGTH: 1869
<212> TYPE: DNA
<213> ORGANISM: Mus musculus

<400> SEQUENCE: 61

```
atgcctcctc agctgcataa cggtctggac ttctctgcca aggtcatcca gggcagcctc      60
gacagcctgc cccaggcagt gaggaagttc gtggaaggca atgctcagct gtgccagccg    120
gagtatatcc acatctgcga tggctccgag gaggagtacg gcagttgct gacccacatg    180
caggaggagg gtgtcatccg caagctgaag aaatatgaca actgttggct ggctctcact    240
```

```
gaccctcgag atgtggccag gatcgaaagc aagacagtca tcatcaccca agagcagaga    300
gacacagtgc ccatcccaa aactggcctc agccagctgg gccgctggat gtcggaagag    360
gactttgaga aagcattcaa cgccaggttc ccagggtgca tgaaaggccg caccatgtat    420
gtcatcccat tcagcatggg gccactgggc tcgccgctgg ccaagattgg tattgaactg    480
acagactcgc cctatgtggt ggccagcatg cggatcatga ctcggatggg catatctgtg    540
ctggaggccc tgggagatgg ggagttcatc aagtgcctgc actctgtggg gtgccctctc    600
cccttaaaaa agcctttggt caacaactgg gcctgcaacc ctgagctgac cctgatcgcc    660
cacctcccgg accgcagaga gatcatctcc tttggaagcg gatatggtgg gaactcacta    720
ctcgggaaga aatgctttgc gttgcggatc gccagccgtc tggctaagga ggaagggtgg    780
ctggcggagc atatgctgat cctgggcata actaaccccg aaggcaagaa gaaataccctg   840 gccgcagcct tccctagtgc ctgtgggaag accaacttgg ccatgatgaa ccccagcctg    900
cccgggtgga aggtcgaatg tgtgggcgat gacatcgcct ggatgaagtt tgatgcccaa    960
ggcaacttaa gggctatcaa cccagaaaac gggttttttg gagttgctcc tggcacctca   1020
gtgaagacaa atccaaatgc cattaaaacc atccagaaaa acaccatctt caccaacgtg   1080
gctgagacta gcgatggggg tgtttactgg gaaggcatcg atgagccgct ggccccggga   1140
gtcaccatca cctcctggaa gaacaaggag tggagaccgc aggacgcgga accatgtgcc   1200
catcccaact cgagattctg cacccctgcc agccagtgcc ccattattga ccctgcctgg   1260
gaatctccag aaggagtacc cattgagggt atcatctttg gtggccgtag acctgaaggt   1320 gtccccttg tctatgaagc cctcagctgg cagcatgggg tgtttgtagg agcagccatg   1380
agatctgagg ccacagctgc tgcagaacac aagggcaaga tcatcatgca cgacccctt    1440 gccatgcgac ccttcttcgg ctacaacttc ggcaaatacc tgcccactg gctgagcatg    1500 gcccaccgcc cagcagccaa gttgcccaag atcttccatg tcaactggtt ccggaaggac   1560
aaagatggca agttcctctg gccaggcttt ggcgagaact cccgggtgct ggagtggatg   1620
ttcgggcgga ttgaagggga agacagcgcc aagctcacgc ccatcggcta catccctaag   1680
gaaaacgcct tgaacctgaa aggcctgggg ggcgtcaacg tggaggagct gtttgggatc   1740
tctaaggagt tctgggagaa ggaggtggag gagatcgaca ggtatctgga ggaccaggtc   1800
aacaccgacc tccccttacga aattgagagg gagctccgag ccctgaaaca gagaatcagc   1860
cagatgtaa                                                          1869
```

<210> SEQ ID NO 62
<211> LENGTH: 622
<212> TYPE: PRT
<213> ORGANISM: Mus musculus

<400> SEQUENCE: 62

```
Met Pro Pro Gln Leu His Asn Gly Leu Asp Phe Ser Ala Lys Val Ile
1               5                   10                  15

Gln Gly Ser Leu Asp Ser Leu Pro Gln Ala Val Arg Lys Phe Val Glu
            20                  25                  30

Gly Asn Ala Gln Leu Cys Gln Pro Glu Tyr Ile His Ile Cys Asp Gly
        35                  40                  45

Ser Glu Glu Glu Tyr Gly Gln Leu Leu Thr His Met Gln Glu Glu Gly
    50                  55                  60

Val Ile Arg Lys Leu Lys Lys Tyr Asp Asn Cys Trp Leu Ala Leu Thr
65                  70                  75                  80
```

-continued

```
Asp Pro Arg Asp Val Ala Arg Ile Glu Ser Lys Thr Val Ile Ile Thr
                85                  90                  95

Gln Glu Gln Arg Asp Thr Val Pro Ile Pro Lys Thr Gly Leu Ser Gln
            100                 105                 110

Leu Gly Arg Trp Met Ser Glu Glu Asp Phe Glu Lys Ala Phe Asn Ala
        115                 120                 125

Arg Phe Pro Gly Cys Met Lys Gly Arg Thr Met Tyr Val Ile Pro Phe
    130                 135                 140

Ser Met Gly Pro Leu Gly Ser Pro Leu Ala Lys Ile Gly Ile Glu Leu
145                 150                 155                 160

Thr Asp Ser Pro Tyr Val Val Ala Ser Met Arg Ile Met Thr Arg Met
                165                 170                 175

Gly Ile Ser Val Leu Glu Ala Leu Gly Asp Gly Glu Phe Ile Lys Cys
            180                 185                 190

Leu His Ser Val Gly Cys Pro Leu Pro Leu Lys Lys Pro Leu Val Asn
        195                 200                 205

Asn Trp Ala Cys Asn Pro Glu Leu Thr Leu Ile Ala His Leu Pro Asp
    210                 215                 220

Arg Arg Glu Ile Ile Ser Phe Gly Ser Gly Tyr Gly Gly Asn Ser Leu
225                 230                 235                 240

Leu Gly Lys Lys Cys Phe Ala Leu Arg Ile Ala Ser Arg Leu Ala Lys
                245                 250                 255

Glu Glu Gly Trp Leu Ala Glu His Met Leu Ile Leu Gly Ile Thr Asn
            260                 265                 270

Pro Glu Gly Lys Lys Tyr Leu Ala Ala Phe Pro Ser Ala Cys
        275                 280                 285

Gly Lys Thr Asn Leu Ala Met Met Asn Pro Ser Leu Pro Gly Trp Lys
    290                 295                 300

Val Glu Cys Val Gly Asp Asp Ile Ala Trp Met Lys Phe Asp Ala Gln
305                 310                 315                 320

Gly Asn Leu Arg Ala Ile Asn Pro Glu Asn Gly Phe Phe Gly Val Ala
                325                 330                 335

Pro Gly Thr Ser Val Lys Thr Asn Pro Asn Ala Ile Lys Thr Ile Gln
            340                 345                 350

Lys Asn Thr Ile Phe Thr Asn Val Ala Glu Thr Ser Asp Gly Gly Val
        355                 360                 365

Tyr Trp Glu Gly Ile Asp Glu Pro Leu Ala Pro Gly Val Thr Ile Thr
    370                 375                 380

Ser Trp Lys Asn Lys Glu Trp Arg Pro Gln Asp Ala Glu Pro Cys Ala
385                 390                 395                 400

His Pro Asn Ser Arg Phe Cys Thr Pro Ala Ser Gln Cys Pro Ile Ile
                405                 410                 415

Asp Pro Ala Trp Glu Ser Pro Glu Gly Val Pro Ile Glu Gly Ile Ile
            420                 425                 430

Phe Gly Gly Arg Arg Pro Glu Gly Val Pro Leu Val Tyr Glu Ala Leu
        435                 440                 445

Ser Trp Gln His Gly Val Phe Val Gly Ala Ala Met Arg Ser Glu Ala
    450                 455                 460

Thr Ala Ala Ala Glu His Lys Gly Lys Ile Ile Met His Asp Pro Phe
465                 470                 475                 480

Ala Met Arg Pro Phe Phe Gly Tyr Asn Phe Gly Lys Tyr Leu Ala His
                485                 490                 495
```

```
Trp Leu Ser Met Ala His Arg Pro Ala Ala Lys Leu Pro Lys Ile Phe
            500                 505                 510

His Val Asn Trp Phe Arg Lys Asp Lys Asp Gly Lys Phe Leu Trp Pro
        515                 520                 525

Gly Phe Gly Glu Asn Ser Arg Val Leu Glu Trp Met Phe Gly Arg Ile
    530                 535                 540

Glu Gly Glu Asp Ser Ala Lys Leu Thr Pro Ile Gly Tyr Ile Pro Lys
545                 550                 555                 560

Glu Asn Ala Leu Asn Leu Lys Gly Leu Gly Val Asn Val Glu Glu
                565                 570                 575

Leu Phe Gly Ile Ser Lys Glu Phe Trp Glu Lys Glu Val Glu Glu Ile
            580                 585                 590

Asp Arg Tyr Leu Glu Asp Gln Val Asn Thr Asp Leu Pro Tyr Glu Ile
        595                 600                 605

Glu Arg Glu Leu Arg Ala Leu Lys Gln Arg Ile Ser Gln Met
610                 615                 620
```

<210> SEQ ID NO 63
<211> LENGTH: 885
<212> TYPE: DNA
<213> ORGANISM: Mus musculus

<400> SEQUENCE: 63

```
atgtggcagt cctccagcgt ggttttccac acgggcgccg gcatcagcac cgcctctggc      60
atccccgact tcagaggccc catggcgtg tggaccatgg aggaacgcgg cctggccccc     120
aagtttgaca ccaccttcga gaatgctcgg ccctcgaaga cccacatggc cctggttcag     180
ctagaacgca tgggcttcct cagcttcctg gtcagccaga acgtagacgg ctgcacgtg     240
cgctcgggct tccccaggga caagctggca gagctgcacg aaacatgtt tgtagaggaa     300
tgtcccaagt gtaagacgca gtacgtcaga gacacggttg tgggcaccat gggcctcaag     360
gccacaggcc ggctctgcac cgtggccaag accaggggac ttcgggcctg tagaggggag     420
ctgagagaca ccattctgga ctgggaggac tcgttgcctg accgggacct gatgctcgct     480
gatgaggcca gcaggaccgc agacctgtct gtcaccctgg gtacctcgct gcagatccgc     540
cccagtggga acctgcccct tgccactaag cgccgaggag gccgtctggt cattgtcaac     600
ctgcaaccca aaaacatga ccgccaggct gacctgcgca tccacggcta cgtggatgag     660
gtgatgtgca gactcatgaa gcatctgggg ctggagattc cagcctggga tggaccctgc     720
gtgctagaca aagccctgcc acctctgcct cgcccagtag cactcaaggc tgagccccc     780
gtgcatctca atggtgcagt gcatgtttcg tataagtcca agcccaacag ccctatactc     840
cacaggcccc ccaaaagagt gaagaccgag gctgccccca gctga                    885
```

<210> SEQ ID NO 64
<211> LENGTH: 294
<212> TYPE: PRT
<213> ORGANISM: Mus musculus

<400> SEQUENCE: 64

```
Met Trp Gln Ser Ser Val Val Phe His Thr Gly Ala Gly Ile Ser
1               5                   10                  15

Thr Ala Ser Gly Ile Pro Asp Phe Arg Gly Pro His Gly Val Trp Thr
            20                  25                  30

Met Glu Glu Arg Gly Leu Ala Pro Lys Phe Asp Thr Thr Phe Glu Asn
        35                  40                  45
```

-continued

```
Ala Arg Pro Ser Lys Thr His Met Ala Leu Val Gln Leu Glu Arg Met
 50                  55                  60

Gly Phe Leu Ser Phe Leu Val Ser Gln Asn Val Asp Gly Leu His Val
 65                  70                  75                  80

Arg Ser Gly Phe Pro Arg Asp Lys Leu Ala Glu Leu His Gly Asn Met
                 85                  90                  95

Phe Val Glu Glu Cys Pro Lys Cys Lys Thr Gln Tyr Val Arg Asp Thr
            100                 105                 110

Val Val Gly Thr Met Gly Leu Lys Ala Thr Gly Arg Leu Cys Thr Val
        115                 120                 125

Ala Lys Thr Arg Gly Leu Arg Ala Cys Arg Gly Glu Leu Arg Asp Thr
130                 135                 140

Ile Leu Asp Trp Glu Asp Ser Leu Pro Asp Arg Asp Leu Met Leu Ala
145                 150                 155                 160

Asp Glu Ala Ser Arg Thr Ala Asp Leu Ser Val Thr Leu Gly Thr Ser
                165                 170                 175

Leu Gln Ile Arg Pro Ser Gly Asn Leu Pro Leu Ala Thr Lys Arg Arg
            180                 185                 190

Gly Gly Arg Leu Val Ile Val Asn Leu Gln Pro Thr Lys His Asp Arg
        195                 200                 205

Gln Ala Asp Leu Arg Ile His Gly Tyr Val Asp Glu Val Met Cys Arg
210                 215                 220

Leu Met Lys His Leu Gly Leu Glu Ile Pro Ala Trp Asp Gly Pro Cys
225                 230                 235                 240

Val Leu Asp Lys Ala Leu Pro Pro Leu Pro Arg Pro Val Ala Leu Lys
                245                 250                 255

Ala Glu Pro Pro Val His Leu Asn Gly Ala Val His Val Ser Tyr Lys
            260                 265                 270

Ser Lys Pro Asn Ser Pro Ile Leu His Arg Pro Pro Lys Arg Val Lys
        275                 280                 285

Thr Glu Ala Ala Pro Ser
    290
```

<210> SEQ ID NO 65
<211> LENGTH: 3369
<212> TYPE: DNA
<213> ORGANISM: Mus musculus

<400> SEQUENCE: 65

| | | | | |
|---|---|---|---|---|
| atgacccgcg | ctcctcgttg | ccccgcggtg | cgctctctgc | tgcgcagccg | ataccgggag | 60 |
| gtgtggccgc | tggcaacctt | tgtgcggcgc | ctggggcccg | agggcaggcg | gcttgtgcaa | 120 |
| cccggggacc | cgaagatcta | ccgcactttg | gttgcccaat | gcctagtgtg | catgcactgg | 180 |
| ggctcacagc | ctccacctgc | cgacctttcc | ttccaccagg | tgtcatccct | gaaagagctg | 240 |
| gtggccaggg | ttgtgcagag | actctgcgag | cgcaacgaga | gaaacgtgct | ggcttttggc | 300 |
| tttgagctgc | ttaacgaggc | cagaggcggg | cctcccatgg | ccttcactag | tagcgtgcgt | 360 |
| agctacttgc | ccaacactgt | tattgagacc | ctgcgtgtca | gtggtgcatg | gatgctactg | 420 |
| ttgagccgag | tggcgacga | cctgctggtc | tacctgctgg | cacactgtgc | tctttatctt | 480 |
| ctggtgcccc | ccagctgtgc | ctaccaggtg | tgtgggtctc | ccctgtacca | aatttgtgcc | 540 |
| accacggata | tctggccctc | tgtgtccgct | agttacaggc | ccacccgacc | cgtgggcagg | 600 |
| aatttcacta | accttaggtt | cttacaacag | atcaagagca | gtagtcgcca | ggaagcaccg | 660 |
| aaacccctgg | ccttgccatc | tcgaggtaca | aagaggcatc | tgagtctcac | cagtacaagt | 720 |

```
gtgccttcag ctaagaaggc cagatgctat cctgtcccga gagtggagga gggaccccac    780
aggcaggtgc taccaacccc atcaggcaaa tcatgggtgc caagtcctgc tcggtccccc    840
gaggtgccta ctgcagagaa agatttgtct tctaaaggaa aggtgtctga cctgagtctc    900
tctgggtcgg tgtgctgtaa acacaagccc agctccacat ctctgctgtc accacccgc     960 caaaatgcct ttcagctcag gccatttatt gagaccagac atttccttta ctccagggga   1020
gatggccaag agcgtctaaa cccctcattc ctactcagca acctccagcc taacttgact   1080
ggggccagga gactggtgga gatcatcttt ctgggctcaa ggcctaggac atcaggacca   1140
ctctgcagga cacaccgtct atcgcgtcga tactggcaga tgcggcccct gttccaacag   1200
ctgctggtga accatgcaga gtgccaatat gtcagactcc tcaggtcaca ttgcaggttt   1260
cgaacagcaa accaacaggt gacagatgcc ttgaacacca gcccaccgca cctcatggat   1320
ttgctccgcc tgcacagcag tccctggcag gtatatggtt ttcttcgggc tgtctctgc    1380 aaggtggtgt ctgctagtct ctggggtacc aggcacaatg agcgccgctt ctttaagaac   1440
ttaaagaagt tcatctcgtt ggggaaatac ggcaagctat cactgcagga actgatgtgg   1500
aagatgaaag tagaggattg ccactggctc cgcagcagcc cggggaagga ccgtgtcccc   1560
gctgcagagc accgtctgag ggagaggatc ctggctacgt tcctgttctg gctgatggac   1620
acatacgtgg tacagctgct taggtcattc ttttacatca cagagagcac attccagaag   1680
aacaggctct tcttctaccg taagagtgtg tggagcaagc tgcagagcat ggagtcagg    1740 caacaccttg agagagtgcg gctacgggag ctgtcacaag aggaggtcag gcatcaccag   1800
gacacctggc tagccatgcc catctgcaga ctgcgcttca tccccaagcc caacggcctg   1860
cggcccattg tgaacatgag ttatagcatg ggtaccagag ctttgggcag aaggaagcag   1920
gcccagcatt tcacccagcg tctcaagact ctcttcagca tgctcaacta tgagcggaca   1980
aaacatcctc accttatggg gtcttctgta ctgggtatga atgacatcta caggacctgg   2040
cgggcctttg tgctgcgtgt gcgtgctctg gaccagacac ccaggatgta ctttgttaag   2100
gcagatgtga ccggggccta tgatgccatc ccccagggta agctggtgga ggttgttgcc   2160
aatatgatca ggcactcgga gagcacgtac tgtatccgcc agtatgcagt ggtccggaga   2220
gatagccaag gccaagtcca caagtccttt aggagacagg tcaccaccct ctctgacctc   2280
cagccataca tgggccagtt ccttaagcat ctgcaggatt cagatgccag tgcactgagg   2340
aactccgttg tcatcgagca gagcatctct atgaatgaga gcagcagcag cctgtttgac   2400
ttcttcctgc acttcctgcg tcacagtgtc gtaaagattg gtgacaggtg ctatacgcag   2460
tgccagggca tcccccaggg ctccagccta tccaccctgc tctgcagtct gtgtttcgga   2520
gacatggaga acaagctgtt tgctgaggtg cagcgggatg ggttgctttt acgttttgtt   2580
gatgactttc tgttggtgac gcctcacttg gaccaagcaa aaaccttcct cagcaccctg   2640
gtccatggcg ttcctgagta tgggtgcatg ataaacttgc agaagacagt ggtgaacttc   2700
cctgtggagc ctggtacccct gggtggtgca gctccatacc agctgcctgc tcactgcctg   2760
tttccctggt gtggcttgct gctggacact cagactttgg aggtgttctg tgactactca   2820
ggttatgccc agacctcaat taagacgagc ctcaccttcc agagtgtctt caaagctggg   2880
aagaccatgc ggaacaagct cctgtcggtc ttgcggttga agtgtcacgg tctatttcta   2940
gacttgcagg tgaacagcct ccagacagtc tgcatcaata tatacaagat cttcctgctt   3000
caggcctaca ggttccatgc atgtgtgatt cagcttccct ttgaccagcg tgttaggaag   3060
```

```
aacctcacat tctttctggg catcatctcc agccaagcat cctgctgcta tgctatcctg    3120
aaggtcaaga atccaggaat gacactaaag gcctctggct cctttcctcc tgaagccgca    3180
cattggctct gctaccaggc cttcctgctc aagctggctg ctcattctgt catctacaaa    3240
tgtctcctgg gacctctgag gacagcccaa aaactgctgt gccggaagct cccagaggcg    3300
acaatgacca tccttaaagc tgcagctgac ccagccctaa gcacagactt tcagaccatt    3360
ttggactaa                                                            3369

<210> SEQ ID NO 66
<211> LENGTH: 1122
<212> TYPE: PRT
<213> ORGANISM: Mus musculus

<400> SEQUENCE: 66
```

| Met | Thr | Arg | Ala | Pro | Arg | Cys | Pro | Ala | Val | Arg | Ser | Leu | Leu | Arg | Ser |
|---|---|---|---|---|---|---|---|---|---|---|---|---|---|---|---|
| 1 | | | | 5 | | | | | 10 | | | | | 15 | |

| Arg | Tyr | Arg | Glu | Val | Trp | Pro | Leu | Ala | Thr | Phe | Val | Arg | Arg | Leu | Gly |
|---|---|---|---|---|---|---|---|---|---|---|---|---|---|---|---|
| | | | 20 | | | | | 25 | | | | | 30 | | |

| Pro | Glu | Gly | Arg | Arg | Leu | Val | Gln | Pro | Gly | Asp | Pro | Lys | Ile | Tyr | Arg |
| | | | 35 | | | | | 40 | | | | | 45 | | |

| Thr | Leu | Val | Ala | Gln | Cys | Leu | Val | Cys | Met | His | Trp | Gly | Ser | Gln | Pro |
| 50 | | | | | 55 | | | | | 60 | | | | | |

| Pro | Pro | Ala | Asp | Leu | Ser | Phe | His | Gln | Val | Ser | Ser | Leu | Lys | Glu | Leu |
| 65 | | | | | 70 | | | | | 75 | | | | | 80 |

| Val | Ala | Arg | Val | Val | Gln | Arg | Leu | Cys | Glu | Arg | Asn | Glu | Arg | Asn | Val |
| | | | | 85 | | | | | 90 | | | | | 95 | |

| Leu | Ala | Phe | Gly | Phe | Glu | Leu | Leu | Asn | Glu | Ala | Arg | Gly | Gly | Pro | Pro |
| | | | 100 | | | | | 105 | | | | | 110 | | |

| Met | Ala | Phe | Thr | Ser | Ser | Val | Arg | Ser | Tyr | Leu | Pro | Asn | Thr | Val | Ile |
| | | | 115 | | | | | 120 | | | | | 125 | | |

| Glu | Thr | Leu | Arg | Val | Ser | Gly | Ala | Trp | Met | Leu | Leu | Leu | Ser | Arg | Val |
| | 130 | | | | | 135 | | | | | 140 | | | | |

| Gly | Asp | Asp | Leu | Leu | Val | Tyr | Leu | Leu | Ala | His | Cys | Ala | Leu | Tyr | Leu |
| 145 | | | | | 150 | | | | | 155 | | | | | 160 |

| Leu | Val | Pro | Pro | Ser | Cys | Ala | Tyr | Gln | Val | Cys | Gly | Ser | Pro | Leu | Tyr |
| | | | | 165 | | | | | 170 | | | | | 175 | |

| Gln | Ile | Cys | Ala | Thr | Thr | Asp | Ile | Trp | Pro | Ser | Val | Ser | Ala | Ser | Tyr |
| | | | 180 | | | | | 185 | | | | | 190 | | |

| Arg | Pro | Thr | Arg | Pro | Val | Gly | Arg | Asn | Phe | Thr | Asn | Leu | Arg | Phe | Leu |
| | | | 195 | | | | | 200 | | | | | 205 | | |

| Gln | Gln | Ile | Lys | Ser | Ser | Arg | Gln | Glu | Ala | Pro | Lys | Pro | Leu | Ala |
| | 210 | | | | | 215 | | | | | 220 | | | | |

| Leu | Pro | Ser | Arg | Gly | Thr | Lys | Arg | His | Leu | Ser | Leu | Thr | Ser | Thr | Ser |
| 225 | | | | | 230 | | | | | 235 | | | | | 240 |

| Val | Pro | Ser | Ala | Lys | Lys | Ala | Arg | Cys | Tyr | Pro | Val | Pro | Arg | Val | Glu |
| | | | | 245 | | | | | 250 | | | | | 255 | |

| Glu | Gly | Pro | His | Arg | Gln | Val | Leu | Pro | Thr | Pro | Ser | Gly | Lys | Ser | Trp |
| | | | 260 | | | | | 265 | | | | | 270 | | |

| Val | Pro | Ser | Pro | Ala | Arg | Ser | Pro | Glu | Val | Pro | Thr | Ala | Glu | Lys | Asp |
| | | | 275 | | | | | 280 | | | | | 285 | | |

| Leu | Ser | Ser | Lys | Gly | Lys | Val | Ser | Asp | Leu | Ser | Leu | Ser | Gly | Ser | Val |
| | 290 | | | | | 295 | | | | | 300 | | | | |

| Cys | Cys | Lys | His | Lys | Pro | Ser | Ser | Thr | Ser | Leu | Leu | Ser | Pro | Pro | Arg |
| 305 | | | | | 310 | | | | | 315 | | | | | 320 |

```
Gln Asn Ala Phe Gln Leu Arg Pro Phe Ile Glu Thr Arg His Phe Leu
                325                 330                 335

Tyr Ser Arg Gly Asp Gly Gln Glu Arg Leu Asn Pro Ser Phe Leu Leu
            340                 345                 350

Ser Asn Leu Gln Pro Asn Leu Thr Gly Ala Arg Arg Leu Val Glu Ile
        355                 360                 365

Ile Phe Leu Gly Ser Arg Pro Arg Thr Ser Gly Pro Leu Cys Arg Thr
    370                 375                 380

His Arg Leu Ser Arg Arg Tyr Trp Gln Met Arg Pro Leu Phe Gln Gln
385                 390                 395                 400

Leu Leu Val Asn His Ala Glu Cys Gln Tyr Val Arg Leu Leu Arg Ser
                405                 410                 415

His Cys Arg Phe Arg Thr Ala Asn Gln Gln Val Thr Asp Ala Leu Asn
            420                 425                 430

Thr Ser Pro Pro His Leu Met Asp Leu Leu Arg Leu His Ser Ser Pro
        435                 440                 445

Trp Gln Val Tyr Gly Phe Leu Arg Ala Cys Leu Cys Lys Val Val Ser
    450                 455                 460

Ala Ser Leu Trp Gly Thr Arg His Asn Glu Arg Arg Phe Phe Lys Asn
465                 470                 475                 480

Leu Lys Lys Phe Ile Ser Leu Gly Lys Tyr Gly Lys Leu Ser Leu Gln
                485                 490                 495

Glu Leu Met Trp Lys Met Lys Val Glu Asp Cys His Trp Leu Arg Ser
            500                 505                 510

Ser Pro Gly Lys Asp Arg Val Pro Ala Ala Glu His Arg Leu Arg Glu
        515                 520                 525

Arg Ile Leu Ala Thr Phe Leu Phe Trp Leu Met Asp Thr Tyr Val Val
    530                 535                 540

Gln Leu Leu Arg Ser Phe Phe Tyr Ile Thr Glu Ser Thr Phe Gln Lys
545                 550                 555                 560

Asn Arg Leu Phe Phe Tyr Arg Lys Ser Val Trp Ser Lys Leu Gln Ser
                565                 570                 575

Ile Gly Val Arg Gln His Leu Glu Arg Val Arg Leu Arg Glu Leu Ser
            580                 585                 590

Gln Glu Glu Val Arg His His Gln Asp Thr Trp Leu Ala Met Pro Ile
        595                 600                 605

Cys Arg Leu Arg Phe Ile Pro Lys Pro Asn Gly Leu Arg Pro Ile Val
    610                 615                 620

Asn Met Ser Tyr Ser Met Gly Thr Arg Ala Leu Gly Arg Arg Lys Gln
625                 630                 635                 640

Ala Gln His Phe Thr Gln Arg Leu Lys Thr Leu Phe Ser Met Leu Asn
                645                 650                 655

Tyr Glu Arg Thr Lys His Pro His Leu Met Gly Ser Ser Val Leu Gly
            660                 665                 670

Met Asn Asp Ile Tyr Arg Thr Trp Arg Ala Phe Val Leu Arg Val Arg
        675                 680                 685

Ala Leu Asp Gln Thr Pro Arg Met Tyr Phe Val Lys Ala Asp Val Thr
    690                 695                 700

Gly Ala Tyr Asp Ala Ile Pro Gln Gly Lys Leu Val Glu Val Val Ala
705                 710                 715                 720

Asn Met Ile Arg His Ser Glu Ser Thr Tyr Cys Ile Arg Gln Tyr Ala
                725                 730                 735
```

```
Val Val Arg Arg Asp Ser Gln Gly Gln Val His Lys Ser Phe Arg Arg
            740                 745                 750

Gln Val Thr Thr Leu Ser Asp Leu Gln Pro Tyr Met Gly Gln Phe Leu
            755                 760                 765

Lys His Leu Gln Asp Ser Asp Ala Ser Ala Leu Arg Asn Ser Val Val
        770                 775                 780

Ile Glu Gln Ser Ile Ser Met Asn Glu Ser Ser Ser Leu Phe Asp
785                 790                 795                 800

Phe Phe Leu His Phe Leu Arg His Ser Val Val Lys Ile Gly Asp Arg
                805                 810                 815

Cys Tyr Thr Gln Cys Gln Gly Ile Pro Gln Gly Ser Ser Leu Ser Thr
            820                 825                 830

Leu Leu Cys Ser Leu Cys Phe Gly Asp Met Glu Asn Lys Leu Phe Ala
            835                 840                 845

Glu Val Gln Arg Asp Gly Leu Leu Leu Arg Phe Val Asp Asp Phe Leu
        850                 855                 860

Leu Val Thr Pro His Leu Asp Gln Ala Lys Thr Phe Leu Ser Thr Leu
865                 870                 875                 880

Val His Gly Val Pro Glu Tyr Gly Cys Met Ile Asn Leu Gln Lys Thr
                885                 890                 895

Val Val Asn Phe Pro Val Glu Pro Gly Thr Leu Gly Gly Ala Ala Pro
            900                 905                 910

Tyr Gln Leu Pro Ala His Cys Leu Phe Pro Trp Cys Gly Leu Leu Leu
            915                 920                 925

Asp Thr Gln Thr Leu Glu Val Phe Cys Asp Tyr Ser Gly Tyr Ala Gln
        930                 935                 940

Thr Ser Ile Lys Thr Ser Leu Thr Phe Gln Ser Val Phe Lys Ala Gly
945                 950                 955                 960

Lys Thr Met Arg Asn Lys Leu Ser Val Leu Arg Leu Lys Cys His
                965                 970                 975

Gly Leu Phe Leu Asp Leu Gln Val Asn Ser Leu Gln Thr Val Cys Ile
            980                 985                 990

Asn Ile Tyr Lys Ile Phe Leu Leu Gln Ala Tyr Arg Phe His Ala Cys
        995                 1000                1005

Val Ile Gln Leu Pro Phe Asp Gln Arg Val Arg Lys Asn Leu Thr
    1010                1015                1020

Phe Phe Leu Gly Ile Ile Ser Ser Gln Ala Ser Cys Cys Tyr Ala
    1025                1030                1035

Ile Leu Lys Val Lys Asn Pro Gly Met Thr Leu Lys Ala Ser Gly
    1040                1045                1050

Ser Phe Pro Pro Glu Ala Ala His Trp Leu Cys Tyr Gln Ala Phe
    1055                1060                1065

Leu Leu Lys Leu Ala Ala His Ser Val Ile Tyr Lys Cys Leu Leu
    1070                1075                1080

Gly Pro Leu Arg Thr Ala Gln Lys Leu Leu Cys Arg Lys Leu Pro
    1085                1090                1095

Glu Ala Thr Met Thr Ile Leu Lys Ala Ala Ala Asp Pro Ala Leu
    1100                1105                1110

Ser Thr Asp Phe Gln Thr Ile Leu Asp
    1115                1120

<210> SEQ ID NO 67
<211> LENGTH: 1428
<212> TYPE: DNA
```

<213> ORGANISM: Mus musculus

<400> SEQUENCE: 67

```
atggcgtcac gcatcgggct gcgcatgcag ctcatgcggg agcaggccca gcaggaggag      60
cagcgagagc gcatgcagca gcaggctgtc atgcattata tgcaacagca gcagcagcag     120
cagcagcagc tgggtgggcc ccccacccca gccatcaaca ccctgtcca cttccagtcg      180
cccccgcctg tgcccgggga ggtgctgaag gtgcagtcct acctggagaa ccccaccctcc   240
taccacctgc aacagtccca gcatcagaag gttcggaagt atctgtctga gacctatggg    300
aacaagtttg ctgcccacgt gagcccagcc caaggttccc cgaagcctgc cccagcagca    360
tccccagggg tgcgggctgg acacgtactg tccacctcgg ccggcaacag tgctcccaac    420
agtcccatgg ccatgctaca tatcagctcc aaccccgaga agagtttga tgatgtcatt     480
gacaacatta tgcgcctgga cagcgtgctg ggctacatca ccctgagat gcagatgcct     540
aacacgctgc ccctgtctag cagccacctg aacgtgtaca gcggtgaccc ccaggtcaca   600
gcctccatgg tgggtgtcac cagcagctcc tgccctgccg acctgactca gaagcgagag    660
ctaacagatg ctgagagcag agccctggcc aaggagcggc agaagaaaga caatcacaac   720
ctaattgaga agaacgcag gttcaacatc aatgaccgga tcaaggagct gggaatgctg     780
atccccaagg ccaacgacct ggacgtgcgc tggaacaaag gcaccatcct caaggcctct    840
gtggattaca tccggaggat gcagaaggac ctgcagaagt cccgggagct ggagaaccac    900
tcccggcgcc tggagatgac taacaagcag ctctggctcc gcatccagga gctggagatg    960
caggcacgcg tgcacggcct ccccaccacc tcgccgtcgg tgtgtaatat ggccgagctg   1020
gcccagcagg tggtgaagca agagttgccc agtgaggatg gcccagggga ggcgctgatg  1080
ctggggcctg aggtccctga gcctgagcaa atgccggctc ttcctcccca ggctccgctg  1140
ccctcggccg cccagccaca gtctccgttc atcacctgg acttcagcca tggcctgagc   1200
tttgggggtg ggggcgacga ggggcccaca ggttaccccg ataccctggg gacagagcac   1260
ggctccccat tccccaacct gtccaagaag gatctggact taatgctcct agatgactcc  1320
ctgctccccc tggcctctga ccccctcttt tctaccatgt ctcctgaggc ctccaaggcc  1380
agcagccgcc ggagcagctt cagcatggag gagggtgatg ttctgtga                1428
```

<210> SEQ ID NO 68
<211> LENGTH: 475
<212> TYPE: PRT
<213> ORGANISM: Mus musculus

<400> SEQUENCE: 68

```
Met Ala Ser Arg Ile Gly Leu Arg Met Gln Leu Met Arg Glu Gln Ala
1               5                  10                  15

Gln Gln Glu Glu Gln Arg Glu Arg Met Gln Gln Gln Ala Val Met His
            20                  25                  30

Tyr Met Gln Gln Gln Gln Gln Gln Gln Leu Gly Gly Pro Pro
        35                  40                  45

Thr Pro Ala Ile Asn Thr Pro Val His Phe Gln Ser Pro Pro Val
    50                  55                  60

Pro Gly Glu Val Leu Lys Val Gln Ser Tyr Leu Glu Asn Pro Thr Ser
65                  70                  75                  80

Tyr His Leu Gln Gln Ser Gln His Gln Lys Val Arg Lys Tyr Leu Ser
                85                  90                  95

Glu Thr Tyr Gly Asn Lys Phe Ala Ala His Val Ser Pro Ala Gln Gly
```

```
                    100             105                 110
Ser Pro Lys Pro Ala Pro Ala Ala Ser Pro Gly Val Arg Ala Gly His
            115                 120                 125

Val Leu Ser Thr Ser Ala Gly Asn Ser Ala Pro Asn Ser Pro Met Ala
    130                 135                 140

Met Leu His Ile Ser Ser Asn Pro Glu Lys Glu Phe Asp Asp Val Ile
145                 150                 155                 160

Asp Asn Ile Met Arg Leu Asp Ser Val Leu Gly Tyr Ile Asn Pro Glu
                165                 170                 175

Met Gln Met Pro Asn Thr Leu Pro Leu Ser Ser His Leu Asn Val
            180                 185                 190

Tyr Ser Gly Asp Pro Gln Val Thr Ala Ser Met Val Gly Val Thr Ser
            195                 200                 205

Ser Ser Cys Pro Ala Asp Leu Thr Gln Lys Arg Glu Leu Thr Asp Ala
    210                 215                 220

Glu Ser Arg Ala Leu Ala Lys Glu Arg Gln Lys Lys Asp Asn His Asn
225                 230                 235                 240

Leu Ile Glu Arg Arg Arg Arg Phe Asn Ile Asn Asp Arg Ile Lys Glu
                245                 250                 255

Leu Gly Met Leu Ile Pro Lys Ala Asn Asp Leu Asp Val Arg Trp Asn
            260                 265                 270

Lys Gly Thr Ile Leu Lys Ala Ser Val Asp Tyr Ile Arg Arg Met Gln
            275                 280                 285

Lys Asp Leu Gln Lys Ser Arg Glu Leu Glu Asn His Ser Arg Arg Leu
    290                 295                 300

Glu Met Thr Asn Lys Gln Leu Trp Leu Arg Ile Gln Glu Leu Glu Met
305                 310                 315                 320

Gln Ala Arg Val His Gly Leu Pro Thr Thr Ser Pro Ser Gly Val Asn
                325                 330                 335

Met Ala Glu Leu Ala Gln Gln Val Val Lys Gln Glu Leu Pro Ser Glu
            340                 345                 350

Asp Gly Pro Gly Glu Ala Leu Met Leu Gly Pro Glu Val Pro Glu Pro
            355                 360                 365

Glu Gln Met Pro Ala Leu Pro Pro Gln Ala Pro Leu Pro Ser Ala Ala
    370                 375                 380

Gln Pro Gln Ser Pro Phe His His Leu Asp Phe Ser His Gly Leu Ser
385                 390                 395                 400

Phe Gly Gly Gly Asp Glu Gly Pro Thr Gly Tyr Pro Asp Thr Leu
                405                 410                 415

Gly Thr Glu His Gly Ser Pro Phe Pro Asn Leu Ser Lys Lys Asp Leu
            420                 425                 430

Asp Leu Met Leu Leu Asp Asp Ser Leu Leu Pro Leu Ala Ser Asp Pro
            435                 440                 445

Leu Phe Ser Thr Met Ser Pro Glu Ala Ser Lys Ala Ser Ser Arg Arg
    450                 455                 460

Ser Ser Phe Ser Met Glu Glu Gly Asp Val Leu
465                 470                 475
```

<210> SEQ ID NO 69
<211> LENGTH: 318
<212> TYPE: DNA
<213> ORGANISM: Mus musculus

<400> SEQUENCE: 69

| | |
|---|---|
| atggtgaagc tgatcgagag caaggaagct tttcaggagg ccctggccgc cgcgggagac | 60 |
| aagcttgtcg tggtggactt ctctgctacg tggtgtggac cttgcaaaat gatcaagccc | 120 |
| ttcttccatt ccctctgtga caagtattcc aatgtggtgt tccttgaagt ggatgtggat | 180 |
| gactgccagg atgttgctgc agactgtgaa gtcaaatgca tgccgacctt ccagttttat | 240 |
| aaaaagggtc aaaaggtggg ggagttctcc ggtgctaaca aggaaaagct tgaagcctct | 300 |
| attactgaat atgcctaa | 318 |

<210> SEQ ID NO 70
<211> LENGTH: 105
<212> TYPE: PRT
<213> ORGANISM: Mus musculus

<400> SEQUENCE: 70

```
Met Val Lys Leu Ile Glu Ser Lys Glu Ala Phe Gln Glu Ala Leu Ala
1               5                   10                  15
Ala Ala Gly Asp Lys Leu Val Val Val Asp Phe Ser Ala Thr Trp Cys
            20                  25                  30
Gly Pro Cys Lys Met Ile Lys Pro Phe Phe His Ser Leu Cys Asp Lys
        35                  40                  45
Tyr Ser Asn Val Val Phe Leu Glu Val Asp Val Asp Cys Gln Asp
    50                  55                  60
Val Ala Ala Asp Cys Glu Val Lys Cys Met Pro Thr Phe Gln Phe Tyr
65                  70                  75                  80
Lys Lys Gly Gln Lys Val Gly Glu Phe Ser Gly Ala Asn Lys Glu Lys
                85                  90                  95
Leu Glu Ala Ser Ile Thr Glu Tyr Ala
            100                 105
```

<210> SEQ ID NO 71
<211> LENGTH: 924
<212> TYPE: DNA
<213> ORGANISM: Mus musculus

<400> SEQUENCE: 71

| | |
|---|---|
| atggtgaacc cgacaacttc cgaagtgcaa cccaccatgg gggtcaagat cttctcagcc | 60 |
| ggagtttcag cttgcctggc agatatcatc accttcccgc tggacactgc aaagtccgc | 120 |
| cttcagatcc aaggtgaagg ccaggcttcc agtaccatta ggtataaagg tgtcctaggg | 180 |
| accatcacca ccctggcaaa aacagaagga ttgccgaaac tgtacagcgg tctgcctgcg | 240 |
| ggcattcaga ggcaaatcag cttttgcctca ctcaggattg cctctacga ctcagtccaa | 300 |
| gagtacttct cttcagggag agaaacacct gcctctctcg aaacaagat ctcagccggc | 360 |
| ttaatgactg gaggtgtggc agtgttcatt gggcagccta cagaggtcgt gaaggtcaga | 420 |
| atgcaagccc agagccatct gcatgggatc aaaccccgct acacggggac ctacaatgct | 480 |
| tacagagtta tagccaccac agaaagcttg tcaacacttt ggaaagggac gacccctaat | 540 |
| ctaatgagaa atgtcatcat caattgtaca gagctggtaa catatgacct catgaagggg | 600 |
| gcccttgtaa acaacaaaat actggcagat gacgtcccct gccatttact gtcagctctt | 660 |
| gttgccgggt tttgcaccac actcctggcc tctccagtgg atgtggtaaa acaagattc | 720 |
| atcaactctc tgccaggaca gtacccaagc gtaccaagct gtgcgatgtc catgtacacc | 780 |
| aaggaaggac cgacggcctt tttcaaaggg tttgtggctt cttttctgcg actcgggtcc | 840 |
| tggaacgtca tcatgtttgt gtgctttgaa cagctgaaaa aagagctgat gaagtccaga | 900 | cagacagtgg attgtaccac ataa                                               924

<210> SEQ ID NO 72
<211> LENGTH: 307
<212> TYPE: PRT
<213> ORGANISM: Mus musculus

<400> SEQUENCE: 72

Met Val Asn Pro Thr Thr Ser Glu Val Gln Pro Thr Met Gly Val Lys
1               5                   10                  15

Ile Phe Ser Ala Gly Val Ser Ala Cys Leu Ala Asp Ile Ile Thr Phe
            20                  25                  30

Pro Leu Asp Thr Ala Lys Val Arg Leu Gln Ile Gln Gly Glu Gly Gln
        35                  40                  45

Ala Ser Ser Thr Ile Arg Tyr Lys Gly Val Leu Gly Thr Ile Thr Thr
    50                  55                  60

Leu Ala Lys Thr Glu Gly Leu Pro Lys Leu Tyr Ser Gly Leu Pro Ala
65                  70                  75                  80

Gly Ile Gln Arg Gln Ile Ser Phe Ala Ser Leu Arg Ile Gly Leu Tyr
                85                  90                  95

Asp Ser Val Gln Glu Tyr Phe Ser Gly Arg Glu Thr Pro Ala Ser
            100                 105                 110

Leu Gly Asn Lys Ile Ser Ala Gly Leu Met Thr Gly Gly Val Ala Val
        115                 120                 125

Phe Ile Gly Gln Pro Thr Glu Val Val Lys Val Arg Met Gln Ala Gln
    130                 135                 140

Ser His Leu His Gly Ile Lys Pro Arg Tyr Thr Gly Thr Tyr Asn Ala
145                 150                 155                 160

Tyr Arg Val Ile Ala Thr Thr Glu Ser Leu Ser Thr Leu Trp Lys Gly
                165                 170                 175

Thr Thr Pro Asn Leu Met Arg Asn Val Ile Ile Asn Cys Thr Glu Leu
            180                 185                 190

Val Thr Tyr Asp Leu Met Lys Gly Ala Leu Val Asn Asn Lys Ile Leu
        195                 200                 205

Ala Asp Asp Val Pro Cys His Leu Leu Ser Ala Leu Val Ala Gly Phe
    210                 215                 220

Cys Thr Thr Leu Leu Ala Ser Pro Val Asp Val Val Lys Thr Arg Phe
225                 230                 235                 240

Ile Asn Ser Leu Pro Gly Gln Tyr Pro Ser Val Pro Ser Cys Ala Met
                245                 250                 255

Ser Met Tyr Thr Lys Glu Gly Pro Thr Ala Phe Phe Lys Gly Phe Val
            260                 265                 270

Ala Ser Phe Leu Arg Leu Gly Ser Trp Asn Val Ile Met Phe Val Cys
        275                 280                 285

Phe Glu Gln Leu Lys Lys Glu Leu Met Lys Ser Arg Gln Thr Val Asp
    290                 295                 300

Cys Thr Thr
305

<210> SEQ ID NO 73
<211> LENGTH: 1659
<212> TYPE: DNA
<213> ORGANISM: Heterocephalus glaber

<400> SEQUENCE: 73
atgcattgtg agaggtttct atgtgtcctg agaataattg gaactacact ttttggagtg     60

```
tctctcctcc tcggaatcac agctgcttat attgttggct accagtttat ccaaacagat    120
aattactact tctcatttgg actgtacggt gccttttag cctcgcatct catcatccaa    180
agcctctttg cctttttgga acaccggaaa atgaagaagt cccttgaaac cccgattaaa    240
ttgaacaaaa cggtagcact ctgcatcgct gcgtaccaag aggaccctga ctacttacgg    300
aaatgtttgc aatctgtgaa aaggctgacc taccctggga ttaaagtcgt gatggtcatc    360
gatgggaact cagacgacga cctttacatg atggacatat tcagcgaagt tatgggcagg    420
gacaaatcgg ccacgtacat ctggaagaac aactttcatg aaaagggacc tggtgagaca    480
gaagagtccc ataagaaag ttcacaacat gtcacccaat ggtcttgtc tagcaaaagt    540 gtttgcatca tgcaaaaatg gggtggaaag agagaagtca tgtacacagc cttcagagca    600
ctggggcgaa gcgtggatta tgtacaggtg tgtgactcag atactatgct tgaccctgcc    660
tcatctgtgg agatggtgaa ggtcttagag gaagacccta tggttggagg tgttggagga    720
gatgtccaga ttttaaacaa gtatgattcc tggatctcct tcctcagcag cgtgagatac    780
tggatggctt ttaatataga aagggcctgc cagtcttatt ttggctgtgt ccagtgcata    840
agcggtcctc tgggaatgta cagaaactcc ttgctgcatg aatttgtgga agactggtac    900
agtcaggaat tcatgggtaa ccaatgcagt tttggtgacg acaggcacct taccaacagg    960
gtgttgagtc tgggctatgc aactaaatac acggctcggt ccaagtgcct tactgaaact   1020
cccatagaat atctgagatg gctgaaccag cagacccgtt ggagcaagtc ctacttccga   1080
gagtggctgt acaatgccat gtggtttcac aagcatcact tgtggatgac ctatgaagct   1140
gttatcactg gattctttcc tttctttctc attgccacag tcatccagct cttctacagg   1200
ggtaaaatct ggaacatcct cctcttcctg ttaactgtcc agctagtggg tctcatcaag   1260
tcatcttttg ccagctgcct tagaggaaat atcgtcatgg tattcatgtc tctgtattca   1320
gtgttataca tgtcaagtct acttcctgcc aagatgtttg caattgcaac cataaacaaa   1380
gctgggtggg gcacatctgg aaggaagacc attgttgtta atttcatagg acttattcca   1440
gtgtccgtgt ggtttacaat ccttctaggt ggtgtaattt tcaccattta taaggaatct   1500
aaaaagccat tttccgaatc caaacagact gttctcatcg tgggaacttt gatctatgca   1560
tgctactggg tcatgctttt gactctctat gtggttctca tcaataagtg tggcaggcgg   1620
aagaagggac aacagtatga catggtgctt gatgtatga                          1659
```

<210> SEQ ID NO 74
<211> LENGTH: 552
<212> TYPE: PRT
<213> ORGANISM: Heterocephalus glaber

<400> SEQUENCE: 74

Met His Cys Glu Arg Phe Leu Cys Val Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro

```
                     85                  90                  95
Asp Tyr Leu Arg Lys Cys Leu Gln Ser Val Lys Arg Leu Thr Tyr Pro
                100                 105                 110
Gly Ile Lys Val Val Met Val Ile Asp Gly Asn Ser Asp Asp Asp Leu
                115                 120                 125
Tyr Met Met Asp Ile Phe Ser Glu Val Met Gly Arg Asp Lys Ser Ala
                130                 135                 140
Thr Tyr Ile Trp Lys Asn Asn Phe His Glu Lys Gly Pro Gly Glu Thr
145                 150                 155                 160
Glu Glu Ser His Lys Glu Ser Ser Gln His Val Thr Gln Leu Val Leu
                165                 170                 175
Ser Ser Lys Ser Val Cys Ile Met Gln Lys Trp Gly Lys Arg Glu
                180                 185                 190
Val Met Tyr Thr Ala Phe Arg Ala Leu Gly Arg Ser Val Asp Tyr Val
                195                 200                 205
Gln Val Cys Asp Ser Asp Thr Met Leu Asp Pro Ala Ser Ser Val Glu
                210                 215                 220
Met Val Lys Val Leu Glu Glu Asp Pro Met Val Gly Val Gly Gly
225                 230                 235                 240
Asp Val Gln Ile Leu Asn Lys Tyr Asp Ser Trp Ile Ser Phe Leu Ser
                245                 250                 255
Ser Val Arg Tyr Trp Met Ala Phe Asn Ile Glu Arg Ala Cys Gln Ser
                260                 265                 270
Tyr Phe Gly Cys Val Gln Cys Ile Ser Gly Pro Leu Gly Met Tyr Arg
                275                 280                 285
Asn Ser Leu Leu His Glu Phe Val Glu Asp Trp Tyr Ser Gln Glu Phe
                290                 295                 300
Met Gly Asn Gln Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Ile Glu Tyr Leu Arg Trp Leu Asn Gln Gln Thr
                340                 345                 350
Arg Trp Ser Lys Ser Tyr Phe Arg Glu Trp Leu Tyr Asn Ala Met Trp
                355                 360                 365
Phe His Lys His His Leu Trp Met Thr Tyr Glu Ala Val Ile Thr Gly
                370                 375                 380
Phe Phe Pro Phe Phe Leu Ile Ala Thr Val Ile Gln Leu Phe Tyr Arg
385                 390                 395                 400
Gly Lys Ile Trp Asn Ile Leu Leu Phe Leu Leu Thr Val Gln Leu Val
                405                 410                 415
Gly Leu Ile Lys Ser Ser Phe Ala Ser Cys Leu Arg Gly Asn Ile Val
                420                 425                 430
Met Val Phe Met Ser Leu Tyr Ser Val Leu Tyr Met Ser Ser Leu Leu
                435                 440                 445
Pro Ala Lys Met Phe Ala Ile Ala Thr Ile Asn Lys Ala Gly Trp Gly
                450                 455                 460
Thr Ser Gly Arg Lys Thr Ile Val Val Asn Phe Ile Gly Leu Ile Pro
465                 470                 475                 480
Val Ser Val Trp Phe Thr Ile Leu Leu Gly Gly Val Ile Phe Thr Ile
                485                 490                 495
Tyr Lys Glu Ser Lys Lys Pro Phe Ser Glu Ser Lys Gln Thr Val Leu
                500                 505                 510
```

Ile Val Gly Thr Leu Ile Tyr Ala Cys Tyr Trp Val Met Leu Leu Thr
                515                 520                 525

Leu Tyr Val Val Leu Ile Asn Lys Cys Gly Arg Arg Lys Lys Gly Gln
        530                 535                 540

Gln Tyr Asp Met Val Leu Asp Val
545                 550

<210> SEQ ID NO 75
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

| ccaaggtata | ttgctgttga | cagtgagcga | cgctgcagat | attccgctct | aagtgaagcc | 60 |
| acagatgtta | gagcggaaaa | tctgcagagc | tgcctactgc | ctcggacttc | aagggggcttg | 120 |
| cggccgccat | ctccatggct | gtaccacctt | gtcggccagg | ttactacaga | tatgtatgtt | 180 |
| gaatctcatt | acatatctgt | tgtaacctgc | tctgacattt | tggtatcttt | catctgacca | 240 |
| cgtactacct | tctatctgat | gtgacagctt | ctgtagcacc | agatgaagat | tgggctcaat | 300 |
| gtttagttat | ttgagcccaa | gcttcatctg | tgtactgcta | gctgtagaac | tccagcttcg | 360 |
| gcctgtaact | tatgatagca | atgtcagcag | tgcctggcag | ccgtggatcg | aataatttaa | 420 |
| gattctaaaa | ttatagtatt | cgatcaacgg | ctgcaaagta | aggttgacca | tactctacag | 480 |
| ttgttgattt | cgtggctaca | gagtttcctt | agcagagctg | gatgcagtgc | agccatatat | 540 |
| ttgtctaaac | tataatatat | ggctgcactg | catatagcta | ctgctaggca | atccttccct | 600 |
| cgataagatg | cagcggcggc | tcctctcccc | atggccctgg | ccttgttgaa | gaggattatc | 660 |
| ctgggctcag | agataatcct | ctacaacaag | ggcagggacc | tggggacccc | ggcaccggca | 720 |
| ggctagc | | | | | | 727 |

<210> SEQ ID NO 76
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

| ggccaaggta | tattgctgtt | gacagtgagc | gacgctgcag | atattccgct | ctaagtgaag | 60 |
| ccacagatgt | tagagcggaa | aatctgcaga | gctgcctact | gcctcggact | tcaagggggct | 120 |
| tgcggccgcc | atctccatgg | ctgtaccacc | ttgtcggcca | ggttactaca | gatatgtatg | 180 |
| ttgaatctca | ttacatatct | gttgtaacct | gctctgacat | tttggtatct | ttcatctgac | 240 |
| cacgtactac | cttctatctg | atgtgacagc | ttctgtagca | ccctgttact | acacatactt | 300 |
| ttgtttagtt | ataaagtatg | tggagtaaca | ggtgtactgc | tagctgtaga | actccagctt | 360 |
| cggcctgtaa | cttatgatag | caatgtcagc | agtgcctcct | gttcccttc | ctaatcattt | 420 |
| aagattctaa | aattataggg | ttaggaatgg | gaacagtaag | taaggttgac | catactctac | 480 |
| agttgttgat | ttcgtggcta | cagagtttcc | ttagcagagc | tgtggcacct | ttattggcta | 540 |
| caatgtctaa | actatttgta | gccaataaag | gtgccctagc | tactgctagg | caatccttcc | 600 |
| ctcgataagt | atggggcctg | gctcgagcag | ggggcgaggg | atgcatctag | tagagcggat | 660 |

```
gattggtccc ctcccttaac aagtcgaact gtcttgtcct tccctcccaa tgaccgcgtc    720
ttcgtcacag tcagcggcgg ctcctctccc catggccctg atgctgtccc tggtccttat    780
gctgggctca gaatacctgg tgtgagtctc agtcagggac ctggggaccc cggcaccggc    840
aggcta                                                                846

<210> SEQ ID NO 77
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
ccaaggtata ttgctgttga cagtgagcga cgctgcagat attccgctct aagtgaagcc     60
acagatgtta gagcggaaaa tctgcagagc tgcctactgc ctcggacttc aagggcttg    120 cggccgccat ctccatggct gtaccacctt gtcggccagg ttactacaga tatgtatgtt    180
gaatctcatt acatatctgt tgtaacctgc tctgacattt tggtatcttt catctgacca    240
cgtactacct tctatctgat gtgacagctt ctgtagcacc ctgttactac acatactttt    300
gtttagttat aaagtatgtg gagtaacagg tgtactgcta gctgtagaac tccagcttcg    360
gcctgtaact tatgatagca atgtcagcag tgcctcctgt tccctttcct aatcatttaa    420
gattctaaaa ttataggatt aggaatggga acagtaagta aggttgacca tactctacag    480
ttgttgattt cgtggctaca gagtttcctt agcagagctg gatgcagtgc agccatatat    540
ttgtctaaac tataatatat ggctgcactg catatagcta ctgctaggca atccttccct    600
cgataagatg cagcggcggc tcctctcccc atggccctgg ccttgttgaa gaggattatc    660
ctgggctcag agataatcct ctacaacaag gcagggacc tggggacccc ggcaccggca    720
ggctagc                                                              727

<210> SEQ ID NO 78
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
ggccaaggta tattgctgtt gacagtgagc gacgctgcag atattccgct ctaagtgaag     60
ccacagatgt tagagcggaa aatctgcaga gctgcctact gcctcggact tcaagggct    120 tgcggccgcc atctccatgg ctgtaccacc ttgtcggcca ggttactaca gatatgtatg    180
ttgaatctca ttacatatct gttgtaacct gctctgacat tttggtatct tcatctgac    240 cacgtactac cttctatctg atgtgacagc ttctgtagca ccctgttact acacatactt    300
ttgtttagtt ataaagtatg tggagtaaca ggtgtactgc tagctgtaga actccagctt    360
cggcctgtaa cttatgatag caatgtcagc agtgcctcct gttccctttc ctaatcattt    420
aagattctaa aattatagga ttaggaatgg gaacagtaag taaggttgac catactctac    480
agttgttgat tcgtggcta cagagtttcc ttagcagagc tgctggatgc agtggcgaca     540
ttttgtctaa actataaatg tcgccactgc atccattagc tactgctagg caatccttcc    600
ctcgataagt atgggggcctg gctcgagcag ggggcgaggg atcagacagt tggacttgtt    660
```

| aaatggtccc ctccctcttg tctgaatcag gtaatgtcct tccctcccaa tgaccgcgtc | 720 |
| ttcgtcacag tcagcggcgg ctcctctccc catggccctg atgctgtccc tggtccttat | 780 |
| gctgggctca gacataagga ccacggacag caacagggac ctggggaccc cggcaccggc | 840 |
| aggcta | 846 |

<210> SEQ ID NO 79
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

| ggccaaggta tattgctgtt gacagtgagc gaccttacct gaatcagaca agaagtgaag | 60 |
| ccacagatgt tcttgtctga atcaggtaat gctgcctact gcctcggact tcaaggggct | 120 |
| tgcggccgcc atctccatgg ctgtaccacc ttgtcgggca tctagtagag cggatgattg | 180 |
| ttgaatctca tttcatccgc tcaactagat ggtctgacat tttggtatct ttcatctgac | 240 |
| cacgtactac cttctatctg atgtgacagc ttctgtagca ccctgttact acacatactt | 300 |
| ttgtttagtt ataaagtatg tggagtaaca ggtgtactgc tagctgtaga actccagctt | 360 |
| cggcctgtaa cttatgatag caatgtcagc agtgcctcct gttccctttc ctaatcattt | 420 |
| aagattctaa aattatagga ttaggaatgg gaacagtaag taaggttgac catactctac | 480 |
| agttgttgat tcgtggcta cagagtttcc ttagcagagc tgctggatgc agtggcgaca | 540 |
| ttttgtctaa actataaatg tcgccactgc atccattagc tactgctagg caatccttcc | 600 |
| ctcgataagt atggggcctg gctcgagcag ggggcgaggg atcagacagt tggacttgtt | 660 |
| aaatggtccc ctccctatga acggtctttc cctctgtcct tccctcccaa tgaccgcgtc | 720 |
| ttcgtcacag tcagcggcgg ctcctctccc catggccctg gccttgttga agaggattat | 780 |
| cctgggctca gacataagga ccacggacag caacagtgac ctggggaccc cggcaccggc | 840 |
| aggcta | 846 |

<210> SEQ ID NO 80
<211> LENGTH: 727
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

| ccaaggtata ttgctgttga cagtgagcga ccttacctga atcagacaag aagtgaagcc | 60 |
| acagatgttc ttgtctgaat caggtaatgc tgcctactgc ctcggacttc aaggggcttg | 120 |
| cggccgccat ctccatggct gtaccacctt gtcgggcatc tagtagagcg gatgattgtt | 180 |
| gaatctcatt tcatccgctc aactagatgg tctgacattt ggtatctttt catctgacca | 240 |
| cgtactacct tctatctgat gtgacagctt ctgtagcacc tgttactac acatactttt | 300 |
| gtttagttat aaagtatgtg gagtaacagg tgtactgcta gctgtagaac tccagcttcg | 360 |
| gcctgtaact tatgatagca atgtcagcag tgcctcctgt tccctttcct aatcatttaa | 420 |
| gattctaaaa ttataggatt aggaatggga acagtaagta aggttgacca tactctacag | 480 |
| ttgttgattt cgtggctaca gagtttcctt agcagagctg ctctaaaga aggcttatga | 540 |
| atgtctaaac tatttcataa gcctacttta gagatagcta ctgctaggca atccttccct | 600 |

```
cgataagtat ggggcctggc tcgagcaggg ggcgagggat gcatctagta gagcggatga    660
ttggtcccct ccctcatccg ctcaactaga tgagtccttc cctcccaatg accgcgtctt    720
ggctagc                                                              727
```

<210> SEQ ID NO 81
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
ccaaggtata ttgctgttga cagtgagcga ctctgagact gacaccaggt atgtgaagcc    60
acagatgata cctggtgtga gtctcagcgc tgcctactgc ctcggacttc aaggggcttg    120
cggccgccat ctccatggct gtaccacctt gtcggtggca cctttattgg ctacaatgtt    180
gaatctcatt tgtagccaat taaggtgcct tctgacattt tggtatcttt catctgacca    240
cgtactacct tctatctgat gtgacagctt ctgtagcacg ccaccctctt cacggccaat    300
gtttagttat ttggccgtga cgagggtggc tgtactgcta gctgtagaac tccagcttcg    360
gcctgtaact tatgatagca atgtcagcag tgcctcgcca ccctcttcac ggccaattaa    420
gattctaaaa ttattgggcc gtgaacaggg tggctaagta aggttgacca tactctacag    480
ttgttgattt cgtggctaca gagtttcctt agcagagctg tggcaccttt attggctaca    540
atgtctaaac tatttgtagc caataaaggt gccctagcta ctgctaggca atccttccct    600
cgataagatg cagcggcggc tcctctcccc atggccctgc ttgggctgtc cctatctttc    660
ctgggctcag agaaagatag ggtcagccca accagggacc tggggacccc ggcaccggca    720
ggctagc                                                              727
```

<210> SEQ ID NO 82
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
ccaaggtata ttgctgttga cagtgagcga ccttgggctg tccctatctt tcgtgaagcc    60
acagatggaa agatagggtc agcccaatgc tgcctactgc ctcggacttc aaggggcttg    120
cggccgccat ctccatggct gtaccacctt gtcggggcag ccgtggatcg ataattgtt     180 gaatctcatt atattcgatc aacgctgcg tctgacattt tggtatcttt catctgacca     240
cgtactacct tctatctgat gtgacagctt ctgtagcacg ccaccctctt cacggccaat    300
gtttagttat ttggccgtga cgagggtggc tgtactgcta gctgtagaac tccagcttcg    360
gcctgtaact tatgatagca atgtcagcag tgcctcgcca ccctcttcac ggccaattaa    420
gattctaaaa ttattgggcc gtgaacaggg tggctaagta aggttgacca tactctacag    480
ttgttgattt cgtggctaca gagtttcctt agcagagctg gatgcagtgc agccatatat    540
ttgtctaaac tataatatat ggctgcactg catatagcta ctgctaggca atccttccct    600
cgataagatg cagcggcggc tcctctcccc atggccctgg ccttgttgaa gaggattatc    660
ctgggctcag agataatcct ctacaacaag ggcagggacc tggggacccc ggcaccggca    720
```

```
                                                  727
ggctagc

<210> SEQ ID NO 83
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
ggccaaggta tattgctgtt gacagtgagc gaccttacct gaatcagaca agaagtgaag    60
ccacagatgt tcttgtctga atcaggtaat gctgcctact gcctcggact tcaagggct    120 tgcggccgcc atctccatgg ctgtaccacc ttgtcgggca tctagtagag cggatgattg    180
ttgaatctca tttcatccgc tcaactagat ggtctgacat tttggtatct ttcatctgac    240
cacgtactac cttctatctg atgtgacagc ttctgtagca cgccaccctc ttcacggcca    300
atgtttagtt atttggccgt gacgagggtg gctgtactgc tagctgtaga actccagctt    360
cggcctgtaa cttatgatag caatgtcagc agtgcctcgc caccctcttc acggccaatt    420
aagattctaa aattattggg ccgtgaacag ggtggctaag taaggttgac catactctac    480
agttgttgat tcgtggcta cagagttttcc ttagcagagc tggatgcagt gcagccatat    540
atttgtctaa actataatat atggctgcac tgcatatagc tactgctagg caatccttcc    600
ctcgataagt atggggcctg gctcgagcag ggggcgaggg atgcatctag tagagcggat    660
gattggtccc ctcccaactg ccactgttga tgtttgtcct tccctcccaa tgaccgcgtc    720
ttcgtcacag tcagcggcgg ctcctctccc catggccctg cgatgcagag tccaggataa    780
tctgggctca gagataatcc tctacaacaa gggcagggac ctggggaccc cggcaccggc    840
aggcta                                                               846

<210> SEQ ID NO 84
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
ggccaaggta tattgctgtt gacagtgagc gacatgctgt ccctggtcct tatggtgaag    60
ccacagatgc ataaggacca cggacagcag gctgcctact gcctcggact tcaagggct    120 tgcggccgcc atctccatgg ctgtaccacc ttgtcggctg gatgcagtgg cgacattttg    180
ttgaatctca ttaatgtcgc cagtgcatcc actctgacat tttggtatct ttcatctgac    240
cacgtactac cttctatctg atgtgacagc ttctgtagca cgccaccctc ttcacggcca    300
atgtttagtt atttggccgt gacgagggtg gctgtactgc tagctgtaga actccagctt    360
cggcctgtaa cttatgatag caatgtcagc agtgcctcgc caccctcttc acggccaatt    420
aagattctaa aattattggg ccgtgaacag ggtggctaag taaggttgac catactctac    480
agttgttgat tcgtggcta cagagttttcc ttagcagagc tggatgcagt gcagccatat    540
atttgtctaa actataatat atggctgcac tgcatatagc tactgctagg caatccttcc    600
ctcgataagt atggggcctg gctcgagcag ggggcgaggg atcgagggaa acaccgttca    660
tattggtccc ctcccttaac aagtcgaact gtcttgtcct tccctcccaa tgaccgcgtc    720
ttcgtcacag tcagcggcgg ctcctctccc catggccctg gccttgttga agaggattat    780
```

```
cctgggctca gagataatcc tctacaacaa gggcagggac ctggggaccc cggcaccggc    840
aggcta                                                              846
```

<210> SEQ ID NO 85
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
ggccaaggta tattgctgtt gacagtgagc gacatgctgt ccctggtcct tatggtgaag     60
ccacagatgc ataaggacca cggacagcag gctgcctact gcctcggact tcaaggggct    120
tgcggccgcc atctccatgg ctgtaccacc ttgtcggctg gatgcagtgg cgacattttg    180
ttgaatctca ttaatgtcgc cagtgcatcc actctgacat tttggtatct ttcatctgac    240
cacgtactac cttctatctg atgtgacagc ttctgtagca cgccaccctc ttcacggcca    300
atgtttagtt atttggccgt gacgagggtg gctgtactgc tagctgtaga actccagctt    360
cggcctgtaa cttatgatag caatgtcagc agtgcctcgc accctcttc acggccaatt     420 aagattctaa aattattggg ccgtgaacag ggtggctaag taaggttgac atactctac     480 agttgttgat tcgtggcta cagagtttcc ttagcagagc tggatgcagt gcagccatat     540
atttgtctaa actataatat atggctgcac tgcatatagc tactgctagg caatccttcc    600
ctcgataagt atggggcctg gctcgagcag ggggcgaggg atcagacagt tggacttgtt    660
aaatggtccc ctccctatga acggtctttc cctctgtcct tccctcccaa tgaccgcgtc    720
ttcgtcacag tcagcggcgg ctcctctccc catggccctg gccttgttga agaggattat    780
cctgggctca gagataatcc tctacaacaa gggcagggac ctggggaccc cggcaccggc    840
aggcta                                                              846
```

<210> SEQ ID NO 86
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
ccaaggtata ttgctgttga cagtgagcga ccctgggctt ctaactttgt tagtgaagcc     60
acagatgtaa caaagttaca agcccagtgc tgcctactgc ctcggacttc aaggggcttg    120
cggccgccat ctccatggct gtaccacctt gtcggccgca tcttaaactt ggagtttgtt    180
gaatctcatt actccaagtt aaagatgcgc tctgacattt tggtatcttt catctgacca    240
cgtactacct tctatctgat gtgacagctt ctgtagcacg ccaccctctt cacggccaat    300
gtttagttat ttggccgtga cgagggtggc tgtactgcta gctgtagaac tccagcttcg    360
gcctgtaact tatgatagca atgtcagcag tgcctcgcca ccctcttcac ggccaattaa    420
gattctaaaa ttattgggcc gtgaacaggg tggctaagta aggttgacca tactctacag    480
ttgttgattt cgtggctaca gagtttcctt agcagagctg cctggagatt gatgcagcaa    540
ttgtctaaac tatattgctg catcaatctc cagttagcta ctgctaggca atccttccct    600
cgataagatg cagcggcggc tcctctcccc atggccctgg cggctgatga agctctatat    660
```

```
ctgggctcag aatatagagc ttgatcagcc ggcagggacc tggggacccc ggcaccggca    720
ggctagc                                                              727
```

<210> SEQ ID NO 87
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
ccaaggtata ttgctgttga cagtgagcga cgcaggtatg tatccaatac atgtgaagcc     60
acagatgatg tattggattc atacctgagc tgcctactgc ctcggacttc aaggggcttg    120
cggccgccat ctccatggct gtaccacctt gtcggcgagg gaaacaccgt tcatattgtt    180
gaatctcatt tatgaacggt cttccctcc tctgacattt tggtatcttt catctgacca     240
cgtactacct tctatctgat gtgacagctt ctgtagcacg ccaccctctt cacggccaat    300
gtttagttat ttggccgtga cgagggtggc tgtactgcta gctgtagaac tccagcttcg    360
gcctgtaact tatgatagca atgtcagcag tgcctcgcca ccctcttcac ggccaattaa    420
gattctaaaa ttattgggcc gtgaacaggg tggctaagta aggttgacca tactctacag    480
ttgttgagac tacgcctggc tcagcaggg ggcgagggat cgagggaaac accgttcata     540
ttggtcccct ccctatgaac ggtctttccc tctgtccttc cctcccaatg accgcgtctt    600
cgtcacagtc agcggcggct cctctcccca tggccctgct tgggctgtcc ctatctttcc    660
tgggctcaga gaaagatagg gtcagcccaa ccagggacct ggggacccg gcaccggcag     720 gctagc                                                               726
```

<210> SEQ ID NO 88
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
ccaaggtata ttgctgttga cagtgagcga cgcggctgat gaagctctat atgtgaagcc     60
acagatgata tagagcttga tcagccgagc tgcctactgc ctcggacttc aaggggcttg    120
cggccgccat ctccatggct gtaccacctt gtcggcctgg agattgatgc agcaattgtt    180
gaatctcatt ttgctgcatc tatctccagc tctgacattt tggtatcttt catctgacca    240
cgtactacct tctatctgat gtgacagctt ctgtagcagc ccttcaagga tatggactat    300
gtttagttat tagtccatat acttgaaggg agtactgcta gctgtagaac tccagcttcg    360
gcctgtaact tatgatagca atgtcagcag tgcctcggat cattgagcgt ctcttattaa    420
gattctaaaa ttattgagag acgctgaatg atcctaagta aggttgacca tactctacag    480
ttgttgattt cgtggctaca gagtttcctt agcagagctg cctggagatt gatgcagcaa    540
ttgtctaaac tatattgctg catcaatctc cagttagcta ctgctaggca atccttccct    600
cgataagatg cagcggcggc tcctctcccc atggccctgc tgagtaatg caaggttatt     660 ctgggctcag aaataacctt gctttactca gccagggacc tggggacccc ggcaccggca    720
gctagc                                                               726
```

```
<210> SEQ ID NO 89
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
ccaaggtata ttgctgttga cagtgagcga ccagaggcta cagattgaac aagtgaagcc      60
acagatgttg ttcaatctct agcctcttgc tgcctactgc ctcggacttc aagggggcttg    120 cggccgccat ctccatggct gtaccacctt gtcggccctt tcattgtgga cctgattgtt    180
gaatctcatt acaggtccac catgaaaggc tctgacattt ggtatctttt catctgacca    240
cgtactacct tctatctgat gtgacagctt ctgtagcacc actcgaacag ctacagctat    300
gtttagttat tagctgtagc ggttcgagtg tgtactgcta gctgtagaac tccagcttcg    360
gcctgtaact tatgatagca atgtcagcag tgcctgctga tccacttctc taccaattaa    420
gattctaaaa ttattgggta gagaactgga tcagaaagta aggttgacca tactctacag    480
ttgttgattt cgtggctaca gagtttcctt agcagagctg acattgttac acagccagta    540
ttgtctaaac tatatactgg ctgtgtaaca atggtagcta ctgctaggca atccttccct    600
cgataagatg cagcggcggc tcctctcccc atggccctgg catggaacat tgtgagaaat    660
ctgggctcag aatttctcac aaagttccat ggcagggacc tggggacccc ggcaccggca    720
ggctagc                                                                727

<210> SEQ ID NO 90
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
ccaaggtata ttgctgttga cagtgagcga ccttacctga atcagacaag aagtgaagcc      60
acagatgttc ttgtctgaat caggtaatgc tgcctactgc ctcggacttc aagggggcttg   120 cggccgccat ctccatggct gtaccacctt gtcgggcatc tagtagagcg gatgattgtt    180
gaatctcatt tcatccgctc aactagatgg tctgacattt ggtatctttt catctgacca    240
cgtactacct tctatctgat gtgacagctt ctgtagcacc tgggcttcta actttgttat    300
gtttagttat taacaaagtt cgaagcccag tgtactgcta gctgtagaac tccagcttcg    360
gcctgtaact tatgatagca atgtcagcag tgcctccgca tcttaaactt ggagttttaa    420
gattctaaaa ttatacctcc aagttaaaga tgcgaaagta aggttgacca tactctacag    480
ttgttgattt cgtggctaca gagtttcctt agcagagctg gcctacatcc tctttgttat    540
ttgtctaaac tataataaca aagacgatgt aggatagcta ctgctaggca atccttccct    600
cgataagtat ggggcctggc tcgagcaggg ggcgagggat gcatctagta gagcggatga    660
ttggtcccct ccctcatccg ctcaactaga tgagtccttc cctcccaatg accgcgtctt    720
ggctagc                                                                727

<210> SEQ ID NO 91
<211> LENGTH: 722
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 91

| | |
|---|---|
| ccaaggtata ttgctgttga cagtgagcga ccctgggctt ctaactttgt tagtgaagcc | 60 |
| acagatgtaa caaagttaca agcccagtgc tgcctactgc ctcggacttc aaggggcttg | 120 |
| cggccgccat ctccatggct gtaccacctt gtcggccgca tcttaaactt ggagtttgtt | 180 |
| gaatctcatt actccaagtt aaagatgcgc tctgacattt tggtatcttt catctgacca | 240 |
| cgtactacct tctatctgat gtgacagctt ctgtagcacc tgggcttcta actttgttat | 300 |
| gtttagttat taacaaagtt cgaagcccag tgtactgcta gctgtagaac tccagcttcg | 360 |
| gccttcacgt ggctacagag tttccttagc agagctgctg gatgcagtgg cgacatttgt | 420 |
| ctaaactata aatgtcgcca ctgcatccat tagctactgc taggcaatcc ttccctcgat | 480 |
| aaatggatgg cctggctcga gcaggggcg agggatcaga cagttggact tgttaaatgg | 540 |
| tccctccct taacaagtcg aactgtcttg tccttccctc ccaatgaccg cgtcttcgtc | 600 |
| acagtcagcg gcggctcctc tccccatggc cctgatgctg tccctggtcc ttatgctggg | 660 |
| ctcagacata aggaccacgg acagcaacag ggacctgggg accccggcac cggcaggcta | 720 |
| gc | 722 |

<210> SEQ ID NO 92
<211> LENGTH: 731
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92

| | |
|---|---|
| ccggccaagg tatattgctg ttgacagtga gcgacgcggc tgatgaagct ctatatgtga | 60 |
| agccacagat gatatagagc ttgatcagcc gagctgccta ctgcctcgga cttcaagggg | 120 |
| cttgcggccg ccatctccat ggctgtacca ccttgtcggc ctggagattg atgcagcaat | 180 |
| tgttgaatct cattttgctg catctatctc cagctctgac attttggtat ctttcatctg | 240 |
| accacgtact accttctatc tgatgtgaca gcttctgtag cagcaggtat gtatccaata | 300 |
| cattgtttag ttatatgtat tggagacata cctgagtact gctagctgta gaactccagc | 360 |
| ttcggcctgt aacttatgat agcaatgtca gcagtgcctc gagggaaaca ccgttcatat | 420 |
| ttaagattct aaaattatag atgaacggtc tttccctcaa agtaaggttg accatactct | 480 |
| acagttgttg atttcgtggc tacagagttt ccttagcaga gctgcctgga gattgatgca | 540 |
| gcaattgtct aaactatatt gctgcatcaa tctccagtta gctactgcta ggcaatcctt | 600 |
| ccctcgataa gtatggggcc tggctcgagc aggggcgag ggatcgaggg aaacaccgtt | 660 |
| catattggtc ccctccctat gaacggtctt tccctctgtc cttccctccc aatgaccgcg | 720 |
| tcttggctag c | 731 |

<210> SEQ ID NO 93
<211> LENGTH: 846
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 93

```
ggccaaggta tattgctgtt gacagtgagc gacgccgtga agcaaatagc agttgtgaag    60
ccacagatga actgctattt ccttcacgga gctgcctact gcctcggact tcaagggggct  120 tgcggccgcc atctccatgg ctgtaccacc ttgtcggcaa ccggatgctc aagatatttg   180
ttgaatctca ttatatcttg aggatccggt tctctgacat tttggtatct ttcatctgac   240
cacgtactac cttctatctg atgtgacagc ttctgtagca gcaggtatgt atccaataca   300
ttgtttagtt atatgtattg gagacatacc tgagtactgc tagctgtaga actccagctt   360
cggcctgtaa cttatgatag caatgtcagc agtgcctcga gggaaacacc gttcatattt   420
aagattctaa aattatagat gaacggtctt tccctcaaag taaggttgac catactctac   480
agttgttgat ttcgtggcta cagagtttcc ttagcagagc tgctggatgc agtggcgaca   540
ttttgtctaa actataaatg tcgccactgc atccattagc tactgctagg caatccttcc   600
ctcgataagt atggggcctg gctcgagcag ggggcgaggg atcagacagt tggacttgtt   660
aaatggtccc ctccctcatc cgctcaacta gatgagtcct tcctcccaa tgaccgcgtc    720 ttcgtcgttt cagcggcggc tcctctcccc atggccctgt ctgagactga caccaggtat   780
ctgggctcag acataaggac cacggacagc aacagggacc tggggacccc ggcaccggca   840
ggctag                                                              846
```

<210> SEQ ID NO 94
<211> LENGTH: 14
<212> TYPE: DNA
<213> ORGANISM: Unknown
<220> FEATURE:
<223> OTHER INFORMATION: Description of Unknown:
     miR16-1-5' sequence

<400> SEQUENCE: 94

```
tgtcagcagt gcct                                                      14
```

<210> SEQ ID NO 95
<211> LENGTH: 14
<212> TYPE: DNA
<213> ORGANISM: Unknown
<220> FEATURE:
<223> OTHER INFORMATION: Description of Unknown:
     miR16-1-3' sequence

<400> SEQUENCE: 95

```
agtaaggttg acca                                                      14
```

<210> SEQ ID NO 96
<211> LENGTH: 18
<212> TYPE: DNA
<213> ORGANISM: Unknown
<220> FEATURE:
<223> OTHER INFORMATION: Description of Unknown:
     mir16-1-stem-loop sequence

<400> SEQUENCE: 96

```
ttaagattct aaaattat                                                  18
```

<210> SEQ ID NO 97
<211> LENGTH: 17
<212> TYPE: DNA
<213> ORGANISM: Unknown
<220> FEATURE:
<223> OTHER INFORMATION: Description of Unknown:
     miR30a-5' sequence

<400> SEQUENCE: 97
tgttgacagt gagcgac                                                    17

<210> SEQ ID NO 98
<211> LENGTH: 16
<212> TYPE: DNA
<213> ORGANISM: Unknown
<220> FEATURE:
<223> OTHER INFORMATION: Description of Unknown:
      miR20a-3' sequence

<400> SEQUENCE: 98
gtactgctag ctgtag                                                     16

<210> SEQ ID NO 99
<211> LENGTH: 16
<212> TYPE: DNA
<213> ORGANISM: Unknown
<220> FEATURE:
<223> OTHER INFORMATION: Description of Unknown:
      mir20a-5' sequence

<400> SEQUENCE: 99
gacagcttct gtagca                                                     16

<210> SEQ ID NO 100
<211> LENGTH: 11
<212> TYPE: DNA
<213> ORGANISM: Unknown
<220> FEATURE:
<223> OTHER INFORMATION: Description of Unknown:
      mir20a-stem-loop sequence

<400> SEQUENCE: 100
tgtttagtta t                                                          11

<210> SEQ ID NO 101
<211> LENGTH: 17
<212> TYPE: DNA
<213> ORGANISM: Unknown
<220> FEATURE:
<223> OTHER INFORMATION: Description of Unknown:
      mir21-3' sequence

<400> SEQUENCE: 101
ctgacatttt ggtatct                                                    17

<210> SEQ ID NO 102
<211> LENGTH: 16
<212> TYPE: DNA
<213> ORGANISM: Unknown
<220> FEATURE:
<223> OTHER INFORMATION: Description of Unknown:
      miR21-5' sequence

<400> SEQUENCE: 102
tgtaccacct tgtcgg                                                     16

<210> SEQ ID NO 103
<211> LENGTH: 14
<212> TYPE: DNA
<213> ORGANISM: Unknown
<220> FEATURE:
<223> OTHER INFORMATION: Description of Unknown:
      mir21-stem-loop sequence

<400> SEQUENCE: 103
tgttgaatct catt                                                    14

<210> SEQ ID NO 104
<211> LENGTH: 15
<212> TYPE: DNA
<213> ORGANISM: Unknown
<220> FEATURE:
<223> OTHER INFORMATION: Description of Unknown:
      mir30a-stem-loop sequence

<400> SEQUENCE: 104
gtgaagccac agatg                                                   15

<210> SEQ ID NO 105
<211> LENGTH: 12
<212> TYPE: DNA
<213> ORGANISM: Unknown
<220> FEATURE:
<223> OTHER INFORMATION: Description of Unknown:
      mir122-stem-loop sequence

<400> SEQUENCE: 105
tgtctaaact at                                                      12

<210> SEQ ID NO 106
<211> LENGTH: 15
<212> TYPE: DNA
<213> ORGANISM: Unknown
<220> FEATURE:
<223> OTHER INFORMATION: Description of Unknown:
      mir150-3' sequence

<400> SEQUENCE: 106
cagggacctg gggac                                                   15

<210> SEQ ID NO 107
<211> LENGTH: 11
<212> TYPE: DNA
<213> ORGANISM: Unknown
<220> FEATURE:
<223> OTHER INFORMATION: Description of Unknown:
      mir150-stem-loop sequence

<400> SEQUENCE: 107
ctgggctcag a                                                       11

<210> SEQ ID NO 108
<211> LENGTH: 17
<212> TYPE: DNA
<213> ORGANISM: Unknown
<220> FEATURE:
<223> OTHER INFORMATION: Description of Unknown:
      miR-30a sequence

<400> SEQUENCE: 108
gctgcctact gcctcgg                                                 17

<210> SEQ ID NO 109
<211> LENGTH: 16
<212> TYPE: DNA
<213> ORGANISM: Unknown
<220> FEATURE:
<223> OTHER INFORMATION: Description of Unknown:
      miR-122 sequence

<400> SEQUENCE: 109
ttccttagca gagctg                                                  16

<210> SEQ ID NO 110
<211> LENGTH: 16
<212> TYPE: DNA
<213> ORGANISM: Unknown
<220> FEATURE:
<223> OTHER INFORMATION: Description of Unknown:
      miR-122 sequence

<400> SEQUENCE: 110
tagctactgc taggca                                                    16

<210> SEQ ID NO 111
<211> LENGTH: 15
<212> TYPE: DNA
<213> ORGANISM: Unknown
<220> FEATURE:
<223> OTHER INFORMATION: Description of Unknown:
      miR-150 sequence

<400> SEQUENCE: 111
ctccccatgg ccctg                                                     15

<210> SEQ ID NO 112
<211> LENGTH: 14
<212> TYPE: DNA
<213> ORGANISM: Unknown
<220> FEATURE:
<223> OTHER INFORMATION: Description of Unknown:
      miR16-1-5' sequence

<400> SEQUENCE: 112
tgtcagcagt gcct                                                      14

<210> SEQ ID NO 113
<211> LENGTH: 248
<212> TYPE: DNA
<213> ORGANISM: Woodchuck hepatitis virus

<400> SEQUENCE: 113
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttag ttcttgccac ggcggaactc    180
atcgccgcct gccttgcccg ctgctggaca ggggctcggc tgttgggcac tgacaattcc    240
gtggtgtt                                                             248

<210> SEQ ID NO 114
<211> LENGTH: 134
<212> TYPE: DNA
<213> ORGANISM: Simian virus 40

<400> SEQUENCE: 114
gctttatttg tgaaatttgt gatgctattg ctttatttgt aaccattata agctgcaata     60
aacaagttaa caacaacaat tgcattcatt ttatgtttca ggttcagggg gagatgtggg    120
aggtttttta aagc                                                      134

<210> SEQ ID NO 115
<211> LENGTH: 3302
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
ccttaattag gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgtagttaa tgattaaccc gccatgctac ttatctacgt    180
agccatgctc taggaagatc ggaattcctt ggctccggtg cccgtcagtg ggcagagcgc    240
acatcgccca cagtccccga aagttgtgg ggaggggtcg gcaattgaac cggtgcctag     300
agaaggtggc gcggggtaaa ctgggaaagt gatgtcgtgt actggctccg ccttttttccc   360
gagggtgggg gagaaccgta tataagtgca gtagtcgccg tgaacgttct ttttcgcaac    420
gggtttgccg ccagaacaca ggtaagtgcc gtgtgtggtt cccgcgggcc tggcctcttt    480
acgggttatg gcccttgcgt gccttgaatt acttccacct ggctgcagta cgtgattctt    540
gatcccgagc ttcgggttgg aagtgggtgg gagagttcga ggccttgcgc ttaaggagcc    600
ccttcgcctc gtgcttgagt tgaggcctgg cctgggcgct ggggccgccg cgtgcgaatc    660
tggtggcacc ttcgcgcctg tctcgctgct ttcgataagt ctctagccat ttaaaatttt    720
tgatgacctg ctgcgacgct ttttttctgg caagatagtc ttgtaaatgc gggccaagat    780
ctgcacactg gtatttcggt ttttgggggcc gcgggcggcg acggggcccg tgcgtcccag   840
cgcacatgtt cggcgaggcg gggcctgcga gcgcggccac cgagaatcgg acgggggtag    900
tctcaagctg gccggcctgc tctggtgcct ggcctcgcgc cgccgtgtat cgccccgccc    960
tgggcggcaa ggctggcccg gtcggcacca gttgcgtgag cggaaagatg gccgcttccc   1020
ggccctgctg cagggagctc aaaatggagg acgcggcgct cgggagagcg ggcgggtgag   1080
tcacccacac aaaggaaaag ggcctttccg tcctcagccg tcgcttcatg tgactccacg   1140
gagtaccggg cgccgtccag gcacctcgat tagttctcga gcttttggag tacgtcgtct   1200
ttaggttggg gggagggggtt ttatgcgatg gagtttcccc acactgagtg ggtggagact   1260
gaagttaggc cagcttggca cttgatgtaa ttctccttgg aatttgcccct ttttgagttt   1320
ggatcttggt tcattctcaa gcctcagaca gtggttcaaa gttttttttct tccatttcag   1380
gtgcggcctg ccaccatggg tcgggggctg ctccggggcc tgtggccgct gcatatcgtc   1440
ctgtggacgc gcatcgccag cacgatcccg ccgcacgttc ccaagtcgga tgtgaaatg    1500
gaagcccaga aagatgcatc catccaccta agctgtaata ggaccatcca tccactgaaa   1560
cattttaaca gtgatgtcat ggccagcgac aatggcggtg cggtcaagct tccacagctg   1620
tgcaagtttt gcgatgtgag actgtccact tgcgacaacc agaagtcctg catgagcaac   1680
tgcagcatca cggccatctg tgagaagccg catgaagtct gcgtggccgt gtggaggaag   1740
aacgacaaga acattactct ggagacggtt tgccacgacc ccaagctcac ctaccacggc   1800
ttcactctgg aagatgccgc ttctcccaag tgtgtcatga aggaaaagaa aagggcgggc   1860
gagactttct tcatgtgtgc ctgtaacatg gaagagtgca acgattacat catcttttcg   1920
gaagaataca ccaccagcag tcccgacccc agagggccca caatcaagcc ctgtcctcca   1980
tgcaaatgcc cagcacctaa cctcgagggt ggaccatccg tcttcatctt ccctccaaag   2040
atcaaggatg tactcatgat ctccctgagc cccatagtca catgtgtggt ggtggatgtg   2100
agcgaggatg acccagatgt ccagatcagc tggtttgtga acaacgtgga agtacacaca   2160
gctcagacac aaacccatag agaggattac aacagtactc tccgggtggt cagtgccctc   2220
cccatccagc accaggactg gatgagtggc aaggcgttcg catgcgcggt caacaacaaa   2280
```

| | | |
|---|---|---|
| gacctcccag cgcccatcga gagaaccatc tcaaaaccca aagggtcagt aagagctcca | 2340 | |
| caggtatatg tcttgcctcc accagaagaa gagatgacta agaaacaggt cactctgacc | 2400 | |
| tgcatggtca cagacttcat gcctgaagac atttacgtgg agtggaccaa caacgggaaa | 2460 | |
| acagagctaa actacaagaa cactgaacca gtcctggact ctgatggttc ttacttcatg | 2520 | |
| tacagcaagc tgagagtgga aaagaagaac tgggtggaaa gaaatagcta ctcctgttca | 2580 | |
| gtggtccacg agggtctgca caatcaccac acgactaaga gcttctcccg gactccgggt | 2640 | |
| aaatgagcta gcaatcaacc tctggattac aaaatttgtg aaagattgac tggtattctt | 2700 | |
| aactatgttg ctccttttac gctatgtgga tacgctgctt taatgccttt gtatcatgct | 2760 | |
| attgcttccc gtatggcttt cattttctcc tccttgtata aatcctggtt agttcttgcc | 2820 | |
| acggcggaac tcatcgccgc ctgccttgcc cgctgctgga caggggctcg gctgttgggc | 2880 | |
| actgacaatt ccgtggtgtt tatttgtgaa atttgtgatg ctattgcttt atttgtaacc | 2940 | |
| attctagctt tatttgtgaa atttgtgatg ctattgcttt atttgtaacc attataagct | 3000 | |
| gcaataaaca agttaacaac aacaattgca ttcattttat gtttcaggtt caggggggaga | 3060 | |
| tgtgggaggt tttttaaagc gggggatcca aattcccgat aaggatcttc ctagagcatg | 3120 | |
| gctacgtaga taagtagcat ggcgggttaa tcattaacta caaggaaccc ctagtgatgg | 3180 | |
| agttggccac tccctctctg cgcgctcgct cgctcactga ggccgggcga ccaaaggtcg | 3240 | |
| cccgacgccc gggctttgcc cgggcggcct cagtgagcga gcgagcgcgc agccttaatt | 3300 | |
| aa | 3302 | |

<210> SEQ ID NO 116
<211> LENGTH: 3854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

| | | |
|---|---|---|
| ccttaattag gctgcgcgct cgctcgctca ctgaggccgc ccgggcaaag cccgggcgtc | 60 | |
| gggcgacctt tggtcgcccg gcctcagtga gcgagcgagc gcgcagagag ggagtggcca | 120 | |
| actccatcac taggggttcc ttgtagttaa tgattaaccc gccatgctac ttatctacgt | 180 | |
| agccatgctc taggaagatc ggaattcctt ggctccggtg cccgtcagtg gcagagcgc | 240 | |
| acatcgccca cagtccccga gaagttgtgg ggaggggtcg gcaattgaac cggtgcctag | 300 | |
| agaaggtggc gcggggtaaa ctgggaaagt gatgtcgtgt actggctccg cctttttccc | 360 | |
| gagggtgggg gagaaccgta tataagtgca gtagtcgccg tgaacgttct ttttcgcaac | 420 | |
| gggtttgccg ccagaacaca ggtaagtgcc gtgtgtggtt cccgcgggcc tggcctcttt | 480 | |
| acgggttatg gcccttgcgt gccttgaatt acttccacct ggctgcagta cgtgattctt | 540 | |
| gatcccgagc ttcgggttgg aagtgggtgg agagttcga ggccttgcgc ttaaggagcc | 600 | |
| ccttcgcctc gtgcttgagt tgaggcctgg cctgggcgct ggggccgccg cgtgcgaatc | 660 | |
| tggtggcacc ttcgcgcctg tctcgctgct ttcgataagt ctctagccat ttaaaattt | 720 | |
| tgatgacctg ctgcgacgct ttttttctgg caagatagtc ttgtaaatgc gggccaagat | 780 | |
| ctgcacactg gtatttcggt ttttggggcc gcgggcggcg acggggcccg tgcgtcccag | 840 | |
| cgcacatgtt cggcgaggcg gggcctgcga gcgcggccac cgagaatcgg acggggtag | 900 | |
| tctcaagctg gccggcctgc tctggtgcct ggcctcgcgc cgccgtgtat cgccccgccc | 960 | |

```
tgggcggcaa ggctggcccg gtcggcacca gttgcgtgag cggaaagatg gccgcttccc      1020
ggccctgctg cagggagctc aaaatggagg acgcggcgct cggagagcg ggcgggtgag       1080 tcacccacac aaaggaaaag ggcctttccg tcctcagccg tcgcttcatg tgactccacg      1140
gagtaccggg cgccgtccag gcacctcgat tagttctcga gcttttggag tacgtcgtct      1200
ttaggttggg gggaggggtt ttatgcgatg gagtttcccc acactgagtg ggtggagact      1260
gaagttaggc cagcttggca cttgatgtaa ttctccttgg aatttgccct ttttgagttt      1320
ggatcttggt tcattctcaa gcctcagaca gtggttcaaa gttttttttct tccatttcag    1380 gtgcggccgc tccgccacca tgatggactt ggagttgcca ccgccaggac tacagtccca     1440
gcaggacatg gatttgattg acatcctttg gaggcaagac atagatcttg gagtaagtcg     1500
agaagtgttt gactttagtc agcgacagaa ggactatgag ttggaaaaac agaaaaaact     1560
cgaaaaggaa agacaagagc aactccagaa ggaacaggag aaggcctttt tcgctcagtt    1620
tcaactggat gaagaaacag gagaattcct cccaattcag ccggcccagc acatccagac    1680
agacactagt ggatccgcca gctactccca ggttgcccac attcccaaac aagatgcctt    1740
gtactttgaa gactgtatgc agcttttggc agagacattc ccatttgttg atgaccatga    1800
gtcgcttgcc ctggatatcc ccagccacgc tgaaagttca gtcttcactg cccctcatca    1860
ggcccagtcc ctcaatagct ctctggaggc agccatgact gatttaagca gcatagagca    1920
ggacatggag caagtttggc aggagctatt ttccattccc gaattacagt gtcttaatac    1980
cgaaaacaag cagctggctg atactaccgc tgttcccagc ccagaagcca cactgacaga    2040
aatggacagc aattaccatt tttactcatc gatctcctcg ctggaaaaag aagtgggcaa    2100
ctgtggtcca catttccttc atggttttga ggattctttc agcagcatcc tctccactga    2160
tgatgccagc cagctgacct ccttagactc aaatcccacc ttaaacacag attttggcga    2220
tgaattttat tctgctttca tagcagagcc cagtgacggt ggcagcatgc cttcctccgc    2280
tgccatcagt cagtcactct ctgaactcct ggacgggact attgaaggct gtgacctgtc    2340
actgtgtaaa gctttcaacc cgaagcacgc tgaaggcaca atggaattca atgactctga    2400
ctctggcatt tcactgaaca caagtcccag ccgagcgtcc ccagagcact ccgtggagtc    2460
ttccatttac ggagacccac cgcctggggtt cagtgactcg gaaatggagg agctagatag   2520
tgcccctgga agtgtcaaac agaacggccc taaagcacag ccagcacatt ctcctggaga    2580
cacagtacag cctctgtcac cagctcaagg gcacagtgct cctatgcgtg aatcccaatg    2640
tgaaaataca acaaaaaaag aagttcccgt gagtcctggt catcaaaaag ccccattcac    2700
aaaagacaaa cattcaagcc gcttagaggc tcatctcaca cgagatgagc ttagggcaaa    2760
agctctccat attccattcc ctgtcgaaaa aatcattaac ctccctgttg atgacttcaa    2820
tgaaatgatg tccaaggagc aattcaatga agctcagctc gcattgatcc gagatatacg    2880
caggagaggt aagaataaag tcgccgccca gaactgtagg aaaaggaagc tggagaacat    2940
tgtcgagctg gagcaagact tgggccactt aaaagacgag agagaaaaac tactcagaga    3000
aaagggagaa aacgacagaa acctccatct actgaaaagg cggctcagca ccttgtatct    3060
tgaagtcttc agcatgttac gtgatgagga tggaaagcct tactctccca gtgaatactc    3120
tctgcagcaa accagagatg gcaatgtgtt ccttgttccc aaaagcaaga agccagatac    3180
aaagaaaaac tagagcgggc tagcaatcaa cctctggatt acaaaatttg tgaaagattg    3240
actggtattc ttaactatgt tgctcctttt acgctatgtg gatacgctgc tttaatgcct    3300
```

```
ttgtatcatg ctattgcttc ccgtatggct ttcattttct cctccttgta taaatcctgg    3360
ttagttcttg ccacggcgga actcatcgcc gcctgccttg cccgctgctg gacagggct     3420 cggctgttgg gcactgacaa ttccgtggtg tttatttgtg aaatttgtga tgctattgct   3480
ttatttgtaa ccattctagc tttatttgtg aaatttgtga tgctattgct ttatttgtaa   3540
ccattataag ctgcaataaa caagttaaca acaacaattg cattcatttt atgtttcagg   3600 ttcagggga gatgtgggag gttttttaaa gcgggggatc caaattcccg ataaggatct    3660
tcctagagca tggctacgta gataagtagc atggcgggtt aatcattaac tacaaggaac   3720
ccctagtgat ggagttggcc actccctctc tgcgcgctcg ctcgctcact gaggccgggc   3780
gaccaaaggt cgcccgacgc ccgggctttg cccgggcggc ctcagtgagc gagcgagcgc   3840
gcagccttaa ttaa                                                    3854

<210> SEQ ID NO 117
<211> LENGTH: 231
<212> TYPE: DNA
<213> ORGANISM: Homo sapiens

<400> SEQUENCE: 117
aggctccggt gcccgtcagt gggcagagcg cacatcgccc acagtccccg agaagttggg    60
gggaggggtc ggcaattgaa ccggtgccta gagaaggtgg cgcggggtaa actgggaaag   120
tgatgtcgtg tactggctcc gccttttttcc cgagggtggg ggagaaccgt atataagtgc  180
agtagtcgcc gtgaacgttc tttttcgcaa cgggtttgcc gccagaacac a            231

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gccaccatgg gtcgggggct gc                                             22

<210> SEQ ID NO 119
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ggacagggct tgattgtggg ccctctgggg tcgggactgc tggtggtgta ttcttccg      58

<210> SEQ ID NO 120
<211> LENGTH: 96
<212> TYPE: DNA
<213> ORGANISM: Canis sp.

<400> SEQUENCE: 120
atgcacagtc aagggcgggg ttgcaacaac acaaaacaaa acaaaacttc cggacttcga    60
cctgcagctg agaagaacat ctcgcaaagc ggcgtt                              96

<210> SEQ ID NO 121
<211> LENGTH: 69
<212> TYPE: DNA
<213> ORGANISM: Unknown
```

```
<220> FEATURE:
<223> OTHER INFORMATION: Description of Unknown:
      mouse/human secretion signal sequence

<400> SEQUENCE: 121
atgggtcggg ggctgctccg gggcctgtgg ccgctgcata tcgtcctgtg gacgcgcatc      60
gccagcacg                                                              69

<210> SEQ ID NO 122
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atgggtcggg ggctgctccg gggcctgtgg ccgctgcata tcgtcctgtg gacgcgcatc      60
gccagcacga ataatgacat gatggtcact gacagcaatg gtgtcatcaa atttccacaa     120
ttgtgtaaat tttgtgatgt gagatcttcc acctgtgaca accagaaatc ttgcatgagc     180
aactgcagca ttacatccat ctgtgagaag ccacatgaag tctgtctggc tgtctggaga     240
aagaatgatg agaacataac actagagact ctctgccatg accccaagga tacctaccat     300
ggaattgttc tcgaagatgc tgcctcttcg aagtgcatta tgaaagaaaa gaaggtgctg     360
ggggagactt tctttatgtg ttcctgtagc tccgacgagt gcaacgacta catcatcttc     420
tctgaagaat atgccaccaa caaccctgac ttgttgttag tcatattcca acccaaaaga     480
gaaaatggaa gagttcctcg cccacctgat tgtcccaaat gcccagcccc tgaaatgctg     540
ggagggcctt cggtcttcat cttttccccg aaacccaagg acaccctctt gattgcccga     600
acacctgagg tcacatgtgt ggtggtggat ctggacccag aagaccctga ggtgcagatc     660
agctggttcg tggacggtaa gcagatgcaa acagccaaga ctcagcctcg tgaggagcag     720
ttcaatggca cctaccgtgt ggtcagtgtc ctccccattg gcaccaggga ctggctcaag     780
gggaagcagt tcacgtgcaa agtcaacaac aaagccctcc catccccgat cgagaggacc     840
atctccaagg ccagagggca agcccatcag cccagtgtgt atgtcctgcc gccatcccgg     900
gaggagttga gcaagaacac agtcagcttg acatgcctga tcaaagactt cttcccacct     960
gacattgatg tggagtggca gagcaatgga cagcaggagc tgagagcaag taccgcacg    1020 accccgcccc agctggacga ggacgggtcc tacttcctgt acagcaagct ctctgtggac    1080
aagagccgct ggcagcgggg agacaccttc atatgtgcgg tgatgcatga agctctacac    1140
aaccactaca cacaggaatc cctctcccat tctccgggta aggagggag tggtgggtcc    1200 gattacaaag atcacgatgg ggactataaa gatcacgaca tcgactataa ggatgacgat    1260
gataaatga                                                           1269

<210> SEQ ID NO 123
<211> LENGTH: 54
<212> TYPE: DNA
<213> ORGANISM: Homo sapiens

<400> SEQUENCE: 123 atggctttc tttggttgct gagctgctgg gcactgctgg gtactacttt tgga             54

<210> SEQ ID NO 124
<211> LENGTH: 18
<212> TYPE: PRT
```

<213> ORGANISM: Homo sapiens

<400> SEQUENCE: 124

Met Ala Phe Leu Trp Leu Leu Ser Cys Trp Ala Leu Leu Gly Thr Thr
1               5                   10                  15

Phe Gly

<210> SEQ ID NO 125
<211> LENGTH: 45
<212> TYPE: DNA
<213> ORGANISM: Unknown
<220> FEATURE:
<223> OTHER INFORMATION: Description of Unknown:
      Trypsinogen sequence

<400> SEQUENCE: 125
atgaacttgc ttctcatcct gactttgtt gcagccgccg tggct                45

<210> SEQ ID NO 126
<211> LENGTH: 57
<212> TYPE: DNA
<213> ORGANISM: Unknown
<220> FEATURE:
<223> OTHER INFORMATION: Description of Unknown:
      Heavy chain sequence

<400> SEQUENCE: 126
atggagttcg ggctttcttg ggtgttcttg gtcgctttgt ttcgggggt ccagtgt    57

<210> SEQ ID NO 127
<211> LENGTH: 19
<212> TYPE: PRT
<213> ORGANISM: Unknown
<220> FEATURE:
<223> OTHER INFORMATION: Description of Unknown:
      Heavy chain sequence

<400> SEQUENCE: 127

Met Glu Phe Gly Leu Ser Trp Val Phe Leu Val Ala Leu Phe Arg Gly
1               5                   10                  15

Val Gln Cys

<210> SEQ ID NO 128
<211> LENGTH: 57
<212> TYPE: DNA
<213> ORGANISM: Unknown
<220> FEATURE:
<223> OTHER INFORMATION: Description of Unknown:
      IL2-ILco1 sequence

<400> SEQUENCE: 128
atgaggatgc aacttctcct cttgatagcc ctttccttgg ctctggtcac caacagc    57

<210> SEQ ID NO 129
<211> LENGTH: 19
<212> TYPE: PRT
<213> ORGANISM: Unknown
<220> FEATURE:
<223> OTHER INFORMATION: Description of Unknown:
      IL2-ILco1 sequence

<400> SEQUENCE: 129

Met Arg Met Gln Leu Leu Leu Leu Ile Ala Leu Ser Leu Ala Leu Val
1               5                   10                  15

Thr Asn Ser

<210> SEQ ID NO 130
<211> LENGTH: 20
<212> TYPE: PRT
<213> ORGANISM: Unknown
<220> FEATURE:
<223> OTHER INFORMATION: Description of Unknown:
      IL2-ILco2 sequence

<400> SEQUENCE: 130

Met Arg Arg Met Gln Leu Leu Leu Leu Ile Ala Leu Ser Leu Ala Leu
1               5                   10                  15

Val Thr Asn Ser
            20

<210> SEQ ID NO 131
<211> LENGTH: 14
<212> TYPE: PRT
<213> ORGANISM: Unknown
<220> FEATURE:
<223> OTHER INFORMATION: Description of Unknown:
      IL2 sequence

<400> SEQUENCE: 131

Met Gln Leu Leu Ser Cys Ile Ala Leu Ile Leu Ala Leu Val
1               5                   10

<210> SEQ ID NO 132
<211> LENGTH: 18
<212> TYPE: PRT
<213> ORGANISM: Homo sapiens

<400> SEQUENCE: 132

Met Lys Trp Val Thr Phe Ile Ser Leu Leu Phe Leu Phe Ser Ser Ala
1               5                   10                  15

Tyr Ser

<210> SEQ ID NO 133
<211> LENGTH: 19
<212> TYPE: PRT
<213> ORGANISM: Homo sapiens

<400> SEQUENCE: 133

Met Thr Arg Leu Thr Val Leu Ala Leu Leu Ala Gly Leu Leu Ala Ser
1               5                   10                  15

Ser Arg Ala

<210> SEQ ID NO 134
<211> LENGTH: 17
<212> TYPE: PRT
<213> ORGANISM: Gaussia sp.

<400> SEQUENCE: 134

Met Gly Val Lys Val Leu Phe Ala Leu Ile Cys Ile Ala Val Ala Glu
1               5                   10                  15

Ala

<210> SEQ ID NO 135
<211> LENGTH: 2679
<212> TYPE: DNA
<213> ORGANISM: Canis sp.

<400> SEQUENCE: 135

```
atggccacct gcattttaca gatgagattc ctaaggctgg ggaagatact gttccactcc      60
agcccacaaa gcacaggtgg cagtggtggg acccggggac ctcgagctcc ggcacagctg     120
cgaacgcagc gtggcacaga taagttagtt gctaagtcag agctcaaggc taaaacggcc     180
caccgcgcgc tggccgacca cttcagggac tacgccgagc tctgcttccg ccacttctgc     240
ggccaggtca agtactggat caccatcgac aaccccctacg tggtggcctg gcacggctac    300
gccaccggtc gcctggcacc cggagtcaga ggcagcccgc ggctcgggta cctggtggcg     360
cacaacctcc tcctggctca cgccaaaatc tggcatctct acaatacttc tttccgccca     420
actcagggag gccaggtatc cattgcccta agctcccact ggatcaatcc tcgaagaatg     480
accgaccata gcatcaaaga atgtcaaaaa tctcttgact ttgtactagg ctggtttgcc     540
aagcccatat ttattgatgg tgactatcct gagagcatga agaataacct gtcatctctt     600
ctgcctgttt ttactgaatc tgagaaaaag ttcatcaagg gaacagctga ctttttttgct   660
cttttcttttg gaccaacttt gagttttcaa ctcttggacc ctcatatgaa gttccaccaa    720
ttagaatctc ccagcctgag gcaactcctt tcttggattg accttgaata taaccaccct     780
caaatattta ttgtggaaaa tggctggttt gtctcaggga ccaccaagag agatgatgcc     840
aaatatatgt attacctcaa aaaattcata atggaaacct taaaagccat caggctggat    900
ggggtggatg tcataggata cacagcgtgg tcccttatgg atggcttcga gtggcacaga     960
ggctacagca tcagacgtgg actcttctac gtggactttc taagccagga taagaaactg    1020
ttgccaaagt cttcagcctt gttctaccaa aagctgatag agaaaaatgg cttccctcct    1080
ttacctgaaa atcagcccct agaagggaca tttccctgtg actttgcttg gggaattgtt    1140
gacaactaca ttcaagtgga caccactctg tctcagttta ccgacccgaa cgtttacctg    1200
tgggacgtcc atcacagcaa gaggctgatt aaggtggacg gctgcgggc caagaagagg     1260
aagccctact gcgtggactt tgccgccatc gggccccagg tggccctgct gcaggagatg    1320
cacgtctcgc attttcactt ctcgctggac tgggccctgc ctcctgccgct gggcaaccag    1380
tcccgggtga ccacgcggc cctgcactac tacggctgcg tggccagcga gctcctgcgc    1440
gccaacatca ccccggtggt ggcgctctgg agaccagccg ctgcgcacca gggtctgcct    1500
ggaccgctgg cacagcgcgg tgcctgggag aacccacgca ccgccctggc gttcgccgag    1560
tacgcgcgcc tgtgcttccg cgccctgggc cgccacgtca aggtgtggat cacgctgcgc    1620
gagccgccca cgcggaacct gacgctccgc gccgggcaca acctgctgcg ggcgcacgcg    1680
ctggcctggc gcgtgtacga cgagcagttc cggggctcgc agcagggaa ggtgtccatc     1740
gccctgcagg ccgactgggt ggagcccgcc tgcccctcct cccagaagga ccgcgaagtg    1800
gccgagaggg ttctggagtt cgacgtcggc tggctggccg agcccatctt cggctccggg    1860
gactacccgc ggctgatgcg cgactggctc acccggagag accattccct cctgccctat    1920
ttcactgacg aagagaagag gctaatccgg ggttcctttg acttcctggc cttgagccat    1980
tacaccacca tcctcgtgga ctgggaaaag gaagacccag tcaaatacaa tgattacctg    2040
gaagtgcagg agatgaccga catcacctgg ctcaactccc ccagtcaggt ggccgtagtg    2100
ccctggggcc tgcgcaaagt gctcaactgg ctcaagttca gtacggaga cctccccatg     2160
tatatcgtat ccaacggcat agatgacgat ccgcgggcag cccaggactc gttgagggtg    2220
tattacatgc agaactatgt aaatgaagct ctgaaagcct acgtattgga tggtatcaat    2280
ctttgtggat actttgccta ctcatttaat gatcgcacag ctccgaagtt tggcctctat    2340
cattatgctg caaaccagtt tgagcccaaa ccgtcggtga agcattacag gaaaattatt    2400
```

```
gacaacaatg gcttcccagg ccctgaaact ttggggcggt tttgtccaga ggaattcacc    2460
ctgtgcaccg aatgcagctt ttttcacacc cgaaagtctt tactggcttt catagctttc    2520 ctacttttg cttttattat ttctctttct ctgattttct actactctag gaaaggcaga    2580
agaagttata aaggagggag tggtgggtcc gattacaaag atcacgatgg ggactataaa    2640
gatcacgaca tcgactataa ggatgacgat gataaatga                           2679
```

```
<210> SEQ ID NO 136
<211> LENGTH: 633
<212> TYPE: DNA
<213> ORGANISM: Canis sp.

<400> SEQUENCE: 136
```

```
atgggctggg ccgaggccgg gttcgagcac ctgggactgt gggtccctgt gctggctgtg      60
cttttgctgg aagcctgccg ggcacatccg atccctgact ccagcccct cctacaattt     120 ggaggtcaag ttcgacagcg gtacctctac accgacgatg cccaggagac agaggcccac    180
ctagagatca gggccgatgg cacagtggtg ggggctgccc gccagagccc tgaaagtctc    240
ctggagctga aagccctaaa gccaggggtc attcaaatct tgggagtcaa acatccagg     300 ttcctgtgcc agggcccaga tgggacacta tatggctcgc tccatttcga ccctgtggcc    360 tgcagttttcc gagaactgct tcttgaggat gggtacaaca tctaccactc cgagacccttt  420 ggtctcccgc ttcgcctgcg ccccacaac tccgcatacc gggacttggc accccgcggg    480
cctgcccgct tcctgccact gccaggcctg cttccagcac cccagagcc tccagggatc    540 ctggccccgg agcctcctga cgtgggctcc tcggaccctc tgagcatggt ggggccttca    600
cagggccgga gtcccagcta tgcttcctga tag                                 633
```

```
<210> SEQ ID NO 137
<211> LENGTH: 727
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(234)
<220> FEATURE:
<221> NAME/KEY: CDS
<222> LOCATION: (238)..(261)
<220> FEATURE:
<221> NAME/KEY: CDS
<222> LOCATION: (277)..(303)
<220> FEATURE:
<221> NAME/KEY: CDS
<222> LOCATION: (313)..(372)
<220> FEATURE:
<221> NAME/KEY: CDS
<222> LOCATION: (379)..(417)
<220> FEATURE:
<221> NAME/KEY: CDS
<222> LOCATION: (421)..(552)
<220> FEATURE:
<221> NAME/KEY: CDS
<222> LOCATION: (556)..(603)
<220> FEATURE:
<221> NAME/KEY: CDS
<222> LOCATION: (607)..(723)

<400> SEQUENCE: 137
```

```
cca agg tat att gct gtt gac agt gag cga cgc tgc aga tat tcc gct        48
Pro Arg Tyr Ile Ala Val Asp Ser Glu Arg Arg Cys Arg Tyr Ser Ala
1               5                   10                  15
```

```
cta agt gaa gcc aca gat gtt aga gcg gaa aat ctg cag agc tgc cta      96
Leu Ser Glu Ala Thr Asp Val Arg Ala Glu Asn Leu Gln Ser Cys Leu
         20                  25                  30 ctg cct cgg act tca agg ggc ttg cgg ccg cca tct cca tgg ctg tac     144
Leu Pro Arg Thr Ser Arg Gly Leu Arg Pro Pro Ser Pro Trp Leu Tyr
     35                  40                  45 cac ctt gtc ggc cag gtt act aca gat atg tat gtt gaa tct cat tac     192
His Leu Val Gly Gln Val Thr Thr Asp Met Tyr Val Glu Ser His Tyr
 50                  55                  60 ata tct gtt gta acc tgc tct gac att ttg gta tct ttc atc tga cca     240
Ile Ser Val Val Thr Cys Ser Asp Ile Leu Val Ser Phe Ile     Pro
 65                  70                  75 cgt act acc ttc tat ctg atg tgacagcttc tgtag cac cct gtt act aca    291
Arg Thr Thr Phe Tyr Leu Met                 His Pro Val Thr Thr
 80              85                                      90 cat act ttt gtt tagttataa agt atg tgg agt aac agg tgt act gct agc   342
His Thr Phe Val           Ser Met Trp Ser Asn Arg Cys Thr Ala Ser
         95                        100                 105 tgt aga act cca gct tcg gcc tgt aac tta tgatag caa tgt cag cag      390
Cys Arg Thr Pro Ala Ser Ala Cys Asn Leu        Gln Cys Gln Gln
                 110                 115 tgc ctc ctg ttc cct ttc cta atc att taa gat tct aaa att ata gga     438
Cys Leu Leu Phe Pro Phe Leu Ile Ile     Asp Ser Lys Ile Ile Gly
120                 125                 130 tta gga atg gga aca gta agt aag gtt gac cat act cta cag ttg ttg     486
Leu Gly Met Gly Thr Val Ser Lys Val Asp His Thr Leu Gln Leu Leu
135                 140                 145                 150 att tcg tgg cta cag agt ttc ctt agc aga gct gga tgc agt gca gcc     534
Ile Ser Trp Leu Gln Ser Phe Leu Ser Arg Ala Gly Cys Ser Ala Ala
             155                 160                 165 ata tat ttg tct aaa cta taa tat atg gct gca ctg cat ata gct act     582
Ile Tyr Leu Ser Lys Leu     Tyr Met Ala Ala Leu His Ile Ala Thr
                 170                 175                 180 gct agg caa tcc ttc cct cga taa gat gca gcg gcg gct cct ctc ccc     630
Ala Arg Gln Ser Phe Pro Arg     Asp Ala Ala Ala Ala Pro Leu Pro
                 185                 190                 195 atg gcc ctg gcc ttg ttg aag agg att atc ctg ggc tca gag ata atc     678
Met Ala Leu Ala Leu Leu Lys Arg Ile Ile Leu Gly Ser Glu Ile Ile
                 200                 205                 210 ctc tac aac aag ggc agg gac ctg ggg acc ccg gca ccg gca ggc tagc   727
Leu Tyr Asn Lys Gly Arg Asp Leu Gly Thr Pro Ala Pro Ala Gly
             215                 220                 225
```

<210> SEQ ID NO 138
<211> LENGTH: 78
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 138

```
Pro Arg Tyr Ile Ala Val Asp Ser Glu Arg Arg Cys Arg Tyr Ser Ala
1               5                   10                  15

Leu Ser Glu Ala Thr Asp Val Arg Ala Glu Asn Leu Gln Ser Cys Leu
             20                  25                  30

Leu Pro Arg Thr Ser Arg Gly Leu Arg Pro Pro Ser Pro Trp Leu Tyr
         35                  40                  45

His Leu Val Gly Gln Val Thr Thr Asp Met Tyr Val Glu Ser His Tyr
     50                  55                  60
```

Ile Ser Val Val Thr Cys Ser Asp Ile Leu Val Ser Phe Ile
65                  70                  75

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Pro Arg Thr Thr Phe Tyr Leu Met
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

His Pro Val Thr Thr His Thr Phe Val
1               5

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Met Trp Ser Asn Arg Cys Thr Ala Ser Cys Arg Thr Pro Ala Ser
1               5                   10                  15

Ala Cys Asn Leu
            20

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Cys Gln Gln Cys Leu Leu Phe Pro Phe Leu Ile Ile
1               5                   10

<210> SEQ ID NO 143
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ser Lys Ile Ile Gly Leu Gly Met Gly Thr Val Ser Lys Val Asp
1               5                   10                  15

His Thr Leu Gln Leu Leu Ile Ser Trp Leu Gln Ser Phe Leu Ser Arg
            20                  25                  30

```
Ala Gly Cys Ser Ala Ala Ile Tyr Leu Ser Lys Leu
         35                  40
```

```
<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Met Ala Ala Leu His Ile Ala Thr Ala Arg Gln Ser Phe Pro Arg
1               5                   10                  15

<210> SEQ ID NO 145
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ala Ala Ala Pro Leu Pro Met Ala Leu Ala Leu Leu Lys Arg
1               5                   10                  15

Ile Ile Leu Gly Ser Glu Ile Ile Leu Tyr Asn Lys Gly Arg Asp Leu
            20                  25                  30

Gly Thr Pro Ala Pro Ala Gly
        35

<210> SEQ ID NO 146
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(258)
<220> FEATURE:
<221> NAME/KEY: CDS
<222> LOCATION: (262)..(456)
<220> FEATURE:
<221> NAME/KEY: CDS
<222> LOCATION: (460)..(486)
<220> FEATURE:
<221> NAME/KEY: CDS
<222> LOCATION: (490)..(576)
<220> FEATURE:
<221> NAME/KEY: CDS
<222> LOCATION: (580)..(846)

<400> SEQUENCE: 146 ggc caa ggt ata ttg ctg ttg aca gtg agc gac atg ctg tcc ctg gtc      48
Gly Gln Gly Ile Leu Leu Leu Thr Val Ser Asp Met Leu Ser Leu Val
1               5                   10                  15 ctt atg gtc aag cca cag atg cat aag gac cac gga cag cag gct gcc      96
Leu Met Val Lys Pro Gln Met His Lys Asp His Gly Gln Gln Ala Ala
            20                  25                  30 tac tgc ctc gga ctt caa ggg gct tgc ggc cgc cat ctc cat ggc tgt     144
Tyr Cys Leu Gly Leu Gln Gly Ala Cys Gly Arg His Leu His Gly Cys
        35                  40                  45 acc acc ttg tcg gct gga tgc agt ggc gac att ttg ttg aat ctc att     192
Thr Thr Leu Ser Ala Gly Cys Ser Gly Asp Ile Leu Leu Asn Leu Ile
    50                  55                  60
```

```
aat gtc gcc agt gca tcc act ctg aca ttt tgg tat ctt tca tct gac     240
Asn Val Ala Ser Ala Ser Thr Leu Thr Phe Trp Tyr Leu Ser Ser Asp
 65              70                  75                  80 cac gta cta cct tct atc tga tgt gac agc ttc tgt agc acg cca ccc     288
His Val Leu Pro Ser Ile     Cys Asp Ser Phe Cys Ser Thr Pro Pro
                 85                  90                  95 tct tca cgg cca atg ttt agt tat ttg gcc gtg acg agg gtg gct gta     336
Ser Ser Arg Pro Met Phe Ser Tyr Leu Ala Val Thr Arg Val Ala Val
            100                 105                 110 ctg cta gct gta gaa ctc cag ctt cgg cct gta act tat gat agc aat     384
Leu Leu Ala Val Glu Leu Gln Leu Arg Pro Val Thr Tyr Asp Ser Asn
        115                 120                 125 gtc agc agt gcc tcg cca ccc tct tca cgg cca att aag att cta aaa     432
Val Ser Ser Ala Ser Pro Pro Ser Ser Arg Pro Ile Lys Ile Leu Lys
    130                 135                 140 tta ttg ggc cgt gaa cag ggt ggc taa gta agg ttg acc ata ctc tac     480
Leu Leu Gly Arg Glu Gln Gly Gly     Val Arg Leu Thr Ile Leu Tyr
145                 150                 155 agt tgt tga ttt cgt ggc tac aga gtt tcc tta gca gag ctg gat gca     528
Ser Cys     Phe Arg Gly Tyr Arg Val Ser Leu Ala Glu Leu Asp Ala
160                 165                 170 gtg cag cca tat att tgt cta aac tat aat ata tgg ctg cac tgc ata     576
Val Gln Pro Tyr Ile Cys Leu Asn Tyr Asn Ile Trp Leu His Cys Ile
    175                 180                 185 tag cta ctg cta ggc aat cct tcc ctc gat aag tat ggg gcc tgg ctc     624
    Leu Leu Gly Asn Pro Ser Leu Asp Lys Tyr Gly Ala Trp Leu
        190                 195                 200 gag cag ggg gcg agg gat cag aca gtt gga ctt gtt aaa tgg tcc cct     672
Glu Gln Gly Ala Arg Asp Gln Thr Val Gly Leu Val Lys Trp Ser Pro
205                 210                 215                 220 ccc tat gaa cgg tct ttc cct ctg tcc ttc cct ccc aat gac cgc gtc     720
Pro Tyr Glu Arg Ser Phe Pro Leu Ser Phe Pro Pro Asn Asp Arg Val
                225                 230                 235 ttc gtc aca gtc agc ggc ggc tcc tct ccc cat ggc cct ggc ctt gtt     768
Phe Val Thr Val Ser Gly Gly Ser Ser Pro His Gly Pro Gly Leu Val
            240                 245                 250 gaa gag gat tat cct ggg ctc aga gat aat cct cta caa caa ggg cag     816
Glu Glu Asp Tyr Pro Gly Leu Arg Asp Asn Pro Leu Gln Gln Gly Gln
        255                 260                 265 gga cct ggg gac ccc ggc acc ggc agg cta                             846
Gly Pro Gly Asp Pro Gly Thr Gly Arg Leu
    270                 275

<210> SEQ ID NO 147
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gly Gln Gly Ile Leu Leu Leu Thr Val Ser Asp Met Leu Ser Leu Val
 1               5                  10                  15

Leu Met Val Lys Pro Gln Met His Lys Asp His Gly Gln Gln Ala Ala
             20                  25                  30

Tyr Cys Leu Gly Leu Gln Gly Ala Cys Gly Arg His Leu His Gly Cys
         35                  40                  45

Thr Thr Leu Ser Ala Gly Cys Ser Gly Asp Ile Leu Leu Asn Leu Ile
     50                  55                  60
```

```
Asn Val Ala Ser Ala Ser Thr Leu Thr Phe Trp Tyr Leu Ser Ser Asp
 65                  70                  75                  80

His Val Leu Pro Ser Ile
                85
```

<210> SEQ ID NO 148
<211> LENGTH: 65
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 148

```
Cys Asp Ser Phe Cys Ser Thr Pro Pro Ser Arg Pro Met Phe Ser
 1               5                  10                  15

Tyr Leu Ala Val Thr Arg Val Ala Val Leu Leu Ala Val Glu Leu Gln
                20                  25                  30

Leu Arg Pro Val Thr Tyr Asp Ser Asn Val Ser Ser Ala Ser Pro Pro
            35                  40                  45

Ser Ser Arg Pro Ile Lys Ile Leu Lys Leu Leu Gly Arg Glu Gln Gly
        50                  55                  60

Gly
 65
```

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 149

```
Val Arg Leu Thr Ile Leu Tyr Ser Cys
 1               5
```

<210> SEQ ID NO 150
<211> LENGTH: 29
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 150

```
Phe Arg Gly Tyr Arg Val Ser Leu Ala Glu Leu Asp Ala Val Gln Pro
 1               5                  10                  15

Tyr Ile Cys Leu Asn Tyr Asn Ile Trp Leu His Cys Ile
                20                  25
```

<210> SEQ ID NO 151
<211> LENGTH: 89
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 151

```
Leu Leu Leu Gly Asn Pro Ser Leu Asp Lys Tyr Gly Ala Trp Leu Glu
 1               5                  10                  15

Gln Gly Ala Arg Asp Gln Thr Val Gly Leu Val Lys Trp Ser Pro Pro
```

-continued

```
                20                  25                  30
Tyr Glu Arg Ser Phe Pro Leu Ser Phe Pro Pro Asn Asp Arg Val Phe
            35                  40                  45

Val Thr Val Ser Gly Gly Ser Ser Pro His Gly Pro Gly Leu Val Glu
        50                  55                  60

Glu Asp Tyr Pro Gly Leu Arg Asp Asn Pro Leu Gln Gln Gly Gln Gly
65                  70                  75                  80

Pro Gly Asp Pro Gly Thr Gly Arg Leu
                85
```